US011633402B2

(12) United States Patent
Kodama et al.

(10) Patent No.: US 11,633,402 B2
(45) Date of Patent: Apr. 25, 2023

(54) RET INHIBITOR

(71) Applicant: CHUGAI SEIYAKU KABUSHIKI KAISHA, Tokyo (JP)

(72) Inventors: Tatsushi Kodama, Kanagawa (JP); Hiroshi Sakamoto, Kanagawa (JP); Toshiyuki Tsukaguchi, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/855,712

(22) Filed: Apr. 22, 2020

(65) Prior Publication Data

US 2020/0246349 A1 Aug. 6, 2020

Related U.S. Application Data

(62) Division of application No. 14/429,834, filed as application No. PCT/JP2013/075621 on Sep. 24, 2013, now Pat. No. 10,668,075.

(30) Foreign Application Priority Data

Sep. 25, 2012 (JP) ................................ 2012-211040

(51) Int. Cl.

| | |
|---|---|
| ***A61K 31/403*** | (2006.01) |
| ***A61K 31/5377*** | (2006.01) |
| ***C07D 401/04*** | (2006.01) |
| ***C12Q 1/6886*** | (2018.01) |
| ***G01N 33/574*** | (2006.01) |
| ***C12Q 1/6883*** | (2018.01) |
| ***G01N 33/573*** | (2006.01) |

(52) U.S. Cl.

CPC ........ *A61K 31/5377* (2013.01); *C07D 401/04* (2013.01); *C12Q 1/6883* (2013.01); *C12Q 1/6886* (2013.01); *G01N 33/573* (2013.01); *G01N 33/57407* (2013.01); *G01N 33/57423* (2013.01); *A61K 31/403* (2013.01); *C12Q 2600/106* (2013.01); *C12Q 2600/156* (2013.01); *G01N 2333/912* (2013.01); *G01N 2800/52* (2013.01)

(58) Field of Classification Search

CPC .... A61K 31/403; A61K 31/5377; A61P 35/00
See application file for complete search history.

(56) References Cited

U.S. PATENT DOCUMENTS

| | | | |
|---|---|---|---|
| 5,721,267 | A | 2/1998 | Broka |
| 5,936,084 | A | 8/1999 | Jirousek et al. |
| 9,126,931 | B2 | 9/2015 | Kinoshita et al. |
| 9,365,514 | B2 | 6/2016 | Furumoto et al. |
| 9,440,922 | B2 | 9/2016 | Kinoshita et al. |
| 9,714,229 | B2 | 7/2017 | Tanaka et al. |
| 10,344,014 | B2 | 7/2019 | Shiraki et al. |
| 10,350,214 | B2 | 7/2019 | Tomimatsu et al. |
| 2004/0072890 | A1 | 4/2004 | Munro et al. |
| 2004/0191254 | A1 | 9/2004 | Fagin |
| 2005/0107364 | A1 | 5/2005 | Hutchinson et al. |
| 2006/0063790 | A1 | 3/2006 | Gillman et al. |
| 2007/0031907 | A1 | 2/2007 | Pinna et al. |
| 2007/0099893 | A1 | 5/2007 | Boyd et al. |
| 2007/0249653 | A1 | 10/2007 | Jagtap et al. |
| 2008/0058320 | A1 | 3/2008 | Herold et al. |
| 2008/0095838 | A1 | 4/2008 | Abou Chacra-Vernet |
| 2008/0262021 | A1 | 10/2008 | Capraro et al. |
| 2009/0209580 | A1 | 8/2009 | Matsui |
| 2009/0221555 | A1 | 9/2009 | Ahmed et al. |
| 2010/0099658 | A1 | 4/2010 | Kondoh et al. |
| 2012/0083488 | A1 | 4/2012 | Kinoshita et al. |
| 2012/0322050 | A1 | 12/2012 | Abassi et al. |

(Continued)

FOREIGN PATENT DOCUMENTS

| | | |
|---|---|---|
| CN | 1902200 A | 1/2007 |
| CN | 103305598 B | 4/2015 |

(Continued)

OTHER PUBLICATIONS

Bilsland et al., "Behavioral and Neurochemical Alterations in Mice Deficient in Anaplastic Lymphoma Kinase Suggest Therapeutic Potential for Psychiatric Indications," Neuropsychopharmacology, 2008, 33:685-700.

(Continued)

*Primary Examiner* — Samira J Jean-Louis

(74) *Attorney, Agent, or Firm* — Foley & Lardner LLP

(57) ABSTRACT

A compound represented by the following general formula (I) [the symbol in the formula are as defined in the description], a salt thereof, or the like is a RET inhibitor or RET tyrosine kinase inhibitor that can he used as an agent for the prevention or treatment of disorders including cancers and cancer metastasis having mutations in RET.

(I)

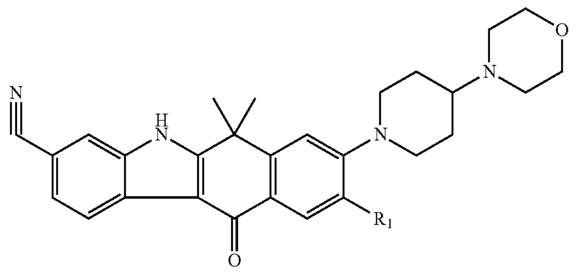

3 Claims, 1 Drawing Sheet

Specification includes a Sequence Listing.

(56) References Cited

U.S. PATENT DOCUMENTS

| | | | |
|---|---|---|---|
| 2013/0116280 | A1 | 5/2013 | Ju et al. |
| 2013/0143877 | A1 | 6/2013 | Furumoto et al. |
| 2014/0221404 | A1 | 8/2014 | Kohno et al. |
| 2015/0150845 | A1 | 6/2015 | Kinoshita et al. |
| 2015/0177246 | A1 | 6/2015 | Shibata et al. |
| 2015/0272958 | A1 | 10/2015 | Kodama et al. |
| 2016/0317494 | A1 | 11/2016 | Furumoto et al. |
| 2016/0340308 | A1 | 11/2016 | Kinoshita et al. |
| 2017/0035773 | A1 | 2/2017 | Tomimatsu et al. |
| 2017/0081306 | A1 | 3/2017 | Tanaka et al. |
| 2017/0119781 | A1 | 5/2017 | Meier et al. |
| 2017/0217927 | A1 | 8/2017 | Shiraki et al. |
| 2019/0284163 | A1 | 9/2019 | Shiraki et al. |
| 2020/0017442 | A1 | 1/2020 | Kinoshita et al. |
| 2020/0038407 | A1 | 2/2020 | Tomimatsu et al. |

FOREIGN PATENT DOCUMENTS

| | | | |
|---|---|---|---|
| EA | 001450 | B1 | 4/2001 |
| EP | 2 253 318 | | 11/2010 |
| JP | 08-092090 | A | 4/1996 |
| JP | 2012-126711 | A | 7/2012 |
| RU | 2162089 | C2 | 1/2001 |
| RU | 2448708 | C2 | 6/2010 |
| WO | WO 00/69856 | A1 | 11/2000 |
| WO | WO 2004/080980 | A1 | 9/2004 |
| WO | WO 2005/009389 | A2 | 2/2005 |
| WO | WO 2005/097765 | A1 | 10/2005 |
| WO | WO 2006/021884 | A2 | 3/2006 |
| WO | WO 2007/023310 | A2 | 3/2007 |
| WO | WO 2007/056497 | A1 | 5/2007 |
| WO | WO 2007/130468 | A2 | 11/2007 |
| WO | WO 2008/021369 | A2 | 2/2008 |
| WO | WO 2008/051547 | A1 | 5/2008 |
| WO | WO 2008/130951 | A1 | 10/2008 |
| WO | WO 2009/008371 | A1 | 1/2009 |
| WO | WO 2009/013126 | A1 | 1/2009 |
| WO | WO 2009/073620 | A2 | 6/2009 |
| WO | WO 2010/128324 | A1 | 11/2010 |
| WO | WO 2010/142423 | A2 | 12/2010 |
| WO | WO 2010/142685 | A1 | 12/2010 |
| WO | WO 2010/143664 | A1 | 12/2010 |
| WO | WO 2011/146945 | A2 | 11/2011 |
| WO | WO 2012/023597 | A1 | 2/2012 |
| WO | WO 2012/138783 | A2 | 10/2012 |
| WO | WO 2012/138789 | A2 | 10/2012 |
| WO | WO 2013/006864 | A2 | 1/2013 |
| WO | WO 2013/018882 | A1 | 2/2013 |
| WO | WO 2013/028817 | A1 | 2/2013 |
| WO | WO 2013/059740 | A1 | 4/2013 |
| WO | WO 2013/066047 | A1 | 5/2013 |
| WO | WO 2013/111668 | A1 | 8/2013 |
| WO | WO 2013/134693 | A1 | 9/2013 |
| WO | WO 2013/141266 | A1 | 9/2013 |
| WO | WO 2013/158859 | A1 | 10/2013 |
| WO | WO 2013/163428 | A1 | 10/2013 |
| WO | WO 2013/169339 | A1 | 11/2013 |
| WO | WO 2014/017491 | A1 | 1/2014 |
| WO | WO 2014/071419 | A2 | 5/2014 |
| WO | WO 2014/130975 | A1 | 8/2014 |
| WO | WO 2014/150300 | A2 | 9/2014 |
| WO | WO 2014/165710 | A2 | 10/2014 |
| WO | WO 2014/172046 | A2 | 10/2014 |

OTHER PUBLICATIONS

Bunz, F., "Chapter 1, The Genetic Basis of Cancer," Principles of Cancer Genetics, 2008, 1-47.
Capalletti et al., "Discovery of recurrent KIF5B-RET fusions and other targetable alterations from clinical NSCLC specimens," J. Clin. Oncol., 2012, 30(suppl.;abstr. No. 7510), 2 pages.
CAS RN 100863-39-6, STN Entry Date Mar. 15, 1986.
CAS RN 222318-66-3, STN Entry Date May 7, 1999.
CAS RN 24716-14-1, STN Entry Date Nov. 16, 1984.
CAS RN 36263-63-5, STN Entry Date Nov. 16, 1984.
CAS RN 4355-38-8, STN Entry Date Nov. 16, 1984.
CAS RN 6008-29-3, STN Entry Date Nov. 16, 1984.
CAS RN 61492-49-7, STN Entry Date Nov. 16, 1984.
CAS RN 74205-47-3, STN Entry Date Nov. 16, 1984.
CAS RN 89579-57-7, STN Entry Date Nov. 16, 1984.
CAS RN 93257-39-7, STN Entry Date Dec. 18, 1984.
Chen et al., "Oncogenic mutations of ALK kinase in neuroblastoma," Nature, Oct. 16, 2008, 455:971-974, and Methods page.
Communication of a Notice of Opposition for corresponding European Application No. 13842266.2 dated May 15, 2019.
Cools et al., "Identification of Novel Fusion Partners of ALK, the Anaplastic Lymphoma Kinase, in Anaplastic Large-Cell Lymphoma and Inflammatory Myofibroblastic Tumor," Genes, Chromosomes & Cancer, 2002, 34:354-362.
Drilon et al., "Response to Bacozantinib in Patients with RET Fusion-Positive Lung Adenocarcinomas," Cancer Discovery, Jun. 2013, 3(6):630-635.
Druker et al., "Section 1: Chronic Myelogenous Leukemia," Cancer: Principles & Practice of Oncology, $7^{th}$ Edition (DeVita et al., Eds.), 2121.
Eng et al., Hum. Mol. Genetics, 1992, 3(2):see abstract.
Faderl et al., "Section 3: Myelodysplastic Syndromes," Cancer: Principles & Practice of Oncology, $7^{th}$ Edition (DeVita et al., Eds.), 2144.
Fine et al., "Section 2: Neoplasms of the Central Nervous System," Cancer: Principles & Practice of Oncology, $7^{th}$ Edition (DeVita et al., Eds.), 1834-1887.
Fischer et al., "A Ki-1(CD30)-Positive Human Cell Line (Karpas 299) Established From a High-Grade Non-Hodgkin's Lymphoma, Showing a 2;5 Translocation and Rearrangement of the T-Cell Receptor β-Chain Gene," Blood, Jul. 1988, 72(1):234-240.
Galkin et al., "Identification of NVP-TAE684, a potent, selective and efficacious inhibitor of NPM-ALK," PNAS, Jan. 2, 2007, 104(1):270-275 (and Corrections published in PNAS, Feb. 6, 2007, 104(6):2024-2025).
Garbett et al., "Extending Nature's Leads: The Anticancer Agent Ellipticine," Curr. Med. Chem.—Anti-Cancer Agents, 2004, 4:149-172.
George et al., "Activating mutations in ALK provide a therapeutic target in neuroblastoma," Nature, 2008, 455:975-978.
Girouard et al., "Neurovascular coupling in the normal brain and in hypertension, stroke, and Alzheimer disease," Journal of Applied Physiology, 2006, 100:328-335.
Glick et al., "Treatment with atypical antipsychotics: new indications and new populations," Journal of Psychiatric Research, 2001, 35:187-191.
Goel et al., "Mice transgenic for BRAF V600E demonstrate phenotype affecting melanocyte and neural lineages," Proceedings of the American Association for Cancer Research, Apr. 2006, 47:#273.
Goodman & Gilman's, Chemotherapy of Neoplastic Diseases, The Pharmacological Basis of Therapeutics, Brunton et al., Eds., 2008, $11^{th}$ Ed., 853-908.
Griffin et al., "Recurrent Involvement of 2p23 in Inflammatory Myofibroblastic Tumors," Cancer Research, Jun. 15, 1999, 59:2776-2780.
Gummadi et al., "Discovery of 7-azaindole based anaplastic lymphoma kinase (ALK) inhibitors: Wild type and mutant (L1196M) active compounds with unique binding mode," Biorganic & Medicinal Chemistry Letters, 2013, 23:4911-4918.
Hallberg et al., "ALK and NSCLC: Targeted therapy with ALK inhibitors," F1000 Reports Medicine, Nov. 1, 2011, 3:21:1-9.
Herbst et al., "ALK Gene Products in Anaplastic Large Cell Lymphomas and Hodgkin's Disease," Blood, Sep. 1, 1995, 86(5):1694-1700.
Huang et al., "An in vivo model to study human GSTP1 polymorphisms in osteosarcoma," Proceedings of the American Association for Cancer Research, Apr. 2006, 47:#271.
Hübinger et al., "CD30-mediated cell cycle arrest associated with induced expression of $p21^{CIP1/WAF1}$ in the anaplastic large cell lymphoma cell line Karpas 299," Oncogene, 2001, 20:590-598.

(56) References Cited

OTHER PUBLICATIONS

Jazii et al., "Identification of squamous cell carcinoma associated proteins by proteomics and loss of beta tropomyosin expression in esophageal cancer," World J. Gastroenterol., Nov. 28, 2006, 12(44):7104-7112.
Jhiang, Sissy M., "The RET proto-oncogene in human cancers," Oncogene, Nov. 20, 2000, 19(49):5590-5597.
Ju et al., "Fusion of KIF5B and RET transforming gene in lung adenocarcinoma revealed from whole-genome and transcriptome sequencing," Genome Research, published online Dec. 22, 2011, 35 pages.
Ju et al., Genome Research, online Dec. 2011, 22:436-445.
Katayama et al., Mechanisms of Acquired Crizotinib Resistance in ALK-Rearranged Lung Cancers,: Sci. Transl. Med., Feb. 8, 2012, 4(120):120ra17, 13 pages.
Kinoshita et al., Design and synthesis of a highly selective, orally active and potent anaplastic lymphoma kinase inhibitor (CH5424802), Bioorganic & Medicinal Chemistry, 2012, 20(3):1271-1280.
Kirsch, Gilbert H., "Heterocyclic Analogues of Carbazole Alkaloids," Current Organic Chemistry, 2001, 5:507-518.
Kiura et al., "A first-in-human phase I/II study of ALK inhibitor CN5424802 in patients with ALK-positive NSCLC," Journal of Clinical Oncology, May 2012, 30(15Suppl):7602, Abstract.
Kodama et al., "Alectinib shows potent antitumor activity against RET-rearranged non-small cell lung cancer," Molecular Cancer Therapeutics, Oct. 27, 2014, 13(12):2910-2918.
Kohno et al., "KIF5B-RET fusions in lung adenocarcinoma," Nature Medicine, published online Feb. 2, 2012, 18(3):375-377.
Kuppen et al., "Tumor structure and extracellular matrix as a possible barrier for therapeutic approaches using immune cells or adenoviruses in colorectal cancer," Histochem. Cell. Biol., 2001, 115:67-72.
Kuster, Bernhard, Ed., Kinase Inhibitors, Methods and Protocols, Methods in Molecular Biology, 2012, vol. 795, Chapter 1 by Fabbro et al., "Targeting Cancer with Small-Molecular-Weight Kinase Inhibitors."
Kwak et al., "Anaplastic Lymphoma Kinase Inhibition in Non-Small-Cell Lung Cancer," The New England Journal of Medicine, Oct. 28, 2010, 363(18):1693-1703.
Lamant et al., "Establishment of a novel anaplastic large-cell lymphoma-cell line (COST) from a 'small-cell variant' of ALCL," Leukemia, 2004, 18:1693-1698.
Latif et al., "Journey of the ALK-inhibitor CH5424802 to phase II clinical trial," Arch. Pharm. Res., 2013, 36(9):1051-1054.
Li et al., "Identification of RET gene fusion by exon array analyses in 'pan-negative' lung cancer from never smokers," Cell Research, 2012, 22:928-931.
Lipson et al., "Identification of new ALK and RET gene fusions from colorectal and lung cancer biopsies," Nature Medicine, 2012, vol. 18, pp. 382-384.
Lissoni et al., "Biotherapy with the pineal hormone melatonin plus aloe and myrrh tincture in untreatable metastatic cancer patients as an essence therapy of cancer," Cancer Therapy, 2009, 7:397-401.
Luo et al., "Principles of Cancer Therapy: Oncogene and Non-oncogene Addiction," Cell, Mar. 6, 2009, 136:823-837.
Mologni, L, "Development of RET Kinase Inhibitors for Targeted Cancer Therapy," Current Medicinal Chemistry, 2011, 18(2):162-175.
Mosse et al., "Identification of ALK as a major familial neuroblastoma predisposition gene," Nature, Oct. 16, 2008, 455:930-935, and Methods page.
National Cancer Institute, http://www.cancer.gov/, "A to Z List of Cancers," downloaded May 29, 2014, 22 pages.
O'Brien et al., "Section 2: Chronic Lymphoid Leukemias," Cancer: Principles & Practice of Oncology, 7$^{th}$ Edition (DeVita et al., Eds.), 2133.
O'Brien et al., "Vascular cognitive impairment," The Lancet Neurology, Feb. 2003, 2:89-98.
Office Action dated Sep. 27, 2016, in JP 2015-040242, with English translation.
Pao et al., "EGF receptor gene mutations are common in lung cancers from 'never smokers' and are associated with sensitivity of tumors to gefitinib and erlotinib," PNAS, Sep. 7, 2004, 101(36):13306-13311.
Piva et al., "Ablation of oncogenic ALK is a viable therapeutic approach for anaplastic large-cell lymphomas," Blood, Jan. 2006, 107(2):689-697.
Rosenwald et al., "t(1;2)(q21;p23) and t(2;3)(p23;q21): Two Novel Variant Translocations of the t(2;5)(p23;q35) in Anaplastic Large Cell Lymphoma," Blood, Jul. 1, 1999, 94(1):362-364.
Sakamoto et al., "ALK inhibitor CH5424802," Bio Clinica, 2013, 28(9):866-871, with English abstract.
Sakamoto et al., "ALK inhibitor CH5424802," Cell, 2013, 45(6):292-296, with English abstract.
Sakamoto et al., "Cancer Cell-D-10-00840R3, Supplemental Information, CH5424802, a Selective ALK Inhibitor Capable of Blocking the Resistant Gatekeeper Mutant," Cancer Cell, May 17, 2011, 19:1-11, XP55248839.
Sakamoto et al., "CH5424802, a Selective ALK Inhibitor Capable of Blocking the Resistant Gatekeeper Mutant," Cancer Cell, May 17, 2011, 19(5):679-690.
Sang et al., "Targeted Inhibition of the Molecular Chaperone Hsp90 Overcomes ALK Inhibitor Resistance in Non-Small Cell Lung Cancer," Cancer Discovery, Mar. 26, 2013, 3(4):430-443.
Scheinberg et al., "Section 2: Management of Acute Leukemias," Cancer: Principles & Practice of Oncology, 7$^{th}$ Edition (DeVita et al., Eds.), 2005, 2088, 2092.
Seto et al., "CH5424802 (RO5424802) for patients with ALK-rearranged advanced non-small-cell lung cancer (AF-001JP study): a single-arm, open-label, phase 1-2 study," Lancet Oncology, 2013, 14(7):590-598.
Shah et al., "Current approaches in the treatment of Alzheimer's disease," Biomedicine & Pharmacotherapy, 2008, 62:199-207.
Shaw et al., "Targeting Anaplastic Lymphoma Kinase in Lung Cancer," Clinical Cancer Research, 2011, 17:2081-2086.
Shujuan, Wang, "The new insights on the diagnosis of malignant histiocytosis," Chinese Journal of Laboratory Medicine, Jan. 30, 2005, 28(1):14-16.
Silverman, Richard B., The Organic Chemistry of Drug Design and Drug Action, Second Ed., Elsevier Academic Press, Northwestern University, Evanston, Illinois, 2004, 29-31, table 2.2.
Soda et al., "Identification of the transforming EML4-ALK fusion gene in non-small-cell lung cancer," Nature, Aug. 2, 2007, 448:561-566, and Methods page.
Solomon et al., "Current Status of Targeted Therapy for Anaplastic Lymphoma Kinase-Rearranged Non-Small Cell Lung Cancer," Clinical Pharmacology & Therapeutics, Jan. 2014, 95(1):15-23.
Soussi, Thierry, "p53 Antibodies in the Sera of Patients with Various Types of Cancer: A Review," Cancer Res., 2000, 60:1777-1788.
Stephens et al., "The landscape of cancer genes and mutational processes in breast cancer," Nature, Jun. 21, 2012, 486:400-406.
Stoica et al., "Identification of Anaplastic Lymphoma Kinase as a Receptor for the Growth Factor Pleiotrophin," J. Biol. Chem., May 18, 2001, 276(20:16772-16779.
Stoica et al., "Midkine Binds to Anaplastic Lymphoma Kinase (ALK) and Acts as a Growth Factor for Different Cell Types," J. Biol. Chem., Sep. 27, 2002, 277(39):35990-35998.
Suzuki et al., "Discovery of novel fusion gene and the drug development study," The Medical Frontline, Dec. 2012, 67(12):2724-2730, with English abstract.
Takeuchi et al., "RET, ROS1 and ALK fusions in lung cancer," Nature Medicine, Mar. 2012, 18(3):378-381.
Utsumi et al., "Novel Anticancer Agent Expected in Lung Cancer Region," Aspiration, 2013, 32(8):717-722, with English abstract.
Wanner et al., "A convenient synthesis of 6-methylellipticine and 6-methylolivacine," Heterocycles, 1982, 19(12):2295-2300.
Wood et al., "Lack of the t(2;5) or Other Mutations Resulting in Expression of Anaplastic Lymphoma Kinase Catalytic Domain in CD30$^+$ Primary Cutaneous Lymphoproliferative Disorders and Hodgkin's Disease," Blood, Sep. 1, 1996, 88(5):1765-1770.
Yun et al., "Novel 2,4-dianilino-5-fluoropyrimidine derivatives possessing ALK inhibitory activities," Arch. Pharm. Res., 2014, 37(7):873-881.

(56) References Cited

OTHER PUBLICATIONS

Zdzalik et al., "Activating mutations in ALK kinase domain confer resistance to structurally unrelated ALK inhibitors in NPM-ALK-positive anaplastic large-cell lymphoma," J. Cancer Res. Clin. Oncol., 2014, 140(4):589-598.
Zhao et al., "The progress of the research on anaplastic lymphoma kinase genetic abnormality of anaplastic large cell lymphoma," Foreign Medical Sciences (Section of Blood Transfusion and Hematology), Oct. 15, 2004, 27(5):403-406.
U.S. Appl. No. 16/862,125, filed Apr. 29, 2020, Kinoshita et al.
U.S. Appl. No. 17/019,896, filed Sep. 14, 2020, Shiraki et al.
U.S. Appl. No. 17/255,707, filed Dec. 23, 2020, Kitayama et al.
U.S. Appl. No. 17/271,437, filed Sep. 3, 2019, Serizawa et al.
Asche et al., "Synthesis, antitumour activity and structure-activity relationships of 5H-benzo[b]carbazoles," Bioorganic & Medicinal Chemistry, 2005, 13:819-837.
Bernardo et al., "Synthesis, Electrochemistry, and Bioactivity of the Cyanobacterial Calothrixins and Related Quinones," J. Med. Chem., 2004, 47:4958-4963.
Boogaard et al., "Ring D Modifications of Ellipticine. Part 2. Chlorination of Ellipticine via its N-oxide and Synthesis and Selective Oxidation of 5,6,11-Trimethyl-5H-Benzo[b]Carbazole," Tetrahedron, 1994, 50(16):4811-4828.
Chang et al., "Polymethacrylates," Handbook of Pharmaceutical Excipients, Rowe et al., Eds., 2009, 6th Ed., 525-533.
Database Accession No. 1:1259(XP55784247), RN 826-55-1, 1907, one page.
Database Accession No. 27:43772 (XP55784257), RN 37828-19-6 CA, 1933, one page.
Database Accession No. 28:22560 (XP55784253), RN 77-55-4, 1934, one page.
Database Accession No. 28:22560 (XP55784254), RN 1135-67-7, 1934, one page.
Database Accession No. 41:3570(XP55784249), RN 6120-95-2, 1946, one page.
Davies, Peter, "Oral Solid Dosage Forms," Drugs and the Pharmaceutical Sciences, Pharmaceutical Preformulation and Formulation, Mark Gibson, Ed., 2009, 2nd Edition, 199:367-430.
Defendant Fresenius Kabi USA, LLC's Initial Invalidity Contentions, filed Oct. 9, 2020 in C.A. No. 20-394 (RGA), *Hoffmann-LaRoche, Inc., Chugai Pharmaceutical Co., Ltd., and Genentech, Inc.* (Plaintiffs and Counterclaim Defendants) v. *Fresenius Kabi USA, LLC* (Defendant and Counterclaim Plantiff), 112 pages.
Gadgeel et al., "A Phase 1 Dose Escalation Study of a New ALK Inhibitor, CH5424802/RO5424802, in ALK Non-Small Cell Lung Cancer (NSCLC) Patients who have Failed Crizotinib (AF-002JG/NP28761, NCT01588028," Journal of Thoracic Oncology, Nov. 2013, 8(2):S199, Abstract O16.06.
Gadgeel et al., "Safety and activity of alectinib against systemic disease and brain metastases in patients with crizotinib-resistant ALK-rearranged non-small-cell lung cancer (AF-002JG): results from the dose-finding portion of a phase 1/2 study," Lancet Oncology, 2014, 15:1119-1128.
Galkin et al., "Identification of NVP-TAE684, a potent, selective and efficacious inhibitor of NPM-ALK," PNAS, Jan. 2, 2007, 104(1):270-275.
Gunby et al., "Structural Insights into the ATP Binding Pocket of the Anaplastic Lymphoma Kinase by Site-Directed Mutagenesis, Inhibitor Binding Analysis, and Homology Modeling," J. Med. Chem., 2006, 49:5759-5768.
Hida et al., "Pharmacologic study (JP28927) of alectinib in Japanese patients with ALK non-small-cell lung cancer with or without prior crizotinib therapy," Cancer Science, 2016, 107:1642-1646.
Hooton, J.C., "Carboxymethylcellulose Calcium," Handbook of Pharmaceutical Excipients, Rowe et al., Eds., 6th Ed., 2009, 117-118.
Inoue et al., "One-year Follow-up of a Phase I/II Study of a Highly Selective ALK Inhibitor CH5424802/RO5424802 in ALK-Rearranged Advanced Non-Small Cell Lung Cancer (NSCLC)," Journal of Thoracic Oncology, Nov. 2013, 8(Supp.2):S1204, Abstract P3.11-034.
Kabir et al., "Hydroxypropyl Cellulose," Handbook of Pharmaceutical Excipients, Rowe et al., Eds., 6th Ed., 2009, 317-322.
Kashyap et al., "Fast Disintegrating Tablet: A Boon to Pediatric and Geriatric," International Journal of Pharma Professional's Research, Apr. 2011, 2(2):318-326.
Kinoshita et al., "Design and synthesis of a highly selective, orally active and potent anaplastic lymphoma kinase inhibitor (CH5424802)," Bioorganic & Medicinal Chemistry, 2012, 20:1271-1280.
Knoelker et al., "Transition Metal Complexes in Organic Synthesis, Part 38. First Total Synthesis of Carbazomycin G and H," Tetrahedron Letters, 1997, 38(23):4051-4054.
Li et al., "Design and Synthesis of 5-Aryl-pyridone-carboxamides as Inhibitors of Anaplastic Lymphoma Kinase," J. Med. Chem., 2006, 49:1006-1015.
Li et al., "Development of Anaplastic Lymphoma Kinase (ALK) Small-Molecule Inhibitors for Cancer Therapy," Medicinal Research Reviews, 2008 (online Aug. 10, 2007), 23(3):372-412.
Liao, Jeffrey Jie-Lou, "Molecular Recognition of Protein Kinase Binding Pockets for Design of Potent and Selective Kinase Inhibitors," Journal of Medicinal Chemistry, Feb. 8, 2007, 50(3):409-424.
Nakagawa et al., "A phase I/II study with a highly selective ALK inhibitor CH5424802/RO5424802 in ALK-positive non-small cell lung cancer (NSCLC) patients: Updated safety and efficacy results from AF-001JP," 49th Annual Meeting of the American Society of Clinical Oncology (ASCO), Chicago, IL, May 31, 2013-Jun. 4, 2013, poster, Abstract No. 8033.
Nakagawa et al., "Antitumor Activity of alectinib (CH5424802/RO5424802) for ALK-Rearranged NSCLC with or without Prior crizotinib Treatment in Bioequivalence Study," 49th Annual Meeting of the American Society of Clinical Oncology (ASCO), Chicago, IL, May 31, 2013-Jun. 4, 2013, poster, Abstract No. 8033.
Ou et al., "Consistent Therapeutic Efficacy of CH5424802/RO5424802 in Brain Metastases Among Crizotinib-Refractory ALK-Positive Non-small Cell Lung Cancer (NSCLC) Patients in an Ongoing Phase I/II Study (AF-002JG/NP28761, NCT01588028)," Journal of Thoracic Oncology, Nov. 2013, 8(2):Abstract O17.07.
Plumb, P., "Sodium Lauryl Sulfate," Handbook of Pharmaceutical Excipients, Rowe et al., Eds., 6th Ed., 2009, 652-653.
Seto et al., "CH5424802 (RO5424802) for patients with ALK-rearranged advanced non-small-cell lung cancer (AF-001JP study): a single-arm, open-label, phase 1-2 study," Lancet Oncology, Jun. 2013, 14:590-598.
Sheridan, Robert P., "The Most Common Chemical Replacements in Drug-Like Compounds," J. Chem. Inf. Comput. Sci., 2002, 42:103-108.
Vendome et al., "Molecular Modeling of Wild-Type and D816V c-Kit Inhibition Based on ATP-Competitive Binding of Ellipticine Derivatives to Tyrosine Kinases," J. Med. Chem., 2005, 48:6194-6201.
Wendling, Patrice, "Alectinib active in ALK-positive, crizotinib-refractory NSCLC," Chest Physician, Oct. 9, 2013, 4 pages.
Ars, Elisabeth, "Methods of genetic diagnosis of hereditary renal diseases. Genetic counseling," Nephrogenetics, May 2011, 2(1):1-119, DOI: 10.3265/Nephrology Supplement Extraordinary.pre2011. Mar. 10890, with English translation, 41 pages.

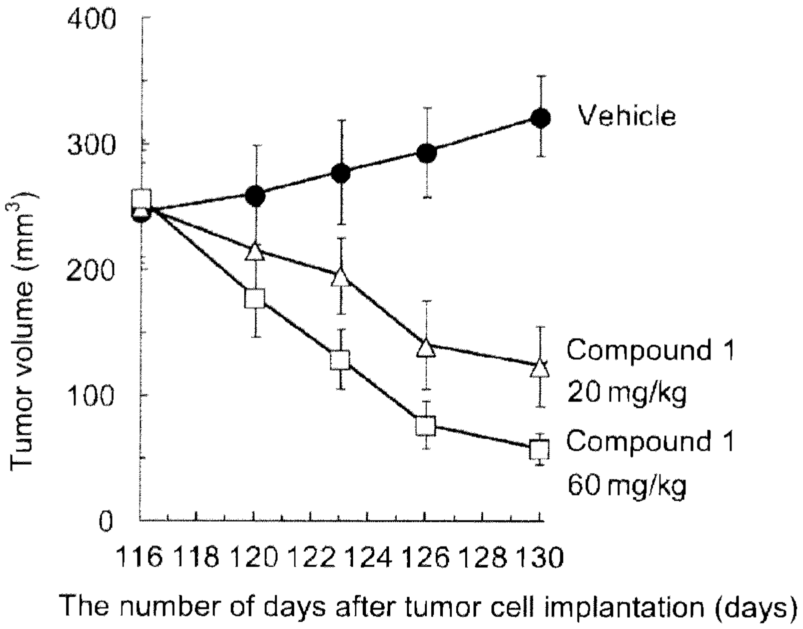
400
300
200
100
0
Tumor volume (mm3)
Vehicle
Compound 1
20 mg/kg
Compound 1
60 mg/kg
116 118 120 122 124 126 128 130
The number of days after tumor cell implantation (days)

RET INHIBITOR

CROSS-REFERENCE TO RELATED APPLICATIONS

This application is a Divisional of U.S. application Ser. No. 14/429,834, which is the National Stage application of PCT/JP2013/075621, filed Sep. 24, 2013, which claims priority from Japanese application JP 2012-211040, filed Sep. 25, 2012.

The instant application contains a Sequence Listing which has been submitted in ASCII format via EFS-WEB and is hereby incorporated by reference in its entirety. Said ASCII copy, created on Apr. 21, 2020, is named sequence.txt and is 308,211 bytes.

TECHNICAL FIELD

The present invention relates to a RET inhibitor, an inhibitor of RET tyrosine kinase, a prophylactic or therapeutic agent for diseases including cancers with a mutation in RET and their metastasis, a method for identifying a target patient, and the like, each of which comprises a tetracyclic compound or a salt thereof or a solvate thereof.

BACKGROUND ART

Rearranged during transfection (RET) is a member of the receptor tyrosine kinases belonging to the cadherin superfamily (Surgery, 2007, vol. 141, p. 96-99). RET tyrosine kinase has a transmembrane region in the middle and has a tyrosine kinase region at the carboxyl-terminal side and an extracellular region at the amino-terminal side. It is known that there are three types of proteins due to differences in carboxyl-terminal splicing (TRENDS in Genetics, 2006, vol. 22, p. 627-636: Reference a). RET forms a dimer via a ligand/GFR complex to thereby phosphorylate and activate its own tyrosine (Reference a).

There are reports showing that RET will be involved in oncogenesis upon alterations (point mutation, chromosomal translocation, chromosomal inversion, gene amplification) in RET gene. For example, in thyroid medullary cancer, it is reported that a point mutation in RET gene results in the expression of RET tyrosine kinase with oncogenic ability (Reference a). Moreover, in thyroid papillary cancer, it is reported that RET gene is fused with another gene (e.g., coiled-coil domain containing 6 (CCDC6) gene or nuclear receptor coactivator 4 (NCOA4) gene) by chromosomal inversion or chromosomal translocation to cause the expression of fused tyrosine kinase RET/PTC with oncogenic ability (European Journal of Endocrinology, 2006, vol. 155, p. 645-653). Further, in non-small cell lung cancer, it is reported that RET is fused with kinesin family protein 5B (KIF5B) gene, which is one of the molecules constituting motor protein complexes involved in intracellular microtubule transport, or with CCDC6 gene to cause non-small cell lung cancer by the constitutive tyrosine kinase activity of fused tyrosine kinase KIF5B-RET or CCDC6-RET with oncogenic ability (Nature Medicine. 2012, 18, p. 378-381, WO2012/014795). Moreover, it is reported that the fused tyrosine kinase NCOA4-RET or TRIM33-RET in which RET gene is fused with NCOA4 gene or TRIM33 (tripartite motif-containing 33) gene is present in non-small cell lung cancer patients (J Clin Oncol, 30 (35), Dec. 10, 2012, p. 4352-9; and Cancer Discov 2013 June, 3 (6), June 2013, p. 630-5).

In view of the foregoing, compounds having an inhibitory effect against RET tyrosine kinase are very useful for cancer prevention and treatment.

As inhibitory substances of RET tyrosine kinase, multi-kinase inhibitors such as sorafenih, sunitinib, XL184, vandetanib and ponatinib are reported to have a cell growth inhibitory effect against cell lines expressing KIF5B-RET (Non-patent Document 1: J Clin Oncol 30, 2012, suppl; Abstract no: 7510). Moreover, it is reported that two patients who have RET fusion gene-positive non-small cell lung cancer exhibited partial response to the multi-kinase inhibitor cabozantinib (Non-Patent Document 2: Cancer Discov, 3 (6), June 2013, p. 630-5).

On the other hand, a tetracyclic compound having the following general formula is reported as an inhibitor of anaplastic lymphoma kinase (ALK), a receptor tyrosine kinase belonging to the insulin receptor family (Patent Document 1: WO2010/143664, Patent Document 2: WO2012/023597, Patent Document 3: Japanese Patent Laid-Open No. 2012-126711). This compound is useful as a therapeutic and/or prophylactic agent for tumors with a mutation in ALK gene.

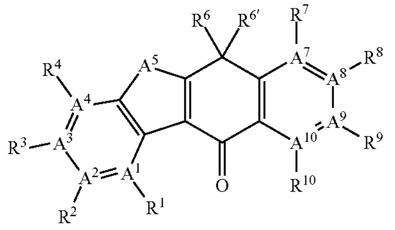

(see the above patent gazette or details of substituents, etc.)

Moreover, it is reported that the following compound with a high concentration (1,000 nM) inhibits many kinases including RET in the Ambit Kinase Screening test (Non-Patent Document 3: Cancer Cell, 19 (5), p. 679-690, 2011, Supplemental Information):

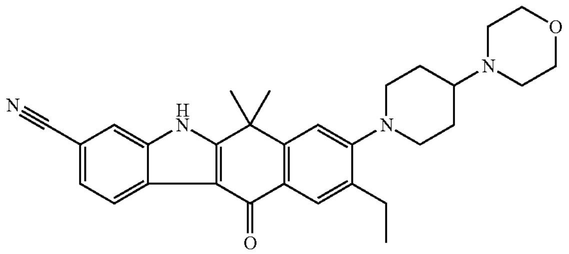 [SMILES: CCc1cc2c(cc1N1CCC(N3CCOCC3)CC1)C(C)(C)c1[nH]c3cc(C#N)ccc3c1C2=O]

However, there is no report showing that the tetracyclic compound found in Patent Document 1 and Non-patent Document 3 is useful as a therapeutic or prophylactic agent for cancers with a mutation in RET.

Moreover, it is reported that the ALK inhibitor crizotinih has no cell growth inhibitory activity against KIF5B-RET-expressing cells (Non-Patent Document 4: Nature Medicine. 2012, 18, p. 378-381).

DOCUMENT LIST

Patent Document

[Patent Document 1] WO2010/143664
[Patent Document 2] WO02012/023597
[Patent Document 3] JP2012-126711A Non-Patent Document

[Non-Patent Document 1] J Clin Oncol 30, 2012, suppl; Abstract no: 7510

[Non-Patent Document 2] Cancer Discov, 3 (6), Jun 2013, p. 630-5

[Non-Patent Document 3] Cancer Cell, 19 (5), p. 679-690, 2011, Supplemental Information

[Non-Patent Document 4] Nature Medicine. 2012, 18, p. 378-381

SUMMARY OF THE INVENTION

Problem to be Solved by the Invention

Cancers caused by a mutation in ALK gene and cancers caused by a mutation in RET gene differ in their mechanism of cancer development, the three-dimensional protein structure of their respective kinases, etc., and hence a specific therapeutic and/or prophylactic method is required for each cancer. In lung cancer, it is reported that a group of patients with a mutation in ALK gene does not overlap with a group of patients with a mutation in RET (Nat Med, 2012 Feb. 12, 18 (3), 375-7). These patient groups arc clearly distinguished from each other for treatment, and the patients in each group require a specific treatment and/or prevention method.

On the other hand, a compound which inhibits multiple kinases at the same time is known to show a lower therapeutic effect in some cases, because its effective therapeutic range is narrow. Thus, a drug which selectively inhibits a small number of kinases can be regarded as having desired properties in terms of therapeutic effect, and hence there is a demand for such a drug.

Means to Solve the Problem

As a result of extensive and intensive efforts made to solve the above problem, the inventors of the present invention have found, ahead of others, that a tetracyclic compound represented by the following formula (I) or a salt thereof or a solvate thereof has not only inhibitory activity against ALK but also potent inhibitory activity against RET, selectively inhibits RET, is useful for treatment and prevention of diseases including cancers with a mutation in RET and their metastasis, and also has high therapeutic efficacy on these diseases. This finding led to the completion of the present invention.

(I)

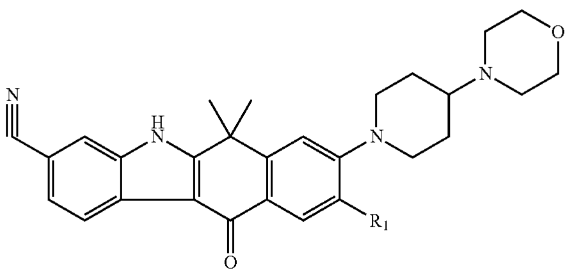

wherein $R_1$ is a $C_{1-6}$ alkyl group.

Namely, according to one aspect of the present invention, the present invention is directed to a therapeutic or prophylactic agent for cancers with a mutation in RET and their metastasis, which comprises a tetracyclic compound shown blow or a salt thereof, etc. According to another aspect, the present invention provides a method for identifying a cancer or a target patient responsive to treatment with the above compound or the like.

More specifically, the present invention is as follows,

[1] A therapeutic and/or prophylactic agent for a tumor with a mutation in RET or for metastasis of the tumor, which comprises a compound represented by formula (I), a salt thereof or a solvate thereof as an active ingredient:

(I)

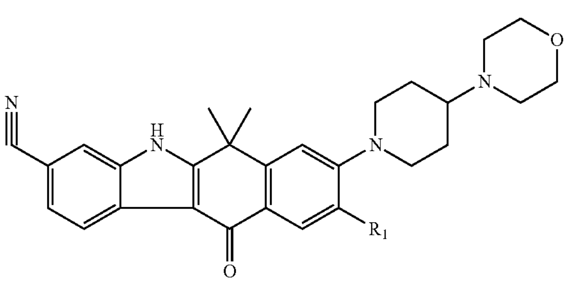

wherein $R_1$ is a $C_{1-6}$ alkyl group.

The therapeutic and/or prophylactic agent according to [1] above, wherein the tumor is selected from the group consisting of acute myelogenous leukemia, chronic myelogenous leukemia, acute lymphocytic leukemia, chronic lymphocytic leukemia, Hodgkin's lymphoma, non-Hodgkin's lymphoma, brain tumor, neuroblastoma, glioma, thyroid cancer, myelodysplastic syndrome, head and neck cancer, esophageal cancer, gastric cancer, colorectal cancer, breast cancer, ovarian cancer, lung cancer. pancreatic cancer, liver cancer, gallbladder cancer, skin cancer, malignant melanoma, kidney cancer, renal pelvic and ureteral cancer, bladder cancer, uterine cancer, testicular cancer, prostate cancer, and tumors metastasized from these tumors.

[3] The therapeutic and/or prophylactic agent according to [1] or [2] above, wherein the tumor is thyroid cancer or lung cancer.

[4] The therapeutic and/or prophylactic agent according to any one of [1] to [3] above, wherein the tumor is thyroid medullary cancer or non-small cell lung cancer.

[4-1] The therapeutic and/or prophylactic agent according to [1] to [4] above, wherein the tumor is a tumor confirmed to show activated RET tyrosine kinase in the tumor tissue.

[4-2] the therapeutic and/or prophylactic agent according to [1] to [4] above, wherein the tumor is a tumor with a mutation which induces activation of RET tyrosine kinase,

[4-2-1] The therapeutic and/or prophylactic agent according to any one of [1] to [4-2] above, wherein the tumor is a tumor with (a) a mutation in the cysteine-rich domain of RET tyrosine kinase, (b) a mutation in the tyrosine kinase domain of RET tyrosine kinase, or (c) a fusion gene of RET and/or a fusion protein of RET.

[4-2-2] The therapeutic and/or prophylactic agent according to any one of [1] to [4-2] above, wherein the tumor is a tumor with a fusion gene of RET and/or a fusion protein of RET.

[4-2-3] The therapeutic and/or prophylactic agent according to any one of [1] to [4-2] and [4-2-2] above, wherein the tumor is a tumor with KIF5B-RET, CCDC6-RET, NCOA4-RET or TRIM33-RET.

[4-3] The therapeutic and/or prophylactic agent according to [1] to [4-2] above, wherein the tumor is a tumor with (a) a mutation in the cysteine-rich domain of RET tyrosine kinase, (b) a mutation in the tyrosine kinase domain of RET tyrosine kinase, or (c) a fusion gene between RET gene and another gene and/or a fusion protein between RET protein and another protein.

[5] The therapeutic and/or prophylactic agent according to any one of [1] to [4-2] above, wherein the tumor is a tumor with a fusion gene between RET gene and another gene and/or a fusion protein between RET protein and another protein.

[5-1] The therapeutic and/or prophylactic agent according to [5] above, wherein the another gene and protein arc the gene and protein of KIF5B, CCDC6 or NCOA4 or TRIM33.

[5-2] The therapeutic and/or prophylactic agent according to [5] or [5-1] above, wherein the fusion gene and protein comprises the tyrosine kinase domain of RET gene or protein and the coiled-coil domain of another gene or protein.

[5-2-1] The therapeutic and/or prophylactic agent according to any one of [5] to [5-2] above, wherein a polypeptide constituting the RET protein and a polynucleotide constituting the REF gene are any of the following polypeptides and any of polynucleotides encoding the polypeptides:

(a) a polypeptide consisting of the amino acid sequence shown in SEQ ID NO: 3 or 4;

(b) a polypeptide consisting of an amino acid sequence with substitution, deletion or insertion of one or more amino acids in the polypeptide shown in SEQ ID NO: 3 or 4; and (c) a polypeptide consisting of an amino acid sequence with 80% or higher identity to the amino acid sequence shown in SEQ ID NO: 3 or 4.

[5-2-2] The therapeutic and/or prophylactic agent according to [5-1] or [5-2-1] above, wherein a polypeptide constituting each of the KIF5B, CCDC6, NCOA4 and TRIM33 proteins and a polynucleotide constituting each of the KIF5B, CCDC6, NCOA4 and TRIM33 genes are any of the following polypeptides and any of polynucleotides encoding the polypeptides:

(1) the polypeptide constituting the KIF5B protein is (a) a polypeptide consisting of the amino acid sequence shown in SEQ ID NO: 30, (b) a polypeptide consisting of an amino acid sequence with substitution, deletion or insertion of one or more amino acids in the amino acid sequence shown in SEQ ID NO: 30, or (c) a polypeptide consisting of an amino acid sequence with 80% or higher identity to the amino acid sequence shown in SEQ ID NO: 30;

(2) the polypeptide constituting the CCDC6 protein is (a) a polypeptide consisting of the amino acid sequence shown in SEQ ID NO: 31, (b) a polypeptide consisting of an amino acid sequence with substitution, deletion or insertion of one or more amino acids in the amino acid sequence shown in SEQ ID NO: 31, or (c) a polypeptide consisting of an amino acid sequence with 80% or higher identity to the amino acid sequence shown in SEQ ID NO: 31;

(3) the polypeptide constituting the NCOA4 protein is (a) a polypeptide consisting of an amino acid sequence selected from the group consisting of SEQ ID NOs: 38 to 42, (b) a polypeptide consisting of an amino acid sequence with substitution, deletion or insertion of one or more amino acids in an amino acid sequence selected from the group consisting of SEQ ID NOs: 38 to 42, or (c) a polypeptide consisting of an amino acid sequence with 80% or higher identity to an amino acid sequence selected from the group consisting of SEQ ID NOs: 38 to 42; and (4) the polypeptide constituting the TRIM33 protein is (a) a polypeptide consisting of the amino acid sequence shown in SEQ ID NO: 45 or 46, (b) a polypeptide consisting of an amino acid sequence with substitution, deletion or insertion of one or more amino acids in the amino acid sequence shown in SEQ ID NO: 45 or 46, or (e) a polypeptide consisting of amino acid sequence with 80% or higher identity to the amino acid sequence shown in SEQ ID NO: 45 or 46.

[5-2-3] The therapeutic and/or prophylactic agent according to [4-2-2], [5] or [5-2] above, wherein a polypeptide constituting the fusion protein and a polynucleotide constituting the fusion gene are any of the following polypeptides (a) to (f) and any of polynucleotides encoding the polypeptides:

(a) a polypeptide consisting of an amino acid sequence selected from the group consisting of SEQ ID NOs: 15 to 24;

(b) a polypeptide comprising an amino acid sequence selected from the group consisting of SEQ ID NOs: 15 to 24, or a polypeptide comprising an amino acid sequence with substitution, deletion or insertion of one or more amino acids in an amino acid sequence selected from the group consisting of SEQ ID NOs: 15 to 24;

(c) a polypeptide comprising an amino acid sequence with 80% or higher identity to an amino acid sequence selected from the group consisting of SEQ ID NOs: 15 to 24;

(d) a polypeptide consisting of the amino acid sequence shown in SEQ ID NO: 27 or 28;

(e) a polypeptide comprising the amino acid sequence shown in SEQ ID NO: 27 or 28, or a polypeptide comprising an amino acid sequence with substitution, deletion or insertion of one or more amino acids in the amino acid sequence shown in SEQ ID NO: 27 or 28; and (f) a polypeptide comprising an amino acid sequence with 80% or higher identity to the amino acid sequence shown in SEQ ID NO: 27 or 28.

[5-2-4] The therapeutic and/or prophylactic agent according to [4-2-2], [5] or [5-2] above, wherein a polypeptide constituting the fusion protein and a polynucleotide constituting the fusion gene are any of the following polypeptides (a) to (f) and any of polynucleotides encoding the polypeptides:

(a) a polypeptide consisting of an amino acid sequence selected from the group consisting of SEQ ID NOs: 15 to 24;

(b) a polypeptide which comprises an amino acid sequence selected from the group consisting of SEQ ID NOs: 15 to 24 and which carriers activated tyrosine kinase, or a polypeptide which comprises an amino acid sequence with substitution, deletion or insertion of 1 to 10 amino acids in an amino acid sequence selected from the group consisting of SEQ ID NOs: 15 to 24 and which has tyrosine kinase activity;

(c) a polypeptide which comprises an amino acid sequence with 90% or higher identity to an amino acid sequence selected from the group consisting of SEQ ID NOs: 15 to 24 and which has tyrosine kinase activity;

(d) a polypeptide consisting of the amino acid sequence shown in SEQ ID NO: 27 or 28;

(e) a polypeptide which comprises the amino acid sequence shown in SEQ ID NO: 27 or 28 and which carries activated RET tyrosine kinase, or a polypeptide which comprises an amino acid sequence with substitution, deletion or insertion of 1 to 10 amino acids in the amino acid sequence shown in SEQ ID NO: 27 or 28 and which has tyrosine kinase activity; and (f) a polypeptide which comprises an amino acid sequence with 90% or higher identity to the amino acid sequence shown in SEQ ID NO: 27 or 28 and which has tyrosine kinase activity.

[5-3] The therapeutic and/or prophylactic agent according to [5-2] above, wherein the fusion gene is any of (a) to (d) shown below:

(a) a fusion gene which comprises a polynucleotide having a nucleotide sequence selected from the group consisting of SEQ ID NOs: 5 to 14;

(b) a fusion gene consisting of a polynucleotide which hybridizes under stringent conditions to DNA consisting of a nucleotide sequence complementary to a nucleotide sequence selected from the group consisting of SEQ ID NOs: 5 to 14 and which encodes a polypeptide having tyrosine kinase activity;

(c) a fusion gene which comprises a polynucleotide encoding a polypeptide having an amino acid sequence selected from the group consisting of SEQ ID NOs: 15 to 24; or (d) a fusion gene comprising a polynucleotide encoding a polypeptide which has substitution, deletion or insertion of one or more (e.g., several tens, 1 to 10, 1 to 5, 1 to 3) amino acids in a polypeptide having an amino acids sequence selected from the group consisting of SEQ ID NOs: 15 to 24 and which has tyrosine kinase activity.

[6] The therapeutic and/or prophylactic agent according to any one of [1] to [4-2] above, wherein the tumor is a tumor with a point mutation in RET gene and/or protein.

[6-1] The therapeutic and/or prophylactic agent according to [6] above, wherein the point mutation is a mutation in the nucleotide 2091G, 2261G, 2494G, 2562A, 2600G, 2861T or 2943T of a polynucleotide having the nucleotide sequence shown in SEQ ID NO: 1.

[6-1-1] The therapeutic and/or prophylactic agent according to [6] or [6-1] above, wherein the point mutation is a mutation in the nucleotide 2091G, 2261G, 2494G, 2562A or 2861T of a polynucleotide having the nucleotide sequence shown in SEQ ID NO: 1.

[6-2] The therapeutic and/or prophylactic agent according to [6] or [6-1] above, wherein the point mutation is a mutation in the nucleotide 2091G, 2494G, 2600G or 2943T of a polynucleotide having the nucleotide sequence shown in SEQ ID NO: 1.

[6-3] The therapeutic and/or prophylactic agent according to [6] or [6-1] above, wherein the point mutation is 2091G>T, 2261G>A, 2494G>C, 2562A>T, 2600G>A. 2600G>C, 2861T>G or 2943T>C in a polynucleotide having the nucleotide sequence shown in SEQ ID NO: 1.

[6-3-1] The therapeutic and/or prophylactic agent according to [6], [6-1] or [6-3] above, wherein the point mutation is 2091G>T, 2261G>A, 2494G>C, 2562A>T or 2861T>G in a polynucleotide having the nucleotide sequence shown in SEQ ID NO: 1.

[6-4] The therapeutic and/or prophylactic agent according to [6], [6-1], [6-2] or [6-3] above, wherein the point mutation is 2091G>T, 2494G>C, 2600G>A or 2943T>C in a polynucleotide having the nucleotide sequence shown in SEQ ID NO: 1.

[6-5] The therapeutic and/or prophylactic agent according to [6] above, wherein the point mutation is a mutation in the amino acid C609, C611, C618, C620, C630, C634, G691, E768, Y791, V804, S891, A883 or M918 of a polypeptide having the amino acid sequence shown in SEQ ID NO: 3.

[6-5-1] The therapeutic and/or prophylactic agent according to [6] or [6-5] above, wherein the point mutation is a mutation in the amino acid C609, C611, C618, C620, C630, C634, G691, E768, Y791, S891 or A883 of a polypeptide having the amino acid sequence shown in SEQ ID NO: 3.

[6-6] The therapeutic and/or prophylactic agent according to [6] or [6-5] above, wherein the point mutation is a mutation in the amino acid C609, C611, C618, C620, C630, C634, E768, V804, S891, A883 or M918 of a polypeptide having the amino acid sequence shown in SEQ ID NO: 3.

[6-7] The therapeutic and/or prophylactic agent according to [6] or [6-5] above, wherein the point mutation is C634W, C634Y, G691S, E768D, Y791F, V804M, V804L, S891A or M918T in a polypeptide having the amino acid sequence shown in SEQ ID NO: 3.

[6-7-1] The therapeutic and/or prophylactic agent according to [6], [6-5] or [6-7] above, wherein the point mutation is C634W, C634Y, G691 S, E768D, Y791F or S891A in a polypeptide having the amino acid sequence shown in SEQ ID NO: 3.

[6-8] The therapeutic and/or prophylactic agent according to [6] or [6-6] above, wherein the point mutation is C634W, C634Y, E768D, V804M or M918T in a polypeptide having the amino acid sequence shown in. SEQ ID NO: 3.

[7] A therapeutic and/or prophylactic agent for a tumor used for a patient with a mutation in RET or for metastasis of the tumor, which comprises a compound represented by formula (I), a salt thereof or a solvate thereof as an active ingredient.

[8] The therapeutic and/or prophylactic agent according to [7] above, wherein the tumor is thyroid cancer or lung cancer.

[8-1] The therapeutic and/or prophylactic agent according to [7] or [8] above, wherein the patient is a patient confirmed to show activated RET tyrosine kinase in the tumor tissue.

[8-2] The therapeutic and/or prophylactic agent according to [7] or [8] above, wherein the patient is a patient with a mutation which induces activation of RET tyrosine kinase.

[8-2-1] The therapeutic and/or prophylactic agent according to any one of [7] to [8-2] above, wherein the patient is a patient with (a) a mutation in the cysteine-rich domain of RET tyrosine kinase, (b) a mutation in the tyrosine kinase domain of RET tyrosine kinase, or (c) a fusion gene of RET and/or a fusion protein of RET.

[8-2-2] The therapeutic and/or prophylactic agent according to any one of [7] to [8-2-1] above, wherein the patient is a patient with a fusion gene of RET and/or a fusion protein of RET.

[8-2-3] The therapeutic and/or prophylactic agent according to any one of [7] to [8-2] and [8-2-2] above, wherein the patient is a patient with KIF5B-RET, CCDC6-RET, NCOA4-RET or TRIM33-RET.

[8-3] The therapeutic and/or prophylactic agent according to any one of [7] to [8-2] above, wherein the patient is a patient with (a) a mutation in the cysteine-rich domain of RET tyrosine kinase, (b) a mutation in the tyrosine kinase domain of RET tyrosine kinase, or (c) a fusion gene between RET gene and another gene and/or a fusion protein between RET protein and another protein.

[9] The therapeutic and/or prophylactic agent according to [7] or [8] above, wherein the patient is a patient with a fusion gene between RET gene and another gene and/or a fusion protein between RET protein and another protein.

[9-1] The therapeutic and/or prophylactic agent according to [8-3] or [9] above, wherein the another gene and protein arc KIF5B, CCDC6, NCOA4 or TRIM33,

[9-2] The therapeutic and/or prophylactic agent according to [9] or [9-1] above, wherein the fusion gene and fusion protein comprises the tyrosine kinase domain of RET gene or protein and the coiled-coil domain of another gene or protein.

[9-2-1] The therapeutic and/or prophylactic agent according to any one of [9] to [9-2] above, wherein a polypeptide constituting the RET protein and a polynucleotide constituting the RET gene are any of the following polypeptides and any of polynucleotides encoding the polypeptides:

(a) a polypeptide consisting of the amino acid sequence shown in SEQ ID NO: 3 or 4;

(b) a polypeptide consisting of an amino acid sequence with substitution, deletion or insertion of one or more amino acids in the polypeptide shown in SEQ ID NO: 3 or 4: and (c) a polypeptide consisting of an amino acid sequence with 80% or higher identity to the amino acid sequence shown in SEQ ID NO: 3 or 4.

[9-2-2] The therapeutic and/or prophylactic agent according to [9-1] above, wherein a polypeptide constituting each of the KIF5B, CCDC6, NCOA4 and TRIM33 proteins and a polynucleotide constituting each of the KIF5B, CCDC6, NCOA4 and TRIM33 genes are any of the following polypeptides and any of polynucleotides encoding the polypeptides:

(1) the polypeptide constituting the KIF5B protein is (a) a polypeptide consisting of the amino acid sequence shown in SEQ ID NO: 30, (b) a polypeptide consisting of an amino acid sequence with substitution, deletion or insertion of one or more amino acids in the amino acid sequence shown in SEQ ID NO: 30, or (c) a polypeptide consisting of an amino acid sequence with 80% or higher identity to the amino acid sequence shown in SEQ ID NO: 30;

(2) the polypeptide constituting the CCDC6 protein is (a) a polypeptide consisting of the amino acid sequence shown in SEQ ID NO: 31, (b) a polypeptide consisting of an amino acid sequence with substitution, deletion or insertion of one or more amino acids in the amino acid sequence shown in SEQ ID NO: 31, or (c) a polypeptide consisting of an amino acid sequence with 80% or higher identity to the amino acid sequence shown in SEQ ID NO: 31;

(3) the poly/peptide constituting the NCOA4 protein is (a) a polypeptide consisting of an amino acid sequence selected from the group consisting of SEQ ID NOs: 38 to 42, (b) a polypeptide consisting of an amino acid sequence with substitution, deletion or insertion of one or more amino acids in an amino acid sequence selected from the group consisting of SEQ ID NOs: 38 to 42, or (c) a polypeptide consisting of an amino acid sequence with 80% or higher identity to an amino acid sequence selected from the group consisting of SEQ ID NOs: 38 to 42; and (4) the polypeptide constituting the TRIM33 protein is (a) a polypeptide consisting of the amino acid sequence shown in SEQ ID NO: 45 or 46, (b) a polypeptide consisting of an amino acid sequence with substitution, deletion or insertion of one or more amino acids in the amino acid sequence shown in SEQ ID NO: 45 or 46, or (c) a polypeptide consisting of an amino acid sequence with 80% or higher identity to the amino acid sequence shown in SEQ ID NO: 45 or 46.

[9-2-3] The therapeutic and/or prophylactic agent according to [8-2-2] or [9] above, wherein a polypeptide constituting the fusion protein and a polynucleotide constituting the fusion gene are any of the following polypeptides (a) to (f) and any of polynucleotides encoding the polypeptides:

(a) a polypeptide consisting of an amino acid sequence selected from the group consisting of SEQ ID NOs: 15 to 24;

(b) a polypeptide comprising an amino acid sequence selected from the group consisting of SEQ ID NOs: 15 to 24, or a polypeptide comprising an amino acid sequence with substitution, deletion or insertion of one or more amino acids in an amino acid sequence selected from the group consisting of SEQ ID NOs: 15 to 24;

(c) a polypeptide comprising an amino acid sequence with 80% or higher identity to an amino acid sequence selected from the group consisting of SEQ ID NOs: 15 to 24;

(d) a polypeptide consisting of the amino acid sequence shown in SEQ ID NO: 27 or 28;

(e) a polypeptide comprising the amino acid sequence shown in SEQ ID NO: 27 or 28, or a polypeptide comprising an amino acid sequence with substitution, deletion or insertion of one or more amino acids in the amino acid sequence shown in SEQ ID NO: 27 or 28; and (f) a polypeptide comprising an amino acid sequence with 80% or higher identity to the amino acid sequence shown in SEQ ID NO: 27 or 28.

[9-2-4] The therapeutic and/or prophylactic agent according to [8-2-2] or [9] above, wherein a polypeptide constituting the fusion protein and a polynucleotide constituting the fusion gene are any of the following polypeptides (a) to (f) and any of polynucleotides encoding the polypeptides:

(a) a polypeptide consisting of an amino acid sequence selected from the group consisting of SEQ ID NOs: 15 to 24;

(b) a polypeptide which comprises an amino acid sequence selected from the group consisting of SEQ ID NOs: 15 to 24 and which carriers activated tyrosine kinase, or a polypeptide which comprises an amino acid sequence with substitution, deletion or insertion of 1 to 10 amino acids in an amino acid sequence selected from the group consisting of SEQ ID NOs: 15 to 24 and which has tyrosine kinase activity;

(c) a polypeptide which comprises an amino acid sequence with 90% or higher identity to an amino acid sequence selected from the group consisting of SEQ ID NOs: 15 to 24 and which has tyrosine kinase activity;

(d) a polypeptide consisting of the amino acid sequence shown in SEQ ID NO: 27 or 28;

(e) a polypeptide which comprises the amino acid sequence shown in SEQ ID NO: 27 or 28 and which carries activated RET tyrosine kinase, or a polypeptide which comprises an amino acid sequence with substitution, deletion or insertion of 1 to 10 amino acids in the amino acid sequence shown in SEQ ID NO: 27 or 28 and which has tyrosine kinase activity; and (f) a polypeptide which comprises an amino acid sequence with 90% or higher identity to the amino acid sequence shown in SEQ ID NO: 27 or 28 and which has tyrosine kinase activity.

[9-3] The therapeutic and/or prophylactic agent according to [9] or [9-2] above, wherein the fusion gene is any of (a) to (d) shown below:

(a) a fusion gene which comprises a polynucleotide having a nucleotide sequence selected from the group consisting of SEQ ID NOs: 5 to 14;

(b) a fusion gene consisting of a polynucleotide which hybridizes under stringent conditions to DNA consisting of a nucleotide sequence complementary to a nucleotide sequence selected from the group consisting of SEQ ID NOs: 5 to 14 and which encodes a polypeptide having tyrosine kinase activity;

(c) a fusion gene which comprises a polynucleotide encoding a polypeptide having an amino acid sequence selected from the group consisting of SEQ ID NOs: 15 to 24; or (d) a fusion gene comprising a polynucleotide encoding a polypeptide which has substitution, deletion or insertion of one or more (e.g., several tens, 1 to 10, 1 to 5, 1 to 3) amino acids in a polypeptide having an amino acids sequence selected from the group consisting of SEQ ID NOs: 15 to 24 and which has tyrosine kinase activity.

[10] The therapeutic and/or prophylactic agent according to [7] or [8] above, wherein the patient is a patient with a point mutation in RET gene and/or protein.

[10-1] The therapeutic and/or prophylactic agent according to [10] above, wherein the point mutation in RET is a point mutation in the cysteine-rich domain or in the tyrosine kinase domain of RET tyrosine kinase.

[10-2] The therapeutic and/or prophylactic agent according to [10] or [10-1] above, wherein the point mutation is a mutation in the nucleotide 2091G, 2261G, 2494G, 2562A, 2600G, 2861T or 2943T of a polynucleotide having the nucleotide sequence shown in SEQ ID NO: 1.

[10-2-1] The therapeutic and/or prophylactic agent according to any one of [10] to [10-2] above, wherein the point mutation is a mutation in the nucleotide 2091G, 2261G, 2494G, 2562A or 2861T of a polynucleotide having the nucleotide sequence shown in SEQ ID NO: 1.

[10-3] The therapeutic and/or prophylactic agent according to any one of [10] to [10-2],wherein the point mutation in RET is a mutation in the nucleotide 2091G, 2494G, 2600G or 2943T of a polynucleotide having the nucleotide sequence shown in SEQ ID NO: 1.

[10-4] The therapeutic and/or prophylactic agent according to any one of [10] to [10-2] above, wherein the point mutation is 2091G>T, 2261G>A. 2494G>C, 2562A>T, 2600G>A, 2600G>C, 2861T>G or 2943T>C in a polynucleotide having the nucleotide sequence shown in SEQ ID NO: 1.

[10-4-1] The therapeutic and/or prophylactic agent according to any one of

[10] to [10-2] and [10-4] above, wherein the point mutation is 2091G>T, 2261G>A, 2494G>C, 2562A>T or 2861T>G in a polynucleotide having the nucleotide sequence shown in SEQ ID NO: 1.

[10-5] The therapeutic and/or prophylactic agent according to any one of [10] to [10-2], [10-4] above, wherein the point mutation in RFT is 2091G>T, 2494G>C, 2600G>A or 2943T>C in a polynucleotide having the nucleotide sequence shown in SEQ ID NO: 1.

[10-6] The therapeutic and/or prophylactic agent according to [10] or [10-1] above, wherein the point mutation is a mutation in the amino acid C609, C611, C618, C620, C630, C634, G691, E768, Y791, V804, S891, A883 or M918 of a polypeptide having the amino acid sequence shown in SEQ ID NO: 3.

[10-6-1] The therapeutic and/or prophylactic agent according to [10], [10-1] or [10-6] above, wherein the point mutation is a mutation in the amino acid C609, C611, C618, C620, C630, C634, G691, E768, Y791, S891 or A883 of a polypeptide having the amino acid sequence shown in SEQ ID NO: 3.

[10-7] The therapeutic and/or prophylactic agent according to [10], [10-1] or [10-6] above, wherein the point mutation in RET is a mutation in the amino acid C609, C611, C618, C620, C630, C634, E768, V804, S891, A883 or M918 of a polypeptide having the amino acid sequence shown in SEQ ID NO: 3.

[10-8] The therapeutic and/or prophylactic agent according to [10], [10-1] or [10-6] above, wherein the point mutation is C634W, C634Y, G691S, E768D, Y791F, V804M, V804L, S891A or M918T in a polypeptide having the amino acid sequence shown in SEQ ID NO: 3.

[10-8-1] The therapeutic and/or prophylactic agent according to [10], [10-1],

[10-6] or [10-8] above, wherein the point mutation is C634W, C634Y, G691S. E768D, Y791F or S891A in a polypeptide having the amino acid sequence shown in SEQ ID NO: 3.

[10-9] The therapeutic and/or prophylactic agent according to any one of [10], [10-1] or [10-6] to [10-8] above, wherein the point mutation in RET is C634Y, E768D, V804M or M918T in a polypeptide having the amino acid sequence shown in SEQ ID NO: 3.

[10-10] The therapeutic and/or prophylactic agent according to any one of [10] to [10-9] above, wherein the patient is a patient detected for the presence of a mutation in RET by Sanger sequencing or FISH method.

[11] The therapeutic and/or prophylactic agent according to any one of [1] to [10-10] above, wherein $R^1$ is ethyl.

[11-1] The therapeutic and/or prophylactic agent according to any one of [1] to [11] above, wherein the compound is a hydrochloride.

[11-2] The therapeutic and/or prophylactic agent according to any one of [1] to [11-1] above, wherein the therapeutic and/or prophylactic agent selectively inhibits RET.

[12] A RET inhibitor, which comprises a compound of formula (I), a salt thereof or a solvate thereof as an active ingredient.

[12-1] Use of a compound of formula (I), a salt thereof or a solvate thereof for inhibition of RET.

[12-2] A method for preventing and/or treating a tumor with a mutation in RET and metastasis of the tumor, which comprises administering a patient with an effective therapeutic amount of a compound represented by formula (I), a salt thereof or a solvate thereof.

[12-3] Use of a compound represented by formula (1), a salt thereof or a solvate thereof for prevention and/or treatment of a tumor with a mutation in RET and metastasis of the tumor.

[12-3-1] The use according to [12-3] above, wherein the mutation in RET is (a) a mutation in the cysteine-rich domain of RET tyrosine kinase, (h) a mutation in the tyrosine kinase domain of RET tyrosine kinase, or (c) the formation of a fusion gene of RET and/or a fusion protein of RET.

[12-3-2] The use according to [12-3] or [12-3-1] above, wherein the mutation in RET results in the formation of a fusion gene of RET and/or a fusion protein of RET.

[12-3-3] The use according to any one of [12] to [12-2-2] above, wherein the mutation in RET results in the formation of KIF5B-RET, CCDC6-RET, NCOA4-RET or TRIM33-RET.

[12-3-4] The use according to any one of [12-3] to [12-3-3] above, wherein the compound of formula (I), the salt thereof or the solvate thereof selectively inhibits RET.

[12-3-5] The use according to any one of [12-3] to [12-3-4] above, wherein $R^1$ is ethyl.

[12-3-6] The use according to any one of [12-3] to [12-3-5] above, wherein the compound is a hydrochloride.

[12-3-7] The use according to any one of [12-3] to [12-3-6] above, wherein the tumor is thyroid cancer or lung cancer.

[13] A method for identifying a subject to be administered with a compound represented by formula (I), a salt thereof or a solvate thereof, which comprises the step of detecting a mutation in RET in a tissue from the subject.

[13-1] The method according to [13] above, wherein the tissue is a tissue confirmed to show activated RET tyrosine kinase.

[13-2] The method according to [13] above, wherein the tissue has a mutation which induces activation of RET tyrosine kinase.

[13-2-1] The method according to any one of [13] to [13-2] above, wherein the mutation in RET is (a) a mutation in the cysteine-rich domain of RET tyrosine kinase, (b) a mutation in the tyrosine kinase domain of RET tyrosine kinase, or (c) the formation of a fusion gene of RET and/or a fusion protein of RET.

[13-2-2] The method according to any one of [13] to [13-2-1] above, wherein the mutation in RET results in the formation of a fusion gene of RET and/or a fusion protein of RET.

[13-2-3] The method according to any one of [13] to [13-2-2] above, wherein the mutation in RET results in the formation of KIF5B-RET, CCDC6-RET, NCOA4-RET or TRIM33-RET.

[13-3] The method according to any one of [13] to [13-2] above, wherein the tissue has (a) a mutation in the cysteine-rich domain of RET tyrosine kinase, (b) a mutation in the tyrosine kinase domain of RET tyrosine kinase, or (c) a fusion gene between RET gene and another gene and/or a fusion protein between RET protein and another protein.

[13-4] The method according to any one of [13] to [13-3] above, wherein the mutation in RET results in the formation of a fusion gene between RET gene and another gene and/or a fusion protein between RET protein and another protein.

[13-5] The method according to [13-4] above, wherein another gene and protein are KIF5B, CCDC6, NCOA4 or TRIM33.

[13-6] The method according to [13-5] above, wherein the fusion gene and fusion protein comprise the tyrosine kinase domain of RET gene or protein and the coiled-coil domain of another gene or protein.

[13-6-1] The method according to any one of [13-4] to [13-6] above, wherein a polypeptide constituting the RET protein and a polynucleotide constituting the RET gene are any of the following polypeptides and any of polynucleotides encoding the polypeptides:

(a) a polypeptide consisting of the amino acid sequence shown in SEQ ID NO: 3 or 4;

(b) a polypeptide consisting of an amino acid sequence with substitution, deletion or insertion of one or more amino acids in the polypeptide shown in SEQ ID NO: 3 or 4; and (c) a polypeptide consisting of an amino acid sequence with 80% or higher identity to the amino acid sequence shown in SEQ ID NO: 3 or 4.

[13-6-2] The method according to [13-5] above, wherein a polypeptide constituting each of the KIF5B, CCDC6, NCOA4 and TRIM33 proteins and a polynucleotide constituting each of the KIF5B, CCDC6, NCOA4 and TRIM33 genes are any of the following polypeptides and any of polynucleotides encoding the polypeptides:

(1) the polypeptide constituting the KIF5B protein is (a) a polypeptide consisting of the amino acid sequence shown in SEQ ID NO: 30, (b) a polypeptide consisting of an amino acid sequence with substitution, deletion or insertion of one or more amino acids in the amino acid sequence shown in SEQ ID NO: 30, or (c) a polypeptide consisting of an amino acid sequence with 80% or higher identity to the amino acid sequence shown in SEQ ID NO: 30;

(2) the polypeptide constituting the CCDC6 protein is (a) a polypeptide consisting of the amino acid sequence shown in SEQ ID NO: 31, (b) a polypeptide consisting of an amino acid sequence with substitution, deletion or insertion of one or more amino acids in the amino acid sequence shown in SEQ ID NO: 31, or (c) a polypeptide consisting of an amino acid sequence with 80% or higher identity to the amino acid sequence shown in SEQ ID NO: 31;

(3) the polypeptide constituting the NCOA4 protein is (a) a polypeptide consisting of an amino acid sequence selected from the group consisting of SEQ ID NOs: 38 to 42, (b) a polypeptide consisting of an amino acid sequence with substitution, deletion or insertion of one or more amino acids in an amino acid sequence selected from the group consisting of SEQ ID NOs: 38 to 42, or (c) a polypeptide consisting of an amino acid sequence with 80% or higher identity to an amino acid sequence selected from the group consisting of SEQ ID NOs: 38 to 42; and (4) the polypeptide constituting the TRIM33 protein is (a) a polypeptide consisting of the amino acid sequence shown in SEQ ID NO: 45 or 46, (b) a polypeptide consisting of an amino acid sequence with substitution, deletion or insertion of one or more amino acids in the amino acid sequence shown in SEQ ID NO: 45 or 46, or (c) a polypeptide consisting of an amino acid sequence with 80% or higher identity to the amino acid sequence shown in SEQ ID NO: 45 or 46.

[13-6-3] The method according to [13-2-1], [13-2-2], [13-3] or [13-4] above, wherein a polypeptide constituting the fusion protein and a polynucleotide constituting the fusion gene arc any of the following polypeptides (a) to (f) and any of polynucleotides encoding the polypeptides:

(a) a polypeptide consisting of an amino acid sequence selected from the group consisting of SEQ ID NOs: 15 to 24;

(b) a polypeptide comprising an amino acid sequence selected from the group consisting of SEQ ID NOs: 15 to 24, or a polypeptide comprising an amino acid sequence with substitution, deletion or insertion of one or more amino acids in an amino acid sequence selected from the group consisting of SEQ ID NOs: 15 to 24;

(c) a polypeptide comprising an amino acid sequence with 80% or higher identity to an amino acid sequence selected from the group consisting of SEQ ID NOs: 15 to 24;

(d) a polypeptide consisting of the amino acid sequence shown in SEQ ID NO: 27 or 28;

(e) a polypeptide comprising the amino acid sequence shown in SEQ ID NO: 27 or 28, or a polypeptide comprising an amino acid sequence with substitution, deletion or insertion of one or more amino acids in the amino acid sequence shown in SEQ ID NO: 27 or 28; and (f) a polypeptide comprising an amino acid sequence with 80% or higher identity to the amino acid sequence shown in SEQ ID NO: 27 or 28.

[13-6-4] The method according to [13-2-1], [13-2-2], [13-3], [13-4] or [13-6-3] above, wherein a polypeptide constituting the fusion protein and a polynucleotide constituting the fusion gene are any of the following polypeptides (a) to (f) and any of polynucleotides encoding the polypeptides:

(a) a polypeptide consisting of an amino acid sequence selected from the group consisting of SEQ ID NOs: 15 to 24;

(b) a polypeptide which comprises an amino acid sequence selected from the group consisting of SEQ ID NOs: 15 to 24 and which carriers activated tyrosine kinase, or a polypeptide which comprises an amino acid sequence with substitution, deletion or insertion of 1 to 10 amino acids in an amino acid sequence selected from the group consisting of SEQ ID NOs: 15 to 24 and which has tyrosine kinase activity;

(c) a polypeptide which comprises an amino acid sequence with 90% or higher identity to an amino acid sequence selected from the group consisting of SEQ ID NOs: 15 to 24 and which has tyrosine kinase activity;

(d) a polypeptide consisting of the amino acid sequence shown in SEQ ID NO: 27 or 28;

(e) a polypeptide which comprises the amino acid sequence shown in SEQ ID NO: 27 or 28 and which carries activated RET tyrosine kinase, or a polypeptide which comprises an ammo acid sequence with substitution, deletion or insertion of 1 to 10 amino acids in the amino acid sequence shown in SEQ ID NO: 27 or 28 and which has tyrosine kinase activity; and (f) a polypeptide which comprises an amino acid sequence with 90% or higher identity to the amino acid sequence shown in SEQ ID NO: 27 or 28 and which has tyrosine kinase activity.

[13-7] The method according to [13-6] above, wherein the fusion gene is any of (a) to (d) shown below:

(a) a fusion gene which comprises a polynucleotide having a nucleotide sequence selected from the group consisting of SEQ ID NOs: 5 to 14;

(b) a fusion gene consisting of a polynucleotide which hybridizes under stringent conditions to DNA consisting of a nucleotide sequence complementary to a nucleotide sequence selected from the group consisting of SEQ ID NOs: 5 to 14 and which encodes a polypeptide having tyrosine kinase activity;

(c) a fusion gene which comprises a polynucleotide encoding a polypeptide having an amino acid sequence selected from the group consisting of SEQ ID NOs: 15 to 24; or (d) a fusion gene comprising a polynucleotide encoding a polypeptide which has substitution, deletion or insertion of one or more (e.g., several tens, 1 to 10, 1 to 5, 1 to 3) amino acids in a polypeptide having an amino acids sequence selected from the group consisting of SEQ ID NOs: 15 to 24 and which has tyrosine kinase activity.

[13-8] The method according to [13] to [13-2] above, wherein the tissue has a point mutation in RET.

[13-9] The method according to [13-8] above, wherein the tissue has a point mutation in the cysteine-rich domain or in the tyrosine kinase domain of RET tyrosine kinase.

[13-10] The method according to [13-8] or [13-9] above, wherein the point mutation is a mutation in the nucleotide 2091G, 2261G, 2494G, 2562A, 2600G, 2861T or 2943T of a polynucleotide having the nucleotide sequence shown in SEQ ID NO: 1.

[13-10-1] The method according to any one of [13-8] to [13-10] above, wherein the point mutation is a mutation in the nucleotide 2091G, 2261G, 2494G, 2562A or 2861T of a polynucleotide having the nucleotide sequence shown in SEQ ID NO: 1.

[13-11] The method according to any one of [13-8] to [13-10] above, wherein the point mutation is a mutation in the nucleotide 2091G, 2494G, 2600G or 2943T of a polynucleotide having the nucleotide sequence shown in SEQ ID NO: 1.

[13-12] The method according to any one of [13-8] to [13-10] above, wherein the point mutation is 2091G>T, 2261G>A, 2494G>C, 2562A>T, 2600G>A, 2600G>C, 2861T>6 or 2943T>C in a polynucleotide having the nucleotide sequence shown in SEQ ID NO: 1.

[13-12-1] The method according to any one of [13-8] to [13-10] and [13-12] above, wherein the point mutation is 2091G>T, 2261G>A, 2494G>C, 2562A>T or 2861T>G in a polynucleotide having the nucleotide sequence shown in SEQ ID NO: 1.

[13-13] The method according to any one of [13-8] to [13-12] above, wherein the point mutation is 2091G>T, 2494G>C, 2600G>A or 2943T>C in a polynucleotide having the nucleotide sequence shown in SEQ ID NO: 1.

[13-14] The method according to [13-8] or [13-9] above, wherein the point mutation is a mutation in the amino acid C609, C611, C618, C620, C630, C634, G691, E768, Y791, V804, S891, A883 or M918 of a polypeptide having the amino acid sequence shown in SEQ ID NO: 3.

[13-14-1] The method according to [13-8], [13-9] or [13-14] above, wherein the point mutation is a mutation in the amino acid C609, C611, C618, C620, C630, C634, G691, E768, Y791, S891 or A883 of a polypeptide having the amino acid sequence shown in SEQ ID NO: 3.

[13-15] The method according to [13-8], [13-9] or [13-14] above, wherein the point mutation is a mutation in the amino acid C609, C611, C618, C620, C630, C634, E768, V804, S891, A883 or M918 of a polypeptide having the amino acid sequence shown in SEQ ID NO: 3.

[13-16] The method according to [13-8], [13-9] or [13-14] above, wherein the point mutation is C634W, C634Y, G691S, E768D, Y791F, V804M, V804L, S891A or M918T in a polypeptide having the amino acid sequence shown in SEQ ID NO: 3.

[13-16-1] The method according to [13-8], [13-9] or [13-14] above, wherein the point mutation is C634W, C634Y, G691S, E768D, Y791F or S891A in a polypeptide having the amino acid sequence shown in SEQ ID NO: 3.

[13-17] The method according to any one of [13-8] to [13-16] above, wherein the point mutation in RET is C634Y, E768D, V804M or M918T in a polypeptide having the amino acid sequence shown in SEQ ID NO: 3.

[13-18] The method according to any one of [13] to [13-17] above, wherein the method identifies a subject to he administered with a compound represented by formula (I), a salt thereof or a solvate thereof for treatment and/or prevention of a tumor with a mutation in RET or metastasis of the tumor.

[13-19] The method according to any one of [13] to [13-18] above, wherein the tumor is thyroid cancer or lung cancer.

[13-20] The method according to any one of [13] to [13-19] above, wherein the compound represented by formula (I), the salt thereof or the solvate thereof selectively inhibits RET.

[13-21] The method according to any one of [13] to [13-20] above, wherein $R^1$ is ethyl.

[13-22] The method according to any one of [13] to [13-21] above, wherein the compound of formula (I), the salt thereof or the solvate thereof is hydrochloride of the compound of formula (I).

[14] A prophylactic and/or therapeutic method for a tumor with a mutation in RET and for metastasis of the tumor, which comprises identifying a patient with a mutation in RET and administering the patient with an effective therapeutic amount of a compound represented by formula (I), a salt thereof or a solvate thereof.

[15] A method for identifying or preliminarily identifying a patient sensitive to a compound represented by formula (I), a salt thereof or a solvate thereof, which comprises the steps of:

detecting the presence of a mutation in RET in a sample obtained from the patient; and determining or preliminarily determining that the patient has sensitivity to the compound, the salt thereof or the solvate thereof, on the basis of the presence of a mutation in RET in the sample.

[15-1] The method according to [15] above, further comprising the step of detecting activation of RET tyrosine kinase.

[15-2] The method according to [15] above, wherein the mutation in RET is a mutation which induces activation of RET tyrosine kinase.

[15-2-1] The method according to any one of [15] to [15-2] above, wherein the mutation in RET is (a) a mutation in the cysteine-rich domain of RET tyrosine kinase, (b) a mutation in the tyrosine kinase domain of RET tyrosine kinase, or (c) the formation of a fusion gene of RET and/or a fusion protein of RET.

[15-2-2] The method according to any one of [15] to [15-2-1] above, wherein the mutation in RET results in the formation of a fusion gene of RET and/or a fusion protein of RET.

[15-2-3] The method according to any one of [15] to [15-2-2] above, wherein the mutation in RET results in the formation of KIF5B-RET, CCDC6-RET, NCOA4-RET or TRIM33-RET.

[15-3] The method according to any one of [15] to [15-2] above, wherein the mutation in RET is (a) a mutation in the cysteine-rich domain of RET tyrosine kinase, (b) a mutation in the tyrosine kinase domain of RET tyrosine kinase, or (c) the formation of a fusion gene between RET gene and another gene and/or a fusion protein between RET protein and another protein.

[15-4] The method according to any one of [15] to [15-3] above, wherein the mutation in RET results in the formation of a fusion gene between RET gene and another gene and/or a fusion protein between RET protein and another protein.

[15-5] The method according to [15-4] above, wherein the other gene and protein are KIF5B, CCDC6, NCOA4 or TRIM33.

[15-6] The method according to [15-4] or [15-5] above, wherein the fusion gene between RET gene and another gene and the fusion protein between RET protein and another protein comprise the tyrosine kinase domain of RET gene or protein and the coiled-coil domain of another gene or protein.

[15-6-1] The method according to any one of [15-4] to [15-6] above, wherein a polypeptide constituting the RET protein and a polynucleotide constituting the RET gene are any of the following polypeptides and any of polynucleotides encoding the polypeptides:

(a) a polypeptide consisting of the amino acid sequence shown in SEQ ID NO: 3 or 4:

(b) a polypeptide consisting of an amino acid sequence with substitution, deletion or insertion of one or more amino acids in the polypeptide shown in SEQ ID NO: 3 or 4; and (c) a polypeptide consisting of an amino acid sequence with 80% or higher identity to the amino acid sequence shown in SEQ ID NO: 3 or 4.

[15-6-2] The method according to [15-5] above, wherein a polypeptide constituting each of the KIF5B, CCDC6, NCOA4 and TRIM33 proteins and a polynucleotide constituting each of the KIF5B, CCDC6, NCOA4 and FRIM33 genes are any of the following polypeptides and any of polynucleotides encoding the polypeptides:

(1) the polypeptide constituting the KIF5B protein is (a) a polypeptide consisting of the amino acid sequence shown in SEQ ID NO: 30, (b) a polypeptide consisting of an amino acid sequence with substitution, deletion or insertion of one or more amino acids in the amino acid sequence shown in SEQ ID NO: 30, or (c) a polypeptide consisting of an amino acid sequence with 80% or higher identity to the amino acid sequence shown in SEQ ID NO: 30;

(2) the polypeptide constituting the CCDC6 protein is (a) a polypeptide consisting of the amino acid sequence shown in. SEQ ID NO: 31, (b) a polypeptide consisting of an amino acid sequence with substitution, deletion or insertion of one or more amino acids in the amino acid sequence shown in SEQ ID NO: 31, or (c) a polypeptide consisting of an amino acid sequence with 80% or higher identity to the amino acid sequence shown in SEQ ID NO: 31;

(3) the polypeptide constituting the NCOA4 protein is (a) a polypeptide consisting of an amino acid sequence selected from the group consisting of SEQ ID NOs: 38 to 42, (b) a polypeptide consisting of an amino acid sequence with substitution, deletion or insertion of one or more amino acids in an amino acid sequence selected from the group consisting of SEQ ID NOs: 38 to 42, or (c) a poly-peptide consisting of an amino acid sequence with 80% or higher identity to an amino acid sequence selected from the group consisting of SEQ ID NOs: 38 to 42; and (4) the polypeptide constituting the TRIM33 protein is (a) a polypeptide consisting of the amino acid sequence shown in SEQ ID NO: 45 or 46, (b) a polypeptide consisting of an amino acid sequence with substitution, deletion or insertion of one or more amino acids in the amino acid sequence shown in SEQ ID NO: 45 or 46, or (c) a polypeptide consisting of an amino acid sequence with 80% or higher identity to the amino acid sequence shown in SEQ ID NO: 45 or 46.

[15-6-3] The method according to [15-2-1], [15-2-2], [15-3] or [15-4] above, wherein a polypeptide constituting the fusion protein and a polynucleotide constituting the fusion gene are any of the following polypeptides (a) to (f) and any of polynucleotides encoding the polypeptides:

(a) a polypeptide consisting of an amino acid sequence selected from the group consisting of SEQ ID NOs: 15 to 24;

(b) a polypeptide comprising an amino acid sequence selected from the group consisting of SEQ ID NOs: 15 to 24, or a polypeptide comprising an amino acid sequence with substitution, deletion or insertion of one or more amino acids in an amino acid sequence selected from the group consisting of SEQ ID NOs: 15 to 24;

(c) a polypeptide comprising an amino acid sequence with 80% or higher identity to an amino acid sequence selected from the group consisting of SEQ ID NOs: 15 to 24;

(d) a polypeptide consisting of the amino acid sequence shown in SEQ ID NO: 27 or 28;

(e) a polypeptide comprising the amino acid sequence shown in SEQ ID NO: 27 or 28, or a polypeptide comprising an amino acid sequence with substitution, deletion or insertion of one or more amino acids in the amino acid sequence shown in SEQ ID NO: 27 or 28; and (f) a polypeptide comprising an amino acid sequence with 80% or higher identity to the amino acid sequence shown in SEQ ID NO: 27 or 28.

[15-6-4] The method according to [15-2-1], [15-2-2], [15-3] or [15-4] above, wherein a polypeptide constituting the fusion protein and a polynucleotide constituting the fusion gene are any of the following polypeptides (a) to (f) and any of polynucleotides encoding the polypeptides:

(a) a polypeptide consisting of an amino acid sequence selected from the group consisting of SEQ ID NOs: 15 to 24;

(b) a polypeptide which comprises an amino acid sequence selected from the group consisting of SEQ ID NOs: 15 to 24 and which carriers activated tyrosine kinase, or a polypeptide which comprises an amino acid sequence with substitution, deletion or insertion of 1 to 10 amino acids in an amino acid sequence selected from the group consisting of SEQ ID NOs: 15 to 24 and which has tyrosine kinase activity;

(c) a polypeptide which comprises an amino acid sequence with 90% or higher identity to an amino acid sequence selected from the group consisting of SEQ ID NOs: 15 to 24 and which has tyrosine kinase activity;

(d) a polypeptide consisting of the amino acid sequence shown in SEQ ID NO: 27 or 28;

(e) a polypeptide which comprises the amino acid sequence shown in SEQ ID NO: 27 or 28 and which carries activated RET tyrosine kinase, or a polypeptide which comprises an amino acid sequence with substitution, deletion or insertion of 1 to 10 amino acids in the amino acid sequence shown in SFQ ID NO: 27 or 28 and which has tyrosine kinase activity; and (f) a polypeptide which comprises an amino acid sequence with 90% or higher identity to the amino acid sequence shown in SEQ ID NO: 27 or 28 and which has tyrosine kinase activity.

[15-6-5] The method according to [15-3] or [15-4] above, wherein the fusion gene is any of (a) to (d) shown below:

(a) a fusion gene which comprises a polynucleotide having a nucleotide sequence selected front the group consisting of SEQ ID NOs: 5 to 14;

(b) a fusion gene consisting of a polynucleotide which hybridizes under stringent conditions to DNA consisting of a nucleotide sequence complementary to a nucleotide sequence selected from the group consisting of SEQ ID NOs: 5 to 14 and which encodes a polypeptide having tyrosine kinase activity;

(c) a fusion gene which comprises a polynucleotide encoding a polypeptide having an amino acid sequence selected from the group consisting of SEQ ID NOs: 15 to 24; or (d) a fusion gene comprising a polynucleotide encoding a polypeptide which has substitution, deletion or insertion of one or more (e.g., several tens, 1 to 10, 1 to 5, 1 to 3) amino acids in a polypeptide having an amino acids sequence selected from the group consisting of SEQ ID NOs: 15 to 24 and which has tyrosine kinase activity.

[15-7] The method according to any one of [15] to [15-2] above, wherein the mutation in RET is a point mutation.

[15-8] The method according to [15-7] above, wherein the point mutation is a point mutation in the cysteine-rich domain or in the tyrosine kinase domain of RET tyrosine kinase.

[15-9] The method according to [15-7] or [15-8] above, wherein the point mutation is a mutation in the nucleotide 2091G, 2261G, 2494G, 2562A, 2600G, 2861T or 2943T of a polynucleotide having the nucleotide sequence shown in SEQ ID NO: 1.

[15-9-1] The method according to any one of [15-7] to [15-9] above, wherein the point mutation is a mutation in the nucleotide 2091G, 2261 G, 2494G, 2562A or 2861T of a polynucleotide having the nucleotide sequence shown in SEQ ID NO: 1.

[15-10] The method according to any one of [15-7] or [15-9] above, wherein the point mutation is a mutation in the nucleotide 2091G, 2494G, 2600G or 2943T of a polynucleotide having the nucleotide sequence shown in SEQ ID NO: 1.

[15-11] The method according to any one of [15-7] to [15-9] above, wherein the point mutation is 2091G>T, 2261G>A, 2494G>C, 2562A>T, 2600G>A, 2600G>C, 2861T>G or 2943T>C in a polynucleotide having the nucleotide sequence shown in SEQ ID NO: 1.

[15-11-1] The method according to any one of [15-7] to [15-9-1] and [15-11] above, wherein the point mutation is 2091G>T, 2261G>A, 2494G>C, 2562A>T or 2861T>6 in a polynucleotide having the nucleotide sequence shown in SEQ ID NO: 1.

[15-12] The method according to any one of [15-7] to [15-11] above, wherein the point mutation is 2091G>T, 2494G>T, 2600G>A or 2493T>C in a polynucleotide having the nucleotide sequence shown in SEQ ID NO: 1.

[15-13] The method according to [15-7] or [15-8] above, wherein the point mutation is a mutation in the amino acid C609, C611, C618, C620, C630, C634, G691, E768, Y791, V804, S891, A883 or M918 of a polypeptide having the amino acid sequence shown in SEQ ID NO: 3.

[15-13-1] The method according to [15-7], [15-8] or [15-13] above, wherein the point mutation is a mutation in the amino acid C609, C611, C618, C620, C630, C634, G691, E768, Y7911, S891 or A883 of a polypeptide having the amino acid sequence shown in SEQ ID NO: 3.

[15-14] The method according to [15-7], [15-8] or [15-13] above, wherein the point mutation is a mutation in the amino acid C609, C611, C618, C620, C630, C634, E768, V804, S891, A883 or M918 of a polypeptide having the amino acid sequence shown in SEQ ID NO: 3.

[15-15] The method according to [15-7], [15-8] or [15-13] above, wherein the point mutation is C634W, C634Y, G691 S, E768D, Y791F, V804M, V804L, S891A or M918T in a polypeptide having the amino acid sequence shown in SEQ ID NO: 3.

[15-15-1] The method according to [15-7], [15-8], [15-13] or [15-15] above, wherein the point mutation is C634W, C634Y, 6691S, E768D, Y791F or S891A in a polypeptide having the amino acid sequence shown in SEQ ID NO: 3.

[15-16] The method according to any one of [15-7] to [15-15],wherein the point mutation is C634W, C634Y, E768D, V804M or M918T in a polypeptide having the amino acid sequence shown in SEQ ID NO: 3.

[15-17] The method according to any one of [15] to [15-16] above, wherein the patient is a patient with thyroid cancer or lung cancer.

[15-18] The method according to any one of [15] to [15-17] above, wherein the patient is a patient with thyroid medullary cancer or non-small cell lung cancer.

[15-19] file method according to any one of [15] to [15-18] above, wherein the compound of formula (I), the salt thereof or the solvate thereof selectively inhibits RET.

[15-20] The method according to any one of [15] to [15-18] above, wherein $R^1$ is ethyl. [15-21] The method according to any one of [15] to [15-19] above, wherein the compound is a hydrochloride.

[16] A method for predicting the sensitivity of a patient to a compound of formula (I), a salt thereof or a solvate thereof, which comprises the steps of:

(1) confirming the presence or absence of a mutation in RET in a sample obtained from the patient; and (2) determining or preliminarily determining that the patient has sensitivity to the compound of formula (I), the salt thereof or the solvate thereof, provided that the mutation in RET is present.

EFFECTS OF THE INVENTION

The therapeutic and/or prophylactic agent of the present invention has a potent inhibitory effect against RET, particularly against RET tyrosine kinase, and is useful as a prophylactic or therapeutic agent (particularly therapeutic agent) for proliferative diseases. Moreover, the active ingredient in the present invention is useful as a prophylactic or therapeutic agent (particularly therapeutic agent) for diseases including various types of cancers, such as leukemia (e.g., acute myelogenous leukemia, chronic myelogenous leukemia, acute lymphocytic leukemia, chronic lymphocytic leukemia), malignant lymphoma (e.g., Hodgkin's lymphoma, non-Hodgkin's lymphoma), brain tumor, neuroblastoma, glioma, thyroid cancer, myelodysplastic syndrome, head and neck cancer, esophageal cancer, gastric cancer, colorectal cancer, breast cancer, ovarian cancer, lung cancer, pancreatic cancer, liver cancer, gallbladder cancer, skin cancer, malignant melanoma, kidney cancer, renal pelvic and ureteral cancer, bladder cancer, uterine cancer, testicular cancer and prostate cancer. The active ingredient in the present invention is further useful as a prophylactic or therapeutic agent (particularly therapeutic agent) for infiltration and metastasis of solid cancers.

The present invention achieves the identification of a cancer or a patient with a mutation in RET and achieves the effective treatment, etc. of such a patient using the compound represented by formula (I) or the like.

BRIEF DESCRIPTION OF THE DRAWING

FIG. 1 shows the antitumor activity of compound 1 using xenograft mouse models having CCDC6-RET fusion gene (Example 6).

MODE FOR CARRYING OUT THE INVENTION

An explanation will be given below of the therapeutic or prophylactic agent of the present invention and preparation procedures thereof.

Definitions

In the context of the present invention, the term "$C_{1-6}$ alkyl group" refers to a monovalent group derived from a linear or branched aliphatic hydrocarbon containing 1 to 6 carbon atoms by removing any one of the hydrogen atoms. More specifically, examples include a methyl group, an ethyl group, an isopropyl group, a butyl group, a n-butyl group, an isobutyl group, a sec-butyl group, a t-butyl group, a pentyl group, an isopentyl group, a 2,3-dimethylpropyl group, a hexyl group, a 2,3-dimethylhexyl group, a 1,1-dimethylpentyl group, a heptyl group and an octyl group. Preferred is a $C_{1-6}$ alkyl group, more preferred is a $C_{1-5}$ alkyl group, even more preferred is a $C_{1-4}$ alkyl group, and still even more preferred is a $C_{1-3}$ alkyl group.

In the context of the present invention, the expression "with a mutation in RET", "a mutation in RET" or "a mutation of RET" is intended to mean that a mutation occurs in RET gene and/or RET protein. In the context of the present invention, the expression "with a mutation in RET", "a mutation in RET" includes a point mutation, a deletion mutation or an insertion mutation in RET gene and/or RET protein, translocation- or inversion-mediated fusion between RET gene and another gene, as well as fusion protein formation between RET protein and another protein. The expression "with a mutation in RET", "a mutation in RET" or "a mutation of RET" further includes amplification of RET gene and/or amplification of RET protein, caused by an increased number of DNA regions on the genome compared to the normal state upon cleavage and rejoining of RET gene, impairment in the repair functions for RET gene, etc.

In the context of the present invention, the term "RET gene" is intended to mean a gene encoding RET (rearranged during transfection) tyrosine kinase. The RET gene of the present invention is intended to mean RET gene of any origin. Specifically, examples include, but are not limited to, a gene having a polynucleotide consisting of the nucleotide sequence shown in SEQ ID NO: 1 or 2, and a polynucleotide encoding a polypeptide consisting of the amino acid sequence shown in SEQ ID NO: 3 or 4.

In the context of the present invention, the term "RET protein" is intended to mean a protein consisting of an amino acid sequence constituting RET tyrosine kinase. The RET protein of the present invention is intended to mean RET protein of any origin. Specifically, examples include, but are not limited to, a protein having a polypeptide consisting of the amino acid sequence shown in SEQ ID NO: 3 or 4. It is known that there are three types of proteins RET9, RET43 and RET51 for RET tyrosine kinase due to differences in carboxyl-terminal splicing (TRENDS in Genetics. 2006, vol. 22, p. 627-636), and polypeptides consisting of amino acids constituting these three types of proteins also fall within "RET protein."

In the present invention, the polypeptide constituting the RET protein and the polynucleotide constituting the. RET gene include the following polypeptides and genes encoding the polypeptides:

a polypeptide consisting of an amino acid sequence with substitution, deletion or insertion of one or more (preferably 1 to 10, particularly preferably 1 to 5) amino acids in the polypeptide shown in SEQ ID NO: 3 or 4; and a polypeptide consisting of an amino acid sequence with 80% or higher (preferably 85% or higher, more preferably 90% or higher, further preferably 95% or higher) identity to the amino acid sequence shown in SEQ ID NO: 3 or 4.

In the context of the present invention, the expression "polynucleotide encoding a polypeptide" encompasses every polynucleotide capable of encoding a specific polypeptide and encompasses any of genomic DNA and cDNA. The polynucleotide includes even a degenerate polynucleotide composed of any codon encoding the same amino acid.

In the present invention, the identity of an amino acid sequence can be calculated by: properly aligning at least two sequences to be compared with each other; determining identical amino acid residues between the sequences; determining the number of matching sites; and subsequently dividing the number of the matching sites by the total number of residues in the sequence region to be compared and multiplying the obtained numeric value by 100. For example, the identity of a specific amino acid sequence to the amino acid sequence shown in SEQ ID NO: 3 can he calculated by: determining the number of matching sites between two sequences, i.e., the amino acid sequence shown in SEQ ID NO: 3 and the specific amino acid sequence, by the above method; and subsequently dividing the number of the matching sites by the total number of residues in the amino acid sequence shown in SEQ ID NO: 3 and multiplying the obtained numeric value by 100.

Alternatively, the identity of an amino acid sequence may be determined by the Karlin-Altschul BLAST algorithm (Prot. Natl. Acad. Sci. USA (1993) 90: 5873-7). On the basis of this algorithm, a program called BLASTN or BLASTX has been developed (Altschul et al., J. Mol. Biol. (1990) 215: 403-10). Each nucleotide sequence can be analyzed by BLASTN on the basis of BLAST using parameters set to, for example, score=100 and wordlength=12. Also, each amino acid sequence can be analyzed by BLASTX on the basis of BLAST using parameters set to, for example, score=50 and wordlength=3. In the case of using BLAST and Gapped BLAST programs, the default parameters of each program are used. Specific approaches of these analysis methods are known in the art (see information provided by the website of BLAST (Basic Local Alignment Search Tool), NCBI (National Center for Biotechnology Information)).

In the context of the present invention, the term "hybridizing" is intended to mean hybridizing to a target DNA or polynucleotide under stringent conditions. The stringent conditions can be determined on the basis of the melting temperature (Tm) of a nucleic acid to form a complex according to a routine method. Specifically, the stringent conditions involve "5×SSPE, 5×Denhardt's solution, 0.5% SDS, 50% formamide, 200 μg/ml salmon sperm DNA, 42° C. overnight" as conditions for hybridization and "0.5×SSC, 0.1% SDS, 42° C." as conditions for washing. More stringent conditions involve "5×SSPE, 5×Denhardt's solution, 0.5% SDS, 50% formamide, 200 μg/ml salmon sperm DNA, 42° C. overnight" as conditions for hybridization and "0.2×SSC, 0.1% SDS, 65° C." as conditions for washing.

The expression "with a mutation in RET", "a mutation in RET" or "a mutation of RET" further includes a state where a mutation which induces activation of RET tyrosine kinase or a mutation which activates RET tyrosine kinase and induces oncogenesis (e.g., thyroid cancer, lung cancer) has occurred in RET gene and/or RET protein. The activation of RET tyrosine kinase can be confirmed by detecting phosphorylated RET in a tumor tissue by immunostaining or the like using an anti-phosphorylated RET antibody.

In the context of the present invention, the expression "activation of RET tyrosine kinase" or "state where REF tyrosine kinase has been activated" is intended to mean that an amino acid residue (e.g., a tyrosine residue) contained in RET tyrosine kinase has been phosphorylated, and includes the amount of phosphorylated RET tyrosine kinase protein is increased in a subject (e.g., a sample taken from a subject) (e.g.. when compared to a normal subject). In addition, the expression "activation of RET tyrosine kinase" or "state where RET tyrosine kinase has been activated" includes a state where phosphorylated RET tyrosine kinase induces phosphorylation of a protein serving as a target of RET tyrosine kinase (hereinafter referred to as a target protein). The expression "activation of RET tyrosine kinase" or "state where RET tyrosine kinase has been activated" include not only the amount of phosphorylated RET tyrosine kinase protein, but also the amount of the above target protein in a phosphorylated form is increased.

In the context of the present invention, the expression "having tyrosine kinase activity" is intended to mean having activity as an enzyme that phosphorylates an amino acid residue, for example, a tyrosine residue, contained in tyrosine kinase. The tyrosine kinase activity of a polypeptide constituting the RET protein can be confirmed by, for example, the above method. In addition, the expression "having tyrosine kinase activity" includes having activity as an enzyme that phosphorylates an amino acid residue of a targeted protein.

Mutations reported to induce activation of RET tyrosine kinase include (1) a mutation in the cysteine-rich domain of RET, (2) a mutation in the tyrosine kinase domain of RET, and (3) formation of a fusion gene between RET gene and another gene or a fusion protein between RET protein and another protein (TRENDS in Genetics, 2006, vol. 22, p. 627-636). The human RET gene is located on chromosome 10 (10q11.2) and composed of 21 exons. The "cysteine-rich domain of RET" refers to a region rich in cysteine found in RET tyrosine kinase, and a polynucleotide encoding this domain is located at exons 10 and 11. The "tyrosine kinase domain of RET" refers to a region having tyrosine kinase activity found in RET tyrosine kinase, and a polynucleotide encoding this domain is located at exons 12 to 18 (TRENDS in Genetics, 2006, vol. 22, p. 627-636).

Specific examples of the above mutations (1) to (3) include those listed below. In the context of the present invention, the expression "with a mutation in RET" or "a mutation in RET" includes a state where any of these mutations (1) to (3) has occurred in RET gene and/or RET protein.

(1) Mutation in the Cysteine-Rich Domain

A mutation in C609, C611, C618, C620, C630, C634 or elsewhere in the amino acid sequence shown in SEQ ID NO: 3 (e.g., C634W, C634Y)

(2) Mutation in the Tyrosine Kinase Domain

A mutation in E768, V804, S891, A883, M918 or elsewhere in the amino acid sequence shown in SEQ ID NO: 3 (e.g., E768D, V804M, V804L, M918T)

(3) Formation of a Fusion Gene Between RET Gene and Another Gene or a Fusion Protein Between RET Protein and Another Protein Formation of KIF5B-RET fusion gene and/or fusion protein comprising the coiled-coil domain of KIF5B and the tyrosine kinase domain of RET Formation of CCDC6-RET fusion gene and/or fusion protein comprising the coiled-coil domain of CCDC6 and the tyrosine kinase domain of RET Formation of NCOA4-RET fusion gene and/or fusion protein comprising the coiled-coil domain of NCOA4 and the tyrosine kinase domain of RET Formation of TRIM33-RET fusion gene and/or fusion protein comprising the coiled-coil domain of TRIM33 and the tyrosine kinase domain of RET In the context of the present invention, the expression "gene of KIF5B" or "KIF5B gene" is intended to mean a gene encoding KIF5B (Kinesin family protein 5B), and the expression "protein of KIF5B" or "KIF5B protein" is intended to mean a protein consisting of an amino acid sequence constituting KIF5B. These terms are intended to mean a gene or a protein of KIF5B of any origin. Examples of a polynucleotide constituting the KIF5B gene and a polypeptide constituting the KIF5I3 protein specifically include, but are not limited to, a polynucleotide consisting of the nucleotide sequence shown in SEQ ID NO: 29 and a polypeptide consisting of the amino acid sequence shown in SEQ ID NO: 30. The polypeptide constituting the KIF5B protein and the polynucleotide constituting the KIF5B gene further include the following polypeptides and polynucleotides encoding the polypeptides:

a polypeptide consisting of an amino acid sequence with substitution, deletion or insertion of one or more (preferably 1 to 10, particularly preferably 1 to 5) amino acids in the amino acid sequence shown in SEQ ID NO: 30; and a polypeptide consisting of an amino acid sequence with 80% or higher (preferably 85% or higher, more preferably 90% or higher, further preferably 95% or higher) identity to the amino acid sequence shown in SEQ ID NO: 30.

The human KIF5B gene is located in chromosome 10 and composed of 26 exons. Candidates for the nucleotide sequence of KIF5B-RET fusion gene include, but are not limited to, those shown in SEQ ID NO: 5, SEQ ID NO: 6, SEQ ID NO: 7, SEQ ID NO: 8, SEQ ID NO: 9, SEQ ID NO: 10, SEQ ID NO: 11. SEQ ID NO: 12, SEQ ID NO: 13 and SEQ ID NO: 14. Candidates for the amino acid sequence of KIF5B-RET fusion protein include, but are not limited to, those shown in SEQ ID NO: 15, SEQ ID NO: 16, SEQ ID NO: 17. SEQ ID NO: 18, SEQ ID NO: 19, SEQ ID NO: 20, SEQ ID NO: 21, SEQ ID NO: 22, SEQ ID NO: 23 and SEQ ID NO: 24. Such KIF5B-RET fusion gene and fusion protein are reported to comprise the coiled-coil domain of KIF5B and the kinase domain of RET (Nature Medicine. 2012, 18, p. 378-381, Nature Medicine. 2012, 18, p. 382-384). In the present invention, the polypeptide constituting the KIF5B-RET fusion protein and the polynucleotide constituting the KIF5B-RET fusion gene additionally include the following polypeptides and polynucleotides encoding the polypeptides:

(i) a polypeptide comprising an amino acid sequence selected from the group consisting of SEQ ID NOs: 15 to 24, or a polypeptide comprising an amino acid sequence with substitution, deletion or insertion of one or more (preferably 1 to 10, particularly preferably 1 to 5) amino acids in an amino acid sequence selected from the group consisting of SEQ ID NOs: 15 to 24;

(ii) a polypeptide comprising an amino acid sequence with 80% or higher (preferably 85% or higher, more preferably 90% or higher, further preferably 95% or higher) identity to an amino acid sequence selected from the group consisting of SEQ ID NOs: 15 to 24; and (iii) a polypeptide which is the polypeptide (i) or (ii) and which has tyrosine kinase activity.

In the context of the present invention, the expression "gene of CCDC6" or "CCDC6 gene" is intended to mean a gene encoding CCDC6 (coiled-coil domain containing 6), and the expression "protein of CCDC6" or "CCDC6 protein" is intended to mean a protein consisting of an amino acid sequence constituting CCDC6. These terms are intended to mean a gene or a protein of CCDC6 of any origin. Examples of a polynucleotide constituting the CCDC6 gene and a polypeptide constituting the CCDC6 protein specifically include, but are not limited to, a polynucleotide consisting of the nucleotide sequence shown in SEQ ID NO: 31 and a polypeptide consisting of the amino acid sequence shown in SEQ ID NO: 32. The polypeptide constituting the CCDC6 protein and the polynucleotide constituting the CCDC6 gene further include the following polypeptides and polynucleotides encoding the polypeptides:

a polypeptide consisting of an amino acid sequence with substitution, deletion or insertion of one or more (preferably 1 to 10, particularly preferably 1 to 5) amino acids in the amino acid sequence shown in SEQ ID NO: 31; and a polypeptide consisting of an amino acid sequence with 80% or higher (preferably 85% or higher, more preferably 90% or higher, further preferably 95% or higher) identity to the amino acid sequence shown in SEQ ID NO: 31.

Human CCDC6 is located in chromosome 10 and composed of 9 exons.

Examples of the nucleotide sequence of CCDC6-RET fusion gene include, but are not limited to, those shown in SEQ ID NOs: 25 and 26. Examples of the amino acid sequence of the CCDC6-RET fusion protein include, but are not limited to, those shown in SEQ ID NOs: 27 and 28. Such CCDC6-RET fusion gene and fusion protein are reported to comprise the coiled-coil domain of CCDC6 and the tyrosine kinase domain of RET (Nat Med. 2012 Feb 12; 18 (3): 378-81).

Examples of the polypeptide constituting the CCDC6-RET fusion protein and the polynucleotide constituting the CCDC6-RET fusion gene additionally include the following polypeptides and polynucleotides encoding the polypeptides:) a polypeptide comprising the amino acid sequence shown in SEQ ID NO: 27 or 28, or a polypeptide comprising an amino acid sequence with substitution, deletion or insertion of one or more (preferably 1 to 10, particularly preferably 1 to 5) amino acids in the amino acid sequence shown in SEQ ID NO: 27 or 28; (ii) a polypeptide comprising an amino acid sequence with 80% or higher (preferably 85% or higher, more preferably 90% or higher, further preferably 95% or higher) identity to the amino acid sequence shown in SEQ ID NO: 27 or 28; and (iii) a polypeptide which is the polypeptide (i) or (ii) and which has tyrosine kinase activity.

In the context of the present invention, the expression "gene of NCOA4" or "NCOA4 gene" is intended to mean a gene encoding NCOA4 (nuclear receptor coactivator 4), and the expression "protein of NCOA4" or "NCOA4 protein" is intended to mean a protein consisting of an amino acid sequence constituting NCOA4. These terms are intended to mean a gene or a protein of NCOA4 of any origin. Examples of a polynucleotide constituting the NCOA4 gene and a polypeptide constituting the NCOA4 protein specifically include, but are not limited to, a polynucleotide consisting of a nucleotide sequence selected from the group consisting of SEQ ID NOs: 33 to 37 and a polypeptide consisting of an amino acid sequence selected from the group consisting of SEQ ID NOs: 38 to 42. The polypeptide constituting the NCOA4 protein and the polynucleotide constituting the NCOA4 gene further include the following polypeptides and polynucleotides encoding the polypeptides:

a polypeptide consisting of an amino acid sequence with substitution, deletion or insertion of one or more (preferably 1 to 10, particularly preferably 1 to 5) amino acids in an amino acid sequence selected from the group consisting of SEQ ID NOs: 38 to 42; and a polypeptide consisting of an amino acid sequence with 80% or higher (preferably 85% or higher, more preferably 90% or higher. further preferably 95% or higher) identity to an amino acid sequence selected from the group consisting of SEQ ID NOs: 35 to 42.

Human NCOA4 is located in chromosome 10. A gene in which NCOA4 exon 6 is fused with RET exon 12 is reported as a NCOA4-RET fusion gene. This fusion gene and its fusion protein are reported to comprise the coiled-coil domain of NCOA4 and the tyrosine kinase domain of RET (J Clin Oncol, 30 (35), Dec 10, 2012, p. 4352-9).

In the context of the present invention. the expression "gene of TRIM33" or "TRIM33 gene" is intended to mean a gene encoding TRIM33 (tripartite motif-containing 33), and the expression "protein of TRIM33" or "TRIM33 protein" is intended to mean a protein consisting of an amino acid sequence constituting TRIM33. These terms are intended to mean a gene or a protein of TRIM33 of any origin. Examples of a polynucleotide constituting the TRIM33 gene and a polypeptide constituting the TRIM33 protein specifically include, but arc not limited to, a polynucleotide consisting of the nucleotide sequence shown in SEQ ID NO: 43 or 44 and a polypeptide consisting of the amino acid sequence shown in SEQ ID NO: 45 or 46. The polypeptide constituting the TRIM33 protein and the polynucleotide constituting the TRIM33 gene further include the following polypeptides and polynucleotides encoding the polypeptides:

a polypeptide consisting of an amino acid sequence with substitution, deletion or insertion of one or more (preferably 1 to 10, particularly preferably 1 to 5) amino acids in the amino acid sequence shown in SEQ ID NO: 45 or 46; and a polypeptide consisting of an amino acid sequence with 80% or higher (preferably 85% or higher, more preferably 90% or higher, further preferably 95% or higher) identity to the amino acid sequence shown in SEQ ID NO: 45 or 46.

Human TRIM33 is located in chromosome 1. A gene in which TRIM33 exon 14 is fused with RET exon 12 is reported as a TRIM33-RET fusion gene. This fusion gene and its fusion protein are reported to comprise the coiled-coil domain of TRIM33 and the tyrosine kinase domain of RET (Cancer Discov, 3 (6), Jun 2013, p. 630-5).

The coiled-coil domain is a domain involved in protein dimerization. KIF5B-RET, CCDC6-RET, NCOA4-RET and TRIM33-RET are therefore considered to form dimers through their coiled-coil domains. These proteins are considered to cause the abnormal activation of RET tyrosine kinase via the dimerization between their coiled-coil domains to induce oncogenesis (Nature Medicine. 2012, 18, p. 378-381; Nature Medicine. 2012, 18, p. 382-384; J Clin Oncol, 30 (35), Dec. 10, 2012, p. 4352-9; and Cancer Discos' 2013 June, 3 (6), June 2013, p. 630-5).

Examples of a mutation in RET protein in thyroid cancer (e.g., thyroid medullary cancer) include C634W, C634Y, E768D, V804M, V804L and M918T mutations in the amino acid sequence shown in SEQ ID NO: 3 (the amino acid sequence of RET). The expressions "C634W," "C634Y," "E768D," "V804M," "V804L" and "M918T" each represent an amino acid mutation, expressed with a numeral representing a specific position which is sandwiched between single-letter symbols of amino acids before and after the mutation. For example, "C634W" denotes a Cys to Trp substitution in the 634th amino acid from the N-terminus of a specific amino acid sequence. Namely, the numeral represents the amino acid position counted from the N-terminus of a specific amino acid sequence, while the single-letter symbols of amino acids appearing before and after the numeral represent amino acids before and after the substitution, respectively.

Mutations in RET gene corresponding to the above mutations include 2091G>T, 2494G>C, 2600G>A, 2600G>C and 2943T>C mutations in the nucleotide sequence shown in SEQ ID NO: 1 (the nucleotide sequence of REF). The expressions "2091G>T," "2494G>C," "2600G>A," "2600G>C" and "2943T>C" each represent a nucleotide mutation, expressed with a numeral representing a specific position followed by bases before and after the mutation. For example, "2091G>T" denotes a G to T substitution in the 2091st nucleotide from the 5' end of a specific base sequence. Namely, the numeral represents the base position counted from the 5' end of a specific base sequence, while the base appearing after the numeral and before the symbol ">" represents a base before the substitution and the base appearing after the symbol ">" represents a base after the substitution.

Examples of a mutation in RET in lung cancer (e.g., non-small cell lung cancer)include the formation of KIF5B-RET fusion gene and/or protein, CCDC6-RET fusion gene and/or protein, NCOA4-RET fusion gene and/or protein, TRIM33-(ET fusion gene and/or protein, etc. More specifically, examples include, hut are not limited to, those listed below.

Formation of KIF5B-RET fusion gene and/or fusion protein comprising the coiled-coil domain of KIF5B and the tyrosine kinase domain of RET Formation of CCDC6-RET fusion gene and/or fusion protein comprising the coiled-coil domain of CCDC6 and the tyrosine kinase domain of RET Formation of NCOA4-RET fusion gene and/or fusion protein comprising the coiled-coil domain of NCOA4 and the tyrosine kinase domain of RET Formation of TRIM33-RET fusion gene and/or fusion protein comprising the coiled-coil domain of TRIM33 and the tyrosine kinase domain of RET In the context of the present invention, the expression "fusion gene of RET," "fusion gene between RET gene and another gene" refers to a gene in which all or a part of RET gene is fused with all or a part of another gene (e.g., KIF5B gene, CCDC6 gene. NCOA4 gene).

In the context of the present invention, the term "KIF5B-RET fusion gene" refers to a gene in which all or a part of RET gene is fused with all or a part of KIF5B gene. The term "CCDC6-RET fusion gene" refers to a gene in which all or a part of RET gene is fused with all or a part of CCDC6 gene. The term "NCOA4-RET fusion gene" refers to a gene in which all or a part of RET gene is fused with all or a part of NCOA4 gene. The term "TRIM33-RET fusion gene" refers to a gene in which all or a part of RET gene is fused with all or a part of TRIM33 gene.

In the context of the present invention, the expression "fusion protein of RET," "fusion protein between RET protein and another protein" refers to a protein in which all or a part of RET protein is fused with all or a part of another protein (e.g., KIF5B protein, CCDC6 protein, NCOA4 protein, TRIM33 protein).

In the context of the present invention, the term "KIF5B-RET fusion protein" refers to a protein in which all or a part of RET protein is fused with all or a part of KIF5B protein. The term "CCDC6-RET fusion protein" refers to a protein in which all or a part of RET protein is fused with all or a part of CCDC6 protein. The term "NCOA4-RET fusion protein" refers to a protein in which all or a part of RET protein is fused with all or a part of NCOA4 protein. The term “TRIM33-RET fusion protein” refers to a protein in which all or a part of RET protein is fused with all or a part of TRIM33 protein.

In the context of the present invention, the term “KIF5B-RET” is intended to mean KIF5B-RET fusion gene and/or KIF5B-RET fusion protein. The term “CCDC6-RET” is intended to mean CCDC6-RET fusion gene and/or CCDC6-RET fusion protein. The term “NCOA4-RET” is intended to mean NCOA4-RET fusion gene and/or NCOA4-RET fusion protein. The term “TRIM33-RET” is intended to mean TRIM33-RET fusion gene and/or TRIM33-RET fusion protein.

The expression “tumor with a mutation in RET” is intended to mean a tumor with a mutation in RET gene and/or protein in tumor cells.

The term “therapeutic agent” is intended to mean a pharmaceutical agent for directly or indirectly ameliorating a target disease or for preventing exacerbations of the target disease. More specifically, it is intended to mean a pharmaceutical agent for use in growth inhibition or size reduction of tumor tissues, inhibition of metastasis, reduction of tumor markers, amelioration of systemic symptoms or extension of survival period in a patient, etc.

The term “prophylactic agent” is intended to mean a pharmaceutical agent for use in pre-treatment of a patient at risk of suffering from a target disease such that the target disease is not developed.

The expression “metastasis of the tumor” is intended to mean metastasis of the primary tumor to other tissues. A therapeutic agent for “metastasis of the tumor” is intended to mean a pharmaceutical agent for inhibiting or suppressing metastasis of the tumor, or a pharmaceutical agent for growth inhibition or size reduction of tumor recurring as a result of metastasis. A prophylactic agent for “metastasis of the tumor” is intended to mean a pharmaceutical agent for use in pre-treatment such that the tumor does not metastasize or does not recur as a result of metastasis.

The expression “tumors metastasized from tumors” is intended to mean that the tumors listed as primary tumors metastasize to other tissues and develop therein.

The expression “subject to he administered” is intended to mean a subject for which a pharmaceutical agent can be expected to provide a therapeutic effect based on its mechanism of action. More specifically, it is intended to mean a patient with a proliferative disease for which growth inhibition or size reduction of tumor tissues, inhibition of metastasis, reduction of tumor markers, and amelioration of systemic symptoms in the patient can be expected.

The expression “tissue from the subject” is intended to mean a tissue contained in blood, alveoli, a biopsy sample, a sputum sample or the like taken from a subject such as a patient.

The expression “patient with a mutation in RET” is intended to mean that the patient has a mutation in RET gene and/or protein either in tumor or non-tumor tissue taken from a patient.

The term “RET inhibitor” is intended to mean a pharmaceutical agent which inhibits the activity of RET kinase, preferably a pharmaceutical agent which binds to RET kinase and has an inhibitory effect against the activity of RET kinase.

The expression “selectively inhibiting RET” is intended to mean that inhibitory activity against RET tyrosine kinase is high in terms of $IC_{50}$ value when compared with inhibitory activity against many other kinases (e.g., ABL, EGFR, FGFR2, HER2, IGF1R, JAK1, KIT, MET, AKT1, MEK1) except for ALK.

The expression “preliminarily determining” or “preliminarily identifying” is intended to mean providing information about the presence of a mutation in RET in order to determine or identify a sensitive patient.

In the present invention, the salt of the compound represented by formula (I) includes, for example: hydrochloride, hydrobromide, hydroiodide, phosphate, phosphonate and sulfate; sulfonates such as methanesulfonate and p-toluenesulfonate; carboxylate such as acetate, citrate, malate, tartrate, succinate and salicylate; alkali metal salts such as sodium salt and potassium salt; alkaline earth metal salts such as magnesium salt and calcium salt; and ammonium salts such as ammonium salt, alkylammonium salt. dialkylammonium salt, trialkylammonium salt and tetraalkylammonium salt. Preferred examples include hydrochloride and methanesulfonate. Hydrochloride is more preferred.

Such a salt is produced by contacting the compound with an acid or a base available in pharmaceutical production.

In the present invention, the compound represented by formula (I) or the salt thereof may be anhydrous or may form a solvate such as a hydrate. The term “solvation” used herein refers to a phenomenon where solute molecules or ions in a solution strongly attract solvent molecules adjacent thereto to create one molecular population and refers to, for example, hydration if the solvent is water. The solvate may be a hydrate or a non-hydrate. An alcohol (e.g., methanol, ethanol, n-propanol), dimethylformamide, or the like can be used as the non-hydrate.

Also, the compound or the salt thereof used in the present invention can exist in some tautomeric forms, for example, enol and imine forms, keto and enamine forms and mixtures thereof. The tautomers exist as a mixture of tautomeric sets in a solution. One tautomer is usually dominant in a solid form. The expression “one tautomer” in the present invention includes all tautomers of the compound used in the present invention.

The present invention includes all of stereoisomers (e.g., enantiomers, diastereomers (including cis and trans geometric isomers)) of the compound represented by formula (I), racemates of the isomers and other mixtures. The compound used in the present invention may have, for example, one or more asymmetric points in formula (I). The present invention includes racemic mixtures, diastereomeric mixtures and enantiomers of such compounds.

The compound according to the present invention may be obtained in a free form. In such a case, the free from can be converted to a salt that may be formed by the compound or to a hydrate or solvate thereof according to a routine method. Alternatively, he compound according to the present invention may he obtained as a salt, hydrate or solvate of the compound. In such a case, these forms can be converted to a free form of the compound according to a routine method.

Also, a substance used in the present invention includes a prodrug of the compound of formula (I). In this context, the term “prodrug” is intended to mean a derivative of the compound of formula (I) that is converted to the compound of formula (I) or a pharmaceutically acceptable salt thereof through enzymatic or nonenzymatic degradation under physiological conditions after administration. The prodrug may be inactive when administered to a patient, but exists in vivo as the active compound of formula (I) converted therefrom.

The prodrug, for example, converts to a desired drug form when a specific pH is reached or through the action of an enzyme.

Typical Production Method

The compound represented by formula (I) that serves as the active ingredient of the therapeutic or prophylactic agent of the present invention can be produced according to a method described in International Publication No. WO2010/143664, though the method for producing the compound represented by formula (I) is not limited thereto.

Therapeutic and/or Prophylactic Agent of the Present Invention

The term “therapeutic and/or prophylactic agent” used in the present invention refers to a pharmaceutical agent that is used for treatment or prevention or for treatment and prevention and specifically refers to a pharmaceutical agent that is used, for example, for treating or preventing the target disease or for suppressing progression (preventing exacerbations or maintaining the status quo) of the disease state.

The therapeutic and/or prophylactic agent of the present invention can be used as a pharmaceutical composition comprising a selected compound useful for the present invention and additionally a pharmaceutically acceptable carrier.

The term “pharmaceutically acceptable carrier” used herein is intended to mean one or more compatible solid or liquid excipients or encapsulating materials that are suitable for administration to mammals. The term “acceptable” used herein is intended to mean that the compound of interest and other ingredients are miscible in a composition in such a manner that reaction substantially reducing the pharmaceutical effectiveness of the composition does not occur therebetween under ordinary use conditions. As a matter of course, the pharmaceutically acceptable carrier must have sufficiently high purity and sufficiently low toxicity suitable for administration to, preferably an animal, more preferably a mammal, to be treated.

Examples of a material that may be used as the pharmaceutically acceptable carrier include: sugars such as lactose, glucose and sucrose; starches such as corn starch and potato starch; cellulose and its derivatives such as carboxymethylcellulose sodium, ethylcellulose and methylcellulose; tragacanth gum powder; malt; gelatin; talc; solid lubricants such as stearic acid and magnesium stearate; calcium sulfate; plant oils such as peanut oil, cottonseed oil, sesame oil, olive oil, corn oil and cacao oil; polyhydric alcohols such as propylene glycol, glycerin, sorbitol, mannitol and polyethylene glycol; alginic acid; emulsifiers such as TWEEN; wetting agents such as lecithin; colorants; flavors; tableting agents; stabilizers; antioxidants; antiseptics; pyrogen-free water; isotonic saline; and phosphate buffer solutions.

Examples of a method for administering the therapeutic and/or prophylactic agent of the present invention include oral, rectal, parenteral (intravenous, intramuscular, subcutaneous), intracisternal, intravaginal, intraperitoneal, intravesical and local (drip, powder, ointment, gel or cream) routes and inhalation (into oral cavity or using nasal sprays). Examples of the dosage form thereof include: solid preparations such as tablets, capsules, granules, powders and pills; liquid preparations such as aqueous and nonaqueous oral solutions and suspensions, and parenteral solutions charged in containers adapted to division into individual doses; and freeze-dried preparations that can be dissolved in use. Alternatively, the dosage form may be adapted to various administration methods encompassing controlled-release formulations as in subcutaneous implantation.

These preparations arc produced by a well known method using additives such as excipients, lubricants (coating agents), binders, disintegrants, stabilizers, flavoring agents and diluents.

Examples of the excipients can include starches such as starch, potato starch and corn starch, lactose, crystalline cellulose and calcium hydrogen phosphate.

Examples of the coating agents can include ethylcellulose, hyciroxypropylcellulose, hydroxypropylmethylcellulose, shellac, talc, carnauba wax and paraffin.

Examples of the hinders can include polyvinylpyrrolidone Macrogol and the compounds similar to the excipients.

Examples of the disintegrants can include compounds similar to the excipients and chemically modified starches and celluloses such as croscarmellose sodium, carboxymethyl starch sodium and cross-linked polyvinylpyrrolidone.

Examples of the stabilizers can include: p-hydroxyhenzoate esters such as methylparaben and propylparaben: alcohols such as chlorobutanol, benzyl alcohol and phenylethyl alcohol; benzalkonium chloride; phenols such as phenol and cresol; thimerosal; dehydroacetic acid; and sorhic acid.

Examples of the flavoring agents can include sweeteners, acidulants and flavors usually used.

The liquid preparations can be produced using a solvent such as ethanol, phenol, chlorocresol, purified water or distilled water.

Examples of the surfactants or emulsifiers can include polysorbate 80, polyoxyl 40 stearate, sodium lauryl sulfate and Lauromacrogol.

The amount of the prophylactic and/or therapeutic agent of the present invention used differs depending on symptom, age, body weight, relative health conditions, the presence of other medications, administration methods, etc. In the case of oral agents, a general effective amount, for example, for a patient (warm-blooded animal, particularly a human) is preferably 0.001 to 3000 mg/kg body weight, more preferably 0.01 to 300 mg/kg body weight, per day in terms of the amount of the active ingredient (compound represented by formula (I)), and the daily dose in an adult patient having a normal body weight is in the range of preferably 1 to 800 mg. In the case of parenteral agents, a general effective amount is preferably 0,001 to 1000 mg/kg body weight, more preferably 0.01 to 300 mg/kg body weight, per day. Desirably, this amount is administered at a single dose or several divided doses per day according to symptom.

The prophylactic and/or therapeutic agent of the present invention may be formulated by a method described in International Publication No. W02012/023597.

The therapeutic and/or prophylactic agent of the present invention may he used in combination with one or more pharmaceutical agents selected from, for example, other chemotherapeutic agents, hormone therapeutic agents, immunotherapeutic agents and molecular target drugs (hereinafter, collectively referred to as concomitant agents). Such an active ingredient may be a low-molecular-weight compound. Alternatively, such an active ingredient may be a low-molecular-weight compound, may be a high-molecular-weight protein, polypeptide or antibody, or may he a vaccine or the like. Moreover, two or more of these active ingredients may he mixed for use at an appropriate ratio.

Examples of the “chemotherapeutic agents” include alkylating agents, platinum preparations, metabolic antagonists, topoisomerase inhibitors, anticancer antibiotics and plant-derived anticancer agents. Examples of the “alkylating agents” include nitrogen mustard, nitrogen mustard-N-oxide hydrochloride. chlorambucil, cyclophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylenemelamine, carmustine, lomustine, streptozocin, pipobroman, ethoglucid, altretamine, ambamustine, dibrospidium hydrochloride, fotemustine, prednimustine, pumitepa, ribomustin, temozolomide, treosulfan, trofosfamide, zinostatin stimalamer, adozelesin, cystemustine and bizelesin. Examples of the "platinum preparations" include carboplatin, cisplatin, miboplatin, nedaplatin and oxaliplatin. Examples of the "metabolic antagonists" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, galocitabine, emitefur), aminopterin, leucovorin calcium, tabloid, butocin, calcium folinate, calcium levofolinate, cladribine, fiudarabine, gemcitabinc, hydroxycarbamide, pentostatin, piritrexim, idoxuridine, mitoguazone, tiazofurin and ambamustine. Examples of topoisomerase I inhibitors (e.g., irinotecan, topotecan), topoisomerase II inhibitors (e.g.. solluzoxane) and the "anticancer antibiotics" include anthracycline anticancer agents (doxorubicin hydrochloride, daunorubicin hydrochloride, aclarubicin hydrochloride, pirarubicin hydrochloride, epirubicin hydrochloride, etc.), actinomycin D, actinomycin C, mitomycin C, chromomycin A3, bleomycin hydrochloride, bleomycin sulfate, peplomycin sulfate, neocarzinostatin, mithramycin, sarkomycin, carzinophilin, mitotane, zorubicin hydrochloride, mitoxantrone hydrochloride and idarubicin hydrochloride. Examples of the "plant-derived anticancer agents" include vinca alkaloid anticancer agents (vinblastine sulfate, vincristine sulfate, vindesine sulfate, etc.), taxane anticancer agents (paclitaxel, docetaxel, etc.) etoposide, etoposide phosphate, teniposide and vinorelbine.

Examples of the "hormone therapeutic agents" include adrenocortical hormone drugs (e.g., dexamethasone, prednisolone, betamethasone, triamcinolone). Among them, prednisolone is preferred.

Examples of the "immunotherapeutic agents (biological response modifiers: BRMs)" include Picibanil, Krestin, sizofiran, lentinan, ubenimex, interferons. interleukins, macrophage colony-stimulating factors, granulocyte colony-stimulating factors, lymphotoxins, BCG vaccines, *Corynebacterium parvum*, levamisole, polysaccharide K and procodazole.

The "molecular target drugs" include, for example, "pharmaceutical agents that inhibit the action of cell growth factors and their receptors". The "cell growth factors" may be any substance that promotes cell growth, and examples typically include peptides with a molecular weight of 20,000 or lower which are factors that exert action at lower concentrations through binding to their receptors and specifically include (1) EGF (epidermal growth factor) and substances having substantially the same activity thereas [e.g., EGF, heregulin (HER2 ligand)], (2) insulin and substances having substantially the same activity thereas [e.g., insulin, IGF (insulin-like growth factor)-1, IGF-2],(3) FGF (fibroblast growth factor) and substances having substantially the same activity thereas [e.g., acidic FGF, basic FGF, KGF (keratinocyte growth factor), FGF-10] (4) VEGF (vascular endothelial growth factor) and (5) other cell growth factors [e.g CSF (colony stimulating factor), EPO (erythropoietin), IL-2 (interleukin-2), NGF (nerve growth factor), PDGF (platelet-derived growth factor), TGFβ (transforming growth factor β), HOF (hepatocyte growth factor)].

The "cell growth factor receptors" may be any receptor having the ability to bind to the above cell growth factors, and specific examples include EGF receptors, heregulin receptors (IIER2), insulin receptors, IGF receptors, FGF receptor-1 or FGF receptor-2, HOF receptors (c-met), VEGF receptors and SCF receptors (c-kit). Examples of the "pharmaceutical agents that inhibit the action of cell growth factors" include Herceptin (HER2 antibody). GLEEVEC (c-kit, abl inhibitor) and Tarceva (EGF receptor inhibitor).

The molecular target drugs also include pharmaceutical agents each inhibiting the actions of a plurality of cell growth factors, and pharmaceutical agents that block intracellular signals generated by cell growth factors.

In addition to the above pharmaceutical agents, L-asparaginase, aceglatone, procarbazine hydochloride, protoporphyrin-cobalt complex salts, mercury-hematoporphyrin sodium, differentiation inducers (e.g., retinoid, vitamin Ds), angiogenesis inhibitors, α-blockers (e.g., tamsulosin hydrochloride), and the like can also be used.

Among those described above, a platinum complex (e.g., carboplatin, cisplatin, oxaliplatin), a metabolic antagonist (e.g., gemcitabine, pemetrexed), a topoisomerase J inhibitor (e.g., irinotecan, topotecan), a plant-derived anticancer agent (taxane drugs (e.g., paclitaxel, docetaxel), vinorelbine), an anticancer antibiotic (e.g., mitomycin C), a hormone therapeutic agent (e.g., prednisolone), an immunotherapeutic agent (e.g., Picibanil, Krestin), a molecular target drug (e.g., anti-VEGF antibodies such as bevacizumab, EGFR inhibitors such as erlotinib, VEGFR inhibitors such as sunitinib), or the like is preferred as a concomitant agent. Cisplatin, gemcitabine, paclitaxel, bevacizumab, or the like is more preferred. Alternatively, the therapeutic and/or prophylactic agent of the present invention may be used in combination with a combination therapy using these pharmaceutical agents. Examples include combined use with a combination therapy of cisplatin, vinblastine and mitomycin C, cisplatin and vinorelbine, cisplatin and paclitaxel, cisplatin and gemcitabine, carboplatin and paclitaxel, pemetrexed and cisplatin, or bevacizumab, cisplatin and pemetrexed.

In the present invention, the timings of administration of the active ingredient of the present invention and the concomitant agent are not limited, and they may be administered simultaneously or at a time interval to a subject to be administered. Alternatively, the active ingredient of the present invention and the concomitant agent may he administered as a single preparation comprising them to a subject to be administered. For example, they may he administered by a multidrug therapy which involves drip-injecting a plurality of drugs in combination over 3 to 6 months or by a method which involves taking oral agents over approximately 2 years.

Also, a preoperative adjuvant therapy such as "chemotherapy" may be performed before execution of surgery in order to inhibit already spread tumor (cancer) cells to prevent recurrence as a result of metastasis or for the purpose of reducing the extent of surgery.

A postoperative adjuvant therapy such as "chemotherapy" may be further performed in order to inhibit the growth of tumor (cancer) cells that have not been removed by local treatment such as surgery or radiation to prevent recurrence as a result of metastasis.

The anticancer agent that may be used in combination with the active ingredient of the present invention may act on not only cancer cells but also normal cells, resulting in the occurrence of adverse reactions. Typical adverse reactions include nausea caused by gastrointestinal mucosal damage, vomiting, anorexia, stomatitis, diarrhea or constipation, taste abnormality, decrease in leukocyte, erythrocyte or platelet level or alopecia caused by bone marrow damage, immune compromise, etc. The active ingredient of the present invention and the concomitant agent may be used in combination with an adverse reaction-reducing agent in order to prevent these adverse reactions. Examples include antiemetics effectively suppressing nausea (e.g., granisetron hydrochloride) and drugs promoting recovery from bone marrow damage (e.g., erythropoietin, G-CSF, GM-CSF).

The dose of the concomitant agent can he appropriately selected with reference to a dose clinically used. The mixing ratio between the active ingredient of the present invention and the concomitant agent can he appropriately selected according to the subject to be administered, administration routes, the target disease, symptom, combination of the pharmaceutical agents, etc. For example, when the subject to be administered is a human, 0.01 to 100 parts by weight of the concomitant agent may he used with respect to 100 parts by weight of a preparation comprising the active ingredient of the present invention.

Method for Detecting Mutation in RET

The therapeutic and/or prophylactic agent of the invention of the present application is expected to be therapeutically and/or prophylactically effective by administration to a subject confirmed to have a mutation in RET. This suggests that a patient confirmed to have a mutation in RET is sensitive to the therapeutic and/or prophylactic agent of the invention of the present application. In the present invention, the method for detecting a mutation in RET includes a method for detecting a mutation in RET gene and a method for detecting a mutation in RET protein.

The method for detecting a mutation in RE'l gene comprises the step of detecting the presence of a RET gene-related specific polynucleotide shown below in a sample obtained from the subject and the amplification of the specific polynucleotide_

Specifically, the method comprises the following steps (1) to (3):

(1) A sample (blood, pulmonary alveolus, a biopsied sample, an expectoration sample, etc.) is taken from the subject;
(2) Genomic DNA or a transcript thereof (e.g., mRNA, cDNA, protein) is extracted from the sample. The genomic DNA can be extracted by a method known in the art. This extraction can be conveniently performed using a commercially available DNA extraction kit.
(3) The presence of a specific polynucleotide in the extracted genomic DNA or transcript thereof (e.g., mRNA, cDNA, protein) and the presence or absence of amplification of the specific polynucleotide are detected.

The presence of the specific polynucleotide can he detected using gene analysis methods known in the art (e.g., methods such as PCR, reverse transcription PCR, Sanger sequencing, in situ hybridization and microarray method) singly or in combination.

In the event of detecting the presence of the specific polynucleotide sequence by using mRNA. the detection can be performed by gene amplification reaction such as reverse transcription PCR using primers designed to be capable of specifically amplifying the polynucleotide sequence to he detected. The primer design can he performed using primer design software (e.g., Primer Express; PE Biosystems) or the like.

In addition, the PCR products which arc obtained by PCR and reverse transcription PCR are analyzed by agarose gel electrophoresis, and the successful obtainment of an amplification fragment with a size of interest can he confirmed by ethidium bromide staining or the like. The successful obtainment of an amplification fragment with a size of interest shows that the specific polynucleotide is present in the sample obtained from the subject.

A point mutation, deletion mutation or insertion mutation in RET gene can be detected by detecting the presence of the specific polynucleotide using, for example, a combined method of the above reverse transcription PCR and Sanger sequencing, or a single-nucleotide extension reaction method known in the art.

A fusion gene between RET gene and another gene can be detected by a method for detecting the presence of the specific polynucleotide using a combined method of the above reverse transcription PCR and Sanger sequencing or using an in situ hybridization technique. The detection using the in situ hybridization technique can be performed by, for example, fluorescent in situ hybridization (FISH), chromogenic in situ hybridization (CISH) or silver in situ hybridization (SISH) known in the art.

A probe which can be used in hybridization is a nucleic acid molecule of at least 32 consecutive nucleotides (16 upstream nucleotides and 16 downstream nucleotides flanking the fusion point) that hybridizes under stringent conditions (preferably under more stringent conditions) to the specific polynucleotide or its complementary strand, but not limited to. A probe comprising the sequence of a specific portion in a polynucleotide having a nucleotide sequence selected from the group consisting of SEQ ID NOs: 5 to 14, 25 and 26. or its complementary strand can also be used, The stringent conditions can be determined on the basis of the melting temperature (Tm) of a nucleic acid to form a complex according to a routine method. Specifically, the stringent conditions involve "5×SSPE, 5×Denhardt's solution, 0.5% SDS, 50% formamide, 200 μg/ml salmon sperm DNA. 42° C. overnight" as conditions for hybridization and "0.5×SSC, 0.1% SDS, 42° C." as conditions for washing. More stringent conditions involve "5×SSPE, 5×Denhardt's solution, 0.5% SDS, 50% formamide, 200 μg/ml salmon sperm DNA, 42° C. overnight" as conditions for hybridization and "0.2×SSC, 0.1% SDS, 65° C." as conditions for washing.

Detection of the amplification of RET gene can be conducted by detecting the amplification of the specific polynucleotide by the above in situ hybridization technique or by comparative genomic hybridization (CGH) using genomic DNA.

The specific polynucleotide to be detected refers to a polynucleotide having a base varied due to a point mutation, deletion mutation or insertion mutation in polynucleotide constituting RET gene, a polynucleotide constituting the fusion gene between RET gene and another gene (e.g., KIF5B gene, CCDC6 gene, NCOA4 gene, TRIM33 gene), or amplified polynucleotide constituting RET gene. Examples of such a polynucleotide include, but are not limited to. the polynucleotides shown below and polynucleotides hybridizing under stringent conditions to polynucleotides consisting of sequences complementary to these polynucleotides (particularly polynucleotides encoding polypeptides having tyrosine kinase activity).

(1) Polynucleotide Constituting Fusion Gene Between RET Gene and KIF5B Gene:

Polynucleotide comprising the nucleotide sequence shown in SEQ ID NO: 5

Polynucleotide comprising the nucleotide sequence shown in SEQ ID NO: 6

Polynucleotide comprising the nucleotide sequence shown in SEQ ID NO: 7

Polynucleotide comprising the nucleotide sequence shown in SEQ ID NO: 8

Polynucleotide comprising the nucleotide sequence shown in SEQ ID NO: 9

Polynucleotide comprising the nucleotide sequence shown in SEQ ID NO: 10

Polynucleotide comprising the nucleotide sequence shown in SEQ ID NO: 11

Polynucleotide comprising the nucleotide sequence shown in SEQ ID NO: 12

Polynucleotide comprising the nucleotide sequence shown in SEQ ID NO: 13

Polynucleotide comprising the nucleotide sequence shown in SEQ ID NO: 14

(2) Polynucleotide Constituting Fusion Gene Between RET Gen and CCDC6 Gene:

Polynucleotide comprising the nucleotide sequence shown in SEQ ID NO: 25

Polynucleotide comprising the nucleotide sequence shown in SEQ ID NO: 26

(3) Polynucleotide Constituting RET Gene:

Polynucleotide comprising the nucleotide sequence shown in SEQ ID NO: 1

Polynucleotide comprising the nucleotide sequence shown in SEQ ID NO: 2

(4) Polynucleotide Having a Base Varied Due to a Point Mutation, Deletion Mutation or Insertion Mutation in Polynucleotide Constituting RET Gene:

Polynucleotide comprising a nucleotide sequence with a mutation in the nucleotide 2091G, 2261G, 2494G, 2562A, 2600G, 2861T or 2943T (e.g., 2091G>T, 2261G>A, 2494G>C, 2562A>T, 2600G>A, 2600G>C, 2861T>G or 2943T>C mutation) of a polynucleotide having the nucleotide sequence shown in SEQ ID NO: 1

Polynucleotide comprising a polynucleotide encoding a polypeptide with a mutation in the amino acid C609, C611, C618, C620, C630, C634, E768, V804, S891, A883 or M918 (e.g., C634W, C634Y, E768D, V804M, V804L or M918T mutation) of a polypeptide having the amino acid sequence shown in SEQ ID NO: 3

The method for detecting a mutation in RET further includes a method for detecting a mutation in RET protein in addition to the above method.

The method for detecting a mutation in RET comprises the step of detecting the presence of a specific polypeptide (hereinafter, referred to as a polypeptide to be detected) in a sample obtained from the subject. The step of detecting a polypeptide to be detected involves preparing a lysate from a sample obtained from the subject (e.g., cancer tissues or cells obtained from the subject).

In the event that a polypeptide to he detected is fusion protein between RET protein and another protein, the presence of polypeptide to be detected can he detected by for example. immunoassay or enzyme activity assay using an antibody against KIF5B, CCDC6, NCOA4 or TRIM33 and an anti-RET antibody in combination. Preferably, an approach such as enzyme immunoassay, two-antibody sandwich ELISA, fluorescent immunoassay, radioimmunoassay or Western blotting using a monoclonal or polyclonal antibody specific for the polypeptide to be detected can he used. In addition to above mentioned method, detection of a mutation (including a point mutation, a deletion mutation and an insertion mutation) in RET protein can be conducted by detecting the presence of a polypeptide to he detected using Western blotting, mass spectrometry, or the like.

Examples of the polypeptide to be detected include, but are not limited to, the polypeptides shown below and polypeptides with deletion, substitution and/or insertion of one or more amino acids (e.g., 1 to 10, 1 to 5, or 1 to 3 amino acids) in these polypeptides (particularly polypeptides having tyrosine kinase activity).

(1) Polypeptide Constituting Fusion Protein Between RET Protein and KIF5B Protein:

Polypeptide comprising the amino acid sequence shown in SEQ ID NO: 15

Polypeptide comprising the amino acid sequence shown in SEQ ID NO: 16

Polypeptide comprising the amino acid sequence shown in SEQ ID NO: 17

Polypeptide comprising the amino acid sequence shown in SEQ ID NO: 18

Polypeptide comprising the amino acid sequence shown in SEQ ID NO: 19

Polypeptide comprising the amino acid sequence shown in SEQ ID NO: 20

Polypeptide comprising the amino acid sequence shown in SEQ ID NO: 21

Polypeptide comprising the amino acid sequence shown in SEQ ID NO: 22

Polypeptide comprising the amino acid sequence shown in SEQ ID NO: 23

Polypeptide comprising the amino acid sequence shown in SEQ ID NO: 24

(2) Polypeptide Constituting Fusion Protein Between RET Protein and CCDC6 Protein:

Polypeptide comprising the amino acid sequence shown in SEQ ID NO: 27

Polypeptide comprising the amino acid sequence shown in SEQ ID NO: 28

(3) Polypeptide Constituting RET Protein

Polypeptide comprising the amino acid sequence shown in SEQ ID NO: 3

Polypeptide comprising the amino acid sequence shown in SEQ ID NO: 4

(4) Polypeptide Having a Point Mutation in a Polypeptide Constituting RET Protein Polypeptide encoded by a polynucleotide comprising a nucleotide sequence with a mutation in the nucleotide 2091G, 2261G, 2494G, 2562A, 2600G, 2861T or 2943T (e.g., 2091G>T, 2261G>A, 2494G>C, 2562A>T, 2600G>A, 2600G>C, 2861T>G or 2943T>C mutation) of a polynucleotide having the nucleotide sequence shown in SEQ ID NO: 1

Polypeptide with a mutation in the amino acid C609, C611l, C618, C620, C630, C634, G691, E768, Y791, V804, S891, A883 or M918 (e.g., C634W, C634Y, G691 S, E768D, Y791F, V804M, V804L, S891A or M918T mutation) of a polypeptide having the amino acid sequence shown in SEQ ID NO: 3

In addition, the presence of the fusion gene between RET gene and KIF5B gene or other fusion genes can he detected by methods described in International Publication No. WO2012/014795, Nature Medicine, 2012, 18, p. 378-381, J Clin Oncol, 30 (35), Dec. 10, 2012, p. 4352-9, Cancer Discov 2013 June, 3 (6). June 2013, p. 630-5, etc.

In addition to the above method, the activation of RET tyrosine kinase may be detected. The activation of RET tyrosine kinase can be confirmed by detecting phosphorylated RET in a tumor tissue by immunostaining or the like using an anti-phosphorylated RET antibody.

EXAMPLES

Hereinafter, the present invention will be described more specifically with reference to Examples. However, the present invention is not intended to be limited to these Examples.

Compound 1 (9-ethyl-6,6-dimethyl-8-(4-morpholin-4-yl-piperidin-1-yl)-11-oxo-6,11-dihydro-5H-benzo[b]carbazole-3-carbonitrile, or 9-ethyl-6,6-dimethyl-8-[4-(morpholin-4-yl)piperidin-1-yl]-11-oxo-6,11-dihydro-5H-benzo[b]

carbazole-3-carbonitrile) represented by formula II (compound described in Example 366 of WO2010/143664) was subjected to pharmacological tests described in Examples 1 to 6.

(II)

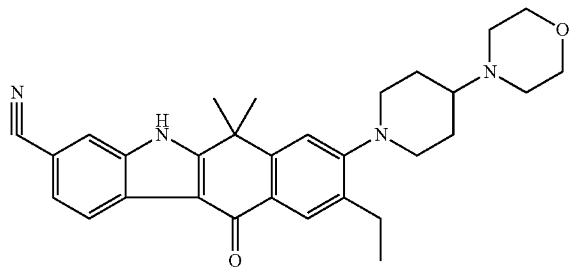

Example 1

Evaluation of RET Kinase Inhibitory Activity and Binding Affinity

The RET kinase inhibitory activity of compound 1 was evaluated with inhibitory activity against the phosphorylation reaction of a biotinylated peptide (EGPWLEEEEE-AYGWMDF) as an index using RET kinase containing a N-terminally GST-tagged RET kinase domain (Curia Biosciences). The phosphorylated biotinylated peptide was detected by the TR-FRET (time-resolved fluorescence resonance energy transfer) method using an europium labeled anti-phosphorylation antibody. 50% inhibition concentration ($IC_{50}$ value) was calculated by the logistic regression method. As a result, compound 1 exhibited RET kinase inhibitory activity with an $IC_{50}$ value of 4.8 nM.

The dissociation constant (Kd value) of compound 1 for RET kinase was also measured by $KINOME_{SCAN}$™ (DiscoveRx). As a result, compound 1 exhibited binding affinity to RET with Kd value of 7.6 nM.

Example 2

Establishment of KIF5B-RET-Expressing Cells and Evaluation of Cell Growth Inhibitory Activity Against these Cells An expression plasmid CS-GS104J-M67 (GeneCopoeia) containing KIF5B-RET variant 1 (gene in which a region from the N-terminus of KIF5B CDS to exon 15 was fused with a region from exon 12 of RET CDS to the C-terminus) (SEQ ID NO: 5) was transfected into mouse lymphocytes Ba/F3 (RIK FN Cell Bank) by electroporation. After transfection, the cells were cultured overnight in an RPMI-1640 medium (Sigma-Aldrich) containing 10% FBS (Bovogen Biologicals) and 1 ng/mL recombinant mouse IL-3 (R&D systems). Then, the culture supernatant was replaced with an RPMl-1640 medium containing 10% LBS. The cells were seeded into a 96-well plate by the limiting dilution method. Approximately 2 weeks later, the expression of phosphorylated RET in cells grown in the absence of IL-3 was detected by Western blotting. This was used as an index to establish a cell line Ba/F3 KIF5B-RET stably expressing KIF5B-RET.

The Ba/F3 KIF5B-RET cells were seeded into a 96-well plate at a concentration of 2,500 cells/well in an RPMI-1640 medium containing 10% FBS. A hydrochloride salt of compound 1 was diluted to 1 nM to 10 μM (final concentrations) with dimethyl sulfoxide and added to the 96-well plate. Dimethyl sulfoxide was added as a negative control. After culture at 37° C. for 2 days in the presence of 5% $CO_2$, a cell counting reagent CellTiter-Glo® Luminescent Cell Viability Assay (Pronged Corporation) was added thereto and stirred, followed by the measurement of luminescence intensity using a luminescence measurement apparatus Envision (PerkinElmer). The measurement value in a well supplemented with only a medium was defined as a cell viability of 0%, while the measurement value in a well supplemented with dimethyl sulfoxide was defined as a cell viability of 100%. The cell viability of the Ba/F3 KIF5B-RET cells was calculated at each concentration of compound 1. The $IC_{50}$ value was determined from the obtained values by the logistic regression method. As a result, compound 1 inhibited cell growth of Ba/F3 KIF5B-RET cells with $IC_{50}$ value of 86 nM.

These results demonstrated that compound 1 can inhibit the kinase activity of RET and can inhibit the growth of a cell line expressing KIF5B-RET.

Example 3

Evaluation of Cell Growth Inhibitory Activity Against Thyroid Medullary Cancer Cell Line TT Cell growth inhibitory activity was evaluated using a thyroid medullary cancer cell line TT (American Type Culture Collection) with a RET kinase active mutation (C634W).

The TT cells were seeded into a 96-well plate at a concentration of 5,000 cells/well in F-12K Nutrient Mixture (Life Technologies Corporation) containing 10% FBS and cultured overnight at 37° C. in the presence of 5% $CO_2$. Then, a hydrochloride salt of compound 1 was diluted to 1 nM to 10 μM (final concentrations) with dimethyl sulfoxide and added to the 96-well plate. Dimethyl sulfoxide was added as a negative control. After culture at 37° C. for 5 days in the presence of 5% $CO_2$. a cell counting reagent CellTiter-Glo® Luminescent Cell Viability Assay was added thereto and stirred, followed by the measurement of luminescence intensity using a luminescence measurement apparatus Envision. The measurement value in a well supplemented with only a medium was defined as a cell viability of 0%, while the measurement value in a well supplemented with dimethyl sulfoxide was defined as a survival rate of 100%. The cell viability of the TT cells was calculated at each concentration of compound 1. The $IC_{50}$ value was determined from the obtained values by the logistic regression method. As a result compound 1 inhibited cell growth of TT cells with IC50 value of 190 nM.

Example 4

RET Kinase Mutant Inhibitory Activity

The RET kinase mutant inhibitory activity of compound 1 was evaluated with inhibitory activity against the phosphorylation reaction of a biotinylated peptide (EGPWLEEEEEAYGWMDF) as an index using a RET kinase mutant containing a N-terminally GST-tagged RET kinase domain (Carna Biosciences, Millipore). The phosphorylated biotinylated peptide was detected by the TR-FRET method using an europium labeled anti-phosphorylation antibody. The $IC_{50}$ value was calculated by the logistic regression method. The test results are shown in Table 1. Compound 1 exhibited inhibitory activity against each mutant of RET kinase with a mutation (V804L, V804M) in a gatekeeper residue.

TABLE 1

| RET mutant | $IC_{50}$ (nM) |
|---|---|
| RET G691S | 9.5 |
| RET Y791F | 14 |
| RET V804L | 32 |
| RET V804M | 53 |
| RET S891A | 8.3 |
| RET M918T | 5.7 |

Example 5

Evaluation of Cell Growth Inhibitory Activity Against Non-Small Cell Lung Cancer Cell Line LC-2/ad Cell growth inhibitory activity was evaluated using a non-small cell lung cancer cell line LC-tad (R1KEN, J Thorac Oncol. 2012 December, 7 (12), 1872-6) harboring CCDC6-RET fusion gene.

The LC-2/ad cells were seeded into a 96-well plate at a concentration of 2,000 cells/well in a medium of a 1:1 mixture of RPMI-1640 and Ham containing 15% FBS and 25 mM HEPES and cultured overnight at 37° C. in the presence of 5% $CO_2$. Then, a hydrochloride salt of compound 1 was diluted to 1 nM to 1 μM (final concentrations) with dimethyl sulfoxide and added to the 96-well plate. Dimethyl sulfoxide was added as a negative control. After culture at 37° C. for 5 days in the presence of 5% $CO_2$, a cell counting reagent CellTiter-Glo® Luminescent Cell Viability Assay was added thereto and stirred, followed by the measurement of luminescence intensity using a luminescence measurement apparatus Envision. The measurement value in a well supplemented with only a medium was defined as a cell viability of 0%, while the measurement value in a well supplemented with dimethyl sulfoxide was defined as a cell viability of 100%. The cell viability of the LC-2/ad cells was calculated at each concentration of compound 1. The $IC_{50}$ value was determined from the obtained values by the logistic regression method. As a result, compound 1 inhibited cell growth of LC-2/ad cells with $IC_{50}$ value of 190 nM.

Example 6

Evaluation of Antitumor Activity in Xenograft Mouse Model Harboring CCDC6-RET Fusion Gene The in vivo antitumor activity of compound 1 was evaluated in non-small cell lung cancer cell line LC-2/ad-implanted mouse models. LC-2/ad was subcutaneously implanted to SCID mice and randomized after tumor size reached 200 to 350 $mm^3$. The administration of the compound was started on the day of randomization. The vehicles used for dissolving the compound were 0.02 N HCl, 10% dimethyl sulfoxide. 10% Cremophor EL, 15% PEG400 and 15% HPCD (2-hydroxypropyl-β-cyclodextrin) (indicated by final concentration). Compound 1 was orally administered once a day to each mouse at a dose of 20 mg/kg or 60 mg/kg for 14 days. As a result, a dose-dependent tumor growth inhibitory effect and tumor regression were confirmed for all tumors. During this test, a significant body weight loss of a mouse was not observed at any dose. The results about the antitumor activity are shown in FIG. 1.

The invention claimed is:

1. A method for identifying a patient sensitive to a compound represented by formula (I), a salt thereof or a solvate thereof, the method comprising detecting a mutation in RET in a sample obtained from the patient; and determining or preliminarily determining that the patient has sensitivity to the compound, the salt thereof or the solvate thereof, based on the mutation in RET detected in the sample, said compound represented by formula (I) having the following structure:

(I)

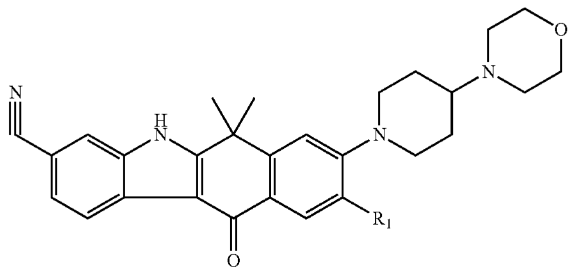

wherein $R^1$ is a $C_{1-6}$ alkyl group, wherein the mutation is (a) a fusion gene between (i) a RET gene and (ii) another gene, which is KIF5B or CCDC6, and/or (b) a fusion protein of a RET protein and another protein, which is KIF5B or CCDC6.

2. The method according to claim 1, wherein the patient is a patient with thyroid cancer or lung cancer.

3. The method according to claim 1, wherein the patient is a patient with thyroid medullary cancer or non-small cell lung cancer.

* * * * *

UNITED STATES PATENT AND TRADEMARK OFFICE

CERTIFICATE OF CORRECTION

PATENT NO. : 11,633,402 B2
APPLICATION NO. : 16/855712
DATED : April 25, 2023
INVENTOR(S) : Kodama et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 74 days.

Signed and Sealed this
Thirty-first Day of December, 2024

Derrick Brent
*Acting Director of the United States Patent and Trademark Office*

SEQUENCE LISTING

```
<160> NUMBER OF SEQ ID NOS: 46

<210> SEQ ID NO 1
<211> LENGTH: 4174
<212> TYPE: DNA
<213> ORGANISM: Homo sapiens
<220> FEATURE:
<221> NAME/KEY: misc_feature
<223> OTHER INFORMATION: RET transcript variant 4 (NM_020630.4 )

<400> SEQUENCE: 1

agtcccgcga ccgaagcagg gcgcgcagca gcgctgagtg ccccggaacg tgcgtcgcgc      60

ccccagtgtc cgtcgcgtcc gccgcgcccc gggcggggat ggggcggcca gactgagcgc     120

cgcacccgcc atccagaccc gccggcccta gccgcagtcc ctccagccgt ggccccagcg     180

cgcacgggcg atggcgaagg cgacgtccgg tgccgcgggg ctgcgtctgc tgttgctgct     240

gctgctgccg ctgctaggca aagtggcatt gggcctctac ttctcgaggg atgcttactg     300

ggagaagctg tatgtggacc aggcggccgg cacgcccttg ctgtacgtcc atgccctgcg     360

ggacgcccct gaggaggtgc ccagcttccg cctgggccag catctctacg gcacgtaccg     420

cacacggctg catgagaaca actggatctg catccaggag gacaccggcc tcctctacct     480

taaccggagc ctggaccata gctcctggga gaagctcagt gtccgcaacc gcggctttcc     540

cctgctcacc gtctacctca aggtcttcct gtcacccaca tcccttcgtg agggcgagtg     600

ccagtggcca ggctgtgccc gcgtatactt ctccttcttc aacacctcct ttccagcctg     660

cagctccctc aagccccggg agctctgctt cccagagaca aggccctcct tccgcattcg     720

ggagaaccga cccccaggca ccttccacca gttccgcctg ctgcctgtgc agttcttgtg     780

ccccaacatc agcgtggcct acaggctcct ggagggtgag ggtctgccct tccgctgcgc     840
```

-continued

```
cccggacagc ctggaggtga gcacgcgctg ggccctggac cgcgagcagc gggagaagta    900
cgagctggtg gccgtgtgca ccgtgcacgc cggcgcgcgc gaggaggtgg tgatggtgcc    960
cttcccggtg accgtgtacg acgaggacga ctcggcgccc accttccccg cgggcgtcga   1020
caccgccagc gccgtggtgg agttcaagcg gaaggaggac accgtggtgg ccacgctgcg   1080
tgtcttcgat gcagacgtgg tacctgcatc aggggagctg gtgaggcggt acacaagcac   1140
gctgctcccc ggggacacct gggcccagca gaccttccgg gtggaacact ggcccaacga   1200
gacctcggtc caggccaacg gcagcttcgt gcgggcgacc gtacatgact ataggctggt   1260
tctcaaccgg aacctctcca tctcggagaa ccgcaccatg cagctggcgg tgctggtcaa   1320
tgactcagac ttccagggcc caggagcggg cgtcctcttg ctccacttca acgtgtcggt   1380
gctgccggtc agcctgcacc tgcccagtac ctactccctc tccgtgagca ggagggctcg   1440
ccgatttgcc cagatcggga aagtctgtgt ggaaaactgc caggcattca gtggcatcaa   1500
cgtccagtac aagctgcatt cctctggtgc caactgcagc acgctagggg tggtcacctc   1560
agccgaggac acctcgggga tcctgtttgt gaatgacacc aaggccctgc ggcggcccaa   1620
gtgtgccgaa cttcactaca tggtggtggc caccgaccag cagacctcta ggcaggccca   1680
ggcccagctg cttgtaacag tggaggggtc atatgtggcc gaggaggcgg gctgccccct   1740
gtcctgtgca gtcagcaaga gacggctgga gtgtgaggag tgtggcggcc tgggctcccc   1800
aacaggcagg tgtgagtgga ggcaaggaga tggcaaaggg atcaccagga acttctccac   1860
ctgctctccc agcaccaaga cctgccccga cggccactgc gatgttgtgg agacccaaga   1920
catcaacatt tgccctcagg actgcctccg ggcagcatt gttgggggac acgagcctgg   1980
ggagccccgg gggattaaag ctggctatgg cacctgcaac tgcttccctg aggaggagaa   2040
gtgcttctgc gagcccgaag acatccagga tccactgtgc gacgagctgt gccgcacggt   2100
gatcgcagcc gctgtcctct tctccttcat cgtctcggtg ctgctgtctg ccttctgcat   2160
ccactgctac cacaagtttg cccacaagcc acccatctcc tcagctgaga tgaccttccg   2220
gaggcccgcc caggccttcc cggtcagcta ctcctcttcc ggtgcccgcc ggccctcgct   2280
ggactccatg gagaaccagg tctccgtgga tgccttcaag atcctggagg atccaaagtg   2340
ggaattccct cggaagaact tggttcttgg aaaaactcta ggagaaggcg aatttggaaa   2400
agtggtcaag gcaacggcct tccatctgaa aggcagagca gggtacacca cggtggccgt   2460
gaagatgctg aaagagaacg cctccccgag tgagcttcga gacctgctgt cagagttcaa   2520
cgtcctgaag caggtcaacc acccacatgt catcaaattg tatggggcct gcagccagga   2580
tggcccgctc ctcctcatcg tggagtacgc caaatacggc tccctgcggg gcttcctccg   2640
cgagagccgc aaagtggggc ctggctacct gggcagtgga ggcagccgca actccagctc   2700
cctggaccac ccggatgagc gggccctcac catgggcgac ctcatctcat ttgcctggca   2760
gatctcacag gggatgcagt atctggccga gatgaagctc gttcatcggg acttggcagc   2820
cagaaacatc ctggtagctg aggggcggaa gatgaagatt tcggatttcg gcttgtcccg   2880
agatgtttat gaagaggatt cctacgtgaa gaggagccag ggtcggattc cagttaaatg   2940
gatggcaatt gaatcccttt ttgatcatat ctacaccacg caaagtgatg tatggtcttt   3000
tggtgtcctg ctgtgggaga tcgtgaccct agggggaaac ccctatcctg ggattcctcc   3060
tgagcggctc ttcaaccttc tgaagaccgg ccaccggatg gagaggccag acaactgcag   3120
cgaggagatg taccgcctga tgctgcaatg ctggaagcag gagccggaca aaaggccggt   3180
```

```
gtttgcggac atcagcaaag acctggagaa gatgatggtt aagaggagag actacttgga   3240

ccttgcggcg tccactccat ctgactccct gatttatgac gacggcctct cagaggagga   3300

gacaccgctg gtggactgta ataatgcccc cctccctcga gccctccctt ccacatggat   3360

tgaaaacaaa ctctatggta gaatttccca tgcatttact agattctagc accgctgtcc   3420

cctctgcact atccttcctc tctgtgatgc tttttaaaaa tgtttctggt ctgaacaaaa   3480

ccaaagtctg ctctgaacct ttttatttgt aaatgtctga ctttgcatcc agtttacatt   3540

taggcattat tgcaactatg tttttctaaa aggaagtgaa aataagtgta attaccacat   3600

tgcccagcaa cttaggatgg tagaggaaaa aacagatcag ggcggaactc tcaggggaga   3660

ccaagaacag gttgaataag gcgcttctgg ggtgggaatc aagtcatagt acttctactt   3720

taactaagtg gataaatata caaatctggg gaggtattca gttgagaaag gagccaccag   3780

caccactcag cctgcactgg gagcacagcc aggttccccc agacccctcc tgggcaggca   3840

ggtgcctctc agaggccacc cggcactggc gagcagccac tggccaagcc tcagccccag   3900

tcccagccac atgtcctcca tcaggggtag cgaggttgca ggagctggct ggccctggga   3960

ggacgcaccc ccactgctgt tttcacatcc tttcccttac ccaccttcag gacggttgtc   4020

acttatgaag tcagtgctaa agctggagca gttgcttttt gaaagaacat ggtctgtggt   4080

gctgtggtct tacaatggac agtaaatatg gttcttgcca aaactccttc ttttgtcttt   4140

gattaaatac tagaaattta aaaaaaaaaa aaaa                               4174
```

<210> SEQ ID NO 2
<211> LENGTH: 5629
<212> TYPE: DNA
<213> ORGANISM: Homo sapiens
<220> FEATURE:
<221> NAME/KEY: misc_feature
<223> OTHER INFORMATION: RET transcript variant 2 (NM_020975.4)

<400> SEQUENCE: 2

```
agtcccgcga ccgaagcagg gcgcgcagca gcgctgagtg ccccggaacg tgcgtcgcgc     60

ccccagtgtc cgtcgcgtcc gccgcgcccc gggcggggat ggggcggcca gactgagcgc    120

cgcacccgcc atccagaccc gccggcccta gccgcagtcc ctccagccgt ggccccagcg    180

cgcacgggcg atggcgaagg cgacgtccgg tgccgcgggg ctgcgtctgc tgttgctgct    240

gctgctgccg ctgctaggca aagtggcatt gggcctctac ttctcgaggg atgcttactg    300

ggagaagctg tatgtggacc aggcggccgg cacgcccttg ctgtacgtcc atgccctgcg    360

ggacgcccct gaggaggtgc ccagcttccg cctgggccag catctctacg gcacgtaccg    420

cacacggctg catgagaaca actggatctg catccaggag gacaccggcc tcctctacct    480

taaccggagc ctggaccata gctcctggga gaagctcagt gtccgcaacc gcggctttcc    540

cctgctcacc gtctacctca aggtcttcct gtcacccaca tcccttcgtg agggcgagtg    600

ccagtggcca ggctgtgccc gcgtatactt ctccttcttc aacacctcct ttccagcctg    660

cagctccctc aagccccggg agctctgctt cccagagaca aggccctcct tccgcattcg    720

ggagaaccga cccccaggca ccttccacca gttccgcctg ctgcctgtgc agttcttgtg    780

ccccaacatc agcgtggcct acaggctcct ggagggtgag ggtctgccct tccgctgcgc    840

cccggacagc ctggaggtga gcacgcgctg ggccctggac cgcgagcagc gggagaagta    900

cgagctggtg gccgtgtgca ccgtgcacgc cggcgcgcgc gaggaggtgg tgatggtgcc    960

cttcccggtg accgtgtacg acgaggacga ctcggcgccc accttccccg cgggcgtcga   1020
```

-continued caccgccagc gccgtggtgg agttcaagcg gaaggaggac accgtggtgg ccacgctgcg 1080
tgtcttcgat gcagacgtgg tacctgcatc aggggagctg gtgaggcggt acacaagcac 1140
gctgctcccc ggggacacct gggcccagca gaccttccgg gtggaacact ggcccaacga 1200
gacctcggtc caggccaacg gcagcttcgt gcgggcgacc gtacatgact ataggctggt 1260
tctcaaccgg aacctctcca tctcggagaa ccgcaccatg cagctggcgg tgctggtcaa 1320
tgactcagac ttccagggcc caggagcggg cgtcctcttg ctccacttca acgtgtcggt 1380
gctgccggtc agcctgcacc tgcccagtac ctactccctc tccgtgagca ggagggctcg 1440
ccgatttgcc cagatcggga aagtctgtgt ggaaaactgc caggcattca gtggcatcaa 1500
cgtccagtac aagctgcatt cctctggtgc caactgcagc acgctagggg tggtcacctc 1560
agccgaggac acctcgggga tcctgtttgt gaatgacacc aaggccctgc ggcggcccaa 1620
gtgtgccgaa cttcactaca tggtggtggc caccgaccag cagacctcta ggcaggccca 1680
ggcccagctg cttgtaacag tggaggggtc atatgtggcc gaggaggcgg gctgccccct 1740
gtcctgtgca gtcagcaaga gacggctgga gtgtgaggag tgtggcggcc tgggctcccc 1800
aacaggcagg tgtgagtgga ggcaaggaga tggcaaaggg atcaccagga acttctccac 1860
ctgctctccc agcaccaaga cctgccccga cggccactgc gatgttgtgg agacccaaga 1920
catcaacatt tgccctcagg actgcctccg gggcagcatt gttgggggac acgagcctgg 1980
ggagccccgg gggattaaag ctggctatgg cacctgcaac tgcttccctg aggaggagaa 2040
gtgcttctgc gagcccgaag acatccagga tccactgtgc gacgagctgt gccgcacggt 2100
gatcgcagcc gctgtcctct tctccttcat cgtctcggtg ctgctgtctg ccttctgcat 2160
ccactgctac cacaagtttg cccacaagcc acccatctcc tcagctgaga tgaccttccg 2220
gaggcccgcc caggccttcc cggtcagcta ctcctcttcc ggtgcccgcc ggccctcgct 2280
ggactccatg gagaaccagg tctccgtgga tgccttcaag atcctggagg atccaaagtg 2340
ggaattccct cggaagaact tggttcttgg aaaaactcta ggagaaggcg aatttggaaa 2400
agtggtcaag gcaacggcct tccatctgaa aggcagagca gggtacacca cggtggccgt 2460
gaagatgctg aaagagaacg cctccccgag tgagcttcga gacctgctgt cagagttcaa 2520
cgtcctgaag caggtcaacc acccacatgt catcaaattg tatggggcct gcagccagga 2580
tggcccgctc ctcctcatcg tggagtacgc caaatacggc tccctgcggg gcttcctccg 2640
cgagagccgc aaagtggggc ctggctacct gggcagtgga ggcagccgca actccagctc 2700
cctggaccac ccggatgagc gggccctcac catgggcgac ctcatctcat ttgcctggca 2760
gatctcacag gggatgcagt atctggccga gatgaagctc gttcatcggg acttggcagc 2820
cagaaacatc ctggtagctg aggggcggaa gatgaagatt tcggatttcg gcttgtcccg 2880
agatgtttat gaagaggatt cctacgtgaa gaggagccag ggtcggattc cagttaaatg 2940
gatggcaatt gaatcccttt ttgatcatat ctacaccacg caaagtgatg tatggtcttt 3000
tggtgtcctg ctgtgggaga tcgtgaccct agggggaaac ccctatcctg ggattcctcc 3060
tgagcggctc ttcaaccttc tgaagaccgg ccaccggatg gagaggccag acaactgcag 3120
cgaggagatg taccgcctga tgctgcaatg ctggaagcag gagccggaca aaaggccggt 3180
gtttgcggac atcagcaaag acctggagaa gatgatggtt aagaggagag actacttgga 3240
ccttgcggcg tccactccat ctgactccct gatttatgac gacggcctct cagaggagga 3300
gacaccgctg gtggactgta ataatgcccc cctccctcga gccctccctt ccacatggat 3360
tgaaaacaaa ctctatggca tgtcagaccc gaactggcct ggagagagtc ctgtaccact 3420

```
cacgagagct gatggcacta acactgggtt tccaagatat ccaaatgata gtgtatatgc   3480
taactggatg ctttcaccct cagcggcaaa attaatggac acgtttgata gttaacattt   3540
ctttgtgaaa ggtaatggac tcacaagggg aagaaacatg ctgagaatgg aaagtctacc   3600
ggccctttct ttgtgaacgt cacattggcc gagccgtgtt cagttcccag gtggcagact   3660
cgtttttggt agtttgtttt aacttccaag gtggttttac ttctgatagc cggtgatttt   3720
ccctcctagc agacatgcca caccgggtaa gagctctgag tcttagtggt taagcattcc   3780
tttctcttca gtgcccagca gcacccagtg ttggtctgtg tccatcagtg accaccaaca   3840
ttctgtgttc acatgtgtgg gtccaacact tactacctgg tgtatgaaat tggacctgaa   3900
ctgttggatt tttctagttg ccgccaaaca aggcaaaaaa atttaaacat gaagcacaca   3960
cacaaaaaag gcagtaggaa aaatgctggc cctgatgacc tgtccttatt cagaatgaga   4020
gactgcgggg ggggcctggg ggtagtgtca atgcccctcc agggctggag gggaagaggg   4080
gccccgagga tgggcctggg ctcagcattc gagatcttga gaatgatttt tttttaatca   4140
tgcaaccttt ccttaggaag acatttggtt ttcatcatga ttaagatgat tcctagattt   4200
agcacaatgg agagattcca tgccatcttt actatgtgga tggtggtatc agggaagagg   4260
gctcacaaga cacatttgtc ccccgggccc accacatcat cctcacgtgt tcggtactga   4320
gcagccacta cccctgatga gaacagtatg aagaaagggg gctgttggag tcccagaatt   4380
gctgacagca gaggctttgc tgctgtgaat cccacctgcc accagcctgc agcacacccc   4440
acagccaagt agaggcgaaa gcagtggctc atcctacctg ttaggagcag gtagggcttg   4500
tactcacttt aatttgaatc ttatcaactt actcataaag ggacaggcta gctagctgtg   4560
ttagaagtag caatgacaat gaccaaggac tgctacacct ctgattacaa ttctgatgtg   4620
aaaaagatgg tgtttggctc ttatagagcc tgtgtgaaag gcccatggat cagctcttcc   4680
tgtgtttgta atttaatgct gctacaagat gtttctgttt cttagattct gaccatgact   4740
cataagcttc ttgtcattct tcattgcttg tttgtggtca cagatgcaca acactcctcc   4800
agtcttgtgg gggcagcttt tgggaagtct cagcagctct tctggctgtg ttgtcagcac   4860
tgtaacttcg cagaaaagag tcggattacc aaaacactgc ctgctcttca gacttaaagc   4920
actgatagga cttaaaatag tctcattcaa atactgtatt ttatataggc atttcacaaa   4980
aacagcaaaa ttgtggcatt ttgtgaggcc aaggcttgga tgcgtgtgta atagagcctt   5040
gtggtgtgtg cgcacacacc cagagggaga gtttgaaaaa tgcttattgg acacgtaacc   5100
tggctctaat ttgggctgtt tttcagatac actgtgataa gttcttttac aaatatctat   5160
agacatggta aacttttggt tttcagatat gcttaatgat agtcttacta aatgcagaaa   5220
taagaataaa ctttctcaaa ttattaaaaa tgcctacaca gtaagtgtga attgctgcaa   5280
caggtttgtt ctcaggaggg taagaactcc aggtctaaac agctgaccca gtgatgggga   5340
atttatcctt gaccaattta tccttgacca ataacctaat tgtctattcc tgagttataa   5400
aagtccccat ccttattagc tctactggaa ttttcataca cgtaaatgca gaagttacta   5460
agtattaagt attactgagt attaagtagt aatctgtcag ttattaaaat ttgtaaaatc   5520
tatttatgaa aggtcattaa accagatcat gttccttttt ttgtaatcaa ggtgactaag   5580
aaaatcagtt gtgtaaataa aatcatgtat cataaaaaaa aaaaaaaaa               5629
```

<210> SEQ ID NO 3
<211> LENGTH: 1072
<212> TYPE: PRT

```
<213> ORGANISM: Homo sapiens
<220> FEATURE:
<221> NAME/KEY: MISC_FEATURE
<223> OTHER INFORMATION: RET isoform c precursor (NP_065681.1)

<400> SEQUENCE: 3

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380
```

-continued

```
Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605

Cys Asn Cys Phe Pro Glu Glu Glu Lys Cys Phe Cys Glu Pro Glu Asp
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
    690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
    770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
```

-continued

```
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp  Ile Ser Lys Asp Leu  Glu Lys Met
        995                 1000                1005

Met Val  Lys Arg Arg Asp Tyr  Leu Asp Leu Ala Ala  Ser Thr Pro
    1010                1015                1020

Ser Asp  Ser Leu Ile Tyr Asp  Asp Gly Leu Ser Glu  Glu Glu Thr
    1025                1030                1035

Pro Leu  Val Asp Cys Asn Asn  Ala Pro Leu Pro Arg  Ala Leu Pro
    1040                1045                1050

Ser Thr  Trp Ile Glu Asn Lys  Leu Tyr Gly Arg Ile  Ser His Ala
    1055                1060                1065

Phe Thr  Arg Phe
    1070


<210> SEQ ID NO 4
<211> LENGTH: 1114
<212> TYPE: PRT
<213> ORGANISM: Homo sapiens
<220> FEATURE:
<221> NAME/KEY: MISC_FEATURE
<223> OTHER INFORMATION: RET isoform a precursor (NP_066124.1)

<400> SEQUENCE: 4

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80
```

-continued

```
His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
```

-continued

```
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605

Cys Asn Cys Phe Pro Glu Glu Glu Lys Cys Phe Cys Glu Pro Glu Asp
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
    690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
    770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925
```

```
Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp  Ile Ser Lys Asp Leu  Glu Lys Met
        995                 1000                1005

Met Val  Lys Arg Arg Asp Tyr  Leu Asp Leu Ala Ala  Ser Thr Pro
    1010                1015                1020

Ser Asp  Ser Leu Ile Tyr Asp  Asp Gly Leu Ser Glu  Glu Glu Thr
    1025                1030                1035

Pro Leu  Val Asp Cys Asn Asn  Ala Pro Leu Pro Arg  Ala Leu Pro
    1040                1045                1050

Ser Thr  Trp Ile Glu Asn Lys  Leu Tyr Gly Met Ser  Asp Pro Asn
    1055                1060                1065

Trp Pro  Gly Glu Ser Pro Val  Pro Leu Thr Arg Ala  Asp Gly Thr
    1070                1075                1080

Asn Thr  Gly Phe Pro Arg Tyr  Pro Asn Asp Ser Val  Tyr Ala Asn
    1085                1090                1095

Trp Met  Leu Ser Pro Ser Ala  Ala Lys Leu Met Asp  Thr Phe Asp
    1100                1105                1110

Ser


<210> SEQ ID NO 5
<211> LENGTH: 2808
<212> TYPE: DNA
<213> ORGANISM: Homo sapiens
<220> FEATURE:
<221> NAME/KEY: misc_feature
<223> OTHER INFORMATION: KIF5B-RET (K15;R12 variant 4)

<400> SEQUENCE: 5

atggcggacc tggccgagtg caacatcaaa gtgatgtgtc gcttcagacc tctcaacgag     60

tctgaagtga accgcggcga caagtacatc gccaagtttc agggagaaga cacggtcgtg    120

atcgcgtcca agccttatgc atttgatcgg gtgttccagt caagcacatc tcaagagcaa    180

gtgtataatg actgtgcaaa gaagattgtt aaagatgtac ttgaaggata taatggaaca    240

atatttgcat atggacaaac atcctctggg aagacacaca caatggaggg taaacttcat    300

gatccagaag gcatgggaat tattccaaga atagtgcaag atatttttaa ttatatttac    360

tccatggatg aaaatttgga atttcatatt aaggtttcat attttgaaat atatttggat    420

aagataaggg acctgttaga tgtttcaaag accaaccttt cagttcatga agacaaaaac    480

cgagttccct atgtaaaggg gtgcacagag cgttttgtat gtagtccaga tgaagttatg    540

gataccatag atgaaggaaa atccaacaga catgtagcag ttacaaatat gaatgaacat    600

agctctagga gtcacagtat atttcttatt aatgtcaaac aagagaacac acaaacggaa    660

caaaagctga gtggaaaact ttatctggtt gatttagctg gtagtgaaaa ggttagtaaa    720

actggagctg aaggtgctgt gctggatgaa gctaaaaaca tcaacaagtc actttctgct    780

cttggaaatg ttatttctgc tttggctgag ggtagtacat atgttccata tcgagatagt    840

aaaatgacaa gaatccttca agattcatta ggtggcaact gtagaaccac tattgtaatt    900
```

```
tgctgctctc catcatcata caatgagtct gaaacaaaat ctacactctt atttggccaa    960

agggccaaaa caattaagaa cacagtttgt gtcaatgtgg agttaactgc agaacagtgg   1020

aaaaagaagt atgaaaaaga aaaagaaaaa aataagatcc tgcggaacac tattcagtgg   1080

cttgaaaatg agctcaacag atggcgtaat ggggagacgg tgcctattga tgaacagttt   1140

gacaaagaga aagccaactt ggaagctttc acagtggata aagatattac tcttaccaat   1200

gataaaccag caaccgcaat tggagttata ggaaatttta ctgatgctga aagaagaaag   1260

tgtgaagaag aaattgctaa attatacaaa cagcttgatg acaaggatga agaaattaac   1320

cagcaaagtc aactggtaga gaaactgaag acgcaaatgt tggatcagga ggagcttttg   1380

gcatctacca gaagggatca agacaatatg caagctgagc tgaatcgcct tcaagcagaa   1440

aatgatgcct ctaaagaaga agtgaaagaa gttttacagg ccctagaaga acttgctgtc   1500

aattatgatc agaagtctca ggaagttgaa gacaaaacta aggaatatga attgcttagt   1560

gatgaattga atcagaaatc ggcaacttta gcgagtatag atgctgagct tcagaaactt   1620

aaggaaatga ccaaccacca gaaaaaacga gcagctgaga tgatggcatc tttactaaaa   1680

gaccttgcag aaataggaat tgctgtggga aataatgatg taaaggagga tccaaagtgg   1740

gaattccctc ggaagaactt ggttcttgga aaaactctag gagaaggcga atttggaaaa   1800

gtggtcaagg caacggcctt ccatctgaaa ggcagagcag ggtacaccac ggtggccgtg   1860

aagatgctga aagagaacgc ctccccgagt gagctgcgag acctgctgtc agagttcaac   1920

gtcctgaagc aggtcaacca cccacatgtc atcaaattgt atggggcctg cagccaggat   1980

ggcccgctcc tcctcatcgt ggagtacgcc aaatacggct ccctgcgggg cttcctccgc   2040

gagagccgca aagtggggcc tggctacctg ggcagtggag gcagccgcaa ctccagctcc   2100

ctggaccacc cggatgagcg ggccctcacc atgggcgacc tcatctcatt tgcctggcag   2160

atctcacagg ggatgcagta tctggccgag atgaagctcg ttcatcggga cttggcagcc   2220

agaaacatcc tggtagctga ggggcggaag atgaagattt cggatttcgg cttgtcccga   2280

gatgtttatg aagaggattc ctacgtgaag aggagccagg gtcggattcc agttaaatgg   2340

atggcaattg aatccctttt tgatcatatc tacaccacgc aaagtgatgt atggtctttt   2400

ggtgtcctgc tgtgggagat cgtgacccta gggggaaacc cctatcctgg gattcctcct   2460

gagcggctct tcaaccttct gaagaccggc caccggatgg agaggccaga caactgcagc   2520

gaggagatgt accgcctgat gctgcaatgc tggaagcagg agccggacaa aaggccggtg   2580

tttgcggaca tcagcaaaga cctggagaag atgatggtta agaggagaga ctacttggac   2640

cttgcggcgt ccactccatc tgactccctg atttatgacg acggcctctc agaggaggag   2700

acaccgctgg tggactgtaa taatgccccc ctccctcgag ccctcccttc cacatggatt   2760

gaaaacaaac tctatggtag aatttcccat gcatttacta gattctag                2808
```

```
<210> SEQ ID NO 6
<211> LENGTH: 2997
<212> TYPE: DNA
<213> ORGANISM: Homo sapiens
<220> FEATURE:
<221> NAME/KEY: misc_feature
<223> OTHER INFORMATION: KIF5B-RET (K16;R12 variant4)

<400> SEQUENCE: 6

atggcggacc tggccgagtg caacatcaaa gtgatgtgtc gcttcagacc tctcaacgag     60

tctgaagtga accgcggcga caagtacatc gccaagtttc agggagaaga cacggtcgtg    120
```

```
atcgcgtcca agccttatgc atttgatcgg gtgttccagt caagcacatc tcaagagcaa    180
gtgtataatg actgtgcaaa gaagattgtt aaagatgtac ttgaaggata taatggaaca    240
atatttgcat atggacaaac atcctctggg aagacacaca caatggaggg taaacttcat    300
gatccagaag gcatgggaat tattccaaga atagtgcaag atatttttaa ttatatttac    360
tccatggatg aaaatttgga atttcatatt aaggtttcat attttgaaat atatttggat    420
aagataaggg acctgttaga tgtttcaaag accaaccttt cagttcatga agacaaaaac    480
cgagttccct atgtaaaggg gtgcacagag cgttttgtat gtagtccaga tgaagttatg    540
gataccatag atgaaggaaa atccaacaga catgtagcag ttacaaatat gaatgaacat    600
agctctagga gtcacagtat atttcttatt aatgtcaaac aagagaacac acaaacggaa    660
caaaagctga gtggaaaact ttatctggtt gatttagctg gtagtgaaaa ggttagtaaa    720
actggagctg aaggtgctgt gctggatgaa gctaaaaaca tcaacaagtc actttctgct    780
cttggaaatg ttatttctgc tttggctgag ggtagtacat atgttccata tcgagatagt    840
aaaatgacaa gaatccttca agattcatta ggtggcaact gtagaaccac tattgtaatt    900
tgctgctctc catcatcata caatgagtct gaaacaaaat ctacactctt atttggccaa    960
agggccaaaa caattaagaa cacagtttgt gtcaatgtgg agttaactgc agaacagtgg   1020
aaaaagaagt atgaaaaaga aaaagaaaaa aataagatcc tgcggaacac tattcagtgg   1080
cttgaaaatg agctcaacag atggcgtaat ggggagacgg tgcctattga tgaacagttt   1140
gacaaagaga aagccaactt ggaagctttc acagtggata aagatattac tcttaccaat   1200
gataaaccag caaccgcaat tggagttata ggaaatttta ctgatgctga aagaagaaag   1260
tgtgaagaag aaattgctaa attatacaaa cagcttgatg acaaggatga agaaattaac   1320
cagcaaagtc aactggtaga gaaactgaag acgcaaatgt tggatcagga ggagcttttg   1380
gcatctacca gaagggatca agacaatatg caagctgagc tgaatcgcct tcaagcagaa   1440
aatgatgcct ctaaagaaga agtgaaagaa gttttacagg ccctagaaga acttgctgtc   1500
aattatgatc agaagtctca ggaagttgaa gacaaaacta aggaatatga attgcttagt   1560
gatgaattga atcagaaatc ggcaacttta gcgagtatag atgctgagct tcagaaactt   1620
aaggaaatga ccaaccacca gaaaaaacga gcagctgaga tgatggcatc tttactaaaa   1680
gaccttgcag aaataggaat tgctgtggga aataatgatg taaagcagcc tgagggaact   1740
ggcatgatag atgaagagtt cactgttgca agactctaca ttagcaaaat gaagtcagaa   1800
gtaaaaacca tggtgaaacg ttgcaagcag ttagaaagca cacaaactga gagcaacaaa   1860
aaaatggaag aaaatgaaaa ggagttagca gcatgtcagc ttcgtatctc tcaagaggat   1920
ccaaagtggg aattccctcg gaagaacttg gttcttggaa aaactctagg agaaggcgaa   1980
tttggaaaag tggtcaaggc aacggccttc catctgaaag gcagagcagg gtacaccacg   2040
gtggccgtga agatgctgaa agagaacgcc tccccgagtg agcttcgaga cctgctgtca   2100
gagttcaacg tcctgaagca ggtcaaccac ccacatgtca tcaaattgta tggggcctgc   2160
agccaggatg gcccgctcct cctcatcgtg gagtacgcca aatacggctc cctgcggggc   2220
ttcctccgcg agagccgcaa agtggggcct ggctacctgg gcagtggagg cagccgcaac   2280
tccagctccc tggaccaccc ggatgagcgg gccctcacca tgggcgacct catctcattt   2340
gcctggcaga tctcacaggg gatgcagtat ctggccgaga tgaagctcgt tcatcgggac   2400
ttggcagcca gaaacatcct ggtagctgag ggcggaaga tgaagatttc ggatttcggc   2460
```

-continued

```
ttgtcccgag atgtttatga agaggattcg tacgtgaaga ggagccaggg tcggattcca   2520

gttaaatgga tggcaattga atcccttttt gatcatatct acaccacgca aagtgatgta   2580

tggtcttttg gtgtcctgct gtgggagatc gtgaccctag gggaaaccc ctatcctggg    2640

attcctcctg agcggctctt caaccttctg aagaccggcc accggatgga gaggccagac   2700

aactgcagcg aggagatgta ccgcctgatg ctgcaatgct ggaagcagga gccggacaaa   2760

aggccggtgt ttgcggacat cagcaaagac ctggagaaga tgatggttaa gaggagagac   2820

tacttggacc ttgcggcgtc cactccatct gactccctga tttatgacga cggcctctca   2880

gaggaggaga caccgctggt ggactgtaat aatgcccccc tccctcgagc cctcccttcc   2940

acatggattg aaaacaaact ctatggtaga atttcccatg catttactag attctag      2997
```

<210> SEQ ID NO 7
<211> LENGTH: 3522
<212> TYPE: DNA
<213> ORGANISM: Homo sapiens
<220> FEATURE:
<221> NAME/KEY: misc_feature
<223> OTHER INFORMATION: KIF5B-RET (K22;R12 variant4)

<400> SEQUENCE: 7

```
atggcggacc tggccgagtg caacatcaaa gtgatgtgtc gcttcagacc tctcaacgag     60

tctgaagtga accgcggcga caagtacatc gccaagtttc agggagaaga cacggtcgtg    120

atcgcgtcca agccttatgc atttgatcgg gtgttccagt caagcacatc tcaagagcaa    180

gtgtataatg actgtgcaaa gaagattgtt aaagatgtac ttgaaggata taatggaaca    240

atatttgcat atggacaaac atcctctggg aagacacaca caatggaggg taaacttcat    300

gatccagaag gcatgggaat tattccaaga atagtgcaag atatttttaa ttatatttac    360

tccatggatg aaaatttgga atttcatatt aaggtttcat attttgaaat atatttggat    420

aagataaggg acctgttaga tgtttcaaag accaaccttt cagttcatga agacaaaaac    480

cgagttccct atgtaaaggg gtgcacagag cgttttgtat gtagtccaga tgaagttatg    540

gataccatag atgaaggaaa atccaacaga catgtagcag ttacaaatat gaatgaacat    600

agctctagga gtcacagtat atttcttatt aatgtcaaac aagagaacac acaaacggaa    660

caaaagctga gtggaaaact ttatctggtt gatttagctg gtagtgaaaa ggttagtaaa    720

actggagctg aaggtgctgt gctggatgaa gctaaaaaca tcaacaagtc actttctgct    780

cttggaaatg ttatttctgc tttggctgag ggtagtacat atgttccata tcgagatagt    840

aaaatgacaa gaatccttca agattcatta ggtggcaact gtagaaccac tattgtaatt    900

tgctgctctc catcatcata caatgagtct gaaacaaaat ctacactctt atttggccaa    960

agggccaaaa caattaagaa cacagtttgt gtcaatgtgg agttaactgc agaacagtgg   1020

aaaaagaagt atgaaaaaga aaaagaaaaa aataagatcc tgcggaacac tattcagtgg   1080

cttgaaaatg agctcaacag atggcgtaat ggggagacgg tgcctattga tgaacagttt   1140

gacaaagaga aagccaactt ggaagctttc acagtggata aagatattac tcttaccaat   1200

gataaaccag caaccgcaat tggagttata ggaaatttta ctgatgctga aagaagaaag   1260

tgtgaagaag aaattgctaa attatacaaa cagcttgatg acaaggatga agaaattaac   1320

cagcaaagtc aactggtaga gaaactgaag acgcaaatgt tggatcagga ggagcttttg   1380

gcatctacca gaagggatca agacaatatg caagctgagc tgaatcgcct tcaagcagaa   1440

aatgatgcct ctaaagaaga agtgaaagaa gttttacagg ccctagaaga acttgctgtc   1500
```

-continued

```
aattatgatc agaagtctca ggaagttgaa gacaaaacta aggaatatga attgcttagt   1560
gatgaattga atcagaaatc ggcaacttta gcgagtatag atgctgagct tcagaaactt   1620
aaggaaatga ccaaccacca gaaaaaacga gcagctgaga tgatggcatc tttactaaaa   1680
gaccttgcag aaataggaat tgctgtggga aataatgatg taaagcagcc tgagggaact   1740
ggcatgatag atgaagagtt cactgttgca agactctaca ttagcaaaat gaagtcagaa   1800
gtaaaaacca tggtgaaacg ttgcaagcag ttagaaagca cacaaactga gagcaacaaa   1860
aaaatggaag aaaatgaaaa ggagttagca gcatgtcagc ttcgtatctc tcaacatgaa   1920
gccaaaatca agtcattgac tgaatacctt caaaatgtgg aacaaaagaa aagacagttg   1980
gaggaatctg tcgatgccct cagtgaagaa ctagtccagc ttcgagcaca agagaaagtc   2040
catgaaatgg aaaaggagca cttaaataag gttcagactg caaatgaagt taagcaagct   2100
gttgaacagc agatccagag ccatagagaa actcatcaaa aacagatcag tagtttgaga   2160
gatgaagtag aagcaaaagc aaaacttatt actgatcttc aagaccaaaa ccagaaaatg   2220
atgttagagc aggaacgtct aagagtagaa catgagaagt tgaaagccac agatcaggaa   2280
aagagcagaa aactacatga acttacggtt atgcaagata gacgagaaca agcaagacaa   2340
gacttgaagg gtttggaaga gacagtggca aaagaacttc agactttaca caacctgcgc   2400
aaactctttg ttcaggacct ggctacaaga gttaaaaagg aggatccaaa gtgggaattc   2460
cctcggaaga acttggttct tggaaaaact ctaggagaag gcgaatttgg aaaagtggtc   2520
aaggcaacgg ccttccatct gaaaggcaga gcagggtaca ccacggtggc cgtgaagatg   2580
ctgaaagaga acgcctcccc gagtgagctg cgagacctgc tgtcagagtt caacgtcctg   2640
aagcaggtca accacccaca tgtcatcaaa ttgtatgggg cctgcagcca ggatggcccg   2700
ctcctcctca tcgtggagta cgccaaatac ggctccctgc ggggcttcct ccgcgagagc   2760
cgcaaagtgg ggcctggcta cctgggcagt ggaggcagcc gcaactccag ctccctggac   2820
cacccggatg agcgggccct caccatgggc gacctcatct catttgcctg gcagatctca   2880
caggggatgc agtatctggc cgagatgaag ctcgttcatc gggacttggc agccagaaac   2940
atcctggtag ctgaggggcg gaagatgaag atttcggatt tcggcttgtc ccgagatgtt   3000
tatgaagagg attcctacgt gaagaggagc cagggtcgga ttccagttaa atggatggca   3060
attgaatccc tttttgatca tatctacacc acgcaaagtg atgtatggtc ttttggtgtc   3120
ctgctgtggg agatcgtgac cctaggggga aacccctatc ctgggattcc tcctgagcgg   3180
ctcttcaacc ttctgaagac cggccaccgg atggagaggc cagacaactg cagcgaggag   3240
atgtaccgcc tgatgctgca atgctggaag caggagccgg acaaaaggcc ggtgtttgcg   3300
gacatcagca aagacctgga gaagatgatg gttaagagga gagactactt ggaccttgcg   3360
gcgtccactc catctgactc cctgatttat gacgacggcc tctcagagga ggagacaccg   3420
ctggtggact gtaataatgc ccccctccct cgagccctcc cttccacatg gattgaaaac   3480
aaactctatg gtagaatttc ccatgcattt actagattct ag                      3522
```

<210> SEQ ID NO 8
<211> LENGTH: 3627
<212> TYPE: DNA
<213> ORGANISM: Homo sapiens
<220> FEATURE:
<221> NAME/KEY: misc_feature
<223> OTHER INFORMATION: KIF5B-RET (K23;R12 variant4)

<400> SEQUENCE: 8

-continued atggcggacc tggccgagtg caacatcaaa gtgatgtgtc gcttcagacc tctcaacgag 60
tctgaagtga accgcggcga caagtacatc gccaagtttc agggagaaga cacggtcgtg 120
atcgcgtcca agccttatgc atttgatcgg gtgttccagt caagcacatc tcaagagcaa 180
gtgtataatg actgtgcaaa gaagattgtt aaagatgtac ttgaaggata taatggaaca 240
atatttgcat atggacaaac atcctctggg aagacacaca caatggaggg taaacttcat 300
gatccagaag gcatgggaat tattccaaga atagtgcaag atatttttaa ttatatttac 360
tccatggatg aaaatttgga atttcatatt aaggtttcat attttgaaat atatttggat 420
aagataaggg acctgttaga tgtttcaaag accaaccttt cagttcatga agacaaaaac 480
cgagttccct atgtaaaggg gtgcacagag cgttttgtat gtagtccaga tgaagttatg 540
gataccatag atgaaggaaa atccaacaga catgtagcag ttacaaatat gaatgaacat 600
agctctagga gtcacagtat atttcttatt aatgtcaaac aagagaacac acaaacggaa 660
caaaagctga gtggaaaact ttatctggtt gatttagctg gtagtgaaaa ggttagtaaa 720
actggagctg aaggtgctgt gctggatgaa gctaaaaaca tcaacaagtc actttctgct 780
cttggaaatg ttatttctgc tttggctgag ggtagtacat atgttccata tcgagatagt 840
aaaatgacaa gaatccttca agattcatta ggtggcaact gtagaaccac tattgtaatt 900
tgctgctctc catcatcata caatgagtct gaaacaaaat ctacactctt atttggccaa 960
agggccaaaa caattaagaa cacagtttgt gtcaatgtgg agttaactgc agaacagtgg 1020
aaaaagaagt atgaaaaaga aaaagaaaaa aataagatcc tgcggaacac tattcagtgg 1080
cttgaaaatg agctcaacag atggcgtaat ggggagacgg tgcctattga tgaacagttt 1140
gacaaagaga aagccaactt ggaagctttc acagtggata aagatattac tcttaccaat 1200
gataaaccag caaccgcaat tggagttata ggaaatttta ctgatgctga aagaagaaag 1260
tgtgaagaag aaattgctaa attatacaaa cagcttgatg acaaggatga agaaattaac 1320
cagcaaagtc aactggtaga gaaactgaag acgcaaatgt tggatcagga ggagcttttg 1380
gcatctacca gaagggatca agacaatatg caagctgagc tgaatcgcct tcaagcagaa 1440
aatgatgcct ctaaagaaga agtgaaagaa gttttacagg ccctagaaga acttgctgtc 1500
aattatgatc agaagtctca ggaagttgaa gacaaaacta aggaatatga attgcttagt 1560
gatgaattga atcagaaatc ggcaacttta gcgagtatag atgctgagct tcagaaactt 1620
aaggaaatga ccaaccacca gaaaaaacga gcagctgaga tgatggcatc tttactaaaa 1680
gaccttgcag aaataggaat tgctgtggga aataatgatg taaagcagcc tgagggaact 1740
ggcatgatag atgaagagtt cactgttgca agactctaca ttagcaaaat gaagtcagaa 1800
gtaaaaacca tggtgaaacg ttgcaagcag ttagaaagca cacaaactga gagcaacaaa 1860
aaaatggaag aaaatgaaaa ggagttagca gcatgtcagc ttcgtatctc tcaacatgaa 1920
gccaaaatca agtcattgac tgaatacctt caaaatgtgg aacaaaagaa aagacagttg 1980
gaggaatctg tcgatgccct cagtgaagaa ctagtccagc ttcgagcaca agagaaagtc 2040
catgaaatgg aaaaggagca cttaaataag gttcagactg caaatgaagt taagcaagct 2100
gttgaacagc agatccagag ccatagagaa actcatcaaa aacagatcag tagtttgaga 2160
gatgaagtag aagcaaaagc aaaacttatt actgatcttc aagaccaaaa ccagaaaatg 2220
atgttagagc aggaacgtct aagagtagaa catgagaagt tgaaagccac agatcaggaa 2280
aagagcagaa aactacatga acttacggtt atgcaagata gacgagaaca agcaagacaa 2340
gacttgaagg gtttggaaga gacagtggca aaagaacttc agactttaca caacctgcgc 2400

-continued aaactctttg ttcaggacct ggctacaaga gttaaaaaga gtgctgagat tgattctgat 2460
gacaccggag gcagcgctgc tcagaagcaa aaaatctcct ttcttgaaaa taatcttgaa 2520
cagctcacta aagtgcacaa acaggaggat ccaaagtggg aattccctcg gaagaacttg 2580
gttcttggaa aaactctagg agaaggcgaa tttggaaaag tggtcaaggc aacggccttc 2640
catctgaaag gcagagcagg gtacaccacg gtggccgtga agatgctgaa agagaacgcc 2700
tccccgagtg agcttcgaga cctgctgtca gagttcaacg tcctgaagca ggtcaaccac 2760
ccacatgtca tcaaattgta tggggcctgc agccaggatg gcccgctcct cctcatcgtg 2820
gagtacgcca aatacggctc cctgcggggc ttcctccgcg agagccgcaa agtggggcct 2880
ggctacctgg gcagtggagg cagccgcaac tccagctccc tggaccaccc ggatgagcgg 2940
gccctcacca tgggcgacct catctcattt gcctggcaga tctcacaggg gatgcagtat 3000
ctggccgaga tgaagctcgt tcatcgggac ttggcagcca gaaacatcct ggtagctgag 3060
gggcggaaga tgaagatttc ggatttcggc ttgtcccgag atgtttatga agaggattcc 3120
tacgtgaaga ggagccaggg tcggattcca gttaaatgga tggcaattga atcccttttt 3180
gatcatatct acaccacgca aagtgatgta tggtcttttg gtgtcctgct gtgggagatc 3240
gtgaccctag gggaaaccc ctatcctggg attcctcctg agcggctctt caaccttctg 3300
aagaccggcc accggatgga gaggccagac aactgcagcg aggagatgta ccgcctgatg 3360
ctgcaatgct ggaagcagga gccggacaaa aggccggtgt ttgcggacat cagcaaagac 3420
ctggagaaga tgatggttaa gaggagagac tacttggacc ttgcggcgtc cactccatct 3480
gactccctga tttatgacga cggcctctca gaggaggaga caccgctggt ggactgtaat 3540
aatgcccccc tccctcgagc cctcccttcc acatggattg aaaacaaact ctatggtaga 3600
atttcccatg catttactag attctag 3627

<210> SEQ ID NO 9
<211> LENGTH: 4101
<212> TYPE: DNA
<213> ORGANISM: Homo sapiens
<220> FEATURE:
<221> NAME/KEY: misc_feature
<223> OTHER INFORMATION: KIF5B-RET (K24;R11 variant4)

<400> SEQUENCE: 9
atggcggacc tggccgagtg caacatcaaa gtgatgtgtc gcttcagacc tctcaacgag 60
tctgaagtga accgcggcga caagtacatc gccaagtttc agggagaaga cacggtcgtg 120
atcgcgtcca agccttatgc atttgatcgg gtgttccagt caagcacatc tcaagagcaa 180
gtgtataatg actgtgcaaa gaagattgtt aaagatgtac ttgaaggata taatggaaca 240
atatttgcat atggacaaac atcctctggg aagacacaca caatggaggg taaacttcat 300
gatccagaag gcatgggaat tattccaaga atagtgcaag atatttttaa ttatatttac 360
tccatggatg aaaatttgga atttcatatt aaggtttcat attttgaaat atatttggat 420
aagataaggg acctgttaga tgtttcaaag accaaccttt cagttcatga agacaaaaac 480
cgagttccct atgtaaaggg gtgcacagag cgttttgtat gtagtccaga tgaagttatg 540
gataccatag atgaaggaaa atccaacaga catgtagcag ttacaaatat gaatgaacat 600
agctctagga gtcacagtat atttcttatt aatgtcaaac aagagaacac acaaacggaa 660
caaaagctga gtggaaaact ttatctggtt gatttagctg gtagtgaaaa ggttagtaaa 720
actggagctg aaggtgctgt gctggatgaa gctaaaaaca tcaacaagtc actttctgct 780

-continued

```
cttggaaatg ttatttctgc tttggctgag ggtagtacat atgttccata tcgagatagt    840
aaaatgacaa gaatccttca agattcatta ggtggcaact gtagaaccac tattgtaatt    900
tgctgctctc catcatcata caatgagtct gaaacaaaat ctacactctt atttggccaa    960
agggccaaaa caattaagaa cacagtttgt gtcaatgtgg agttaactgc agaacagtgg   1020
aaaaagaagt atgaaaaaga aaaagaaaaa aataagatcc tgcggaacac tattcagtgg   1080
cttgaaaatg agctcaacag atggcgtaat ggggagacgg tgcctattga tgaacagttt   1140
gacaaagaga aagccaactt ggaagctttc acagtggata aagatattac tcttaccaat   1200
gataaaccag caaccgcaat tggagttata ggaaatttta ctgatgctga aagaagaaag   1260
tgtgaagaag aaattgctaa attatacaaa cagcttgatg acaaggatga agaaattaac   1320
cagcaaagtc aactggtaga gaaactgaag acgcaaatgt tggatcagga ggagcttttg   1380
gcatctacca gaagggatca agacaatatg caagctgagc tgaatcgcct tcaagcagaa   1440
aatgatgcct ctaaagaaga agtgaaagaa gttttacagg ccctagaaga acttgctgtc   1500
aattatgatc agaagtctca ggaagttgaa gacaaaacta aggaatatga attgcttagt   1560
gatgaattga atcagaaatc ggcaacttta gcgagtatag atgctgagct tcagaaactt   1620
aaggaaatga ccaaccacca gaaaaaacga gcagctgaga tgatggcatc tttactaaaa   1680
gaccttgcag aaataggaat tgctgtggga aataatgatg taaagcagcc tgagggaact   1740
ggcatgatag atgaagagtt cactgttgca agactctaca ttagcaaaat gaagtcagaa   1800
gtaaaaacca tggtgaaacg ttgcaagcag ttagaaagca cacaaactga gagcaacaaa   1860
aaaatggaag aaaatgaaaa ggagttagca gcatgtcagc ttcgtatctc tcaacatgaa   1920
gccaaaatca agtcattgac tgaatacctt caaaatgtgg aacaaaagaa aagacagttg   1980
gaggaatctg tcgatgccct cagtgaagaa ctagtccagc ttcgagcaca agagaaagtc   2040
catgaaatgg aaaaggagca cttaaataag gttcagactg caaatgaagt taagcaagct   2100
gttgaacagc agatccagag ccatagagaa actcatcaaa aacagatcag tagtttgaga   2160
gatgaagtag aagcaaaagc aaaacttatt actgatcttc aagaccaaaa ccagaaaatg   2220
atgttagagc aggaacgtct aagagtagaa catgagaagt tgaaagccac agatcaggaa   2280
aagagcagaa aactacatga acttacggtt atgcaagata gacgagaaca agcaagacaa   2340
gacttgaagg gtttggaaga gacagtggca aaagaacttc agactttaca caacctgcgc   2400
aaactctttg ttcaggacct ggctacaaga gttaaaaaga gtgctgagat tgattctgat   2460
gacaccggag gcagcgctgc tcagaagcaa aaaatctcct ttcttgaaaa taatcttgaa   2520
cagctcacta aagtgcacaa acagttggta cgtgataatg cagatctccg ctgtgaactt   2580
cctaagttgg aaaagcgact tcgagctaca gctgagagag tgaaagcttt ggaatcagca   2640
ctgaaagaag ctaaagaaaa tgcatctcgt gatcgcaaac gctatcagca agaagtagat   2700
cgcataaagg aagcagtcag gtcaaagaat atggccagaa gagggcattc tgcacagatt   2760
gatccactgt gcgacgagct gtgccgcacg gtgatcgcag ccgctgtcct cttctccttc   2820
atcgtctcgg tgctgctgtc tgccttctgc atccactgct accacaagtt tgcccacaag   2880
ccacccatct cctcagctga gatgaccttc cggaggcccg cccaggcctt cccggtcagc   2940
tactcctctt ccggtgcccg ccggccctcg ctggactcca tggagaacca ggtctccgtg   3000
gatgccttca agatcctgga ggatccaaag tgggaattcc ctcggaagaa cttggttctt   3060
ggaaaaactc taggagaagg cgaatttgga aaagtggtca aggcaacggc cttccatctg   3120
```

-continued

```
aaaggcagag cagggtacac cacggtggcc gtgaagatgc tgaaagagaa cgcctccccg   3180

agtgagcttc gagacctgct gtcagagttc aacgtcctga agcaggtcaa ccacccacat   3240

gtcatcaaat tgtatggggc ctgcagccag gatggcccgc tcctcctcat cgtggagtac   3300

gccaaatacg gctccctgcg gggcttcctc cgcgagagcc gcaaagtggg gcctggctac   3360

ctgggcagtg gaggcagccg caactccagc tccctggacc acccggatga gcgggccctc   3420

accatgggcg acctcatctc atttgcctgg cagatctcac aggggatgca gtatctggcc   3480

gagatgaagc tcgttcatcg ggacttggca gccagaaaca tcctggtagc tgaggggcgg   3540

aagatgaaga tttcggattt cggcttgtcc cgagatgttt atgaagagga ttcctacgtg   3600

aagaggagcc agggtcggat tccagttaaa tggatggcaa ttgaatccct tttgatcat    3660

atctacacca cgcaaagtga tgtatggtct tttggtgtcc tgctgtggga gatcgtgacc   3720

ctagggggaa acccctatcc tgggattcct cctgagcggc tcttcaacct tctgaagacc   3780

ggccaccgga tggagaggcc agacaactgc agcgaggaga tgtaccgcct gatgctgcaa   3840

tgctggaagc aggagccgga caaaaggccg gtgtttgcgg acatcagcaa agacctggag   3900

aagatgatgg ttaagaggag agactacttg gaccttgcgg cgtccactcc atctgactcc   3960

ctgatttatg acgacggcct ctcagaggag gagacaccgc tggtggactg taataatgcc   4020

cccctccctc gagccctccc ttccacatgg attgaaaaca aactctatgg tagaatttcc   4080

catgcattta ctagattcta g                                              4101
```

<210> SEQ ID NO 10
<211> LENGTH: 2934
<212> TYPE: DNA
<213> ORGANISM: Homo sapiens
<220> FEATURE:
<221> NAME/KEY: misc_feature
<223> OTHER INFORMATION: KIF5B-RET (K15;R12 variant2)

<400> SEQUENCE: 10

```
atggcggacc tggccgagtg caacatcaaa gtgatgtgtc gcttcagacc tctcaacgag     60

tctgaagtga accgcggcga caagtacatc gccaagtttc agggagaaga cacggtcgtg    120

atcgcgtcca agccttatgc atttgatcgg gtgttccagt caagcacatc tcaagagcaa    180

gtgtataatg actgtgcaaa gaagattgtt aaagatgtac ttgaaggata taatggaaca    240

atatttgcat atggacaaac atcctctggg aagacacaca caatggaggg taaacttcat    300

gatccagaag gcatgggaat tattccaaga atagtgcaag atatttttaa ttatatttac    360

tccatggatg aaaatttgga atttcatatt aaggtttcat attttgaaat atatttggat    420

aagataaggg acctgttaga tgtttcaaag accaaccttt cagttcatga agacaaaaac    480

cgagttccct atgtaaaggg gtgcacagag cgttttgtat gtagtccaga tgaagttatg    540

gataccatag atgaaggaaa atccaacaga catgtagcag ttacaaatat gaatgaacat    600

agctctagga gtcacagtat atttcttatt aatgtcaaac aagagaacac acaaacggaa    660

caaaagctga gtggaaaact ttatctggtt gatttagctg gtagtgaaaa ggttagtaaa    720

actggagctg aaggtgctgt gctggatgaa gctaaaaaca tcaacaagtc actttctgct    780

cttggaaatg ttatttctgc tttggctgag ggtagtacat atgttccata tcgagatagt    840

aaaatgacaa gaatccttca agattcatta ggtggcaact gtagaaccac tattgtaatt    900

tgctgctctc catcatcata caatgagtct gaaacaaaat ctacactctt atttggccaa    960

agggccaaaa caattaagaa cacagtttgt gtcaatgtgg agttaactgc agaacagtgg   1020
```

-continued

```
aaaaagaagt atgaaaaaga aaaagaaaaa aataagatcc tgcggaacac tattcagtgg   1080
cttgaaaatg agctcaacag atggcgtaat ggggagacgg tgcctattga tgaacagttt   1140
gacaaagaga aagccaactt ggaagctttc acagtggata aagatattac tcttaccaat   1200
gataaaccag caaccgcaat tggagttata ggaaatttta ctgatgctga aagaagaaag   1260
tgtgaagaag aaattgctaa attatacaaa cagcttgatg acaaggatga agaaattaac   1320
cagcaaagtc aactggtaga gaaactgaag acgcaaatgt tggatcagga ggagcttttg   1380
gcatctacca gaagggatca agacaatatg caagctgagc tgaatcgcct tcaagcagaa   1440
aatgatgcct ctaaagaaga agtgaaagaa gttttacagg ccctagaaga acttgctgtc   1500
aattatgatc agaagtctca ggaagttgaa gacaaaacta aggaatatga attgcttagt   1560
gatgaattga atcagaaatc ggcaacttta gcgagtatag atgctgagct tcagaaactt   1620
aaggaaatga ccaaccacca gaaaaaacga gcagctgaga tgatggcatc tttactaaaa   1680
gaccttgcag aaataggaat tgctgtggga aataatgatg taaaggagga tccaaagtgg   1740
gaattccctc ggaagaactt ggttcttgga aaaactctag gagaaggcga atttggaaaa   1800
gtggtcaagg caacggcctt ccatctgaaa ggcagagcag ggtacaccac ggtggccgtg   1860
aagatgctga aagagaacgc ctccccgagt gagctgcgag acctgctgtc agagttcaac   1920
gtcctgaagc aggtcaacca cccacatgtc atcaaattgt atggggcctg cagccaggat   1980
ggcccgctcc tcctcatcgt ggagtacgcc aaatacggct ccctgcgggg cttcctccgc   2040
gagagccgca aagtggggcc tggctacctg ggcagtggag gcagccgcaa ctccagctcc   2100
ctggaccacc cggatgagcg ggccctcacc atgggcgacc tcatctcatt tgcctggcag   2160
atctcacagg ggatgcagta tctggccgag atgaagctcg ttcatcggga cttggcagcc   2220
agaaacatcc tggtagctga ggggcggaag atgaagattt cggatttcgg cttgtcccga   2280
gatgtttatg aagaggattc ctacgtgaag aggagccagg gtcggattcc agttaaatgg   2340
atggcaattg aatccctttt tgatcatatc tacaccacgc aaagtgatgt atggtctttt   2400
ggtgtcctgc tgtgggagat cgtgacccta gggggaaacc cctatcctgg gattcctcct   2460
gagcggctct tcaaccttct gaagaccggc caccggatgg agaggccaga caactgcagc   2520
gaggagatgt accgcctgat gctgcaatgc tggaagcagg agccggacaa aaggccggtg   2580
tttgcggaca tcagcaaaga cctggagaag atgatggtta agaggagaga ctacttggac   2640
cttgcggcgt ccactccatc tgactccctg atttatgacg acggcctctc agaggaggag   2700
acaccgctgg tggactgtaa taatgccccc ctccctcgag ccctcccttc cacatggatt   2760
gaaaacaaac tctatggcat gtcagacccg aactggcctg gagagagtcc tgtaccactc   2820
acgagagctg atggcactaa cactgggttt ccaagatatc caaatgatag tgtatatgct   2880
aactggatgc tttcaccctc agcggcaaaa ttaatggaca cgtttgatag ttaa         2934
```

<210> SEQ ID NO 11
<211> LENGTH: 3123
<212> TYPE: DNA
<213> ORGANISM: Homo sapiens
<220> FEATURE:
<221> NAME/KEY: misc_feature
<223> OTHER INFORMATION: KIF5B-RET (K16;R12 variant2)

<400> SEQUENCE: 11

```
atggcggacc tggccgagtg caacatcaaa gtgatgtgtc gcttcagacc tctcaacgag     60
tctgaagtga accgcggcga caagtacatc gccaagtttc agggagaaga cacggtcgtg    120
```

-continued

```
atcgcgtcca agccttatgc atttgatcgg gtgttccagt caagcacatc tcaagagcaa    180
gtgtataatg actgtgcaaa gaagattgtt aaagatgtac ttgaaggata taatggaaca    240
atatttgcat atggacaaac atcctctggg aagacacaca caatggaggg taaacttcat    300
gatccagaag gcatgggaat tattccaaga atagtgcaag atatttttaa ttatatttac    360
tccatggatg aaaatttgga atttcatatt aaggtttcat attttgaaat atatttggat    420
aagataaggg acctgttaga tgtttcaaag accaaccttt cagttcatga agacaaaaac    480
cgagttccct atgtaaaggg gtgcacagag cgttttgtat gtagtccaga tgaagttatg    540
gataccatag atgaaggaaa atccaacaga catgtagcag ttacaaatat gaatgaacat    600
agctctagga gtcacagtat atttcttatt aatgtcaaac aagagaacac acaaacggaa    660
caaaagctga gtggaaaact ttatctggtt gatttagctg gtagtgaaaa ggttagtaaa    720
actggagctg aaggtgctgt gctggatgaa gctaaaaaca tcaacaagtc actttctgct    780
cttggaaatg ttatttctgc tttggctgag ggtagtacat atgttccata tcgagatagt    840
aaaatgacaa gaatccttca agattcatta ggtggcaact gtagaaccac tattgtaatt    900
tgctgctctc catcatcata caatgagtct gaaacaaaat ctacactctt atttggccaa    960
agggccaaaa caattaagaa cacagtttgt gtcaatgtgg agttaactgc agaacagtgg   1020
aaaaagaagt atgaaaaaga aaaagaaaaa aataagatcc tgcggaacac tattcagtgg   1080
cttgaaaatg agctcaacag atggcgtaat ggggagacgg tgcctattga tgaacagttt   1140
gacaaagaga aagccaactt ggaagctttc acagtggata aagatattac tcttaccaat   1200
gataaaccag caaccgcaat tggagttata ggaaatttta ctgatgctga aagaagaaag   1260
tgtgaagaag aaattgctaa attatacaaa cagcttgatg acaaggatga agaaattaac   1320
cagcaaagtc aactggtaga gaaactgaag acgcaaatgt tggatcagga ggagcttttg   1380
gcatctacca gaagggatca agacaatatg caagctgagc tgaatcgcct tcaagcagaa   1440
aatgatgcct ctaaagaaga agtgaaagaa gttttacagg ccctagaaga acttgctgtc   1500
aattatgatc agaagtctca ggaagttgaa gacaaaacta aggaatatga attgcttagt   1560
gatgaattga atcagaaatc ggcaacttta gcgagtatag atgctgagct tcagaaactt   1620
aaggaaatga ccaaccacca gaaaaaacga gcagctgaga tgatggcatc tttactaaaa   1680
gaccttgcag aaataggaat tgctgtggga aataatgatg taaagcagcc tgagggaact   1740
ggcatgatag atgaagagtt cactgttgca agactctaca ttagcaaaat gaagtcagaa   1800
gtaaaaacca tggtgaaacg ttgcaagcag ttagaaagca cacaaactga gagcaacaaa   1860
aaaatggaag aaaatgaaaa ggagttagca gcatgtcagc ttcgtatctc tcaagaggat   1920
ccaaagtggg aattccctcg gaagaacttg gttcttggaa aaactctagg agaaggcgaa   1980
tttggaaaag tggtcaaggc aacggccttc catctgaaag gcagagcagg gtacaccacg   2040
gtggccgtga agatgctgaa agagaacgcc tccccgagtg agcttcgaga cctgctgtca   2100
gagttcaacg tcctgaagca ggtcaaccac ccacatgtca tcaaattgta tggggcctgc   2160
agccaggatg gcccgctcct cctcatcgtg gagtacgcca aatacggctc cctgcggggc   2220
ttcctccgcg agagccgcaa agtggggcct ggctacctgg gcagtggagg cagccgcaac   2280
tccagctccc tggaccaccc ggatgagcgg gccctcacca tgggcgacct catctcattt   2340
gcctggcaga tctcacaggg gatgcagtat ctggccgaga tgaagctcgt tcatcgggac   2400
ttggcagcca gaaacatcct ggtagctgag gggcggaaga tgaagatttc ggatttcggc   2460
ttgtcccgag atgtttatga agaggattcg tacgtgaaga ggagccaggg tcggattcca   2520
```

```
gttaaatgga tggcaattga atccctttt gatcatatct acaccacgca aagtgatgta   2580

tggtcttttg gtgtcctgct gtgggagatc gtgaccctag gggaaaccc ctatcctggg   2640

attcctcctg agcggctctt caaccttctg aagaccggcc accggatgga gaggccagac   2700

aactgcagcg aggagatgta ccgcctgatg ctgcaatgct ggaagcagga gccggacaaa   2760

aggccggtgt ttgcggacat cagcaaagac ctggagaaga tgatggttaa gaggagagac   2820

tacttggacc ttgcggcgtc cactccatct gactccctga tttatgacga cggcctctca   2880

gaggaggaga caccgctggt ggactgtaat aatgcccccc tccctcgagc cctcccttcc   2940

acatggattg aaaacaaact ctatggcatg tcagacccga actggcctgg agagagtcct   3000

gtaccactca cgagagctga tggcactaac actgggtttc caagatatcc aaatgatagt   3060

gtatatgcta actggatgct ttcaccctca gcggcaaaat taatggacac gtttgatagt   3120

taa                                                                3123
```

<210> SEQ ID NO 12
<211> LENGTH: 3648
<212> TYPE: DNA
<213> ORGANISM: Homo sapiens
<220> FEATURE:
<221> NAME/KEY: misc_feature
<223> OTHER INFORMATION: KIF5B-RET (K22;R12 variant2)

<400> SEQUENCE: 12

```
atggcggacc tggccgagtg caacatcaaa gtgatgtgtc gcttcagacc tctcaacgag     60

tctgaagtga accgcggcga caagtacatc gccaagtttc agggagaaga cacggtcgtg    120

atcgcgtcca agccttatgc atttgatcgg gtgttccagt caagcacatc tcaagagcaa    180

gtgtataatg actgtgcaaa gaagattgtt aaagatgtac ttgaaggata taatggaaca    240

atatttgcat atggacaaac atcctctggg aagacacaca caatggaggg taaacttcat    300

gatccagaag gcatgggaat tattccaaga atagtgcaag atatttttaa ttatatttac    360

tccatggatg aaaatttgga atttcatatt aaggtttcat attttgaaat atatttggat    420

aagataaggg acctgttaga tgtttcaaag accaaccttt cagttcatga agacaaaaac    480

cgagttccct atgtaaaggg gtgcacagag cgttttgtat gtagtccaga tgaagttatg    540

gataccatag atgaaggaaa atccaacaga catgtagcag ttacaaatat gaatgaacat    600

agctctagga gtcacagtat atttcttatt aatgtcaaac aagagaacac acaaacggaa    660

caaaagctga gtggaaaact ttatctggtt gatttagctg gtagtgaaaa ggttagtaaa    720

actggagctg aaggtgctgt gctggatgaa gctaaaaaca tcaacaagtc actttctgct    780

cttggaaatg ttatttctgc tttggctgag ggtagtacat atgttccata tcgagatagt    840

aaaatgacaa gaatccttca agattcatta ggtggcaact gtagaaccac tattgtaatt    900

tgctgctctc catcatcata caatgagtct gaaacaaaat ctacactctt atttggccaa    960

agggccaaaa caattaagaa cacagtttgt gtcaatgtgg agttaactgc agaacagtgg   1020

aaaaagaagt atgaaaaaga aaaagaaaaa aataagatcc tgcggaacac tattcagtgg   1080

cttgaaaatg agctcaacag atggcgtaat ggggagacgg tgcctattga tgaacagttt   1140

gacaaagaga aagccaactt ggaagctttc acagtggata aagatattac tcttaccaat   1200

gataaaccag caaccgcaat tggagttata ggaaatttta ctgatgctga aagaagaaag   1260

tgtgaagaag aaattgctaa attatacaaa cagcttgatg acaaggatga agaaattaac   1320

cagcaaagtc aactggtaga gaaactgaag acgcaaatgt tggatcagga ggagcttttg   1380
```

gcatctacca gaagggatca agacaatatg caagctgagc tgaatcgcct tcaagcagaa 1440
aatgatgcct ctaaagaaga agtgaaagaa gttttacagg ccctagaaga acttgctgtc 1500
aattatgatc agaagtctca ggaagttgaa gacaaaacta aggaatatga attgcttagt 1560
gatgaattga atcagaaatc ggcaacttta gcgagtatag atgctgagct tcagaaactt 1620
aaggaaatga ccaaccacca gaaaaaacga gcagctgaga tgatggcatc tttactaaaa 1680
gaccttgcag aaataggaat tgctgtggga aataatgatg taaagcagcc tgagggaact 1740
ggcatgatag atgaagagtt cactgttgca agactctaca ttagcaaaat gaagtcagaa 1800
gtaaaaacca tggtgaaacg ttgcaagcag ttagaaagca cacaaactga gagcaacaaa 1860
aaaatggaag aaaatgaaaa ggagttagca gcatgtcagc ttcgtatctc tcaacatgaa 1920
gccaaaatca agtcattgac tgaatacctt caaaatgtgg aacaaaagaa aagacagttg 1980
gaggaatctg tcgatgccct cagtgaagaa ctagtccagc ttcgagcaca agagaaagtc 2040
catgaaatgg aaaaggagca cttaaataag gttcagactg caaatgaagt taagcaagct 2100
gttgaacagc agatccagag ccatagagaa actcatcaaa aacagatcag tagtttgaga 2160
gatgaagtag aagcaaaagc aaaacttatt actgatcttc aagaccaaaa ccagaaaatg 2220
atgttagagc aggaacgtct aagagtagaa catgagaagt tgaaagccac agatcaggaa 2280
aagagcagaa aactacatga acttacggtt atgcaagata gacgagaaca agcaagacaa 2340
gacttgaagg gtttggaaga gacagtggca aaagaacttc agactttaca caacctgcgc 2400
aaactctttg ttcaggacct ggctacaaga gttaaaaagg aggatccaaa gtgggaattc 2460
cctcggaaga acttggttct tggaaaaact ctaggagaag gcgaatttgg aaaagtggtc 2520
aaggcaacgg ccttccatct gaaaggcaga gcagggtaca ccacggtggc cgtgaagatg 2580
ctgaaagaga acgcctcccc gagtgagctg cgagacctgc tgtcagagtt caacgtcctg 2640
aagcaggtca accacccaca tgtcatcaaa ttgtatgggg cctgcagcca ggatggcccg 2700
ctcctcctca tcgtggagta cgccaaatac ggctccctgc ggggcttcct ccgcgagagc 2760
cgcaaagtgg ggcctggcta cctgggcagt ggaggcagcc gcaactccag ctccctggac 2820
cacccggatg agcgggccct caccatgggc gacctcatct catttgcctg gcagatctca 2880
caggggatgc agtatctggc cgagatgaag ctcgttcatc gggacttggc agccagaaac 2940
atcctggtag ctgaggggcg gaagatgaag atttcggatt tcggcttgtc ccgagatgtt 3000
tatgaagagg attcctacgt gaagaggagc cagggtcgga ttccagttaa atggatggca 3060
attgaatccc tttttgatca tatctacacc acgcaaagtg atgtatggtc ttttggtgtc 3120
ctgctgtggg agatcgtgac cctaggggga aacccctatc ctgggattcc tcctgagcgg 3180
ctcttcaacc ttctgaagac cggccaccgg atggagaggc cagacaactg cagcgaggag 3240
atgtaccgcc tgatgctgca atgctggaag caggagccgg acaaaaggcc ggtgtttgcg 3300
gacatcagca aagacctgga gaagatgatg gttaagagga gagactactt ggaccttgcg 3360
gcgtccactc catctgactc cctgatttat gacgacggcc tctcagagga ggagacaccg 3420
ctggtggact gtaataatgc ccccctccct cgagccctcc cttccacatg gattgaaaac 3480
aaactctatg gcatgtcaga cccgaactgg cctggagaga gtcctgtacc actcacgaga 3540
gctgatggca ctaacactgg gtttccaaga tatccaaatg atagtgtata tgctaactgg 3600
atgctttcac cctcagcggc aaaattaatg gacacgtttg atagttaa 3648

<210> SEQ ID NO 13

-continued

<211> LENGTH: 3753
<212> TYPE: DNA
<213> ORGANISM: Homo sapiens
<220> FEATURE:
<221> NAME/KEY: misc_feature
<223> OTHER INFORMATION: KIF5B-RET (K23;R12 variant2)

<400> SEQUENCE: 13
atggcggacc tggccgagtg caacatcaaa gtgatgtgtc gcttcagacc tctcaacgag 60
tctgaagtga accgcggcga caagtacatc gccaagtttc agggagaaga cacggtcgtg 120
atcgcgtcca agccttatgc atttgatcgg gtgttccagt caagcacatc tcaagagcaa 180
gtgtataatg actgtgcaaa gaagattgtt aaagatgtac ttgaaggata taatggaaca 240
atatttgcat atggacaaac atcctctggg aagacacaca caatggaggg taaacttcat 300
gatccagaag gcatgggaat tattccaaga atagtgcaag atatttttaa ttatatttac 360
tccatggatg aaaatttgga atttcatatt aaggtttcat attttgaaat atatttggat 420
aagataaggg acctgttaga tgtttcaaag accaaccttt cagttcatga agacaaaaac 480
cgagttccct atgtaaaggg gtgcacagag cgttttgtat gtagtccaga tgaagttatg 540
gataccatag atgaaggaaa atccaacaga catgtagcag ttacaaatat gaatgaacat 600
agctctagga gtcacagtat atttcttatt aatgtcaaac aagagaacac acaaacggaa 660
caaaagctga gtggaaaact ttatctggtt gatttagctg gtagtgaaaa ggttagtaaa 720
actggagctg aaggtgctgt gctggatgaa gctaaaaaca tcaacaagtc actttctgct 780
cttggaaatg ttatttctgc tttggctgag ggtagtacat atgttccata tcgagatagt 840
aaaatgacaa gaatccttca agattcatta ggtggcaact gtagaaccac tattgtaatt 900
tgctgctctc catcatcata caatgagtct gaaacaaaat ctacactctt atttggccaa 960
agggccaaaa caattaagaa cacagtttgt gtcaatgtgg agttaactgc agaacagtgg 1020
aaaaagaagt atgaaaaaga aaaagaaaaa aataagatcc tgcggaacac tattcagtgg 1080
cttgaaaatg agctcaacag atggcgtaat ggggagacgg tgcctattga tgaacagttt 1140
gacaaagaga aagccaactt ggaagctttc acagtggata aagatattac tcttaccaat 1200
gataaaccag caaccgcaat tggagttata ggaaatttta ctgatgctga aagaagaaag 1260
tgtgaagaag aaattgctaa attatacaaa cagcttgatg acaaggatga agaaattaac 1320
cagcaaagtc aactggtaga gaaactgaag acgcaaatgt tggatcagga ggagcttttg 1380
gcatctacca gaagggatca agacaatatg caagctgagc tgaatcgcct tcaagcagaa 1440
aatgatgcct ctaaagaaga agtgaaagaa gttttacagg ccctagaaga acttgctgtc 1500
aattatgatc agaagtctca ggaagttgaa gacaaaacta aggaatatga attgcttagt 1560
gatgaattga atcagaaatc ggcaacttta gcgagtatag atgctgagct tcagaaactt 1620
aaggaaatga ccaaccacca gaaaaaacga gcagctgaga tgatggcatc tttactaaaa 1680
gaccttgcag aaataggaat tgctgtggga aataatgatg taaagcagcc tgagggaact 1740
ggcatgatag atgaagagtt cactgttgca agactctaca ttagcaaaat gaagtcagaa 1800
gtaaaaacca tggtgaaacg ttgcaagcag ttagaaagca cacaaactga gagcaacaaa 1860
aaaatggaag aaaatgaaaa ggagttagca gcatgtcagc ttcgtatctc tcaacatgaa 1920
gccaaaatca agtcattgac tgaatacctt caaaatgtgg aacaaaagaa aagacagttg 1980
gaggaatctg tcgatgccct cagtgaagaa ctagtccagc ttcgagcaca agagaaagtc 2040
catgaaatgg aaaaggagca cttaaataag gttcagactg caaatgaagt taagcaagct 2100

-continued

```
gttgaacagc agatccagag ccatagagaa actcatcaaa aacagatcag tagtttgaga   2160

gatgaagtag aagcaaaagc aaaacttatt actgatcttc aagaccaaaa ccagaaaatg   2220

atgttagagc aggaacgtct aagagtagaa catgagaagt tgaaagccac agatcaggaa   2280

aagagcagaa aactacatga acttacggtt atgcaagata gacgagaaca agcaagacaa   2340

gacttgaagg gtttggaaga gacagtggca aaagaacttc agactttaca caacctgcgc   2400

aaactctttg ttcaggacct ggctacaaga gttaaaaaga gtgctgagat tgattctgat   2460

gacaccggag gcagcgctgc tcagaagcaa aaaatctcct ttcttgaaaa taatcttgaa   2520

cagctcacta aagtgcacaa acaggaggat ccaaagtggg aattccctcg gaagaacttg   2580

gttcttggaa aaactctagg agaaggcgaa tttggaaaag tggtcaaggc aacggccttc   2640

catctgaaag gcagagcagg gtacaccacg gtggccgtga agatgctgaa agagaacgcc   2700

tccccgagtg agcttcgaga cctgctgtca gagttcaacg tcctgaagca ggtcaaccac   2760

ccacatgtca tcaaattgta tggggcctgc agccaggatg gcccgctcct cctcatcgtg   2820

gagtacgcca aatacggctc cctgcggggc ttcctccgcg agagccgcaa agtggggcct   2880

ggctacctgg gcagtggagg cagccgcaac tccagctccc tggaccaccc ggatgagcgg   2940

gccctcacca tgggcgacct catctcattt gcctggcaga tctcacaggg gatgcagtat   3000

ctggccgaga tgaagctcgt tcatcgggac ttggcagcca gaaacatcct ggtagctgag   3060

gggcggaaga tgaagatttc ggatttcggc ttgtcccgag atgtttatga agaggattcc   3120

tacgtgaaga ggagccaggg tcggattcca gttaaatgga tggcaattga atcccttttt   3180

gatcatatct acaccacgca aagtgatgta tggtcttttg gtgtcctgct gtgggagatc   3240

gtgaccctag gggaaaccc ctatcctggg attcctcctg agcggctctt caaccttctg   3300

aagaccggcc accggatgga gaggccagac aactgcagcg aggagatgta ccgcctgatg   3360

ctgcaatgct ggaagcagga gccggacaaa aggccggtgt ttgcggacat cagcaaagac   3420

ctggagaaga tgatggttaa gaggagagac tacttggacc ttgcggcgtc cactccatct   3480

gactccctga tttatgacga cggcctctca gaggaggaga caccgctggt ggactgtaat   3540

aatgcccccc tccctcgagc cctcccttcc acatggattg aaaacaaact ctatggcatg   3600

tcagacccga actggcctgg agagagtcct gtaccactca cgagagctga tggcactaac   3660

actgggtttc caagatatcc aaatgatagt gtatatgcta actggatgct ttcaccctca   3720

gcggcaaaat taatggacac gtttgatagt taa                                3753
```

```
<210> SEQ ID NO 14
<211> LENGTH: 2958
<212> TYPE: DNA
<213> ORGANISM: Homo sapiens
<220> FEATURE:
<221> NAME/KEY: misc_feature
<223> OTHER INFORMATION: KIF5B-RET (K15;R11 variant4)

<400> SEQUENCE: 14

atggcggacc tggccgagtg caacatcaaa gtgatgtgtc gcttcagacc tctcaacgag     60

tctgaagtga accgcggcga caagtacatc gccaagtttc agggagaaga cacggtcgtg    120

atcgcgtcca agccttatgc atttgatcgg gtgttccagt caagcacatc tcaagagcaa    180

gtgtataatg actgtgcaaa gaagattgtt aaagatgtac ttgaaggata taatggaaca    240

atatttgcat atggacaaac atcctctggg aagacacaca caatggaggg taaacttcat    300

gatccagaag gcatgggaat tattccaaga atagtgcaag atatttttaa ttatatttac    360
```

-continued

```
tccatggatg aaaatttgga atttcatatt aaggtttcat attttgaaat atatttggat    420
aagataaggg acctgttaga tgtttcaaag accaaccttt cagttcatga agacaaaaac    480
cgagttccct atgtaaaggg gtgcacagag cgttttgtat gtagtccaga tgaagttatg    540
gataccatag atgaaggaaa atccaacaga catgtagcag ttacaaatat gaatgaacat    600
agctctagga gtcacagtat atttcttatt aatgtcaaac aagagaacac acaaacggaa    660
caaaagctga gtggaaaact ttatctggtt gatttagctg gtagtgaaaa ggttagtaaa    720
actggagctg aaggtgctgt gctggatgaa gctaaaaaca tcaacaagtc actttctgct    780
cttggaaatg ttatttctgc tttggctgag ggtagtacat atgttccata tcgagatagt    840
aaaatgacaa gaatccttca agattcatta ggtggcaact gtagaaccac tattgtaatt    900
tgctgctctc catcatcata caatgagtct gaaacaaaat ctacactctt atttggccaa    960
agggccaaaa caattaagaa cacagtttgt gtcaatgtgg agttaactgc agaacagtgg   1020
aaaaagaagt atgaaaaaga aaaagaaaaa aataagatcc tgcggaacac tattcagtgg   1080
cttgaaaatg agctcaacag atggcgtaat ggggagacgg tgcctattga tgaacagttt   1140
gacaaagaga aagccaactt ggaagctttc acagtggata aagatattac tcttaccaat   1200
gataaaccag caaccgcaat tggagttata ggaaatttta ctgatgctga aagaagaaag   1260
tgtgaagaag aaattgctaa attatacaaa cagcttgatg acaaggatga agaaattaac   1320
cagcaaagtc aactggtaga gaaactgaag acgcaaatgt tggatcagga ggagcttttg   1380
gcatctacca gaagggatca agacaatatg caagctgagc tgaatcgcct tcaagcagaa   1440
aatgatgcct ctaaagaaga agtgaaagaa gttttacagg ccctagaaga acttgctgtc   1500
aattatgatc agaagtctca ggaagttgaa gacaaaacta aggaatatga attgcttagt   1560
gatgaattga atcagaaatc ggcaacttta gcgagtatag atgctgagct tcagaaactt   1620
aaggaaatga ccaaccacca gaaaaaacga gcagctgaga tgatggcatc tttactaaaa   1680
gaccttgcag aaataggaat tgctgtggga aataatgatg taaagtttgc ccacaagcca   1740
cccatctcct cagctgagat gaccttccgg aggcccgccc aggccttccc ggtcagctac   1800
tcctcttccg gtgcccgccg gccctcgctg gactccatgg agaaccaggt ctccgtggat   1860
gccttcaaga tcctggagga tccaaagtgg gaattccctc ggaagaactt ggttcttgga   1920
aaaactctag gagaaggcga atttggaaaa gtggtcaagg caacggcctt ccatctgaaa   1980
ggcagagcag ggtacaccac ggtggccgtg aagatgctga aagagaacgc ctccccgagt   2040
gagctgcgag acctgctgtc agagttcaac gtcctgaagc aggtcaacca cccacatgtc   2100
atcaaattgt atggggcctg cagccaggat ggcccgctcc tcctcatcgt ggagtacgcc   2160
aaatacggct ccctgcgggg cttcctccgc gagagccgca aagtggggcc tggctacctg   2220
ggcagtggag gcagccgcaa ctccagctcc ctggaccacc cggatgagcg ggccctcacc   2280
atgggcgacc tcatctcatt tgcctggcag atctcacagg ggatgcagta tctggccgag   2340
atgaagctcg ttcatcggga cttggcagcc agaaacatcc tggtagctga ggggcggaag   2400
atgaagattt cggatttcgg cttgtcccga gatgtttatg aagaggattc ctacgtgaag   2460
aggagccagg gtcggattcc agttaaatgg atggcaattg aatccctttt tgatcatatc   2520
tacaccacgc aaagtgatgt atggtctttt ggtgtcctgc tgtgggagat cgtgacccta   2580
gggggaaacc cctatcctgg gattcctcct gagcggctct tcaaccttct gaagaccggc   2640
caccggatgg agaggccaga caactgcagc gaggagatgt accgcctgat gctgcaatgc   2700
tggaagcagg agccggacaa aaggccggtg tttgcggaca tcagcaaaga cctggagaag   2760
```

atgatggtta agaggagaga ctacttggac cttgcggcgt ccactccatc tgactccctg 2820
atttatgacg acggcctctc agaggaggag acaccgctgg tggactgtaa taatgccccc 2880
ctccctcgag ccctcccttc cacatggatt gaaaacaaac tctatggtag aatttcccat 2940
gcatttacta gattctag 2958

<210> SEQ ID NO 15
<211> LENGTH: 935
<212> TYPE: PRT
<213> ORGANISM: Homo sapiens
<220> FEATURE:
<221> NAME/KEY: misc_feature
<223> OTHER INFORMATION: KIF5B-RET (K15;R12 variant 4)

<400> SEQUENCE: 15

Met Ala Asp Leu Ala Glu Cys Asn Ile Lys Val Met Cys Arg Phe Arg
1 5 10 15

Pro Leu Asn Glu Ser Glu Val Asn Arg Gly Asp Lys Tyr Ile Ala Lys
20 25 30

Phe Gln Gly Glu Asp Thr Val Val Ile Ala Ser Lys Pro Tyr Ala Phe
35 40 45

Asp Arg Val Phe Gln Ser Ser Thr Ser Gln Glu Gln Val Tyr Asn Asp
50 55 60

Cys Ala Lys Lys Ile Val Lys Asp Val Leu Glu Gly Tyr Asn Gly Thr
65 70 75 80

Ile Phe Ala Tyr Gly Gln Thr Ser Ser Gly Lys Thr His Thr Met Glu
85 90 95

Gly Lys Leu His Asp Pro Glu Gly Met Gly Ile Ile Pro Arg Ile Val
100 105 110

Gln Asp Ile Phe Asn Tyr Ile Tyr Ser Met Asp Glu Asn Leu Glu Phe
115 120 125

His Ile Lys Val Ser Tyr Phe Glu Ile Tyr Leu Asp Lys Ile Arg Asp
130 135 140

Leu Leu Asp Val Ser Lys Thr Asn Leu Ser Val His Glu Asp Lys Asn
145 150 155 160

Arg Val Pro Tyr Val Lys Gly Cys Thr Glu Arg Phe Val Cys Ser Pro
165 170 175

Asp Glu Val Met Asp Thr Ile Asp Glu Gly Lys Ser Asn Arg His Val
180 185 190

Ala Val Thr Asn Met Asn Glu His Ser Ser Arg Ser His Ser Ile Phe
195 200 205

Leu Ile Asn Val Lys Gln Glu Asn Thr Gln Thr Glu Gln Lys Leu Ser
210 215 220

Gly Lys Leu Tyr Leu Val Asp Leu Ala Gly Ser Glu Lys Val Ser Lys
225 230 235 240

Thr Gly Ala Glu Gly Ala Val Leu Asp Glu Ala Lys Asn Ile Asn Lys
245 250 255

Ser Leu Ser Ala Leu Gly Asn Val Ile Ser Ala Leu Ala Glu Gly Ser
260 265 270

Thr Tyr Val Pro Tyr Arg Asp Ser Lys Met Thr Arg Ile Leu Gln Asp
275 280 285

Ser Leu Gly Gly Asn Cys Arg Thr Thr Ile Val Ile Cys Cys Ser Pro
290 295 300

Ser Ser Tyr Asn Glu Ser Glu Thr Lys Ser Thr Leu Leu Phe Gly Gln
305 310 315 320

-continued

```
Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Glu
                565                 570                 575

Asp Pro Lys Trp Glu Phe Pro Arg Lys Asn Leu Val Leu Gly Lys Thr
            580                 585                 590

Leu Gly Glu Gly Glu Phe Gly Lys Val Val Lys Ala Thr Ala Phe His
        595                 600                 605

Leu Lys Gly Arg Ala Gly Tyr Thr Thr Val Ala Val Lys Met Leu Lys
    610                 615                 620

Glu Asn Ala Ser Pro Ser Glu Leu Arg Asp Leu Leu Ser Glu Phe Asn
625                 630                 635                 640

Val Leu Lys Gln Val Asn His Pro His Val Ile Lys Leu Tyr Gly Ala
                645                 650                 655

Cys Ser Gln Asp Gly Pro Leu Leu Leu Ile Val Glu Tyr Ala Lys Tyr
            660                 665                 670

Gly Ser Leu Arg Gly Phe Leu Arg Glu Ser Arg Lys Val Gly Pro Gly
        675                 680                 685

Tyr Leu Gly Ser Gly Gly Ser Arg Asn Ser Ser Ser Leu Asp His Pro
    690                 695                 700

Asp Glu Arg Ala Leu Thr Met Gly Asp Leu Ile Ser Phe Ala Trp Gln
705                 710                 715                 720

Ile Ser Gln Gly Met Gln Tyr Leu Ala Glu Met Lys Leu Val His Arg
                725                 730                 735
```

```
Asp Leu Ala Ala Arg Asn Ile Leu Val Ala Glu Gly Arg Lys Met Lys
            740                 745                 750

Ile Ser Asp Phe Gly Leu Ser Arg Asp Val Tyr Glu Glu Asp Ser Tyr
        755                 760                 765

Val Lys Arg Ser Gln Gly Arg Ile Pro Val Lys Trp Met Ala Ile Glu
    770                 775                 780

Ser Leu Phe Asp His Ile Tyr Thr Thr Gln Ser Asp Val Trp Ser Phe
785                 790                 795                 800

Gly Val Leu Leu Trp Glu Ile Val Thr Leu Gly Gly Asn Pro Tyr Pro
                805                 810                 815

Gly Ile Pro Pro Glu Arg Leu Phe Asn Leu Leu Lys Thr Gly His Arg
            820                 825                 830

Met Glu Arg Pro Asp Asn Cys Ser Glu Glu Met Tyr Arg Leu Met Leu
        835                 840                 845

Gln Cys Trp Lys Gln Glu Pro Asp Lys Arg Pro Val Phe Ala Asp Ile
    850                 855                 860

Ser Lys Asp Leu Glu Lys Met Met Val Lys Arg Arg Asp Tyr Leu Asp
865                 870                 875                 880

Leu Ala Ala Ser Thr Pro Ser Asp Ser Leu Ile Tyr Asp Asp Gly Leu
                885                 890                 895

Ser Glu Glu Glu Thr Pro Leu Val Asp Cys Asn Asn Ala Pro Leu Pro
            900                 905                 910

Arg Ala Leu Pro Ser Thr Trp Ile Glu Asn Lys Leu Tyr Gly Arg Ile
        915                 920                 925

Ser His Ala Phe Thr Arg Phe
    930                 935


<210> SEQ ID NO 16
<211> LENGTH: 998
<212> TYPE: PRT
<213> ORGANISM: Homo sapiens
<220> FEATURE:
<221> NAME/KEY: misc_feature
<223> OTHER INFORMATION: KIF5B-RET (K16;R12 variant4)

<400> SEQUENCE: 16

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160
```

-continued

```
Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575
```

```
Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
    610                 615                 620

Asn Glu Lys Glu Leu Ala Ala Cys Gln Leu Arg Ile Ser Gln Glu Asp
625                 630                 635                 640

Pro Lys Trp Glu Phe Pro Arg Lys Asn Leu Val Leu Gly Lys Thr Leu
                645                 650                 655

Gly Glu Gly Glu Phe Gly Lys Val Val Lys Ala Thr Ala Phe His Leu
            660                 665                 670

Lys Gly Arg Ala Gly Tyr Thr Thr Val Ala Val Lys Met Leu Lys Glu
        675                 680                 685

Asn Ala Ser Pro Ser Glu Leu Arg Asp Leu Leu Ser Glu Phe Asn Val
    690                 695                 700

Leu Lys Gln Val Asn His Pro His Val Ile Lys Leu Tyr Gly Ala Cys
705                 710                 715                 720

Ser Gln Asp Gly Pro Leu Leu Leu Ile Val Glu Tyr Ala Lys Tyr Gly
                725                 730                 735

Ser Leu Arg Gly Phe Leu Arg Glu Ser Arg Lys Val Gly Pro Gly Tyr
            740                 745                 750

Leu Gly Ser Gly Gly Ser Arg Asn Ser Ser Ser Leu Asp His Pro Asp
        755                 760                 765

Glu Arg Ala Leu Thr Met Gly Asp Leu Ile Ser Phe Ala Trp Gln Ile
    770                 775                 780

Ser Gln Gly Met Gln Tyr Leu Ala Glu Met Lys Leu Val His Arg Asp
785                 790                 795                 800

Leu Ala Ala Arg Asn Ile Leu Val Ala Glu Gly Arg Lys Met Lys Ile
                805                 810                 815

Ser Asp Phe Gly Leu Ser Arg Asp Val Tyr Glu Glu Asp Ser Tyr Val
            820                 825                 830

Lys Arg Ser Gln Gly Arg Ile Pro Val Lys Trp Met Ala Ile Glu Ser
        835                 840                 845

Leu Phe Asp His Ile Tyr Thr Thr Gln Ser Asp Val Trp Ser Phe Gly
    850                 855                 860

Val Leu Leu Trp Glu Ile Val Thr Leu Gly Gly Asn Pro Tyr Pro Gly
865                 870                 875                 880

Ile Pro Pro Glu Arg Leu Phe Asn Leu Leu Lys Thr Gly His Arg Met
                885                 890                 895

Glu Arg Pro Asp Asn Cys Ser Glu Glu Met Tyr Arg Leu Met Leu Gln
            900                 905                 910

Cys Trp Lys Gln Glu Pro Asp Lys Arg Pro Val Phe Ala Asp Ile Ser
        915                 920                 925

Lys Asp Leu Glu Lys Met Met Val Lys Arg Arg Asp Tyr Leu Asp Leu
    930                 935                 940

Ala Ala Ser Thr Pro Ser Asp Ser Leu Ile Tyr Asp Asp Gly Leu Ser
945                 950                 955                 960

Glu Glu Glu Thr Pro Leu Val Asp Cys Asn Asn Ala Pro Leu Pro Arg
                965                 970                 975

Ala Leu Pro Ser Thr Trp Ile Glu Asn Lys Leu Tyr Gly Arg Ile Ser
            980                 985                 990

His Ala Phe Thr Arg Phe
```

995

<210> SEQ ID NO 17
<211> LENGTH: 1173
<212> TYPE: PRT
<213> ORGANISM: Homo sapiens
<220> FEATURE:
<221> NAME/KEY: misc_feature
<223> OTHER INFORMATION: KIF5B-RET (K22;R12 variant4)

<400> SEQUENCE: 17

Met Ala Asp Leu Ala Glu Cys Asn Ile Lys Val Met Cys Arg Phe Arg
1 5 10 15

Pro Leu Asn Glu Ser Glu Val Asn Arg Gly Asp Lys Tyr Ile Ala Lys
20 25 30

Phe Gln Gly Glu Asp Thr Val Val Ile Ala Ser Lys Pro Tyr Ala Phe
35 40 45

Asp Arg Val Phe Gln Ser Ser Thr Ser Gln Glu Gln Val Tyr Asn Asp
50 55 60

Cys Ala Lys Lys Ile Val Lys Asp Val Leu Glu Gly Tyr Asn Gly Thr
65 70 75 80

Ile Phe Ala Tyr Gly Gln Thr Ser Ser Gly Lys Thr His Thr Met Glu
85 90 95

Gly Lys Leu His Asp Pro Glu Gly Met Gly Ile Ile Pro Arg Ile Val
100 105 110

Gln Asp Ile Phe Asn Tyr Ile Tyr Ser Met Asp Glu Asn Leu Glu Phe
115 120 125

His Ile Lys Val Ser Tyr Phe Glu Ile Tyr Leu Asp Lys Ile Arg Asp
130 135 140

Leu Leu Asp Val Ser Lys Thr Asn Leu Ser Val His Glu Asp Lys Asn
145 150 155 160

Arg Val Pro Tyr Val Lys Gly Cys Thr Glu Arg Phe Val Cys Ser Pro
165 170 175

Asp Glu Val Met Asp Thr Ile Asp Glu Gly Lys Ser Asn Arg His Val
180 185 190

Ala Val Thr Asn Met Asn Glu His Ser Ser Arg Ser His Ser Ile Phe
195 200 205

Leu Ile Asn Val Lys Gln Glu Asn Thr Gln Thr Glu Gln Lys Leu Ser
210 215 220

Gly Lys Leu Tyr Leu Val Asp Leu Ala Gly Ser Glu Lys Val Ser Lys
225 230 235 240

Thr Gly Ala Glu Gly Ala Val Leu Asp Glu Ala Lys Asn Ile Asn Lys
245 250 255

Ser Leu Ser Ala Leu Gly Asn Val Ile Ser Ala Leu Ala Glu Gly Ser
260 265 270

Thr Tyr Val Pro Tyr Arg Asp Ser Lys Met Thr Arg Ile Leu Gln Asp
275 280 285

Ser Leu Gly Gly Asn Cys Arg Thr Thr Ile Val Ile Cys Cys Ser Pro
290 295 300

Ser Ser Tyr Asn Glu Ser Glu Thr Lys Ser Thr Leu Leu Phe Gly Gln
305 310 315 320

Arg Ala Lys Thr Ile Lys Asn Thr Val Cys Val Asn Val Glu Leu Thr
325 330 335

Ala Glu Gln Trp Lys Lys Lys Tyr Glu Lys Glu Lys Glu Lys Asn Lys
340 345 350

-continued

```
Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
    610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
                645                 650                 655

Lys Arg Gln Leu Glu Glu Ser Val Asp Ala Leu Ser Glu Glu Leu Val
            660                 665                 670

Gln Leu Arg Ala Gln Glu Lys Val His Glu Met Glu Lys Glu His Leu
        675                 680                 685

Asn Lys Val Gln Thr Ala Asn Glu Val Lys Gln Ala Val Glu Gln Gln
    690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
                725                 730                 735

Asn Gln Lys Met Met Leu Glu Gln Glu Arg Leu Arg Val Glu His Glu
            740                 745                 750

Lys Leu Lys Ala Thr Asp Gln Glu Lys Ser Arg Lys Leu His Glu Leu
        755                 760                 765

Thr Val Met Gln Asp Arg Arg Glu Gln Ala Arg Gln Asp Leu Lys Gly
```

```
    770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Glu Asp Pro
                805                 810                 815

Lys Trp Glu Phe Pro Arg Lys Asn Leu Val Leu Gly Lys Thr Leu Gly
            820                 825                 830

Glu Gly Glu Phe Gly Lys Val Val Lys Ala Thr Ala Phe His Leu Lys
        835                 840                 845

Gly Arg Ala Gly Tyr Thr Thr Val Ala Val Lys Met Leu Lys Glu Asn
    850                 855                 860

Ala Ser Pro Ser Glu Leu Arg Asp Leu Leu Ser Glu Phe Asn Val Leu
865                 870                 875                 880

Lys Gln Val Asn His Pro His Val Ile Lys Leu Tyr Gly Ala Cys Ser
                885                 890                 895

Gln Asp Gly Pro Leu Leu Leu Ile Val Glu Tyr Ala Lys Tyr Gly Ser
            900                 905                 910

Leu Arg Gly Phe Leu Arg Glu Ser Arg Lys Val Gly Pro Gly Tyr Leu
        915                 920                 925

Gly Ser Gly Gly Ser Arg Asn Ser Ser Ser Leu Asp His Pro Asp Glu
    930                 935                 940

Arg Ala Leu Thr Met Gly Asp Leu Ile Ser Phe Ala Trp Gln Ile Ser
945                 950                 955                 960

Gln Gly Met Gln Tyr Leu Ala Glu Met Lys Leu Val His Arg Asp Leu
                965                 970                 975

Ala Ala Arg Asn Ile Leu Val Ala Glu Gly Arg Lys Met Lys Ile Ser
            980                 985                 990

Asp Phe Gly Leu Ser Arg Asp Val  Tyr Glu Glu Asp Ser  Tyr Val Lys
        995                 1000                1005

Arg Ser  Gln Gly Arg Ile Pro  Val Lys Trp Met Ala  Ile Glu Ser
    1010                1015                1020

Leu Phe  Asp His Ile Tyr Thr  Thr Gln Ser Asp Val  Trp Ser Phe
    1025                1030                1035

Gly Val  Leu Leu Trp Glu Ile  Val Thr Leu Gly Gly  Asn Pro Tyr
    1040                1045                1050

Pro Gly  Ile Pro Pro Glu Arg  Leu Phe Asn Leu Leu  Lys Thr Gly
    1055                1060                1065

His Arg  Met Glu Arg Pro Asp  Asn Cys Ser Glu Glu  Met Tyr Arg
    1070                1075                1080

Leu Met  Leu Gln Cys Trp Lys  Gln Glu Pro Asp Lys  Arg Pro Val
    1085                1090                1095

Phe Ala  Asp Ile Ser Lys Asp  Leu Glu Lys Met Met  Val Lys Arg
    1100                1105                1110

Arg Asp  Tyr Leu Asp Leu Ala  Ala Ser Thr Pro Ser  Asp Ser Leu
    1115                1120                1125

Ile Tyr  Asp Asp Gly Leu Ser  Glu Glu Glu Thr Pro  Leu Val Asp
    1130                1135                1140

Cys Asn  Asn Ala Pro Leu Pro  Arg Ala Leu Pro Ser  Thr Trp Ile
    1145                1150                1155

Glu Asn  Lys Leu Tyr Gly Arg  Ile Ser His Ala Phe  Thr Arg Phe
    1160                1165                1170

<210> SEQ ID NO 18
```

-continued

<211> LENGTH: 1208
<212> TYPE: PRT
<213> ORGANISM: Homo sapiens
<220> FEATURE:
<221> NAME/KEY: misc_feature
<223> OTHER INFORMATION: KIF5B-RET (K23;R12 variant4)

<400> SEQUENCE: 18

```
Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
```

```
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
    610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
                645                 650                 655

Lys Arg Gln Leu Glu Glu Ser Val Asp Ala Leu Ser Glu Glu Leu Val
            660                 665                 670

Gln Leu Arg Ala Gln Glu Lys Val His Glu Met Glu Lys Glu His Leu
        675                 680                 685

Asn Lys Val Gln Thr Ala Asn Glu Val Lys Gln Ala Val Glu Gln Gln
    690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
                725                 730                 735

Asn Gln Lys Met Met Leu Glu Gln Glu Arg Leu Arg Val Glu His Glu
            740                 745                 750

Lys Leu Lys Ala Thr Asp Gln Glu Lys Ser Arg Lys Leu His Glu Leu
        755                 760                 765

Thr Val Met Gln Asp Arg Arg Glu Gln Ala Arg Gln Asp Leu Lys Gly
    770                 775                 780

Leu Glu Glu Thr Val Ala Lys Glu Leu Gln Thr Leu His Asn Leu Arg
785                 790                 795                 800
```

-continued

```
Lys Leu Phe Val Gln Asp Leu Ala Thr Arg Val Lys Lys Ser Ala Glu
                805                 810                 815

Ile Asp Ser Asp Asp Thr Gly Gly Ser Ala Ala Gln Lys Gln Lys Ile
            820                 825                 830

Ser Phe Leu Glu Asn Asn Leu Glu Gln Leu Thr Lys Val His Lys Gln
        835                 840                 845

Glu Asp Pro Lys Trp Glu Phe Pro Arg Lys Asn Leu Val Leu Gly Lys
    850                 855                 860

Thr Leu Gly Glu Gly Glu Phe Gly Lys Val Val Lys Ala Thr Ala Phe
865                 870                 875                 880

His Leu Lys Gly Arg Ala Gly Tyr Thr Thr Val Ala Val Lys Met Leu
                885                 890                 895

Lys Glu Asn Ala Ser Pro Ser Glu Leu Arg Asp Leu Leu Ser Glu Phe
            900                 905                 910

Asn Val Leu Lys Gln Val Asn His Pro His Val Ile Lys Leu Tyr Gly
        915                 920                 925

Ala Cys Ser Gln Asp Gly Pro Leu Leu Leu Ile Val Glu Tyr Ala Lys
    930                 935                 940

Tyr Gly Ser Leu Arg Gly Phe Leu Arg Glu Ser Arg Lys Val Gly Pro
945                 950                 955                 960

Gly Tyr Leu Gly Ser Gly Gly Ser Arg Asn Ser Ser Ser Leu Asp His
                965                 970                 975

Pro Asp Glu Arg Ala Leu Thr Met Gly Asp Leu Ile Ser Phe Ala Trp
            980                 985                 990

Gln Ile Ser Gln Gly Met Gln Tyr  Leu Ala Glu Met Lys  Leu Val His
        995                 1000                 1005

Arg Asp  Leu Ala Ala Arg Asn  Ile Leu Val Ala Glu  Gly Arg Lys
    1010                 1015                 1020

Met Lys  Ile Ser Asp Phe Gly  Leu Ser Arg Asp Val  Tyr Glu Glu
    1025                 1030                 1035

Asp Ser  Tyr Val Lys Arg Ser  Gln Gly Arg Ile Pro  Val Lys Trp
    1040                 1045                 1050

Met Ala  Ile Glu Ser Leu Phe  Asp His Ile Tyr Thr  Thr Gln Ser
    1055                 1060                 1065

Asp Val  Trp Ser Phe Gly Val  Leu Leu Trp Glu Ile  Val Thr Leu
    1070                 1075                 1080

Gly Gly  Asn Pro Tyr Pro Gly  Ile Pro Pro Glu Arg  Leu Phe Asn
    1085                 1090                 1095

Leu Leu  Lys Thr Gly His Arg  Met Glu Arg Pro Asp  Asn Cys Ser
    1100                 1105                 1110

Glu Glu  Met Tyr Arg Leu Met  Leu Gln Cys Trp Lys  Gln Glu Pro
    1115                 1120                 1125

Asp Lys  Arg Pro Val Phe Ala  Asp Ile Ser Lys Asp  Leu Glu Lys
    1130                 1135                 1140

Met Met  Val Lys Arg Arg Asp  Tyr Leu Asp Leu Ala  Ala Ser Thr
    1145                 1150                 1155

Pro Ser  Asp Ser Leu Ile Tyr  Asp Asp Gly Leu Ser  Glu Glu Glu
    1160                 1165                 1170

Thr Pro  Leu Val Asp Cys Asn  Asn Ala Pro Leu Pro  Arg Ala Leu
    1175                 1180                 1185

Pro Ser  Thr Trp Ile Glu Asn  Lys Leu Tyr Gly Arg  Ile Ser His
    1190                 1195                 1200
```

```
Ala Phe  Thr Arg Phe
    1205


<210> SEQ ID NO 19
<211> LENGTH: 1366
<212> TYPE: PRT
<213> ORGANISM: Homo sapiens
<220> FEATURE:
<221> NAME/KEY: misc_feature
<223> OTHER INFORMATION: KIF5B-RET (K24;R11 variant4)

<400> SEQUENCE: 19

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350
```

-continued

```
Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
    610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
                645                 650                 655

Lys Arg Gln Leu Glu Glu Ser Val Asp Ala Leu Ser Glu Glu Leu Val
            660                 665                 670

Gln Leu Arg Ala Gln Glu Lys Val His Glu Met Glu Lys Glu His Leu
        675                 680                 685

Asn Lys Val Gln Thr Ala Asn Glu Val Lys Gln Ala Val Glu Gln Gln
    690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
                725                 730                 735

Asn Gln Lys Met Met Leu Glu Gln Glu Arg Leu Arg Val Glu His Glu
            740                 745                 750

Lys Leu Lys Ala Thr Asp Gln Glu Lys Ser Arg Lys Leu His Glu Leu
        755                 760                 765
```

-continued

```
Thr Val Met Gln Asp Arg Arg Glu Gln Ala Arg Gln Asp Leu Lys Gly
    770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Ser Ala Glu
                805                 810                 815

Ile Asp Ser Asp Asp Thr Gly Gly Ser Ala Ala Gln Lys Gln Lys Ile
            820                 825                 830

Ser Phe Leu Glu Asn Asn Leu Glu Gln Leu Thr Lys Val His Lys Gln
        835                 840                 845

Leu Val Arg Asp Asn Ala Asp Leu Arg Cys Glu Leu Pro Lys Leu Glu
    850                 855                 860

Lys Arg Leu Arg Ala Thr Ala Glu Arg Val Lys Ala Leu Glu Ser Ala
865                 870                 875                 880

Leu Lys Glu Ala Lys Glu Asn Ala Ser Arg Asp Arg Lys Arg Tyr Gln
                885                 890                 895

Gln Glu Val Asp Arg Ile Lys Glu Ala Val Arg Ser Lys Asn Met Ala
            900                 905                 910

Arg Arg Gly His Ser Ala Gln Ile Asp Pro Leu Cys Asp Glu Leu Cys
        915                 920                 925

Arg Thr Val Ile Ala Ala Ala Val Leu Phe Ser Phe Ile Val Ser Val
    930                 935                 940

Leu Leu Ser Ala Phe Cys Ile His Cys Tyr His Lys Phe Ala His Lys
945                 950                 955                 960

Pro Pro Ile Ser Ser Ala Glu Met Thr Phe Arg Arg Pro Ala Gln Ala
                965                 970                 975

Phe Pro Val Ser Tyr Ser Ser Ser Gly Ala Arg Arg Pro Ser Leu Asp
            980                 985                 990

Ser Met Glu Asn Gln Val Ser Val  Asp Ala Phe Lys Ile  Leu Glu Asp
        995                 1000                1005

Pro Lys  Trp Glu Phe Pro Arg  Lys Asn Leu Val Leu  Gly Lys Thr
    1010                1015                1020

Leu Gly  Glu Gly Glu Phe Gly  Lys Val Val Lys Ala  Thr Ala Phe
    1025                1030                1035

His Leu  Lys Gly Arg Ala Gly  Tyr Thr Thr Val Ala  Val Lys Met
    1040                1045                1050

Leu Lys  Glu Asn Ala Ser Pro  Ser Glu Leu Arg Asp  Leu Leu Ser
    1055                1060                1065

Glu Phe  Asn Val Leu Lys Gln  Val Asn His Pro His  Val Ile Lys
    1070                1075                1080

Leu Tyr  Gly Ala Cys Ser Gln  Asp Gly Pro Leu Leu  Leu Ile Val
    1085                1090                1095

Glu Tyr  Ala Lys Tyr Gly Ser  Leu Arg Gly Phe Leu  Arg Glu Ser
    1100                1105                1110

Arg Lys  Val Gly Pro Gly Tyr  Leu Gly Ser Gly Gly  Ser Arg Asn
    1115                1120                1125

Ser Ser  Ser Leu Asp His Pro  Asp Glu Arg Ala Leu  Thr Met Gly
    1130                1135                1140

Asp Leu  Ile Ser Phe Ala Trp  Gln Ile Ser Gln Gly  Met Gln Tyr
    1145                1150                1155

Leu Ala  Glu Met Lys Leu Val  His Arg Asp Leu Ala  Ala Arg Asn
    1160                1165                1170

Ile Leu  Val Ala Glu Gly Arg  Lys Met Lys Ile Ser  Asp Phe Gly
```

```
    1175                1180                1185

Leu Ser  Arg Asp Val Tyr Glu  Glu Asp Ser Tyr Val  Lys Arg Ser
    1190                1195                1200

Gln Gly  Arg Ile Pro Val Lys  Trp Met Ala Ile Glu  Ser Leu Phe
    1205                1210                1215

Asp His  Ile Tyr Thr Thr Gln  Ser Asp Val Trp Ser  Phe Gly Val
    1220                1225                1230

Leu Leu  Trp Glu Ile Val Thr  Leu Gly Gly Asn Pro  Tyr Pro Gly
    1235                1240                1245

Ile Pro  Pro Glu Arg Leu Phe  Asn Leu Leu Lys Thr  Gly His Arg
    1250                1255                1260

Met Glu  Arg Pro Asp Asn Cys  Ser Glu Glu Met Tyr  Arg Leu Met
    1265                1270                1275

Leu Gln  Cys Trp Lys Gln Glu  Pro Asp Lys Arg Pro  Val Phe Ala
    1280                1285                1290

Asp Ile  Ser Lys Asp Leu Glu  Lys Met Met Val Lys  Arg Arg Asp
    1295                1300                1305

Tyr Leu  Asp Leu Ala Ala Ser  Thr Pro Ser Asp Ser  Leu Ile Tyr
    1310                1315                1320

Asp Asp  Gly Leu Ser Glu Glu  Glu Thr Pro Leu Val  Asp Cys Asn
    1325                1330                1335

Asn Ala  Pro Leu Pro Arg Ala  Leu Pro Ser Thr Trp  Ile Glu Asn
    1340                1345                1350

Lys Leu  Tyr Gly Arg Ile Ser  His Ala Phe Thr Arg  Phe
    1355                1360                1365


<210> SEQ ID NO 20
<211> LENGTH: 977
<212> TYPE: PRT
<213> ORGANISM: Homo sapiens
<220> FEATURE:
<221> NAME/KEY: misc_feature
<223> OTHER INFORMATION: KIF5B-RET (K15;R12 variant2)

<400> SEQUENCE: 20

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160
```

-continued

```
Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Glu
                565                 570                 575

Asp Pro Lys Trp Glu Phe Pro Arg Lys Asn Leu Val Leu Gly Lys Thr
```

-continued

```
            580                 585                 590

Leu Gly Glu Gly Glu Phe Gly Lys Val Val Lys Ala Thr Ala Phe His
        595                 600                 605

Leu Lys Gly Arg Ala Gly Tyr Thr Thr Val Ala Val Lys Met Leu Lys
    610                 615                 620

Glu Asn Ala Ser Pro Ser Glu Leu Arg Asp Leu Leu Ser Glu Phe Asn
625                 630                 635                 640

Val Leu Lys Gln Val Asn His Pro His Val Ile Lys Leu Tyr Gly Ala
                645                 650                 655

Cys Ser Gln Asp Gly Pro Leu Leu Leu Ile Val Glu Tyr Ala Lys Tyr
            660                 665                 670

Gly Ser Leu Arg Gly Phe Leu Arg Glu Ser Arg Lys Val Gly Pro Gly
        675                 680                 685

Tyr Leu Gly Ser Gly Gly Ser Arg Asn Ser Ser Ser Leu Asp His Pro
    690                 695                 700

Asp Glu Arg Ala Leu Thr Met Gly Asp Leu Ile Ser Phe Ala Trp Gln
705                 710                 715                 720

Ile Ser Gln Gly Met Gln Tyr Leu Ala Glu Met Lys Leu Val His Arg
                725                 730                 735

Asp Leu Ala Ala Arg Asn Ile Leu Val Ala Glu Gly Arg Lys Met Lys
            740                 745                 750

Ile Ser Asp Phe Gly Leu Ser Arg Asp Val Tyr Glu Glu Asp Ser Tyr
        755                 760                 765

Val Lys Arg Ser Gln Gly Arg Ile Pro Val Lys Trp Met Ala Ile Glu
    770                 775                 780

Ser Leu Phe Asp His Ile Tyr Thr Thr Gln Ser Asp Val Trp Ser Phe
785                 790                 795                 800

Gly Val Leu Leu Trp Glu Ile Val Thr Leu Gly Gly Asn Pro Tyr Pro
                805                 810                 815

Gly Ile Pro Pro Glu Arg Leu Phe Asn Leu Leu Lys Thr Gly His Arg
            820                 825                 830

Met Glu Arg Pro Asp Asn Cys Ser Glu Glu Met Tyr Arg Leu Met Leu
        835                 840                 845

Gln Cys Trp Lys Gln Glu Pro Asp Lys Arg Pro Val Phe Ala Asp Ile
    850                 855                 860

Ser Lys Asp Leu Glu Lys Met Met Val Lys Arg Arg Asp Tyr Leu Asp
865                 870                 875                 880

Leu Ala Ala Ser Thr Pro Ser Asp Ser Leu Ile Tyr Asp Asp Gly Leu
                885                 890                 895

Ser Glu Glu Glu Thr Pro Leu Val Asp Cys Asn Asn Ala Pro Leu Pro
            900                 905                 910

Arg Ala Leu Pro Ser Thr Trp Ile Glu Asn Lys Leu Tyr Gly Met Ser
        915                 920                 925

Asp Pro Asn Trp Pro Gly Glu Ser Pro Val Pro Leu Thr Arg Ala Asp
    930                 935                 940

Gly Thr Asn Thr Gly Phe Pro Arg Tyr Pro Asn Asp Ser Val Tyr Ala
945                 950                 955                 960

Asn Trp Met Leu Ser Pro Ser Ala Ala Lys Leu Met Asp Thr Phe Asp
                965                 970                 975

Ser
```

<210> SEQ ID NO 21
<211> LENGTH: 1040

<212> TYPE: PRT
<213> ORGANISM: Homo sapiens
<220> FEATURE:
<221> NAME/KEY: misc_feature
<223> OTHER INFORMATION: KIF5B-RET (K16;R12 variant2)

<400> SEQUENCE: 21

```
Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380
```

-continued

```
Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
    610                 615                 620

Asn Glu Lys Glu Leu Ala Ala Cys Gln Leu Arg Ile Ser Gln Glu Asp
625                 630                 635                 640

Pro Lys Trp Glu Phe Pro Arg Lys Asn Leu Val Leu Gly Lys Thr Leu
                645                 650                 655

Gly Glu Gly Glu Phe Gly Lys Val Val Lys Ala Thr Ala Phe His Leu
            660                 665                 670

Lys Gly Arg Ala Gly Tyr Thr Thr Val Ala Val Lys Met Leu Lys Glu
        675                 680                 685

Asn Ala Ser Pro Ser Glu Leu Arg Asp Leu Leu Ser Glu Phe Asn Val
    690                 695                 700

Leu Lys Gln Val Asn His Pro His Val Ile Lys Leu Tyr Gly Ala Cys
705                 710                 715                 720

Ser Gln Asp Gly Pro Leu Leu Leu Ile Val Glu Tyr Ala Lys Tyr Gly
                725                 730                 735

Ser Leu Arg Gly Phe Leu Arg Glu Ser Arg Lys Val Gly Pro Gly Tyr
            740                 745                 750

Leu Gly Ser Gly Gly Ser Arg Asn Ser Ser Ser Leu Asp His Pro Asp
        755                 760                 765

Glu Arg Ala Leu Thr Met Gly Asp Leu Ile Ser Phe Ala Trp Gln Ile
    770                 775                 780

Ser Gln Gly Met Gln Tyr Leu Ala Glu Met Lys Leu Val His Arg Asp
785                 790                 795                 800
```

-continued

```
Leu Ala Ala Arg Asn Ile Leu Val Ala Glu Gly Arg Lys Met Lys Ile
                805                 810                 815

Ser Asp Phe Gly Leu Ser Arg Asp Val Tyr Glu Glu Asp Ser Tyr Val
            820                 825                 830

Lys Arg Ser Gln Gly Arg Ile Pro Val Lys Trp Met Ala Ile Glu Ser
        835                 840                 845

Leu Phe Asp His Ile Tyr Thr Thr Gln Ser Asp Val Trp Ser Phe Gly
    850                 855                 860

Val Leu Leu Trp Glu Ile Val Thr Leu Gly Gly Asn Pro Tyr Pro Gly
865                 870                 875                 880

Ile Pro Pro Glu Arg Leu Phe Asn Leu Leu Lys Thr Gly His Arg Met
                885                 890                 895

Glu Arg Pro Asp Asn Cys Ser Glu Glu Met Tyr Arg Leu Met Leu Gln
            900                 905                 910

Cys Trp Lys Gln Glu Pro Asp Lys Arg Pro Val Phe Ala Asp Ile Ser
        915                 920                 925

Lys Asp Leu Glu Lys Met Met Val Lys Arg Arg Asp Tyr Leu Asp Leu
    930                 935                 940

Ala Ala Ser Thr Pro Ser Asp Ser Leu Ile Tyr Asp Asp Gly Leu Ser
945                 950                 955                 960

Glu Glu Glu Thr Pro Leu Val Asp Cys Asn Asn Ala Pro Leu Pro Arg
                965                 970                 975

Ala Leu Pro Ser Thr Trp Ile Glu Asn Lys Leu Tyr Gly Met Ser Asp
            980                 985                 990

Pro Asn Trp Pro Gly Glu Ser Pro  Val Pro Leu Thr Arg  Ala Asp Gly
        995                 1000                1005

Thr Asn  Thr Gly Phe Pro Arg  Tyr Pro Asn Asp Ser  Val Tyr Ala
    1010                1015                1020

Asn Trp  Met Leu Ser Pro Ser  Ala Ala Lys Leu Met  Asp Thr Phe
    1025                1030                1035

Asp Ser
    1040
```

<210> SEQ ID NO 22
<211> LENGTH: 1215
<212> TYPE: PRT
<213> ORGANISM: Homo sapiens
<220> FEATURE:
<221> NAME/KEY: misc_feature
<223> OTHER INFORMATION: KIF5B-RET (K22;R12 variant2)

<400> SEQUENCE: 22

```
Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110
```

-continued

```
Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525
```

-continued

```
Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
    610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
                645                 650                 655

Lys Arg Gln Leu Glu Glu Ser Val Asp Ala Leu Ser Glu Glu Leu Val
            660                 665                 670

Gln Leu Arg Ala Gln Glu Lys Val His Glu Met Glu Lys Glu His Leu
        675                 680                 685

Asn Lys Val Gln Thr Ala Asn Glu Val Lys Gln Ala Val Glu Gln Gln
    690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
                725                 730                 735

Asn Gln Lys Met Met Leu Glu Gln Glu Arg Leu Arg Val Glu His Glu
            740                 745                 750

Lys Leu Lys Ala Thr Asp Gln Glu Lys Ser Arg Lys Leu His Glu Leu
        755                 760                 765

Thr Val Met Gln Asp Arg Arg Glu Gln Ala Arg Gln Asp Leu Lys Gly
    770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Glu Asp Pro
                805                 810                 815

Lys Trp Glu Phe Pro Arg Lys Asn Leu Val Leu Gly Lys Thr Leu Gly
            820                 825                 830

Glu Gly Glu Phe Gly Lys Val Val Lys Ala Thr Ala Phe His Leu Lys
        835                 840                 845

Gly Arg Ala Gly Tyr Thr Thr Val Ala Val Lys Met Leu Lys Glu Asn
    850                 855                 860

Ala Ser Pro Ser Glu Leu Arg Asp Leu Leu Ser Glu Phe Asn Val Leu
865                 870                 875                 880

Lys Gln Val Asn His Pro His Val Ile Lys Leu Tyr Gly Ala Cys Ser
                885                 890                 895

Gln Asp Gly Pro Leu Leu Leu Ile Val Glu Tyr Ala Lys Tyr Gly Ser
            900                 905                 910

Leu Arg Gly Phe Leu Arg Glu Ser Arg Lys Val Gly Pro Gly Tyr Leu
        915                 920                 925

Gly Ser Gly Gly Ser Arg Asn Ser Ser Ser Leu Asp His Pro Asp Glu
    930                 935                 940

Arg Ala Leu Thr Met Gly Asp Leu Ile Ser Phe Ala Trp Gln Ile Ser
```

-continued 945 950 955 960

Gln Gly Met Gln Tyr Leu Ala Glu Met Lys Leu Val His Arg Asp Leu
965 970 975

Ala Ala Arg Asn Ile Leu Val Ala Glu Gly Arg Lys Met Lys Ile Ser
980 985 990

Asp Phe Gly Leu Ser Arg Asp Val Tyr Glu Glu Asp Ser Tyr Val Lys
995 1000 1005

Arg Ser Gln Gly Arg Ile Pro Val Lys Trp Met Ala Ile Glu Ser
1010 1015 1020

Leu Phe Asp His Ile Tyr Thr Thr Gln Ser Asp Val Trp Ser Phe
1025 1030 1035

Gly Val Leu Leu Trp Glu Ile Val Thr Leu Gly Gly Asn Pro Tyr
1040 1045 1050

Pro Gly Ile Pro Pro Glu Arg Leu Phe Asn Leu Leu Lys Thr Gly
1055 1060 1065

His Arg Met Glu Arg Pro Asp Asn Cys Ser Glu Glu Met Tyr Arg
1070 1075 1080

Leu Met Leu Gln Cys Trp Lys Gln Glu Pro Asp Lys Arg Pro Val
1085 1090 1095

Phe Ala Asp Ile Ser Lys Asp Leu Glu Lys Met Met Val Lys Arg
1100 1105 1110

Arg Asp Tyr Leu Asp Leu Ala Ala Ser Thr Pro Ser Asp Ser Leu
1115 1120 1125

Ile Tyr Asp Asp Gly Leu Ser Glu Glu Glu Thr Pro Leu Val Asp
1130 1135 1140

Cys Asn Asn Ala Pro Leu Pro Arg Ala Leu Pro Ser Thr Trp Ile
1145 1150 1155

Glu Asn Lys Leu Tyr Gly Met Ser Asp Pro Asn Trp Pro Gly Glu
1160 1165 1170

Ser Pro Val Pro Leu Thr Arg Ala Asp Gly Thr Asn Thr Gly Phe
1175 1180 1185

Pro Arg Tyr Pro Asn Asp Ser Val Tyr Ala Asn Trp Met Leu Ser
1190 1195 1200

Pro Ser Ala Ala Lys Leu Met Asp Thr Phe Asp Ser
1205 1210 1215

<210> SEQ ID NO 23
<211> LENGTH: 1250
<212> TYPE: PRT
<213> ORGANISM: Homo sapiens
<220> FEATURE:
<221> NAME/KEY: misc_feature
<223> OTHER INFORMATION: KIF5B-RET (K23;R12 variant2)

<400> SEQUENCE: 23

Met Ala Asp Leu Ala Glu Cys Asn Ile Lys Val Met Cys Arg Phe Arg
1 5 10 15

Pro Leu Asn Glu Ser Glu Val Asn Arg Gly Asp Lys Tyr Ile Ala Lys
20 25 30

Phe Gln Gly Glu Asp Thr Val Val Ile Ala Ser Lys Pro Tyr Ala Phe
35 40 45

Asp Arg Val Phe Gln Ser Ser Thr Ser Gln Glu Gln Val Tyr Asn Asp
50 55 60

Cys Ala Lys Lys Ile Val Lys Asp Val Leu Glu Gly Tyr Asn Gly Thr
65 70 75 80

-continued

```
Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
```

-continued

```
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
    610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
                645                 650                 655

Lys Arg Gln Leu Glu Glu Ser Val Asp Ala Leu Ser Glu Glu Leu Val
            660                 665                 670

Gln Leu Arg Ala Gln Glu Lys Val His Glu Met Glu Lys Glu His Leu
        675                 680                 685

Asn Lys Val Gln Thr Ala Asn Glu Val Lys Gln Ala Val Glu Gln Gln
    690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
                725                 730                 735

Asn Gln Lys Met Met Leu Glu Gln Glu Arg Leu Arg Val Glu His Glu
            740                 745                 750

Lys Leu Lys Ala Thr Asp Gln Glu Lys Ser Arg Lys Leu His Glu Leu
        755                 760                 765

Thr Val Met Gln Asp Arg Arg Glu Gln Ala Arg Gln Asp Leu Lys Gly
    770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Ser Ala Glu
                805                 810                 815

Ile Asp Ser Asp Asp Thr Gly Gly Ser Ala Ala Gln Lys Gln Lys Ile
            820                 825                 830

Ser Phe Leu Glu Asn Asn Leu Glu Gln Leu Thr Lys Val His Lys Gln
        835                 840                 845

Glu Asp Pro Lys Trp Glu Phe Pro Arg Lys Asn Leu Val Leu Gly Lys
    850                 855                 860

Thr Leu Gly Glu Gly Glu Phe Gly Lys Val Val Lys Ala Thr Ala Phe
865                 870                 875                 880

His Leu Lys Gly Arg Ala Gly Tyr Thr Thr Val Ala Val Lys Met Leu
                885                 890                 895

Lys Glu Asn Ala Ser Pro Ser Glu Leu Arg Asp Leu Leu Ser Glu Phe
            900                 905                 910

Asn Val Leu Lys Gln Val Asn His Pro His Val Ile Lys Leu Tyr Gly
        915                 920                 925
```

Ala Cys Ser Gln Asp Gly Pro Leu Leu Leu Ile Val Glu Tyr Ala Lys
    930                 935                 940

Tyr Gly Ser Leu Arg Gly Phe Leu Arg Glu Ser Arg Lys Val Gly Pro
945                 950                 955                 960

Gly Tyr Leu Gly Ser Gly Gly Ser Arg Asn Ser Ser Ser Leu Asp His
                965                 970                 975

Pro Asp Glu Arg Ala Leu Thr Met Gly Asp Leu Ile Ser Phe Ala Trp
            980                 985                 990

Gln Ile Ser Gln Gly Met Gln Tyr  Leu Ala Glu Met Lys  Leu Val His
        995                 1000                1005

Arg Asp  Leu Ala Ala Arg Asn  Ile Leu Val Ala Glu  Gly Arg Lys
    1010                1015                1020

Met Lys  Ile Ser Asp Phe Gly  Leu Ser Arg Asp Val  Tyr Glu Glu
    1025                1030                1035

Asp Ser  Tyr Val Lys Arg Ser  Gln Gly Arg Ile Pro  Val Lys Trp
    1040                1045                1050

Met Ala  Ile Glu Ser Leu Phe  Asp His Ile Tyr Thr  Thr Gln Ser
    1055                1060                1065

Asp Val  Trp Ser Phe Gly Val  Leu Leu Trp Glu Ile  Val Thr Leu
    1070                1075                1080

Gly Gly  Asn Pro Tyr Pro Gly  Ile Pro Pro Glu Arg  Leu Phe Asn
    1085                1090                1095

Leu Leu  Lys Thr Gly His Arg  Met Glu Arg Pro Asp  Asn Cys Ser
    1100                1105                1110

Glu Glu  Met Tyr Arg Leu Met  Leu Gln Cys Trp Lys  Gln Glu Pro
    1115                1120                1125

Asp Lys  Arg Pro Val Phe Ala  Asp Ile Ser Lys Asp  Leu Glu Lys
    1130                1135                1140

Met Met  Val Lys Arg Arg Asp  Tyr Leu Asp Leu Ala  Ala Ser Thr
    1145                1150                1155

Pro Ser  Asp Ser Leu Ile Tyr  Asp Asp Gly Leu Ser  Glu Glu Glu
    1160                1165                1170

Thr Pro  Leu Val Asp Cys Asn  Asn Ala Pro Leu Pro  Arg Ala Leu
    1175                1180                1185

Pro Ser  Thr Trp Ile Glu Asn  Lys Leu Tyr Gly Met  Ser Asp Pro
    1190                1195                1200

Asn Trp  Pro Gly Glu Ser Pro  Val Pro Leu Thr Arg  Ala Asp Gly
    1205                1210                1215

Thr Asn  Thr Gly Phe Pro Arg  Tyr Pro Asn Asp Ser  Val Tyr Ala
    1220                1225                1230

Asn Trp  Met Leu Ser Pro Ser  Ala Ala Lys Leu Met  Asp Thr Phe
    1235                1240                1245

Asp Ser
    1250

<210> SEQ ID NO 24
<211> LENGTH: 985
<212> TYPE: PRT
<213> ORGANISM: Homo sapiens
<220> FEATURE:
<221> NAME/KEY: misc_feature
<223> OTHER INFORMATION: KIF5B-RET (K15;R11 variant4)

<400> SEQUENCE: 24

Met Ala Asp Leu Ala Glu Cys Asn Ile Lys Val Met Cys Arg Phe Arg

-continued

```
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430
```

-continued

```
Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Phe
                565                 570                 575

Ala His Lys Pro Pro Ile Ser Ser Ala Glu Met Thr Phe Arg Arg Pro
            580                 585                 590

Ala Gln Ala Phe Pro Val Ser Tyr Ser Ser Ser Gly Ala Arg Arg Pro
        595                 600                 605

Ser Leu Asp Ser Met Glu Asn Gln Val Ser Val Asp Ala Phe Lys Ile
    610                 615                 620

Leu Glu Asp Pro Lys Trp Glu Phe Pro Arg Lys Asn Leu Val Leu Gly
625                 630                 635                 640

Lys Thr Leu Gly Glu Gly Glu Phe Gly Lys Val Val Lys Ala Thr Ala
                645                 650                 655

Phe His Leu Lys Gly Arg Ala Gly Tyr Thr Thr Val Ala Val Lys Met
            660                 665                 670

Leu Lys Glu Asn Ala Ser Pro Ser Glu Leu Arg Asp Leu Leu Ser Glu
        675                 680                 685

Phe Asn Val Leu Lys Gln Val Asn His Pro His Val Ile Lys Leu Tyr
    690                 695                 700

Gly Ala Cys Ser Gln Asp Gly Pro Leu Leu Leu Ile Val Glu Tyr Ala
705                 710                 715                 720

Lys Tyr Gly Ser Leu Arg Gly Phe Leu Arg Glu Ser Arg Lys Val Gly
                725                 730                 735

Pro Gly Tyr Leu Gly Ser Gly Gly Ser Arg Asn Ser Ser Ser Leu Asp
            740                 745                 750

His Pro Asp Glu Arg Ala Leu Thr Met Gly Asp Leu Ile Ser Phe Ala
        755                 760                 765

Trp Gln Ile Ser Gln Gly Met Gln Tyr Leu Ala Glu Met Lys Leu Val
    770                 775                 780

His Arg Asp Leu Ala Ala Arg Asn Ile Leu Val Ala Glu Gly Arg Lys
785                 790                 795                 800

Met Lys Ile Ser Asp Phe Gly Leu Ser Arg Asp Val Tyr Glu Glu Asp
                805                 810                 815

Ser Tyr Val Lys Arg Ser Gln Gly Arg Ile Pro Val Lys Trp Met Ala
            820                 825                 830

Ile Glu Ser Leu Phe Asp His Ile Tyr Thr Thr Gln Ser Asp Val Trp
        835                 840                 845
```

-continued

```
Ser Phe Gly Val Leu Leu Trp Glu Ile Val Thr Leu Gly Gly Asn Pro
    850                 855                 860

Tyr Pro Gly Ile Pro Pro Glu Arg Leu Phe Asn Leu Leu Lys Thr Gly
865                 870                 875                 880

His Arg Met Glu Arg Pro Asp Asn Cys Ser Glu Glu Met Tyr Arg Leu
                885                 890                 895

Met Leu Gln Cys Trp Lys Gln Glu Pro Asp Lys Arg Pro Val Phe Ala
            900                 905                 910

Asp Ile Ser Lys Asp Leu Glu Lys Met Met Val Lys Arg Arg Asp Tyr
        915                 920                 925

Leu Asp Leu Ala Ala Ser Thr Pro Ser Asp Ser Leu Ile Tyr Asp Asp
    930                 935                 940

Gly Leu Ser Glu Glu Glu Thr Pro Leu Val Asp Cys Asn Asn Ala Pro
945                 950                 955                 960

Leu Pro Arg Ala Leu Pro Ser Thr Trp Ile Glu Asn Lys Leu Tyr Gly
                965                 970                 975

Arg Ile Ser His Ala Phe Thr Arg Phe
            980                 985


<210> SEQ ID NO 25
<211> LENGTH: 1512
<212> TYPE: DNA
<213> ORGANISM: Homo sapiens
<220> FEATURE:
<221> NAME/KEY: misc_feature
<223> OTHER INFORMATION: CCDC6-RET variant a (AB698668.1)

<400> SEQUENCE: 25

atggcggaca gcgccagcga gagcgacacg gacggggcgg ggggcaacag cagcagctcg     60

gccgccatgc agtcgtcctg ctcgtcgacc tcgggcggcg gcggtggcgg cgggggaggc    120

ggcggcggtg ggaagtcggg gggcattgtc atctcgccgt tccgcctgga ggagctcacc    180

aaccgcctgg cctcgctgca gcaagagaac aaggtgctga agatagagct ggagacctac    240

aaactgaagt gcaaggcact gcaggaggag aaccgcgacc tgcgcaaagc cagcgttacc    300

atcgaggatc caaagtggga attccctcgg aagaacttgg ttcttggaaa aactctagga    360

gaaggcgaat ttggaaaagt ggtcaaggca acggccttcc atctgaaagg cagagcaggg    420

tacaccacgg tggccgtgaa gatgctgaaa gagaacgcct ccccgagtga gctgcgagac    480

ctgctgtcag agttcaacgt cctgaagcag gtcaaccacc cacatgtcat caaattgtat    540

ggggcctgca gccaggatgg cccgctcctc ctcatcgtgg agtacgccaa atacggctcc    600

ctgcggggct tcctccgcga gagccgcaaa gtggggcctg gctacctggg cagtggaggc    660

agccgcaact ccagctccct ggaccacccg gatgagcggg ccctcaccat gggcgacctc    720

atctcatttg cctggcagat ctcacagggg atgcagtatc tggccgagat gaagctcgtt    780

catcgggact tggcagccag aaacatcctg gtagctgagg ggcggaagat gaagatttcg    840

gatttcggct tgtcccgaga tgtttatgaa gaggattcct acgtgaagag gagccagggt    900

cggattccag ttaaatggat ggcaattgaa tccctttttg atcatatcta caccacgcaa    960

agtgatgtat ggtcttttgg tgtcctgctg tgggagatcg tgaccctagg gggaaacccc   1020

tatcctggga ttcctcctga gcggctcttc aaccttctga agaccggcca ccggatggag   1080

aggccagaca actgcagcga ggagatgtac cgcctgatgc tgcaatgctg gaagcaggag   1140

ccggacaaaa ggccggtgtt tgcggacatc agcaaagacc tggagaagat gatggttaag   1200

aggagagact acttggacct tgcggcgtcc actccatctg actccctgat ttatgacgac   1260
```

```
ggcctctcag aggaggagac accgctggtg gactgtaata atgccccct ccctcgagcc   1320

ctcccttcca catggattga aaacaaactc tatggcatgt cagacccgaa ctggcctgga   1380

gagagtcctg taccactcac gagagctgat ggcactaaca ctgggtttcc aagatatcca   1440

aatgatagtg tatatgctaa ctggatgctt tcaccctcag cggcaaaatt aatggacacg   1500

tttgatagtt aa                                                        1512
```

<210> SEQ ID NO 26
<211> LENGTH: 1386
<212> TYPE: DNA
<213> ORGANISM: Homo sapiens
<220> FEATURE:
<221> NAME/KEY: misc_feature
<223> OTHER INFORMATION: CCDC6-RET variant c (AB698669.1)

<400> SEQUENCE: 26

```
atggcggaca gcgccagcga gagcgacacg gacggggcgg ggggcaacag cagcagctcg     60

gccgccatgc agtcgtcctg ctcgtcgacc tcgggcggcg gcggtggcgg cgggggaggc    120

ggcggcggtg ggaagtcggg gggcattgtc atctcgccgt tccgcctgga ggagctcacc    180

aaccgcctgg cctcgctgca gcaagagaac aaggtgctga agatagagct ggagacctac    240

aaactgaagt gcaaggcact gcaggaggag aaccgcgacc tgcgcaaagc cagcgttacc    300

atcgaggatc caaagtggga attccctcgg aagaacttgg ttcttggaaa aactctagga    360

gaaggcgaat ttggaaaagt ggtcaaggca acggccttcc atctgaaagg cagagcaggg    420

tacaccacgg tggccgtgaa gatgctgaaa gagaacgcct ccccgagtga gctgcgagac    480

ctgctgtcag agttcaacgt cctgaagcag gtcaaccacc cacatgtcat caaattgtat    540

ggggcctgca gccaggatgg cccgctcctc ctcatcgtgg agtacgccaa atacggctcc    600

ctgcggggct tcctccgcga gagccgcaaa gtggggcctg gctacctggg cagtggaggc    660

agccgcaact ccagctccct ggaccacccg gatgagcggg ccctcaccat gggcgacctc    720

atctcatttg cctggcagat ctcacagggg atgcagtatc tggccgagat gaagctcgtt    780

catcgggact tggcagccag aaacatcctg gtagctgagg ggcggaagat gaagatttcg    840

gatttcggct tgtcccgaga tgtttatgaa gaggattcct acgtgaagag gagccagggt    900

cggattccag ttaaatggat ggcaattgaa tccctttttg atcatatcta caccacgcaa    960

agtgatgtat ggtcttttgg tgtcctgctg tgggagatcg tgaccctagg gggaaacccc   1020

tatcctggga ttcctcctga gcggctcttc aaccttctga agaccggcca ccggatggag   1080

aggccagaca actgcagcga ggagatgtac cgcctgatgc tgcaatgctg gaagcaggag   1140

ccggacaaaa ggccggtgtt tgcggacatc agcaaagacc tggagaagat gatggttaag   1200

aggagagact acttggacct tgcggcgtcc actccatctg actccctgat ttatgacgac   1260

ggcctctcag aggaggagac accgctggtg gactgtaata atgccccct ccctcgagcc   1320

ctcccttcca catggattga aaacaaactc tatggtagaa tttcccatgc atttactaga   1380

ttctag                                                               1386
```

<210> SEQ ID NO 27
<211> LENGTH: 503
<212> TYPE: PRT
<213> ORGANISM: Homo sapiens
<220> FEATURE:
<221> NAME/KEY: misc_feature
<223> OTHER INFORMATION: CCDC6-RET variant a (BAM36435.1)

-continued

<400> SEQUENCE: 27

Met Ala Asp Ser Ala Ser Glu Ser Asp Thr Asp Gly Ala Gly Gly Asn
1 5 10 15

Ser Ser Ser Ser Ala Ala Met Gln Ser Ser Cys Ser Ser Thr Ser Gly
20 25 30

Gly Gly Gly Gly Gly Gly Gly Gly Gly Gly Gly Gly Lys Ser Gly Gly
35 40 45

Ile Val Ile Ser Pro Phe Arg Leu Glu Glu Leu Thr Asn Arg Leu Ala
50 55 60

Ser Leu Gln Gln Glu Asn Lys Val Leu Lys Ile Glu Leu Glu Thr Tyr
65 70 75 80

Lys Leu Lys Cys Lys Ala Leu Gln Glu Glu Asn Arg Asp Leu Arg Lys
85 90 95

Ala Ser Val Thr Ile Glu Asp Pro Lys Trp Glu Phe Pro Arg Lys Asn
100 105 110

Leu Val Leu Gly Lys Thr Leu Gly Glu Gly Glu Phe Gly Lys Val Val
115 120 125

Lys Ala Thr Ala Phe His Leu Lys Gly Arg Ala Gly Tyr Thr Thr Val
130 135 140

Ala Val Lys Met Leu Lys Glu Asn Ala Ser Pro Ser Glu Leu Arg Asp
145 150 155 160

Leu Leu Ser Glu Phe Asn Val Leu Lys Gln Val Asn His Pro His Val
165 170 175

Ile Lys Leu Tyr Gly Ala Cys Ser Gln Asp Gly Pro Leu Leu Leu Ile
180 185 190

Val Glu Tyr Ala Lys Tyr Gly Ser Leu Arg Gly Phe Leu Arg Glu Ser
195 200 205

Arg Lys Val Gly Pro Gly Tyr Leu Gly Ser Gly Gly Ser Arg Asn Ser
210 215 220

Ser Ser Leu Asp His Pro Asp Glu Arg Ala Leu Thr Met Gly Asp Leu
225 230 235 240

Ile Ser Phe Ala Trp Gln Ile Ser Gln Gly Met Gln Tyr Leu Ala Glu
245 250 255

Met Lys Leu Val His Arg Asp Leu Ala Ala Arg Asn Ile Leu Val Ala
260 265 270

Glu Gly Arg Lys Met Lys Ile Ser Asp Phe Gly Leu Ser Arg Asp Val
275 280 285

Tyr Glu Glu Asp Ser Tyr Val Lys Arg Ser Gln Gly Arg Ile Pro Val
290 295 300

Lys Trp Met Ala Ile Glu Ser Leu Phe Asp His Ile Tyr Thr Thr Gln
305 310 315 320

Ser Asp Val Trp Ser Phe Gly Val Leu Leu Trp Glu Ile Val Thr Leu
325 330 335

Gly Gly Asn Pro Tyr Pro Gly Ile Pro Pro Glu Arg Leu Phe Asn Leu
340 345 350

Leu Lys Thr Gly His Arg Met Glu Arg Pro Asp Asn Cys Ser Glu Glu
355 360 365

Met Tyr Arg Leu Met Leu Gln Cys Trp Lys Gln Glu Pro Asp Lys Arg
370 375 380

Pro Val Phe Ala Asp Ile Ser Lys Asp Leu Glu Lys Met Met Val Lys
385 390 395 400

Arg Arg Asp Tyr Leu Asp Leu Ala Ala Ser Thr Pro Ser Asp Ser Leu
405 410 415

```
Ile Tyr Asp Asp Gly Leu Ser Glu Glu Glu Thr Pro Leu Val Asp Cys
            420                 425                 430

Asn Asn Ala Pro Leu Pro Arg Ala Leu Pro Ser Thr Trp Ile Glu Asn
        435                 440                 445

Lys Leu Tyr Gly Met Ser Asp Pro Asn Trp Pro Gly Glu Ser Pro Val
    450                 455                 460

Pro Leu Thr Arg Ala Asp Gly Thr Asn Thr Gly Phe Pro Arg Tyr Pro
465                 470                 475                 480

Asn Asp Ser Val Tyr Ala Asn Trp Met Leu Ser Pro Ser Ala Ala Lys
                485                 490                 495

Leu Met Asp Thr Phe Asp Ser
            500


<210> SEQ ID NO 28
<211> LENGTH: 461
<212> TYPE: PRT
<213> ORGANISM: Homo sapiens
<220> FEATURE:
<221> NAME/KEY: misc_feature
<223> OTHER INFORMATION: CCDC6-RET variant c (BAM36436.1)

<400> SEQUENCE: 28

Met Ala Asp Ser Ala Ser Glu Ser Asp Thr Asp Gly Ala Gly Gly Asn
1               5                   10                  15

Ser Ser Ser Ser Ala Ala Met Gln Ser Ser Cys Ser Ser Thr Ser Gly
            20                  25                  30

Gly Gly Gly Gly Gly Gly Gly Gly Gly Gly Gly Gly Lys Ser Gly Gly
        35                  40                  45

Ile Val Ile Ser Pro Phe Arg Leu Glu Glu Leu Thr Asn Arg Leu Ala
    50                  55                  60

Ser Leu Gln Gln Glu Asn Lys Val Leu Lys Ile Glu Leu Glu Thr Tyr
65                  70                  75                  80

Lys Leu Lys Cys Lys Ala Leu Gln Glu Glu Asn Arg Asp Leu Arg Lys
                85                  90                  95

Ala Ser Val Thr Ile Glu Asp Pro Lys Trp Glu Phe Pro Arg Lys Asn
            100                 105                 110

Leu Val Leu Gly Lys Thr Leu Gly Glu Gly Glu Phe Gly Lys Val Val
        115                 120                 125

Lys Ala Thr Ala Phe His Leu Lys Gly Arg Ala Gly Tyr Thr Thr Val
    130                 135                 140

Ala Val Lys Met Leu Lys Glu Asn Ala Ser Pro Ser Glu Leu Arg Asp
145                 150                 155                 160

Leu Leu Ser Glu Phe Asn Val Leu Lys Gln Val Asn His Pro His Val
                165                 170                 175

Ile Lys Leu Tyr Gly Ala Cys Ser Gln Asp Gly Pro Leu Leu Leu Ile
            180                 185                 190

Val Glu Tyr Ala Lys Tyr Gly Ser Leu Arg Gly Phe Leu Arg Glu Ser
        195                 200                 205

Arg Lys Val Gly Pro Gly Tyr Leu Gly Ser Gly Gly Ser Arg Asn Ser
    210                 215                 220

Ser Ser Leu Asp His Pro Asp Glu Arg Ala Leu Thr Met Gly Asp Leu
225                 230                 235                 240

Ile Ser Phe Ala Trp Gln Ile Ser Gln Gly Met Gln Tyr Leu Ala Glu
                245                 250                 255

Met Lys Leu Val His Arg Asp Leu Ala Ala Arg Asn Ile Leu Val Ala
```

```
            260                 265                 270

Glu Gly Arg Lys Met Lys Ile Ser Asp Phe Gly Leu Ser Arg Asp Val
        275                 280                 285

Tyr Glu Glu Asp Ser Tyr Val Lys Arg Ser Gln Gly Arg Ile Pro Val
    290                 295                 300

Lys Trp Met Ala Ile Glu Ser Leu Phe Asp His Ile Tyr Thr Thr Gln
305                 310                 315                 320

Ser Asp Val Trp Ser Phe Gly Val Leu Leu Trp Glu Ile Val Thr Leu
                325                 330                 335

Gly Gly Asn Pro Tyr Pro Gly Ile Pro Pro Glu Arg Leu Phe Asn Leu
            340                 345                 350

Leu Lys Thr Gly His Arg Met Glu Arg Pro Asp Asn Cys Ser Glu Glu
        355                 360                 365

Met Tyr Arg Leu Met Leu Gln Cys Trp Lys Gln Glu Pro Asp Lys Arg
    370                 375                 380

Pro Val Phe Ala Asp Ile Ser Lys Asp Leu Glu Lys Met Met Val Lys
385                 390                 395                 400

Arg Arg Asp Tyr Leu Asp Leu Ala Ala Ser Thr Pro Ser Asp Ser Leu
                405                 410                 415

Ile Tyr Asp Asp Gly Leu Ser Glu Glu Glu Thr Pro Leu Val Asp Cys
            420                 425                 430

Asn Asn Ala Pro Leu Pro Arg Ala Leu Pro Ser Thr Trp Ile Glu Asn
        435                 440                 445

Lys Leu Tyr Gly Arg Ile Ser His Ala Phe Thr Arg Phe
    450                 455                 460


<210> SEQ ID NO 29
<211> LENGTH: 5905
<212> TYPE: DNA
<213> ORGANISM: Homo sapiens
<220> FEATURE:
<221> NAME/KEY: misc_feature
<223> OTHER INFORMATION: KIF5B (NM_004521.2)

<400> SEQUENCE: 29

ctcctcccgc accgccctgt cgcccaacgg cggcctcagg agtgatcggg cagcagtcgg      60

ccggccagcg gacggcagag cgggcggacg ggtaggcccg gcctgctctt cgcgaggagg     120

aagaaggtgg ccactctccc ggtccccaga acctccccag cccccgcagt ccgcccagac     180

cgtaaagggg gacgctgagg agccgcggac gctctccccg gtgccgccgc cgctgccgcc     240

gccatggctg ccatgatgga tcggaagtga gcattagggt taacggctgc cggcgccggc     300

tcttcaagtc ccggctcccc ggccgcctcc acccggggaa gcgcagcgcg gcgcagctga     360

ctgctgcctc tcacggccct cgcgaccaca agccctcagg tccggcgcgt tccctgcaag     420

actgagcggc ggggagtggc tcccggccgc cggccccggc tgcgagaaag atggcggacc     480

tggccgagtg caacatcaaa gtgatgtgtc gcttcagacc tctcaacgag tctgaagtga     540

accgcggcga caagtacatc gccaagtttc agggagaaga cacggtcgtg atcgcgtcca     600

agccttatgc atttgatcgg gtgttccagt caagcacatc tcaagagcaa gtgtataatg     660

actgtgcaaa gaagattgtt aaagatgtac ttgaaggata taatggaaca atatttgcat     720

atggacaaac atcctctggg aagacacaca caatggaggg taaacttcat gatccagaag     780

gcatgggaat tattccaaga atagtgcaag atatttttaa ttatatttac tccatggatg     840

aaaatttgga atttcatatt aaggtttcat attttgaaat atatttggat aagataaggg     900
```

acctgttaga tgtttcaaag accaaccttt cagttcatga agacaaaaac cgagttccct 960
atgtaaaggg gtgcacagag cgttttgtat gtagtccaga tgaagttatg gataccatag 1020
atgaaggaaa atccaacaga catgtagcag ttacaaatat gaatgaacat agctctagga 1080
gtcacagtat atttcttatt aatgtcaaac aagagaacac acaaacggaa caaaagctga 1140
gtggaaaact ttatctggtt gatttagctg gtagtgaaaa ggttagtaaa actggagctg 1200
aaggtgctgt gctggatgaa gctaaaaaca tcaacaagtc actttctgct cttggaaatg 1260
ttatttctgc tttggctgag ggtagtacat atgttccata tcgagatagt aaaatgacaa 1320
gaatccttca agattcatta ggtggcaact gtagaaccac tattgtaatt tgctgctctc 1380
catcatcata caatgagtct gaaacaaaat ctacactctt atttggccaa agggccaaaa 1440
caattaagaa cacagtttgt gtcaatgtgg agttaactgc agaacagtgg aaaaagaagt 1500
atgaaaaaga aaaagaaaaa aataagatcc tgcggaacac tattcagtgg cttgaaaatg 1560
agctcaacag atggcgtaat ggggagacgg tgcctattga tgaacagttt gacaaagaga 1620
aagccaactt ggaagctttc acagtggata aagatattac tcttaccaat gataaaccag 1680
caaccgcaat tggagttata ggaaatttta ctgatgctga aagaagaaag tgtgaagaag 1740
aaattgctaa attatacaaa cagcttgatg acaaggatga agaaattaac cagcaaagtc 1800
aactggtaga gaaactgaag acgcaaatgt tggatcagga ggagcttttg gcatctacca 1860
gaagggatca agacaatatg caagctgagc tgaatcgcct tcaagcagaa aatgatgcct 1920
ctaaagaaga agtgaaagaa gttttacagg ccctagaaga acttgctgtc aattatgatc 1980
agaagtctca ggaagttgaa gacaaaacta aggaatatga attgcttagt gatgaattga 2040
atcagaaatc ggcaacttta gcgagtatag atgctgagct tcagaaactt aaggaaatga 2100
ccaaccacca gaaaaaacga gcagctgaga tgatggcatc tttactaaaa gaccttgcag 2160
aaataggaat tgctgtggga aataatgatg taaagcagcc tgagggaact ggcatgatag 2220
atgaagagtt cactgttgca agactctaca ttagcaaaat gaagtcagaa gtaaaaacca 2280
tggtgaaacg ttgcaagcag ttagaaagca cacaaactga gagcaacaaa aaaatggaag 2340
aaaatgaaaa ggagttagca gcatgtcagc ttcgtatctc tcaacatgaa gccaaaatca 2400
agtcattgac tgaatacctt caaaatgtgg aacaaaagaa aagacagttg gaggaatctg 2460
tcgatgccct cagtgaagaa ctagtccagc ttcgagcaca agagaaagtc catgaaatgg 2520
aaaaggagca cttaaataag gttcagactg caaatgaagt taagcaagct gttgaacagc 2580
agatccagag ccatagagaa actcatcaaa aacagatcag tagtttgaga gatgaagtag 2640
aagcaaaagc aaaacttatt actgatcttc aagaccaaaa ccagaaaatg atgttagagc 2700
aggaacgtct aagagtagaa catgagaagt tgaaagccac agatcaggaa aagagcagaa 2760
aactacatga acttacggtt atgcaagata gacgagaaca agcaagacaa gacttgaagg 2820
gtttggaaga gacagtggca aaagaacttc agactttaca caacctgcgc aaactctttg 2880
ttcaggacct ggctacaaga gttaaaaaga gtgctgagat tgattctgat gacaccggag 2940
gcagcgctgc tcagaagcaa aaaatctcct ttcttgaaaa taatcttgaa cagctcacta 3000
aagtgcacaa acagttggta cgtgataatg cagatctccg ctgtgaactt cctaagttgg 3060
aaaagcgact tcgagctaca gctgagagag tgaaagcttt ggaatcagca ctgaaagaag 3120
ctaaagaaaa tgcatctcgt gatcgcaaac gctatcagca agaagtagat cgcataaagg 3180
aagcagtcag gtcaaagaat atggccagaa gagggcattc tgcacagatt gctaaaccta 3240
ttcgtcccgg gcaacatcca gcagcttctc caactcaccc aagtgcaatt cgtggaggag 3300

-continued

```
gtgcatttgt tcagaacagc cagccagtgg cagtgcgagg tggaggaggc aaacaagtgt   3360
aatcgtttat acatacccac aggtgttaaa aagtaatcga agtacgaaga ggacatggta   3420
tcaagcagtc attcaatgac tataacctct actcccttgg gattgtagaa ttataacttt   3480
taaaaaaaat gtataaatta tacctggcct gtacagctgt ttcctaccta ctcttcttgt   3540
aaactctgct gcttcccaac acaactagag tgcaattttg gcatcttagg agggaaaaag   3600
gacagtttac aactgtggcc ctatttatta cacagtttgt ctatcgtgtc ttaaatttag   3660
tctttactgt gccaagctaa ctgtacctta taggactgta ctttttgtat tttttgtgta   3720
tgtttatttt ttaatctcag tttaaattac ctagctgcta ctgcttcttg tttttctttt   3780
cctattaaaa cgtcttcctt ttttttctt aagagaaaat ggaacattta ggttaaatgt   3840
ctttaaattt taccacttaa caacactaca tgcccataaa atatatccag tcagtactgt   3900
attttaaaat cccttgaaat gatgatatca gggttaaaat tacttgtatt gtttctgaag   3960
tttgctcctg aaaactactg tttgagcact gaaacgttac aaatgcctaa taggcatttg   4020
agactgagca aggctacttg ttatctcatg aaatgcctgt tgccgagtta ttttgaatag   4080
aaatatttta aagtatcaaa agcagatctt agtttaaggg agtttggaaa aggaattata   4140
tttctctttt tcctgattct gtactcaaca agtcttgatg gaattaaaat actctgcttt   4200
attctggtga gcctgctagc taatataagt attggacagg taataatttg tcatctttaa   4260
tattagtaaa atgaattaag atattatagg attaaacata attttatacg gttagtactt   4320
tattggccga cctaaattta tagcgtgtgg aaattgagaa aaatgaagaa acaggacaga   4380
tatatgatga attaaaaata tatataggtc aattttggtc tgaaatccct gaggtgtttt   4440
taacctgcta cactaatttg tacactaatt tatttcttta gtctagaaat agtaaattgt   4500
ttgcaagtca ctaataatca ttagataaat tattttcttg gccatagccg ataattttgt   4560
aatcagtact aagtgtatac gtatttttgc cactttttcc tcagatgatt aaagtaagtc   4620
aacagcttat tttaggaaac tgtaaaagta atagggaaag agatttcact atttgcttca   4680
tcagtggtag gggggcggtg actgcaactg tgttagcaga aattcacaga gaatggggat   4740
ttaaggttag cagagaaact tggaaagttc tgtgttagga tcttgctggc agaattaact   4800
ttttgcaaaa gttttataca cagatatttg tattaaattt ggagccatag tcagaagact   4860
cagatcataa ttggcttatt tttctatttc cgtaactatt gtaatttcca cttttgtaat   4920
aattttgatt taaaatataa atttatttat ttattttttt aatagtcaaa aatctttgct   4980
gttgtagtct gcaacctcta aaatgattgt gttgctttta ggattgatca gaagaaacac   5040
tccaaaaatt gagatgaaat gttggtgcag ccagttataa gtaatatagt taacaagcaa   5100
aaaaagtgct gccacctttt atgatgattt tctaaatgga gaaacatttg gctgcatcca   5160
catagacctt tatgttttgt tttcagttga aaacttgcct cctttggcaa cattcgtaaa   5220
tgaagcagaa tttttttttc tctttttcc aaatatgtta gttttgttct tgtaagatgt   5280
atcatgggta ttggtgctgt gtaatgaaca acgaatttta attagcatgt ggttcagaat   5340
atacaatgtt aggtttttaa aaagtatctt gatggttctt ttctatttat aatttcagac   5400
tttcataaag tgtaccaaga atttcataaa tttgttttca gtgaactgct ttttgctatg   5460
gtaggtcatt aaacacagca cttactctta aaaatgaaaa tttctgatca tctaggatat   5520
tgacacattt caatttgcag tgtctttttg actggatata ttaacgttcc tctgaatggc   5580
attgatagat ggttcagaag agaaactcaa tgaaataaag agaatattta ttcatggcga   5640
```

-continued

```
ttaattaaat tatttgccta acttaagaaa actactgtgc gtaactctca gtttgtgctt   5700

aactccattt gacatgaggt gacagaagag agtctgagtc tacctgtgga atatgttggt   5760

ttattttcag tgcttgaaga tacattcaca aatacttggt ttgggaagac accgtttaat   5820

tttaagttaa cttgcatgtt gtaaatgcgt tttatgttta aataaagagg aaaatttttt   5880

gaaatgtaaa aaaaaaaaaa aaaaa                                         5905
```

<210> SEQ ID NO 30
<211> LENGTH: 963
<212> TYPE: PRT
<213> ORGANISM: Homo sapiens
<220> FEATURE:
<221> NAME/KEY: misc_feature
<223> OTHER INFORMATION: kinesin-1 heavy chain (NP_004512.1)

<400> SEQUENCE: 30

```
Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
```

-continued

```
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
    610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
                645                 650                 655

Lys Arg Gln Leu Glu Glu Ser Val Asp Ala Leu Ser Glu Glu Leu Val
            660                 665                 670

Gln Leu Arg Ala Gln Glu Lys Val His Glu Met Glu Lys Glu His Leu
        675                 680                 685

Asn Lys Val Gln Thr Ala Asn Glu Val Lys Gln Ala Val Glu Gln Gln
    690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
                725                 730                 735
```

Asn Gln Lys Met Met Leu Glu Gln Glu Arg Leu Arg Val Glu His Glu
740 745 750

Lys Leu Lys Ala Thr Asp Gln Glu Lys Ser Arg Lys Leu His Glu Leu
755 760 765

Thr Val Met Gln Asp Arg Arg Glu Gln Ala Arg Gln Asp Leu Lys Gly
770 775 780

Leu Glu Glu Thr Val Ala Lys Glu Leu Gln Thr Leu His Asn Leu Arg
785 790 795 800

Lys Leu Phe Val Gln Asp Leu Ala Thr Arg Val Lys Lys Ser Ala Glu
805 810 815

Ile Asp Ser Asp Asp Thr Gly Gly Ser Ala Ala Gln Lys Gln Lys Ile
820 825 830

Ser Phe Leu Glu Asn Asn Leu Glu Gln Leu Thr Lys Val His Lys Gln
835 840 845

Leu Val Arg Asp Asn Ala Asp Leu Arg Cys Glu Leu Pro Lys Leu Glu
850 855 860

Lys Arg Leu Arg Ala Thr Ala Glu Arg Val Lys Ala Leu Glu Ser Ala
865 870 875 880

Leu Lys Glu Ala Lys Glu Asn Ala Ser Arg Asp Arg Lys Arg Tyr Gln
885 890 895

Gln Glu Val Asp Arg Ile Lys Glu Ala Val Arg Ser Lys Asn Met Ala
900 905 910

Arg Arg Gly His Ser Ala Gln Ile Ala Lys Pro Ile Arg Pro Gly Gln
915 920 925

His Pro Ala Ala Ser Pro Thr His Pro Ser Ala Ile Arg Gly Gly Gly
930 935 940

Ala Phe Val Gln Asn Ser Gln Pro Val Ala Val Arg Gly Gly Gly Gly
945 950 955 960

Lys Gln Val

<210> SEQ ID NO 31
<211> LENGTH: 5842
<212> TYPE: DNA
<213> ORGANISM: Homo sapiens
<220> FEATURE:
<221> NAME/KEY: misc_feature
<223> OTHER INFORMATION: CCDC6 (NM_005436.4)

<400> SEQUENCE: 31
agtgcaatac tgcccaagcc cgggcggggt ctctgttctc tggcagagga ggtcccttgg 60
cagcgggaag cgccctctct ttctctcgcc gccgctccga gtctgcgccc tggtgccagg 120
cgctcagctc ggcgctcccc tgtgctcgcc cggcgcccac tcattcgcag cccggccttc 180
gtcgccgccg cctccctgct gctcctcctc ctttccccag cccgccgcgg ccatggcgga 240
cagcgccagc gagagcgaca cggacggggc gggggggcaac agcagcagct cggccgccat 300
gcagtcgtcc tgctcgtcga cctcgggcgg cggcggtggc ggcgggggag gcggcggcgg 360
tgggaagtcg gggggcattg tcatctcgcc gttccgcctg gaggagctca ccaaccgcct 420
ggcctcgctg cagcaagaga acaaggtgct gaagatagag ctggagacct acaaactgaa 480
gtgcaaggca ctgcaggagg agaaccgcga cctgcgcaaa gccagcgtga ccatccaagc 540
cagggctgag caggaagaag aattcattag taacacttta ttcaagaaaa ttcaggcttt 600
gcagaaggag aaagaaaccc ttgctgtaaa ttatgagaaa gaagaagaat tcctcactaa 660
tgagctctcc agaaaattga tgcagttgca gcatgagaaa gccgaactag aacagcatct 720

-continued

```
tgaacaagag caggaatttc aggtcaacaa actgatgaag aaaattaaaa aactggagaa    780
tgacaccatt tctaagcaac ttacattaga acagttgaga cgggagaaga ttgaccttga    840
aaatacattg gaacaagaac aagaagcact agttaatcgc ctctggaaaa ggatggataa    900
gcttgaagct gaaaagcgaa tcctgcagga aaaattagac cagcccgtct ctgctccacc    960
atcgcctaga gatatctcca tggagattga ttctccagaa aatatgatgc gtcacatcag   1020
gtttttaaag aatgaagtgg aacggctgaa gaagcaactg agagctgctc agttacagca   1080
ttcagagaaa atggcacagt atctggagga ggaacgtcac atgagagaag agaacttgag   1140
gctccagagg aagctgcaga gggagatgga gagaagagaa gccctctgtc gacagctctc   1200
cgagagtgag tccagcttag aaatggacga cgaaaggtat tttaatgaga tgtctgcaca   1260
aggattaaga cctcgcactg tgtccagccc gatcccttac acaccttctc cgagttcaag   1320
caggcctata tcacctggtc tatcatatgc aagtcacacg gttggtttca cgccaccaac   1380
ttcactgact agagctggaa tgtcttatta caattccccg ggtcttcacg tgcagcacat   1440
gggaacatcc catggtatca caaggccttc accacggaga agcaacagtc ctgacaaatt   1500
caaacggccc acgccgcctc catctcccaa cacacagacc ccagtccagc cacctccgcc   1560
tccacctccg ccacccatgc agcccacggt cccctcagca gccacctcgc agcctactcc   1620
ttcgcaacat tcggcgcacc cctcctccca gccttaatgc atgagcttag tctgaatttc   1680
aagttgggac tcatccaatg gagccgtcta ctcaacgcca aaggcttcct tctctggcat   1740
atttggatat gacttatttg cactgaggtt atctaggctt cactatccat tgtgttgtaa   1800
atgtttgtca gaaatgcagc cagtgttgtg ggtctacaac actaaccaga cgactttttc   1860
catcagtgtt ttacttgaat cttcatgtac gtccattccc tggctggaac cttcgctgtt   1920
tggtatttgg tatttcagca gcagtgtgca atttttgctt ggcccagagc ttcattctcc   1980
tggcttttag gtttgtaaaa gaaaaaggga tatctttttt atattttttt ccatgaatct   2040
gcagaaaatt actgagctgt tgttaccctc ctctcattat aatagtgttt accaaacata   2100
ccaataattc agcactacaa ttcagacctt tgaaaatctg gctttcagtg tagaacagaa   2160
agttagatga atcagtgccc aagacatatt ttctgtttaa cagaactttc tacagataca   2220
tttttttacag gttattttca ttgtgttatt gacatccatg tctctcgtaa aacagatggc   2280
ccaaagtaat gaatcatgtg gctgtacctt ctccacataa atgggatgga taattatcgt   2340
atattaagat gtgattctct tttttatcct taatgttaat ctacttaacc tggcccccctc   2400
taacatgagt cgataaatgt tgtcctactc accggtggtt tcaatggcta attagaatgt   2460
gttatttgat ttctgctgca gaaggcagtg tgattgtaac aaaaacaatg cggcttcccc   2520
ctttcgtact tcatttgtgt tctcttaaaa tagagtttga acaaatattt taaaggtgca   2580
aaataccatt agaaaatact atttgaaatg gacattatcg cattatcttg gcataatggc   2640
cagaaaatat tgtattgctt ggcagaaaag aaaataaggt ctaaaggaaa gtagcacatt   2700
agcattgatg gctgttcatt tcacccagta taagcaagtg cagtgtacaa agaagtatat   2760
tctgaataca ttatttccat tcatttagca caaataaatc atttggtttc actttgcagt   2820
ggaacactga gtcactcttt tcttaacacg tgcaacatct taatttttgt ttttcagcag   2880
ttgctgtttt gtactttggt agtaaagtga tttttaccac ctgtgtttgc atatttatat   2940
atgctgtgga tgaaaataac ttactagaga atgtatattt tatgacaaga atgtgtatct   3000
gttggatata atcagagaac tgaaaagtaa tttatcagta atttttaaga gtccatgttt   3060
```

-continued

```
tgtgacaacc atctctaata gccaactctt tattaaacac actcctaaaa ataaggaacc   3120
atgacattgt agatatttaa tattgtacag tatagaaacc tccatttttg ccttcgaatg   3180
catatttaag agttaacaga atgaaaaaaa aaagtcttgt tggataatag tgtttgacta   3240
gcgttttaag aacttgagag taaaagcaac aataagattt tttcacctct tcctgcttcc   3300
acccccaaac tgagaacatc actcaattgt ttggaagaaa ctgtaggtct atataaattt   3360
tatttataat gtatgtgtaa tatacataat cataatacag ttctcagatg cagggaagaa   3420
gtttggcatt taatcattga ggctttaggt ttttgatgtg atcagactgg gccatgtcaa   3480
acccggaatt ttcaccaaca gttcactcac cctcctggta cattgccatt ccaaggaatt   3540
ctgagagtag gcaaacaaat tttgccttca tggtacagtt ctcagttttt cttataggag   3600
aaatatggta tatgtttata agaatctttt atgagattat agatttcaat gctgtggata   3660
gtgtcttgca cccaaacaag aaagtccata atggaatgat cttccctcag cttcctatcg   3720
atttagttac ctcttgaaag cacaaaaatt aaaacattgc catatgttga atttttaaaa   3780
agcacttgga gtgagcgaac atttcctgat aaatgccttt tagagatagg ttcttgatat   3840
tcagacatct gcagaaatgt tctggttccc aaagtcattt cacttcgaaa taaaacacag   3900
ctccttcaaa cagcactttt tccacataaa tctagttgcc tctccctgtg gacattcaga   3960
actgatagaa caaacactac tcttttgaat ttgatggttc gtgtccttta aagtgtttga   4020
ggacctatgc agagcctgta acacttgggt agtacctgct aggacaattt cttggcaatt   4080
gtcttactac tagggatcag taagatttag attctgagcc cataatggca acagcccccct   4140
cacctatggg aagctgactt ccctcagtcg ggcacttctc atgggggctg aacatggttc   4200
ctgccattct gttacccact ctcccaggtg agccctggat tggctcccag aaggcctttg   4260
taaaatcagt agccgtcctg caggcaggtg ggagcaacag gggcttcagt agcttcattt   4320
tcctgtcttg cagacagaga cccttggcta ccactgtgct gctaatagga taagtactct   4380
gttgccagat taccatgcct tttatacaaa accaaattaa cttacctaat acctgacacc   4440
tctttgggct ctgaactgct ttctctcatc aagcatgcta gcactctaga cagaattcta   4500
gaaatttggc agatagtgga agcctttaat tgaacttact ccttcgttga ctgaaaggag   4560
ttttaaattc tgagctcctg agatactgac tagcaaccat ggaatgaatg tgtgaccaga   4620
aagtggcttt gacaccaagt gctactgtcc ctttgtaatt ggcttctaac agaattcaac   4680
cagaaataat tgataatgtg aatttttgtt aattgttcac ttgtaggaaa atagaacatg   4740
tatcaccctt tgttaggtag acatgaactt ttcctgcaca aagccttgct tttagagaat   4800
gcccaataag gcaagaaaaa gcatagtaac ttgtgctttg agagctcaat atttgtatct   4860
tatcagtaca gaagaaatat ttctgtgtaa cttgatcttc tgtctagtac ttgtcttata   4920
ggtaaccaac actgaaaact ttgtagtgat gactaccaaa gaaatacata gtaaaacaac   4980
cttttatttc caaattgtta aagagccagc cattgatgct gctacatgag ttccatgctc   5040
aagagccatt gtaagagatt aaggggtttc taggtttttg gtgatttttt gtttgttttt   5100
ttctttgttt tttagggttt ttttttcttc tttaattttt tgattaaaac atacacacag   5160
ctgttagcat aaagtcgtgg ggggcatttt ctggaatgct cagcagttct gattaactgc   5220
caagcccagg ttgcctctca tgaggcaact gaaaaaatcc tgtgtcttga tagcatgggt   5280
gctgtgtgtg tgcatgtgtg tgtctgcatt catgccttaa ctcgggttac tgcacaactt   5340
tagttcttga cttagtctgc accgtcatct agattgtatt gtacatctcg gtctgaactt   5400
catcctggca aaaacaaagt tgcaggcaca acagtttaag aatgcattcc tccagaagag   5460
```

```
tatctggtca ggttgacccc tgagccttct ttggacttga tttggaactt agcctggaaa   5520

gcgaaagtgg actgtccaac agaaagatgt caacaaggaa aagaggagag ccaagcgcta   5580

gcatgccttt tgcctctgca tatctgtgca cactgtatgt tgttcatgat agcttgtcta   5640

caacttgact aggttggagt tctggtaata gtggcaatct tgacattctt ggtcagagtt   5700

tagagagatg taagactttc aattaatgtc ttatttactc ctttatgttg attagtcttt   5760

gatacatgtg ctgaatcaga aacctaaata aagataattt tttaaaatgt acctcttgag   5820

ccttaaaaaa aaaaaaaaaa aa                                            5842
```

```
<210> SEQ ID NO 32
<211> LENGTH: 474
<212> TYPE: PRT
<213> ORGANISM: Homo sapiens
<220> FEATURE:
<221> NAME/KEY: misc_feature
<223> OTHER INFORMATION: CCDC6 (NP_005427.2)

<400> SEQUENCE: 32

Met Ala Asp Ser Ala Ser Glu Ser Asp Thr Asp Gly Ala Gly Gly Asn
1               5                   10                  15

Ser Ser Ser Ser Ala Ala Met Gln Ser Ser Cys Ser Ser Thr Ser Gly
            20                  25                  30

Gly Gly Gly Gly Gly Gly Gly Gly Gly Gly Gly Gly Lys Ser Gly Gly
        35                  40                  45

Ile Val Ile Ser Pro Phe Arg Leu Glu Glu Leu Thr Asn Arg Leu Ala
    50                  55                  60

Ser Leu Gln Gln Glu Asn Lys Val Leu Lys Ile Glu Leu Glu Thr Tyr
65                  70                  75                  80

Lys Leu Lys Cys Lys Ala Leu Gln Glu Glu Asn Arg Asp Leu Arg Lys
                85                  90                  95

Ala Ser Val Thr Ile Gln Ala Arg Ala Glu Gln Glu Glu Glu Phe Ile
            100                 105                 110

Ser Asn Thr Leu Phe Lys Lys Ile Gln Ala Leu Gln Lys Glu Lys Glu
        115                 120                 125

Thr Leu Ala Val Asn Tyr Glu Lys Glu Glu Glu Phe Leu Thr Asn Glu
    130                 135                 140

Leu Ser Arg Lys Leu Met Gln Leu Gln His Glu Lys Ala Glu Leu Glu
145                 150                 155                 160

Gln His Leu Glu Gln Glu Gln Glu Phe Gln Val Asn Lys Leu Met Lys
                165                 170                 175

Lys Ile Lys Lys Leu Glu Asn Asp Thr Ile Ser Lys Gln Leu Thr Leu
            180                 185                 190

Glu Gln Leu Arg Arg Glu Lys Ile Asp Leu Glu Asn Thr Leu Glu Gln
        195                 200                 205

Glu Gln Glu Ala Leu Val Asn Arg Leu Trp Lys Arg Met Asp Lys Leu
    210                 215                 220

Glu Ala Glu Lys Arg Ile Leu Gln Glu Lys Leu Asp Gln Pro Val Ser
225                 230                 235                 240

Ala Pro Pro Ser Pro Arg Asp Ile Ser Met Glu Ile Asp Ser Pro Glu
                245                 250                 255

Asn Met Met Arg His Ile Arg Phe Leu Lys Asn Glu Val Glu Arg Leu
            260                 265                 270

Lys Lys Gln Leu Arg Ala Ala Gln Leu Gln His Ser Glu Lys Met Ala
        275                 280                 285
```

-continued

```
Gln Tyr Leu Glu Glu Glu Arg His Met Arg Glu Glu Asn Leu Arg Leu
    290                 295                 300

Gln Arg Lys Leu Gln Arg Glu Met Glu Arg Arg Glu Ala Leu Cys Arg
305                 310                 315                 320

Gln Leu Ser Glu Ser Glu Ser Ser Leu Glu Met Asp Asp Glu Arg Tyr
                325                 330                 335

Phe Asn Glu Met Ser Ala Gln Gly Leu Arg Pro Arg Thr Val Ser Ser
            340                 345                 350

Pro Ile Pro Tyr Thr Pro Ser Pro Ser Ser Ser Arg Pro Ile Ser Pro
        355                 360                 365

Gly Leu Ser Tyr Ala Ser His Thr Val Gly Phe Thr Pro Pro Thr Ser
    370                 375                 380

Leu Thr Arg Ala Gly Met Ser Tyr Tyr Asn Ser Pro Gly Leu His Val
385                 390                 395                 400

Gln His Met Gly Thr Ser His Gly Ile Thr Arg Pro Ser Pro Arg Arg
                405                 410                 415

Ser Asn Ser Pro Asp Lys Phe Lys Arg Pro Thr Pro Pro Pro Ser Pro
            420                 425                 430

Asn Thr Gln Thr Pro Val Gln Pro Pro Pro Pro Pro Pro Pro Pro Pro
        435                 440                 445

Met Gln Pro Thr Val Pro Ser Ala Ala Thr Ser Gln Pro Thr Pro Ser
    450                 455                 460

Gln His Ser Ala His Pro Ser Ser Gln Pro
465                 470


<210> SEQ ID NO 33
<211> LENGTH: 3748
<212> TYPE: DNA
<213> ORGANISM: Homo sapiens
<220> FEATURE:
<221> NAME/KEY: misc_feature
<223> OTHER INFORMATION: NCOA4 variant 1 (NM_001145260.1)

<400> SEQUENCE: 33

agagggcagt caagggcttc tggctgaccc gagcggagat ctcgcgagac tgtcagacgt      60

atggcgagag gtgtgggagg aagattgtgt tgtcgcgaga actctgcctt tgggccgtag     120

gttagtgtgg ggccgtgtct cagtccaccc aaggtctcct cggatcgcct ggagaggcac     180

tcggacctgt tatgtctgga cacattgctt caacatagaa cgcacatgaa caatgtggag     240

gtctaggctg gaatgggggc ccagttgacc acttttgctc tagctggagc agtgaggaga     300

atgaatacct tccaagacca gagtggcagc tccagtaata gagaacccct tttgaggtgt     360

agtgatgcac ggagggactt ggagcttgct attggtggag ttctccgggc tgaacagcaa     420

attaaagata acttgcgaga ggtcaaagct cagattcaca gttgcataag ccgtcacctg     480

gaatgtctta gaagccgtga ggtatggctg tatgaacagg tggaccttat ttatcagctt     540

aaagaggaga cacttcaaca gcaggctcag cagctctact cgttattggg ccagttcaat     600

tgtcttactc atcaactgga gtgtacccaa aacaaagatc tagccaatca agtctctgtg     660

tgcctggaga gactgggcag tttgaccctt aagcctgaag attcaactgt cctgctcttt     720

gaagctgaca caattactct gcgccagacc atcaccacat ttgggtctct caaaaccatt     780

caaattcctg agcacttgat ggctcatgct agttcagcaa atattgggcc cttcctggag     840

aagagaggct gtatctccat gccagagcag aagtcagcat ccggtattgt agctgtccct     900

ttcagcgaat ggctccttgg aagcaaacct gccagtggtt atcaagctcc ttacataccc     960
```

```
agcaccgacc cccaggactg gcttacccaa aagcagacct tggagaacag tcagacttct   1020
tccagagcct gcaatttctt caataatgtc gggggaaacc taaagggctt agaaaactgg   1080
ctcctcaaga gtgaaaaatc aagttatcaa aagtgtaaca gccattccac tactagttct   1140
ttctccattg aaatggaaaa ggttggagat caagagcttc ctgatcaaga tgagatggac   1200
ctatcagatt ggctagtgac tccccaggaa tcccataagc tgcggaagcc tgagaatggc   1260
agtcgtgaaa ccagtgagaa gtttaagctc ttattccagt cctataatgt gaatgattgg   1320
cttgtcaaga ctgactcctg taccaactgt cagggaaacc agcccaaagg tgtggagatt   1380
gaaaacctgg gcaatctgaa gtgcctgaat gaccacttgg aggccaagaa accattgtcc   1440
acccccagca tggttacaga ggattggctt gtccagaacc atcaggaccc atgtaaggta   1500
gaggaggtgt gcagagccaa tgagccctgc acaagctttg cagagtgtgt gtgtgatgag   1560
aattgtgaga aggaggctct gtataagtgg cttctgaaga aagaaggaaa ggataaaaat   1620
gggatgcctg tggaacccaa acctgagcct gagaagcata aagattccct gaatatgtgg   1680
ctctgtccta gaaaagaagt aatagaacaa actaaagcac caaaggcaat gactccttct   1740
agaattgctg attccttcca agtcataaag aacagcccct tgtcggagtg gcttatcagg   1800
cccccataca aagaaggaag tcccaaggaa gtgcctggta ctgaagacag agctggcaaa   1860
cagaagttta aaagccccat gaatacttcc tggtgttcct ttaacacagc tgactgggtc   1920
ctgccaggaa agaagatggg caacctcagc cagttatctt ctggagaaga caagtggctg   1980
cttcgaaaga aggcccagga agtattactt aattcacctc tacaggagga acataacttc   2040
cccccagacc attatggcct ccctgcagtt tgtgatctct ttgcctgtat gcagcttaaa   2100
gttgataaag agaagtggtt atatcgaact cctctacagg catacttcaa aatgaacttt   2160
caagatgtaa ccgttgggaa ttttcagatc ccatgtggat tctagtagtt tatataccta   2220
cctcgaagat gtgaaggaat ggacaagagt tgagcagcct ttctgctgat tatcacacat   2280
catgagctga gtgactgcag cttgccaaat ctttgtgttt ctgggtctga ccaattagct   2340
tagttcttct cctgcctaat tttgaactag taaagcaaag tgagtcatca gattatgagt   2400
tactgtttaa aagaaaaatg ctgtttattc atgctgaggt gattcagttc cctccttctt   2460
acagaagtat tttaattcac cccacactag aaatgcagca tctttgtgga cgtctttttc   2520
acaagcctcc aaggctcctt agattgggtc gttactaaaa gtacattaaa acactcttgt   2580
ttatcgaagt atattgatgt attctaaagc tagtaaactt ccctaacgtt taattgccct   2640
acagatgctt ctcttgctgt gggttttctt ttgttagtgg tctgaaataa ttattttcct   2700
gttctattaa tacatagtgt attttgcaca aaaaaattaa cctggtcaat agtgattacc   2760
aaaatatata ttaataatct tggcaatttt tgacattaat tatgaaacat tttagcccac   2820
gttagttcta cattattctt cacttaaact cagctactgc aaattttgtc tttctgtaaa   2880
tgttattaaa atatccagtg agctctttag aaggactcag tattatttca agactatttt   2940
tgaggtaatt ctagcctttt aaaatattct acagacctac ggggcttaaa agaaccccag   3000
taccgactaa gcaaataggc aaaagacatg ttggaaatgt agtatagtac ttgaaacagt   3060
cactatcata gggataattg gtgcatcctg tgtaaatgga agctgagctt gacacctggt   3120
gcttttaagt agggataaag tcatcctctc actgcaagca cagcatacct gtacctccaa   3180
aagtgacgtt ttagtgaaca ggccgttttc aacacttgtg ccttggggtg ttcattgaag   3240
ctttgtgaaa actactgatg ttttctcagt ctccttaaag ttacgtccat gctttaaaat   3300
```

```
gtctgtgtag gagagaagtg gggtttataa tgttttctct aagatatctt tgctgctttc   3360

cagactttga aactattaag cttcttaact gcctcttacc ggaaatactt ctggggaaac   3420

ttcatggtcc caaaatgtca ttgccataca gcttcactag agttctttga accacagctg   3480

aaaagagctt tgtattattt tttaattccc tccccagata tcatttagga gtattatata   3540

aaggtggtgg gcaaaaacaa tgtaaggagc ctttccagtt atcttgagtt gcagctctgt   3600

agtttcttga ggccaaacac actgtatttt acaagtcaaa atataattta cattaatcac   3660

tatgttaatg agtatgtaaa acattctttt gcattgatga attttgtatc tgcttccatt   3720

aaaagcataa cagccataaa aaaaaaaa                                      3748
```

<210> SEQ ID NO 34
<211> LENGTH: 3659
<212> TYPE: DNA
<213> ORGANISM: Homo sapiens
<220> FEATURE:
<221> NAME/KEY: misc_feature
<223> OTHER INFORMATION: NCOA4 variant 2 (NM_001145261.1)

<400> SEQUENCE: 34

```
agagggcagt caagggcttc tggctgaccc gagcggagat ctcgcgagac tgtcagacgt     60

atggcgagag gtgtgggagg aagattgtgt tgtcgcgaga actctgcctt tgggccgtag    120

gttagtgtgg ggccgtgtct cagtccaccc aaggtctcct cggatcgcct ggagaggcac    180

tcggacctgt tatgtctgga cacattgctt caacatagaa cgcacatgaa caatgtggag    240

gtctaggctg gaatgggggc ccagttgacc acttttgctc tagctggagc agtgaggaga    300

atgaatacct tccaagacca gagtggcagc tccagtaata gagaacccct tttgaggtgt    360

agtgatgcac ggagggactt ggagcttgct attggtggag ttctccgggc tgaacagcaa    420

attaaagata acttgcgaga ggtcaaagct cagattcaca gttgcataag ccgtcacctg    480

gaatgtctta gaagccgtga ggtatggctg tatgaacagg tggaccttat ttatcagctt    540

aaagaggaga cacttcaaca gcaggctcag cagctctact cgttattggg ccagttcaat    600

tgtcttactc atcaactgga gtgtacccaa aacaaagatc tagccaatca agtctctgtg    660

tgcctggaga gactgggcag tttgaccctt aagcctgaag attcaactgt cctgctcttt    720

gaagctgaca caattactct gcgccagacc atcaccacat ttgggtctct caaaaccatt    780

caaattcctg agcacttgat ggctcatgct agttcagcaa atattgggcc cttcctggag    840

aagagaggct gtatctccat gccagagcag aagtcagcat ccggtattgt agctgtccct    900

ttcagcgaat ggctccttgg aagcaaacct gccagtggtt atcaagctcc ttacataccc    960

agcaccgacc cccaggactg gcttacccaa aagcagacct tggagaacag tcagacttct   1020

tccagagcct gcaatttctt caataatgtc gggggaaacc taaagggctt agaaaactgg   1080

ctcctcaaga gtgaaaaatc aagttatcaa aagtgtaaca gccattccac tactagttct   1140

ttctccattg aaatggaaaa ggttggagat caagagcttc ctgatcaaga tgagatggac   1200

ctatcagatt ggctagtgac tccccaggaa tcccataagc tgcggaagcc tgagaatggc   1260

agtcgtgaaa ccagtgagaa gtttaagctc ttattccagt cctataatgt gaatgattgg   1320

cttgtcaaga ctgactcctg taccaactgt cagggaaacc agcccaaagg tgtggagatt   1380

gaaaacctgg gcaatctgaa gtgcctgaat gaccacttgg aggccaagaa accattgtcc   1440

acccccagca tggttacaga ggattggctt gtccagaacc atcaggaccc atgtaaggta   1500

gaggaggtgt gcagagccaa tgagccctgc acaagctttg cagagtgtgt gtgtgatgag   1560
```

-continued

```
aattgtgaga aggaggctct gtataagtgg cttctgaaga aagaaggaaa ggataaaaat   1620
gggatgcctg tggaacccaa acctgagcct gagaagcata aagattccct gaatatgtgg   1680
ctctgtccta gaaaagaagt aatagaacaa actaaagcac caaaggcaat gactccttct   1740
agaattgctg attccttcca agtcataaag aacagcccct tgtcggagtg gcttatcagg   1800
cccccataca aagaaggaag tcccaaggaa gtgcctggta ctgaagacag agctggcaaa   1860
cagaagttta aaagccccat gaatacttcc tggtgttcct ttaacacagc tgactgggtc   1920
ctgccaggaa agaagatggg caacctcagc cagttatctt ctggagaaga caagtggctg   1980
cttcgaaaga aggcccagga agtattactt aattcacctc tacaggagga acataacttc   2040
cccccagacc attatggcct ccctgcagtt tgtgatctct ttgcctgtat gcagcttaaa   2100
gttgataaag agaagtggtt atatcgaact cctctacaga tgtgaaggaa tggacaagag   2160
ttgagcagcc tttctgctga ttatcacaca tcatgagctg agtgactgca gcttgccaaa   2220
tctttgtgtt tctgggtctg accaattagc ttagttcttc tcctgcctaa ttttgaacta   2280
gtaaagcaaa gtgagtcatc agattatgag ttactgttta aaagaaaaat gctgtttatt   2340
catgctgagg tgattcagtt ccctccttct tacagaagta ttttaattca ccccacacta   2400
gaaatgcagc atctttgtgg acgtcttttt cacaagcctc caaggctcct tagattgggt   2460
cgttactaaa agtacattaa aacactcttg tttatcgaag tatattgatg tattctaaag   2520
ctagtaaact tccctaacgt ttaattgccc tacagatgct tctcttgctg tgggtttttct  2580
tttgttagtg gtctgaaata attattttcc tgttctatta atacatagtg tattttgcac   2640
aaaaaaatta acctggtcaa tagtgattac caaaatatat attaataatc ttggcaattt   2700
ttgacattaa ttatgaaaca ttttagccca cgttagttct acattattct tcacttaaac   2760
tcagctactg caaattttgt ctttctgtaa atgttattaa aatatccagt gagctcttta   2820
gaaggactca gtattatttc aagactattt ttgaggtaat tctagccttt taaaatattc   2880
tacagaccta cggggcttaa aagaacccca gtaccgacta agcaaatagg caaaagacat   2940
gttggaaatg tagtatagta cttgaaacag tcactatcat agggataatt ggtgcatcct   3000
gtgtaaatgg aagctgagct tgacacctgg tgcttttaag tagggataaa gtcatcctct   3060
cactgcaagc acagcatacc tgtacctcca aaagtgacgt tttagtgaac aggccgtttt   3120
caacacttgt gccttggggt gttcattgaa gctttgtgaa aactactgat gttttctcag   3180
tctccttaaa gttacgtcca tgctttaaaa tgtctgtgta ggagagaagt ggggtttata   3240
atgttttctc taagatatct ttgctgcttt ccagactttg aaactattaa gcttcttaac   3300
tgcctcttac cggaaatact tctggggaaa cttcatggtc ccaaaatgtc attgccatac   3360
agcttcacta gagttctttg aaccacagct gaaaagagct ttgtattatt ttttaattcc   3420
ctccccagat atcatttagg agtattatat aaaggtggtg ggcaaaaaca atgtaaggag   3480
cctttccagt tatcttgagt tgcagctctg tagtttcttg aggccaaaca cactgtattt   3540
tacaagtcaa aatataattt acattaatca ctatgttaat gagtatgtaa aacattcttt   3600
tgcattgatg aattttgtat ctgcttccat taaaagcata acagccataa aaaaaaaaa    3659
```

<210> SEQ ID NO 35
<211> LENGTH: 3588
<212> TYPE: DNA
<213> ORGANISM: Homo sapiens
<220> FEATURE:
<221> NAME/KEY: misc_feature
<223> OTHER INFORMATION: NCOA4 variant 3 (NM_001145262.1)

-continued

<400> SEQUENCE: 35

```
attgattcaa ttttacactg tgccaggcat tgtggcattc cacacaaatg gtgagaagct     60
aaaagtgaga aatttggcac aggtgaagaa ggctgggtaa cacatttgaa agactgctaa    120
acaggtcttg catgactggc ctaagtgcaa agtgaagcag cccatcacgc tccagctctc    180
caaatcggag ccggcatttc acccatgtga tacaggagca gtgaggagaa tgaatacctt    240
ccaagaccag agtggcagct ccagtaatag agaacccctt ttgaggtgta gtgatgcacg    300
gagggacttg gagcttgcta ttggtggagt tctccgggct gaacagcaaa ttaaagataa    360
cttgcgagag gtcaaagctc agattcacag ttgcataagc cgtcacctgg aatgtcttag    420
aagccgtgag gtatggctgt atgaacaggt ggaccttatt tatcagctta aagaggagac    480
acttcaacag caggctcagc agctctactc gttattgggc cagttcaatt gtcttactca    540
tcaactggag tgtacccaaa acaaagatct agccaatcaa gtctctgtgt gcctggagag    600
actgggcagt ttgaccctta agcctgaaga ttcaactgtc ctgctctttg aagctgacac    660
aattactctg cgccagacca tcaccacatt tgggtctctc aaaaccattc aaattcctga    720
gcacttgatg gctcatgcta gttcagcaaa tattgggccc ttcctggaga agagaggctg    780
tatctccatg ccagagcaga agtcagcatc cggtattgta gctgtccctt tcagcgaatg    840
gctccttgga agcaaacctg ccagtggtta tcaagctcct tacataccca gcaccgaccc    900
ccaggactgg cttacccaaa agcagacctt ggagaacagt cagacttctt ccagagcctg    960
caatttcttc aataatgtcg ggggaaacct aaagggctta gaaaactggc tcctcaagag   1020
tgaaaaatca agttatcaaa agtgtaacag ccattccact actagttctt tctccattga   1080
aatggaaaag gttggagatc aagagcttcc tgatcaagat gagatggacc tatcagattg   1140
gctagtgact ccccaggaat cccataagct gcggaagcct gagaatggca gtcgtgaaac   1200
cagtgagaag tttaagctct tattccagtc ctataatgtg aatgattggc ttgtcaagac   1260
tgactcctgt accaactgtc agggaaacca gcccaaaggt gtggagattg aaaacctggg   1320
caatctgaag tgcctgaatg accacttgga ggccaagaaa ccattgtcca cccccagcat   1380
ggttacagag gattggcttg tccagaacca tcaggaccca tgtaaggtag aggaggtgtg   1440
cagagccaat gagccctgca caagctttgc agagtgtgtg tgtgatgaga attgtgagaa   1500
ggaggctctg tataagtggc ttctgaagaa agaaggaaag gataaaaatg ggatgcctgt   1560
ggaacccaaa cctgagcctg agaagcataa agattccctg aatatgtggc tctgtcctag   1620
aaaagaagta atagaacaaa ctaaagcacc aaaggcaatg actccttcta gaattgctga   1680
ttccttccaa gtcataaaga acagcccctt gtcggagtgg cttatcaggc cccccataca   1740
agaaggaagt cccaaggaag tgcctggtac tgaagacaga gctggcaaac agaagtttaa   1800
aagccccatg aatacttcct ggtgttcctt taacacagct gactgggtcc tgccaggaaa   1860
gaagatgggc aacctcagcc agttatcttc tggagaagac aagtggctgc ttcgaaagaa   1920
ggcccaggaa gtattactta attcacctct acaggaggaa cataacttcc ccccagacca   1980
ttatggcctc cctgcagttt gtgatctctt tgcctgtatg cagcttaaag ttgataaaga   2040
gaagtggtta tatcgaactc ctctacagat gtgaaggaat ggacaagagt tgagcagcct   2100
ttctgctgat tatcacacat catgagctga gtgactgcag cttgccaaat ctttgtgttt   2160
ctgggtctga ccaattagct tagttcttct cctgcctaat tttgaactag taaagcaaag   2220
tgagtcatca gattatgagt tactgtttaa aagaaaaatg ctgtttattc atgctgaggt   2280
gattcagttc cctccttctt acagaagtat tttaattcac cccacactag aaatgcagca   2340
```

```
tctttgtgga cgtctttttc acaagcctcc aaggctcctt agattgggtc gttactaaaa   2400

gtacattaaa acactcttgt ttatcgaagt atattgatgt attctaaagc tagtaaactt   2460

ccctaacgtt taattgccct acagatgctt ctcttgctgt gggtttttctt ttgttagtgg   2520

tctgaaataa ttattttcct gttctattaa tacatagtgt attttgcaca aaaaaattaa   2580

cctggtcaat agtgattacc aaaatatata ttaataatct tggcaatttt tgacattaat   2640

tatgaaacat tttagcccac gttagttcta cattattctt cacttaaact cagctactgc   2700

aaattttgtc tttctgtaaa tgttattaaa atatccagtg agctctttag aaggactcag   2760

tattatttca agactatttt tgaggtaatt ctagcctttt aaaatattct acagacctac   2820

ggggcttaaa agaaccccag taccgactaa gcaaataggc aaaagacatg ttggaaatgt   2880

agtatagtac ttgaaacagt cactatcata gggataattg gtgcatcctg tgtaaatgga   2940

agctgagctt gacacctggt gcttttaagt agggataaag tcatcctctc actgcaagca   3000

cagcatacct gtacctccaa aagtgacgtt ttagtgaaca ggccgttttc aacacttgtg   3060

ccttggggtg ttcattgaag ctttgtgaaa actactgatg ttttctcagt ctccttaaag   3120

ttacgtccat gctttaaaat gtctgtgtag gagagaagtg ggtttataa tgttttctct   3180

aagatatctt tgctgctttc cagactttga aactattaag cttcttaact gcctcttacc   3240

ggaaatactt ctggggaaac ttcatggtcc caaaatgtca ttgccataca gcttcactag   3300

agttctttga accacagctg aaaagagctt tgtattattt tttaattccc tccccagata   3360

tcatttagga gtattatata aaggtggtgg gcaaaaacaa tgtaaggagc ctttccagtt   3420

atcttgagtt gcagctctgt agtttcttga ggccaaacac actgtatttt acaagtcaaa   3480

atataattta cattaatcac tatgttaatg agtatgtaaa acattctttt gcattgatga   3540

attttgtatc tgcttccatt aaaagcataa cagccataaa aaaaaaaa                3588
```

```
<210> SEQ ID NO 36
<211> LENGTH: 3562
<212> TYPE: DNA
<213> ORGANISM: Homo sapiens
<220> FEATURE:
<221> NAME/KEY: misc_feature
<223> OTHER INFORMATION: NCOA4 variant 4 (NM_001145263.1)

<400> SEQUENCE: 36

agagggcagt caagggcttc tggctgaccc gagcggagat ctcgcgagac tgtcagacgt     60

atggcgagag gtgtgggagg aagattgtgt tgtcgcgaga actctgcctt tgggccgtag    120

gttagtgtgg ggccgtgtct cagtccaccc aaggtctcct cggatcgcct ggagaggcac    180

tcggacctgg agcagtgagg agaatgaata ccttccaaga ccagagtggc agctccagta    240

atagagaacc ccttttgagg tgtagtgatg cacggaggga cttggagctt gctattggtg    300

gagttctccg ggctgaacag caaattaaag ataacttgcg agaggtcaaa gctcagattc    360

acagttgcat aagccgtcac ctggaatgtc ttagaagccg tgaggtatgg ctgtatgaac    420

aggtggacct tatttatcag cttaaagagg agacacttca acagcaggct cagcagctct    480

actcgttatt gggccagttc aattgtctta ctcatcaact ggagtgtacc caaaacaaag    540

atctagccaa tcaagtctct gtgtgcctgg agagactggg cagtttgacc cttaagcctg    600

aagattcaac tgtcctgctc tttgaagctg acacaattac tctgcgccag accatcacca    660

catttgggtc tctcaaaacc attcaaattc ctgagcactt gatggctcat gctagttcag    720

caaatattgg gcccttcctg gagaagagag gctgtatctc catgccagag cagaagtcag    780
```

-continued

```
catccggtat tgtagctgtc cctttcagcg aatggctcct tggaagcaaa cctgccagtg    840
gttatcaagc tccttacata cccagcaccg acccccagga ctggcttacc caaaagcaga    900
ccttggagaa cagtcagact tcttccagag cctgcaattt cttcaataat gtcgggggaa    960
acctaaaggg cttagaaaac tggctcctca agagtgaaaa atcaagttat caaaagtgta   1020
acagccattc cactactagt tctttctcca ttgaaatgga aaaggttgga gatcaagagc   1080
ttcctgatca agatgagatg gacctatcag attggctagt gactccccag gaatcccata   1140
agctgcggaa gcctgagaat ggcagtcgtg aaaccagtga gaagtttaag ctcttattcc   1200
agtcctataa tgtgaatgat tggcttgtca agactgactc ctgtaccaac tgtcagggaa   1260
accagcccaa aggtgtggag attgaaaacc tgggcaatct gaagtgcctg aatgaccact   1320
tggaggccaa gaaaccattg tccaccccca gcatggttac agaggattgg cttgtccaga   1380
accatcagga cccatgtaag gtagaggagg tgtgcagagc caatgagccc tgcacaagct   1440
ttgcagagtg tgtgtgtgat gagaattgtg agaaggaggc tctgtataag tggcttctga   1500
agaaagaagg aaaggataaa aatgggatgc ctgtggaacc caaacctgag cctgagaagc   1560
ataaagattc cctgaatatg tggctctgtc ctagaaaaga agtaatagaa caaactaaag   1620
caccaaaggc aatgactcct tctagaattg ctgattcctt ccaagtcata aagaacagcc   1680
ccttgtcgga gtggcttatc aggcccccat acaaagaagg aagtcccaag gaagtgcctg   1740
gtactgaaga cagagctggc aaacagaagt ttaaaagccc catgaatact tcctggtgtt   1800
cctttaacac agctgactgg gtcctgccag gaaagaagat gggcaacctc agccagttat   1860
cttctggaga agacaagtgg ctgcttcgaa agaaggccca ggaagtatta cttaattcac   1920
ctctacagga ggaacataac ttcccccag accattatgg cctccctgca gtttgtgatc   1980
tctttgcctg tatgcagctt aaagttgata aagagaagtg gttatatcga actcctctac   2040
agatgtgaag gaatggacaa gagttgagca gcctttctgc tgattatcac acatcatgag   2100
ctgagtgact gcagcttgcc aaatctttgt gtttctgggt ctgaccaatt agcttagttc   2160
ttctcctgcc taattttgaa ctagtaaagc aaagtgagtc atcagattat gagttactgt   2220
ttaaaagaaa aatgctgttt attcatgctg aggtgattca gttccctcct tcttacagaa   2280
gtattttaat tcaccccaca ctagaaatgc agcatctttg tggacgtctt tttcacaagc   2340
ctccaaggct ccttagattg ggtcgttact aaaagtacat taaaacactc ttgtttatcg   2400
aagtatattg atgtattcta aagctagtaa acttccctaa cgtttaattg ccctacagat   2460
gcttctcttg ctgtgggttt tcttttgtta gtggtctgaa ataattattt tcctgttcta   2520
ttaatacata gtgtattttg cacaaaaaaa ttaacctggt caatagtgat taccaaaata   2580
tatattaata atcttggcaa tttttgacat taattatgaa acattttagc ccacgttagt   2640
tctacattat tcttcactta aactcagcta ctgcaaattt tgtctttctg taaatgttat   2700
taaaatatcc agtgagctct ttagaaggac tcagtattat ttcaagacta tttttgaggt   2760
aattctagcc ttttaaaata ttctacagac ctacggggct taaaagaacc ccagtaccga   2820
ctaagcaaat aggcaaaaga catgttggaa atgtagtata gtacttgaaa cagtcactat   2880
catagggata attggtgcat cctgtgtaaa tggaagctga gcttgacacc tggtgctttt   2940
aagtagggat aaagtcatcc tctcactgca agcacagcat acctgtacct ccaaaagtga   3000
cgttttagtg aacaggccgt tttcaacact tgtgccttgg ggtgttcatt gaagctttgt   3060
gaaaactact gatgttttct cagtctcctt aaagttacgt ccatgcttta aaatgtctgt   3120
```

```
gtaggagaga agtggggttt ataatgtttt ctctaagata tctttgctgc tttccagact   3180

ttgaaactat taagcttctt aactgcctct taccggaaat acttctgggg aaacttcatg   3240

gtcccaaaat gtcattgcca tacagcttca ctagagttct ttgaaccaca gctgaaaaga   3300

gctttgtatt attttttaat tccctcccca gatatcattt aggagtatta tataaaggtg   3360

gtgggcaaaa acaatgtaag gagcctttcc agttatcttg agttgcagct ctgtagtttc   3420

ttgaggccaa acacactgta ttttacaagt caaaatataa tttacattaa tcactatgtt   3480

aatgagtatg taaaacattc ttttgcattg atgaattttg tatctgcttc cattaaaagc   3540

ataacagcca taaaaaaaaa aa                                             3562
```

```
<210> SEQ ID NO 37
<211> LENGTH: 3502
<212> TYPE: DNA
<213> ORGANISM: Homo sapiens
<220> FEATURE:
<221> NAME/KEY: misc_feature
<223> OTHER INFORMATION: NCOA4 variant 5 (NM_005437.3)

<400> SEQUENCE: 37
```

```
gaactggagt tgccgtgtga cgcgtgggcg ggacgaggcc cgggctcggg gacctttcgc     60

actcgggtca ggggtaaagc agcctgtcgc ttgccgggca gctggtgagt cggtgacctg    120

gcctgtgagg agcagtgagg agaatgaata ccttccaaga ccagagtggc agctccagta    180

atagagaacc ccttttgagg tgtagtgatg cacggaggga cttggagctt gctattggtg    240

gagttctccg ggctgaacag caaattaaag ataacttgcg agaggtcaaa gctcagattc    300

acagttgcat aagccgtcac ctggaatgtc ttagaagccg tgaggtatgg ctgtatgaac    360

aggtggacct tatttatcag cttaaagagg agacacttca acagcaggct cagcagctct    420

actcgttatt gggccagttc aattgtctta ctcatcaact ggagtgtacc caaaacaaag    480

atctagccaa tcaagtctct gtgtgcctgg agagactggg cagtttgacc cttaagcctg    540

aagattcaac tgtcctgctc tttgaagctg acacaattac tctgcgccag accatcacca    600

catttgggtc tctcaaaacc attcaaattc ctgagcactt gatggctcat gctagttcag    660

caaatattgg gcccttcctg gagaagagag gctgtatctc catgccagag cagaagtcag    720

catccggtat tgtagctgtc cctttcagcg aatggctcct tggaagcaaa cctgccagtg    780

gttatcaagc tccttacata cccagcaccg acccccagga ctggcttacc caaaagcaga    840

ccttggagaa cagtcagact tcttccagag cctgcaattt cttcaataat gtcgggggaa    900

acctaaaggg cttagaaaac tggctcctca agagtgaaaa atcaagttat caaaagtgta    960

acagccattc cactactagt tctttctcca ttgaaatgga aaaggttgga gatcaagagc   1020

ttcctgatca agatgagatg gacctatcag attggctagt gactccccag gaatcccata   1080

agctgcggaa gcctgagaat ggcagtcgtg aaaccagtga gaagtttaag ctcttattcc   1140

agtcctataa tgtgaatgat tggcttgtca agactgactc ctgtaccaac tgtcagggaa   1200

accagcccaa aggtgtggag attgaaaacc tgggcaatct gaagtgcctg aatgaccact   1260

tggaggccaa gaaaccattg tccacccccca gcatggttac agaggattgg cttgtccaga   1320

accatcagga cccatgtaag gtagaggagg tgtgcagagc caatgagccc tgcacaagct   1380

ttgcagagtg tgtgtgtgat gagaattgtg agaaggaggc tctgtataag tggcttctga   1440

agaaagaagg aaaggataaa aatgggatgc ctgtggaacc caaacctgag cctgagaagc   1500

ataaagattc cctgaatatg tggctctgtc ctagaaaaga agtaatagaa caaactaaag   1560
```

```
caccaaaggc aatgactcct tctagaattg ctgattcctt ccaagtcata aagaacagcc   1620
ccttgtcgga gtggcttatc aggcccccat acaaagaagg aagtcccaag gaagtgcctg   1680
gtactgaaga cagagctggc aaacagaagt ttaaaagccc catgaatact tcctggtgtt   1740
cctttaacac agctgactgg gtcctgccag gaaagaagat gggcaacctc agccagttat   1800
cttctggaga agacaagtgg ctgcttcgaa agaaggccca ggaagtatta cttaattcac   1860
ctctacagga ggaacataac ttccccccag accattatgg cctccctgca gtttgtgatc   1920
tctttgcctg tatgcagctt aaagttgata aagagaagtg gttatatcga actcctctac   1980
agatgtgaag gaatggacaa gagttgagca gcctttctgc tgattatcac acatcatgag   2040
ctgagtgact gcagcttgcc aaatctttgt gtttctgggt ctgaccaatt agcttagttc   2100
ttctcctgcc taattttgaa ctagtaaagc aaagtgagtc atcagattat gagttactgt   2160
ttaaaagaaa aatgctgttt attcatgctg aggtgattca gttccctcct tcttacagaa   2220
gtattttaat tcaccccaca ctagaaatgc agcatctttg tggacgtctt tttcacaagc   2280
ctccaaggct ccttagattg ggtcgttact aaaagtacat taaaacactc ttgtttatcg   2340
aagtatattg atgtattcta aagctagtaa acttccctaa cgtttaattg ccctacagat   2400
gcttctcttg ctgtgggttt tcttttgtta gtggtctgaa ataattattt tcctgttcta   2460
ttaatacata gtgtattttg cacaaaaaaa ttaacctggt caatagtgat taccaaaata   2520
tatattaata atcttggcaa tttttgacat taattatgaa acattttagc ccacgttagt   2580
tctacattat tcttcactta aactcagcta ctgcaaattt tgtctttctg taaatgttat   2640
taaaatatcc agtgagctct ttagaaggac tcagtattat ttcaagacta tttttgaggt   2700
aattctagcc ttttaaaata ttctacagac ctacggggct taaaagaacc ccagtaccga   2760
ctaagcaaat aggcaaaaga catgttggaa atgtagtata gtacttgaaa cagtcactat   2820
catagggata attggtgcat cctgtgtaaa tggaagctga gcttgacacc tggtgctttt   2880
aagtagggat aaagtcatcc tctcactgca agcacagcat acctgtacct ccaaaagtga   2940
cgttttagtg aacaggccgt tttcaacact tgtgccttgg ggtgttcatt gaagctttgt   3000
gaaaactact gatgttttct cagtctcctt aaagttacgt ccatgcttta aaatgtctgt   3060
gtaggagaga agtggggttt ataatgtttt ctctaagata tctttgctgc tttccagact   3120
ttgaaactat taagcttctt aactgcctct taccggaaat acttctgggg aaacttcatg   3180
gtcccaaaat gtcattgcca tacagcttca ctagagttct ttgaaccaca gctgaaaaga   3240
gctttgtatt attttttaat tccctcccca gatatcattt aggagtatta tataaaggtg   3300
gtgggcaaaa acaatgtaag gagcctttcc agttatcttg agttgcagct ctgtagtttc   3360
ttgaggccaa acacactgta ttttacaagt caaaatataa tttacattaa tcactatgtt   3420
aatgagtatg taaaacattc ttttgcattg atgaatttttg tatctgcttc cattaaaagc  3480
ataacagcca taaaaaaaaa aa                                            3502
```

<210> SEQ ID NO 38
<211> LENGTH: 650
<212> TYPE: PRT
<213> ORGANISM: Homo sapiens
<220> FEATURE:
<221> NAME/KEY: misc_feature
<223> OTHER INFORMATION: NCOA4 isoform 1 (NP_001138732.1)

<400> SEQUENCE: 38

```
Met Gly Ala Gln Leu Thr Thr Phe Ala Leu Ala Gly Ala Val Arg Arg
1               5                   10                  15
```

```
Met Asn Thr Phe Gln Asp Gln Ser Gly Ser Ser Ser Asn Arg Glu Pro
            20                  25                  30

Leu Leu Arg Cys Ser Asp Ala Arg Arg Asp Leu Glu Leu Ala Ile Gly
        35                  40                  45

Gly Val Leu Arg Ala Glu Gln Gln Ile Lys Asp Asn Leu Arg Glu Val
    50                  55                  60

Lys Ala Gln Ile His Ser Cys Ile Ser Arg His Leu Glu Cys Leu Arg
65                  70                  75                  80

Ser Arg Glu Val Trp Leu Tyr Glu Gln Val Asp Leu Ile Tyr Gln Leu
                85                  90                  95

Lys Glu Glu Thr Leu Gln Gln Gln Ala Gln Gln Leu Tyr Ser Leu Leu
            100                 105                 110

Gly Gln Phe Asn Cys Leu Thr His Gln Leu Glu Cys Thr Gln Asn Lys
        115                 120                 125

Asp Leu Ala Asn Gln Val Ser Val Cys Leu Glu Arg Leu Gly Ser Leu
    130                 135                 140

Thr Leu Lys Pro Glu Asp Ser Thr Val Leu Leu Phe Glu Ala Asp Thr
145                 150                 155                 160

Ile Thr Leu Arg Gln Thr Ile Thr Thr Phe Gly Ser Leu Lys Thr Ile
                165                 170                 175

Gln Ile Pro Glu His Leu Met Ala His Ala Ser Ser Ala Asn Ile Gly
            180                 185                 190

Pro Phe Leu Glu Lys Arg Gly Cys Ile Ser Met Pro Glu Gln Lys Ser
        195                 200                 205

Ala Ser Gly Ile Val Ala Val Pro Phe Ser Glu Trp Leu Leu Gly Ser
    210                 215                 220

Lys Pro Ala Ser Gly Tyr Gln Ala Pro Tyr Ile Pro Ser Thr Asp Pro
225                 230                 235                 240

Gln Asp Trp Leu Thr Gln Lys Gln Thr Leu Glu Asn Ser Gln Thr Ser
                245                 250                 255

Ser Arg Ala Cys Asn Phe Phe Asn Asn Val Gly Gly Asn Leu Lys Gly
            260                 265                 270

Leu Glu Asn Trp Leu Leu Lys Ser Glu Lys Ser Ser Tyr Gln Lys Cys
        275                 280                 285

Asn Ser His Ser Thr Thr Ser Ser Phe Ser Ile Glu Met Glu Lys Val
    290                 295                 300

Gly Asp Gln Glu Leu Pro Asp Gln Asp Glu Met Asp Leu Ser Asp Trp
305                 310                 315                 320

Leu Val Thr Pro Gln Glu Ser His Lys Leu Arg Lys Pro Glu Asn Gly
                325                 330                 335

Ser Arg Glu Thr Ser Glu Lys Phe Lys Leu Leu Phe Gln Ser Tyr Asn
            340                 345                 350

Val Asn Asp Trp Leu Val Lys Thr Asp Ser Cys Thr Asn Cys Gln Gly
        355                 360                 365

Asn Gln Pro Lys Gly Val Glu Ile Glu Asn Leu Gly Asn Leu Lys Cys
    370                 375                 380

Leu Asn Asp His Leu Glu Ala Lys Lys Pro Leu Ser Thr Pro Ser Met
385                 390                 395                 400

Val Thr Glu Asp Trp Leu Val Gln Asn His Gln Asp Pro Cys Lys Val
                405                 410                 415

Glu Glu Val Cys Arg Ala Asn Glu Pro Cys Thr Ser Phe Ala Glu Cys
            420                 425                 430
```

```
Val Cys Asp Glu Asn Cys Glu Lys Glu Ala Leu Tyr Lys Trp Leu Leu
        435                 440                 445

Lys Lys Glu Gly Lys Asp Lys Asn Gly Met Pro Val Glu Pro Lys Pro
    450                 455                 460

Glu Pro Glu Lys His Lys Asp Ser Leu Asn Met Trp Leu Cys Pro Arg
465                 470                 475                 480

Lys Glu Val Ile Glu Gln Thr Lys Ala Pro Lys Ala Met Thr Pro Ser
                485                 490                 495

Arg Ile Ala Asp Ser Phe Gln Val Ile Lys Asn Ser Pro Leu Ser Glu
            500                 505                 510

Trp Leu Ile Arg Pro Pro Tyr Lys Glu Gly Ser Pro Lys Glu Val Pro
        515                 520                 525

Gly Thr Glu Asp Arg Ala Gly Lys Gln Lys Phe Lys Ser Pro Met Asn
    530                 535                 540

Thr Ser Trp Cys Ser Phe Asn Thr Ala Asp Trp Val Leu Pro Gly Lys
545                 550                 555                 560

Lys Met Gly Asn Leu Ser Gln Leu Ser Ser Gly Glu Asp Lys Trp Leu
                565                 570                 575

Leu Arg Lys Lys Ala Gln Glu Val Leu Leu Asn Ser Pro Leu Gln Glu
            580                 585                 590

Glu His Asn Phe Pro Pro Asp His Tyr Gly Leu Pro Ala Val Cys Asp
        595                 600                 605

Leu Phe Ala Cys Met Gln Leu Lys Val Asp Lys Glu Lys Trp Leu Tyr
    610                 615                 620

Arg Thr Pro Leu Gln Ala Tyr Phe Lys Met Asn Phe Gln Asp Val Thr
625                 630                 635                 640

Val Gly Asn Phe Gln Ile Pro Cys Gly Phe
                645                 650


<210> SEQ ID NO 39
<211> LENGTH: 630
<212> TYPE: PRT
<213> ORGANISM: Homo sapiens
<220> FEATURE:
<221> NAME/KEY: misc_feature
<223> OTHER INFORMATION: NCOA4 isoform 2 (NP_001138733.1)

<400> SEQUENCE: 39

Met Gly Ala Gln Leu Thr Thr Phe Ala Leu Ala Gly Ala Val Arg Arg
1               5                   10                  15

Met Asn Thr Phe Gln Asp Gln Ser Gly Ser Ser Ser Asn Arg Glu Pro
            20                  25                  30

Leu Leu Arg Cys Ser Asp Ala Arg Arg Asp Leu Glu Leu Ala Ile Gly
        35                  40                  45

Gly Val Leu Arg Ala Glu Gln Gln Ile Lys Asp Asn Leu Arg Glu Val
    50                  55                  60

Lys Ala Gln Ile His Ser Cys Ile Ser Arg His Leu Glu Cys Leu Arg
65                  70                  75                  80

Ser Arg Glu Val Trp Leu Tyr Glu Gln Val Asp Leu Ile Tyr Gln Leu
                85                  90                  95

Lys Glu Glu Thr Leu Gln Gln Gln Ala Gln Gln Leu Tyr Ser Leu Leu
            100                 105                 110

Gly Gln Phe Asn Cys Leu Thr His Gln Leu Glu Cys Thr Gln Asn Lys
        115                 120                 125

Asp Leu Ala Asn Gln Val Ser Val Cys Leu Glu Arg Leu Gly Ser Leu
    130                 135                 140
```

-continued

```
Thr Leu Lys Pro Glu Asp Ser Thr Val Leu Leu Phe Glu Ala Asp Thr
145                 150                 155                 160

Ile Thr Leu Arg Gln Thr Ile Thr Thr Phe Gly Ser Leu Lys Thr Ile
                165                 170                 175

Gln Ile Pro Glu His Leu Met Ala His Ala Ser Ser Ala Asn Ile Gly
            180                 185                 190

Pro Phe Leu Glu Lys Arg Gly Cys Ile Ser Met Pro Glu Gln Lys Ser
        195                 200                 205

Ala Ser Gly Ile Val Ala Val Pro Phe Ser Glu Trp Leu Leu Gly Ser
    210                 215                 220

Lys Pro Ala Ser Gly Tyr Gln Ala Pro Tyr Ile Pro Ser Thr Asp Pro
225                 230                 235                 240

Gln Asp Trp Leu Thr Gln Lys Gln Thr Leu Glu Asn Ser Gln Thr Ser
                245                 250                 255

Ser Arg Ala Cys Asn Phe Phe Asn Asn Val Gly Gly Asn Leu Lys Gly
            260                 265                 270

Leu Glu Asn Trp Leu Leu Lys Ser Glu Lys Ser Ser Tyr Gln Lys Cys
        275                 280                 285

Asn Ser His Ser Thr Thr Ser Ser Phe Ser Ile Glu Met Glu Lys Val
    290                 295                 300

Gly Asp Gln Glu Leu Pro Asp Gln Asp Glu Met Asp Leu Ser Asp Trp
305                 310                 315                 320

Leu Val Thr Pro Gln Glu Ser His Lys Leu Arg Lys Pro Glu Asn Gly
                325                 330                 335

Ser Arg Glu Thr Ser Glu Lys Phe Lys Leu Leu Phe Gln Ser Tyr Asn
            340                 345                 350

Val Asn Asp Trp Leu Val Lys Thr Asp Ser Cys Thr Asn Cys Gln Gly
        355                 360                 365

Asn Gln Pro Lys Gly Val Glu Ile Glu Asn Leu Gly Asn Leu Lys Cys
    370                 375                 380

Leu Asn Asp His Leu Glu Ala Lys Lys Pro Leu Ser Thr Pro Ser Met
385                 390                 395                 400

Val Thr Glu Asp Trp Leu Val Gln Asn His Gln Asp Pro Cys Lys Val
                405                 410                 415

Glu Glu Val Cys Arg Ala Asn Glu Pro Cys Thr Ser Phe Ala Glu Cys
            420                 425                 430

Val Cys Asp Glu Asn Cys Glu Lys Glu Ala Leu Tyr Lys Trp Leu Leu
        435                 440                 445

Lys Lys Glu Gly Lys Asp Lys Asn Gly Met Pro Val Glu Pro Lys Pro
    450                 455                 460

Glu Pro Glu Lys His Lys Asp Ser Leu Asn Met Trp Leu Cys Pro Arg
465                 470                 475                 480

Lys Glu Val Ile Glu Gln Thr Lys Ala Pro Lys Ala Met Thr Pro Ser
                485                 490                 495

Arg Ile Ala Asp Ser Phe Gln Val Ile Lys Asn Ser Pro Leu Ser Glu
            500                 505                 510

Trp Leu Ile Arg Pro Pro Tyr Lys Glu Gly Ser Pro Lys Glu Val Pro
        515                 520                 525

Gly Thr Glu Asp Arg Ala Gly Lys Gln Lys Phe Lys Ser Pro Met Asn
    530                 535                 540

Thr Ser Trp Cys Ser Phe Asn Thr Ala Asp Trp Val Leu Pro Gly Lys
545                 550                 555                 560
```

```
Lys Met Gly Asn Leu Ser Gln Leu Ser Ser Gly Glu Asp Lys Trp Leu
                565                 570                 575

Leu Arg Lys Lys Ala Gln Glu Val Leu Leu Asn Ser Pro Leu Gln Glu
            580                 585                 590

Glu His Asn Phe Pro Pro Asp His Tyr Gly Leu Pro Ala Val Cys Asp
        595                 600                 605

Leu Phe Ala Cys Met Gln Leu Lys Val Asp Lys Glu Lys Trp Leu Tyr
    610                 615                 620

Arg Thr Pro Leu Gln Met
625                 630


<210> SEQ ID NO 40
<211> LENGTH: 614
<212> TYPE: PRT
<213> ORGANISM: Homo sapiens
<220> FEATURE:
<221> NAME/KEY: misc_feature
<223> OTHER INFORMATION: NCOA4 isoform 3 (NP_001138734.1)

<400> SEQUENCE: 40

Met Asn Thr Phe Gln Asp Gln Ser Gly Ser Ser Ser Asn Arg Glu Pro
1               5                   10                  15

Leu Leu Arg Cys Ser Asp Ala Arg Arg Asp Leu Glu Leu Ala Ile Gly
            20                  25                  30

Gly Val Leu Arg Ala Glu Gln Gln Ile Lys Asp Asn Leu Arg Glu Val
        35                  40                  45

Lys Ala Gln Ile His Ser Cys Ile Ser Arg His Leu Glu Cys Leu Arg
    50                  55                  60

Ser Arg Glu Val Trp Leu Tyr Glu Gln Val Asp Leu Ile Tyr Gln Leu
65                  70                  75                  80

Lys Glu Glu Thr Leu Gln Gln Gln Ala Gln Gln Leu Tyr Ser Leu Leu
                85                  90                  95

Gly Gln Phe Asn Cys Leu Thr His Gln Leu Glu Cys Thr Gln Asn Lys
            100                 105                 110

Asp Leu Ala Asn Gln Val Ser Val Cys Leu Glu Arg Leu Gly Ser Leu
        115                 120                 125

Thr Leu Lys Pro Glu Asp Ser Thr Val Leu Leu Phe Glu Ala Asp Thr
    130                 135                 140

Ile Thr Leu Arg Gln Thr Ile Thr Thr Phe Gly Ser Leu Lys Thr Ile
145                 150                 155                 160

Gln Ile Pro Glu His Leu Met Ala His Ala Ser Ser Ala Asn Ile Gly
                165                 170                 175

Pro Phe Leu Glu Lys Arg Gly Cys Ile Ser Met Pro Glu Gln Lys Ser
            180                 185                 190

Ala Ser Gly Ile Val Ala Val Pro Phe Ser Glu Trp Leu Leu Gly Ser
        195                 200                 205

Lys Pro Ala Ser Gly Tyr Gln Ala Pro Tyr Ile Pro Ser Thr Asp Pro
    210                 215                 220

Gln Asp Trp Leu Thr Gln Lys Gln Thr Leu Glu Asn Ser Gln Thr Ser
225                 230                 235                 240

Ser Arg Ala Cys Asn Phe Phe Asn Asn Val Gly Gly Asn Leu Lys Gly
                245                 250                 255

Leu Glu Asn Trp Leu Leu Lys Ser Glu Lys Ser Ser Tyr Gln Lys Cys
            260                 265                 270

Asn Ser His Ser Thr Thr Ser Ser Phe Ser Ile Glu Met Glu Lys Val
        275                 280                 285
```

```
Gly Asp Gln Glu Leu Pro Asp Gln Asp Glu Met Asp Leu Ser Asp Trp
    290                 295                 300

Leu Val Thr Pro Gln Glu Ser His Lys Leu Arg Lys Pro Glu Asn Gly
305                 310                 315                 320

Ser Arg Glu Thr Ser Glu Lys Phe Lys Leu Leu Phe Gln Ser Tyr Asn
                325                 330                 335

Val Asn Asp Trp Leu Val Lys Thr Asp Ser Cys Thr Asn Cys Gln Gly
            340                 345                 350

Asn Gln Pro Lys Gly Val Glu Ile Glu Asn Leu Gly Asn Leu Lys Cys
        355                 360                 365

Leu Asn Asp His Leu Glu Ala Lys Lys Pro Leu Ser Thr Pro Ser Met
    370                 375                 380

Val Thr Glu Asp Trp Leu Val Gln Asn His Gln Asp Pro Cys Lys Val
385                 390                 395                 400

Glu Glu Val Cys Arg Ala Asn Glu Pro Cys Thr Ser Phe Ala Glu Cys
                405                 410                 415

Val Cys Asp Glu Asn Cys Glu Lys Glu Ala Leu Tyr Lys Trp Leu Leu
            420                 425                 430

Lys Lys Glu Gly Lys Asp Lys Asn Gly Met Pro Val Glu Pro Lys Pro
        435                 440                 445

Glu Pro Glu Lys His Lys Asp Ser Leu Asn Met Trp Leu Cys Pro Arg
    450                 455                 460

Lys Glu Val Ile Glu Gln Thr Lys Ala Pro Lys Ala Met Thr Pro Ser
465                 470                 475                 480

Arg Ile Ala Asp Ser Phe Gln Val Ile Lys Asn Ser Pro Leu Ser Glu
                485                 490                 495

Trp Leu Ile Arg Pro Pro Tyr Lys Glu Gly Ser Pro Lys Glu Val Pro
            500                 505                 510

Gly Thr Glu Asp Arg Ala Gly Lys Gln Lys Phe Lys Ser Pro Met Asn
        515                 520                 525

Thr Ser Trp Cys Ser Phe Asn Thr Ala Asp Trp Val Leu Pro Gly Lys
    530                 535                 540

Lys Met Gly Asn Leu Ser Gln Leu Ser Ser Gly Glu Asp Lys Trp Leu
545                 550                 555                 560

Leu Arg Lys Lys Ala Gln Glu Val Leu Leu Asn Ser Pro Leu Gln Glu
                565                 570                 575

Glu His Asn Phe Pro Pro Asp His Tyr Gly Leu Pro Ala Val Cys Asp
            580                 585                 590

Leu Phe Ala Cys Met Gln Leu Lys Val Asp Lys Glu Lys Trp Leu Tyr
        595                 600                 605

Arg Thr Pro Leu Gln Met
    610
```

<210> SEQ ID NO 41
<211> LENGTH: 614
<212> TYPE: PRT
<213> ORGANISM: Homo sapiens
<220> FEATURE:
<221> NAME/KEY: misc_feature
<223> OTHER INFORMATION: NCOA4 isoform 3 (NP_001138735.1)

<400> SEQUENCE: 41

```
Met Asn Thr Phe Gln Asp Gln Ser Gly Ser Ser Ser Asn Arg Glu Pro
1               5                   10                  15

Leu Leu Arg Cys Ser Asp Ala Arg Arg Asp Leu Glu Leu Ala Ile Gly
```

-continued

```
            20                  25                  30

Gly Val Leu Arg Ala Glu Gln Gln Ile Lys Asp Asn Leu Arg Glu Val
        35                  40                  45

Lys Ala Gln Ile His Ser Cys Ile Ser Arg His Leu Glu Cys Leu Arg
    50                  55                  60

Ser Arg Glu Val Trp Leu Tyr Glu Gln Val Asp Leu Ile Tyr Gln Leu
65                  70                  75                  80

Lys Glu Glu Thr Leu Gln Gln Gln Ala Gln Gln Leu Tyr Ser Leu Leu
                85                  90                  95

Gly Gln Phe Asn Cys Leu Thr His Gln Leu Glu Cys Thr Gln Asn Lys
            100                 105                 110

Asp Leu Ala Asn Gln Val Ser Val Cys Leu Glu Arg Leu Gly Ser Leu
        115                 120                 125

Thr Leu Lys Pro Glu Asp Ser Thr Val Leu Leu Phe Glu Ala Asp Thr
    130                 135                 140

Ile Thr Leu Arg Gln Thr Ile Thr Thr Phe Gly Ser Leu Lys Thr Ile
145                 150                 155                 160

Gln Ile Pro Glu His Leu Met Ala His Ala Ser Ser Ala Asn Ile Gly
                165                 170                 175

Pro Phe Leu Glu Lys Arg Gly Cys Ile Ser Met Pro Glu Gln Lys Ser
            180                 185                 190

Ala Ser Gly Ile Val Ala Val Pro Phe Ser Glu Trp Leu Leu Gly Ser
        195                 200                 205

Lys Pro Ala Ser Gly Tyr Gln Ala Pro Tyr Ile Pro Ser Thr Asp Pro
    210                 215                 220

Gln Asp Trp Leu Thr Gln Lys Gln Thr Leu Glu Asn Ser Gln Thr Ser
225                 230                 235                 240

Ser Arg Ala Cys Asn Phe Phe Asn Asn Val Gly Gly Asn Leu Lys Gly
                245                 250                 255

Leu Glu Asn Trp Leu Leu Lys Ser Glu Lys Ser Ser Tyr Gln Lys Cys
            260                 265                 270

Asn Ser His Ser Thr Thr Ser Ser Phe Ser Ile Glu Met Glu Lys Val
        275                 280                 285

Gly Asp Gln Glu Leu Pro Asp Gln Asp Glu Met Asp Leu Ser Asp Trp
    290                 295                 300

Leu Val Thr Pro Gln Glu Ser His Lys Leu Arg Lys Pro Glu Asn Gly
305                 310                 315                 320

Ser Arg Glu Thr Ser Glu Lys Phe Lys Leu Leu Phe Gln Ser Tyr Asn
                325                 330                 335

Val Asn Asp Trp Leu Val Lys Thr Asp Ser Cys Thr Asn Cys Gln Gly
            340                 345                 350

Asn Gln Pro Lys Gly Val Glu Ile Glu Asn Leu Gly Asn Leu Lys Cys
        355                 360                 365

Leu Asn Asp His Leu Glu Ala Lys Lys Pro Leu Ser Thr Pro Ser Met
    370                 375                 380

Val Thr Glu Asp Trp Leu Val Gln Asn His Gln Asp Pro Cys Lys Val
385                 390                 395                 400

Glu Glu Val Cys Arg Ala Asn Glu Pro Cys Thr Ser Phe Ala Glu Cys
                405                 410                 415

Val Cys Asp Glu Asn Cys Glu Lys Glu Ala Leu Tyr Lys Trp Leu Leu
            420                 425                 430

Lys Lys Glu Gly Lys Asp Lys Asn Gly Met Pro Val Glu Pro Lys Pro
        435                 440                 445
```

```
Glu Pro Glu Lys His Lys Asp Ser Leu Asn Met Trp Leu Cys Pro Arg
    450                 455                 460

Lys Glu Val Ile Glu Gln Thr Lys Ala Pro Lys Ala Met Thr Pro Ser
465                 470                 475                 480

Arg Ile Ala Asp Ser Phe Gln Val Ile Lys Asn Ser Pro Leu Ser Glu
                485                 490                 495

Trp Leu Ile Arg Pro Pro Tyr Lys Glu Gly Ser Pro Lys Glu Val Pro
            500                 505                 510

Gly Thr Glu Asp Arg Ala Gly Lys Gln Lys Phe Lys Ser Pro Met Asn
        515                 520                 525

Thr Ser Trp Cys Ser Phe Asn Thr Ala Asp Trp Val Leu Pro Gly Lys
    530                 535                 540

Lys Met Gly Asn Leu Ser Gln Leu Ser Ser Gly Glu Asp Lys Trp Leu
545                 550                 555                 560

Leu Arg Lys Lys Ala Gln Glu Val Leu Leu Asn Ser Pro Leu Gln Glu
                565                 570                 575

Glu His Asn Phe Pro Pro Asp His Tyr Gly Leu Pro Ala Val Cys Asp
            580                 585                 590

Leu Phe Ala Cys Met Gln Leu Lys Val Asp Lys Glu Lys Trp Leu Tyr
        595                 600                 605

Arg Thr Pro Leu Gln Met
    610


<210> SEQ ID NO 42
<211> LENGTH: 614
<212> TYPE: PRT
<213> ORGANISM: Homo sapiens
<220> FEATURE:
<221> NAME/KEY: misc_feature
<223> OTHER INFORMATION: NCOA4 isoform 3 (NP_005428.1)

<400> SEQUENCE: 42

Met Asn Thr Phe Gln Asp Gln Ser Gly Ser Ser Ser Asn Arg Glu Pro
1               5                   10                  15

Leu Leu Arg Cys Ser Asp Ala Arg Arg Asp Leu Glu Leu Ala Ile Gly
            20                  25                  30

Gly Val Leu Arg Ala Glu Gln Gln Ile Lys Asp Asn Leu Arg Glu Val
        35                  40                  45

Lys Ala Gln Ile His Ser Cys Ile Ser Arg His Leu Glu Cys Leu Arg
    50                  55                  60

Ser Arg Glu Val Trp Leu Tyr Glu Gln Val Asp Leu Ile Tyr Gln Leu
65                  70                  75                  80

Lys Glu Glu Thr Leu Gln Gln Gln Ala Gln Gln Leu Tyr Ser Leu Leu
                85                  90                  95

Gly Gln Phe Asn Cys Leu Thr His Gln Leu Glu Cys Thr Gln Asn Lys
            100                 105                 110

Asp Leu Ala Asn Gln Val Ser Val Cys Leu Glu Arg Leu Gly Ser Leu
        115                 120                 125

Thr Leu Lys Pro Glu Asp Ser Thr Val Leu Leu Phe Glu Ala Asp Thr
    130                 135                 140

Ile Thr Leu Arg Gln Thr Ile Thr Thr Phe Gly Ser Leu Lys Thr Ile
145                 150                 155                 160

Gln Ile Pro Glu His Leu Met Ala His Ala Ser Ser Ala Asn Ile Gly
                165                 170                 175

Pro Phe Leu Glu Lys Arg Gly Cys Ile Ser Met Pro Glu Gln Lys Ser
```

```
            180                 185                 190

Ala Ser Gly Ile Val Ala Val Pro Phe Ser Glu Trp Leu Leu Gly Ser
        195                 200                 205

Lys Pro Ala Ser Gly Tyr Gln Ala Pro Tyr Ile Pro Ser Thr Asp Pro
    210                 215                 220

Gln Asp Trp Leu Thr Gln Lys Gln Thr Leu Glu Asn Ser Gln Thr Ser
225                 230                 235                 240

Ser Arg Ala Cys Asn Phe Phe Asn Asn Val Gly Gly Asn Leu Lys Gly
                245                 250                 255

Leu Glu Asn Trp Leu Leu Lys Ser Glu Lys Ser Ser Tyr Gln Lys Cys
            260                 265                 270

Asn Ser His Ser Thr Thr Ser Ser Phe Ser Ile Glu Met Glu Lys Val
        275                 280                 285

Gly Asp Gln Glu Leu Pro Asp Gln Asp Glu Met Asp Leu Ser Asp Trp
    290                 295                 300

Leu Val Thr Pro Gln Glu Ser His Lys Leu Arg Lys Pro Glu Asn Gly
305                 310                 315                 320

Ser Arg Glu Thr Ser Glu Lys Phe Lys Leu Leu Phe Gln Ser Tyr Asn
                325                 330                 335

Val Asn Asp Trp Leu Val Lys Thr Asp Ser Cys Thr Asn Cys Gln Gly
            340                 345                 350

Asn Gln Pro Lys Gly Val Glu Ile Glu Asn Leu Gly Asn Leu Lys Cys
        355                 360                 365

Leu Asn Asp His Leu Glu Ala Lys Lys Pro Leu Ser Thr Pro Ser Met
    370                 375                 380

Val Thr Glu Asp Trp Leu Val Gln Asn His Gln Asp Pro Cys Lys Val
385                 390                 395                 400

Glu Glu Val Cys Arg Ala Asn Glu Pro Cys Thr Ser Phe Ala Glu Cys
                405                 410                 415

Val Cys Asp Glu Asn Cys Glu Lys Glu Ala Leu Tyr Lys Trp Leu Leu
            420                 425                 430

Lys Lys Glu Gly Lys Asp Lys Asn Gly Met Pro Val Glu Pro Lys Pro
        435                 440                 445

Glu Pro Glu Lys His Lys Asp Ser Leu Asn Met Trp Leu Cys Pro Arg
    450                 455                 460

Lys Glu Val Ile Glu Gln Thr Lys Ala Pro Lys Ala Met Thr Pro Ser
465                 470                 475                 480

Arg Ile Ala Asp Ser Phe Gln Val Ile Lys Asn Ser Pro Leu Ser Glu
                485                 490                 495

Trp Leu Ile Arg Pro Pro Tyr Lys Glu Gly Ser Pro Lys Glu Val Pro
            500                 505                 510

Gly Thr Glu Asp Arg Ala Gly Lys Gln Lys Phe Lys Ser Pro Met Asn
        515                 520                 525

Thr Ser Trp Cys Ser Phe Asn Thr Ala Asp Trp Val Leu Pro Gly Lys
    530                 535                 540

Lys Met Gly Asn Leu Ser Gln Leu Ser Ser Gly Glu Asp Lys Trp Leu
545                 550                 555                 560

Leu Arg Lys Lys Ala Gln Glu Val Leu Leu Asn Ser Pro Leu Gln Glu
                565                 570                 575

Glu His Asn Phe Pro Pro Asp His Tyr Gly Leu Pro Ala Val Cys Asp
            580                 585                 590

Leu Phe Ala Cys Met Gln Leu Lys Val Asp Lys Glu Lys Trp Leu Tyr
        595                 600                 605
```

```
Arg Thr Pro Leu Gln Met
    610


<210> SEQ ID NO 43
<211> LENGTH: 8339
<212> TYPE: DNA
<213> ORGANISM: Homo sapiens
<220> FEATURE:
<221> NAME/KEY: misc_feature
<223> OTHER INFORMATION: TRIM33 transcript variant a (NM_015906.3)

<400> SEQUENCE: 43

ctgcggctgg ggctgggggc ggcggcggcg gcgacgcggg cggcgggcgg cgcggggcgg     60

tccggcgggt tcaaagagga aaacatggcg gaaaacaaag gcggcggcga ggctgagagc    120

ggcggcgggg gcagcggcag cgcgccggta actgccgggg ccgccgggcc cgccgcgcag    180

gaggcggagc cgcctctcac cgcggtgctg gtggaggagg aggaggagga aggcggcagg    240

gccggcgctg agggcggcgc ggccgggccc gacgacgggg gggtggccgc ggcctcctcg    300

ggctcggccc aggctgcttc atctcctgcg gcctcagtgg gcactggagt tgccgggggc    360

gcagtatcga cgccggctcc agctccagcc tcggctcccg ctccgggtcc ctcggcaggg    420

ccgcctcctg gaccgccagc ctcgctcctg gacacctgcg ccgtgtgtca gcagagcttg    480

cagagccggc gtgaggcgga gcccaagctg ctgccctgtc ttcactcctt ctgcctgcgc    540

tgcctgcccg agccggagcg ccagctcagc gtgcccatcc cgggggggcag caacggcgac    600

atccagcaag ttggtgtaat acggtgccca gtatgccgcc aagaatgcag acagatagac    660

cttgtggata attattttgt gaaagacaca tctgaagctc ctagcagttc tgatgaaaaa    720

tcagaacagg tatgtactag ttgtgaagac aatgcaagtg cagttggctt ttgtgtagaa    780

tgtggagagt ggctatgtaa gacatgtatc gaagcacatc aaagagtaaa atttactaaa    840

gatcacttga tcaggaagaa agaagatgtc tcagagtctg ttggagcatc tggtcaacgc    900

cctgttttct gccctgtaca caaacaagaa cagttgaaac ttttctgtga aacatgtgat    960

agattgacat gtagagactg tcagctattg gaacacaaag aacataggta tcagtttttg   1020

gaagaagctt ttcaaaatca gaagggtgca attgagaatc tactggcgaa acttcttgag   1080

aagaagaatt atgttcattt tgcagctact caggtgcaga ataggataaa agaagtaaat   1140

gagactaaca aacgagtaga acaggaaatt aaagtggcca ttttcaccct tatcaatgaa   1200

attaataaga aaggaaaatc tctcttacaa cagctagaga atgttacaaa ggaaagacag   1260

atgaagttac tacagcagca gaatgacatc acaggccttt cccggcaggt gaagcatgtt   1320

atgaacttca caaattgggc aattgcaagt ggcagcagca cagcactact atacagcaag   1380

cgactgatta ctttccagtt gcgtcatatt ttgaaagcac ggtgtgatcc tgtccctgct   1440

gctaatggag caatacgttt ccattgtgat cccaccttct gggcaaagaa tgtagtcaat   1500

ttaggtaatc tagtaataga gagtaaacca gctcctggtt atactcctaa tgttgtagtt   1560

gggcaagttc ctccagggac aaaccacatt agtaaaaccc ctggacagat taacttagca   1620

cagcttcgac tccagcacat gcaacaacaa gtatatgcac agaaacatca gcagttgcaa   1680

cagatgagga tgcagcaacc accagcacct gtaccaacta caacaacaac aacacaacag   1740

catcctagac aagcagcccc tcagatgtta caacaacagc ctcctcgatt gatcagtgtg   1800

caaacaatgc aaagaggcaa catgaactgt ggagcttttc aagcccatca gatgagactg   1860

gctcagaatg ctgccagaat accagggata cccaggcaca gcggccctca atattccatg   1920
```

-continued

```
atgcagccac acctccaaag acaacactca aacccagggc atgctggacc ctttcccgta   1980
gtatcggtac acaacaccac aatcaaccca acgagcccta ctacagcaac tatggcaaat   2040
gcaaaccgag gtcccaccag cccatctgtt acagcaatag agctaatccc ctcagttacc   2100
aatccagaaa accttccatc gctgccagat attccaccca tacagttgga agatgctggc   2160
tcaagtagtt tagataatct actaagtaga tacatctcag gcagtcacct acccccacag   2220
cctacaagca ccatgaatcc ttctccaggt ccctctgccc tttctccggg atcatcaggt   2280
ttatccaatt ctcacacacc tgtgagaccc ccaagtactt ctagtactgg cagtcgaggc   2340
agctgtgggt catcaggaag aactgctgag aagacaagtc ttagtttcaa atctgatcag   2400
gtgaaggtca agcaagaacc tgggactgaa gatgaaatat gtagcttttc aggaggtgta   2460
aaacaagaaa aaacagagga tggcaggagg agtgcttgca tgttgagcag tcctgagagt   2520
agcttgacac cacctctctc aaccaacctg catctagaaa gtgaattgga tgcattggca   2580
agcctggaaa accatgtgaa aattgaacct gcagatatga atgaaagctg caaacagtca   2640
gggctcagca gccttgttaa tggaaagtcc ccaattcgaa gcctcatgca caggtcggca   2700
aggattggag gagatggcaa caataaagat gatgacccaa atgaagactg gtgtgctgtc   2760
tgccaaaacg gaggagatct cttgtgctgc gaaaaatgtc caaaggtctt tcatctaact   2820
tgtcatgttc caacactact tagctttcca agtggggact ggatatgcac attttgtaga   2880
gatattggaa agccagaagt tgaatatgat tgtgataatt tgcaacatag taagaagggg   2940
aaaactgcgc aggggttaag ccccgtggac caaaggaaat gtgaacgtct tctgctttac   3000
ctctattgcc atgaattaag tattgaattc caggagcctg ttcctgcttc gataccaaac   3060
tactataaaa ttataaagaa accaatggat ttatccaccg tgaaaaagaa gcttcagaaa   3120
aaacattccc aacactacca aatcccggat gactttgtgg ccgatgtccg tttgatcttc   3180
aagaactgtg aaaggtttaa tgaaatgatg aaagttgttc aagtttatgc agacacacaa   3240
gagattaatt tgaaggctga ttcagaagta gctcaggcag ggaaagcagt tgcattgtac   3300
tttgaagata aactcacaga gatctactca gacaggacct tcgcaccttt gccagagttt   3360
gagcaggaag aggatgatgg tgaggtaact gaggactctg atgaagactt tatacagccc   3420
cgcagaaaac gcctaaagtc agatgagaga ccagtacata taaagtaaaa tgacatggat   3480
ttaaatcaat tgtttaaaaa aaaaaaaacg aaaaaaaaaa aaaaaacaca aaaaacccag   3540
aaaactttta agtgttgctg gaatatcctg cctacagtgg gcacctcctt gaagaagctg   3600
atagctttta cacagtatta gattgaaata atggacagaa acacattctt gtcaagaaag   3660
ggggagagaa gtctgtttgc aagtttcaaa gcaaaaagca aaagtgaaat gatttgagga   3720
tttctgttct aatggagatg attctctgat tgttagaaat ggcaaatatt gatgattgtg   3780
tgctattgat tggtgcagga tacttggtat acgagtaaat acttgagact cgtgtcactt   3840
gataaatttt ctttttggac taggtcgcac agttattaaa acaactttta accctccccc   3900
ttcacacaca tacatatcag gttgttttct agttaaaaac ccaagtagct cagattctac   3960
tttaatgtca gtgcagattt gcattgaatc atgccattat gtttttctc atttttatgc    4020
tgttgggtct tagtttttaa attgatataa agaactcagc aatggtttta ttttctactc   4080
atacttaggg tttaggaaac actaccacta gttatcattt aatcaacttc aatggtctac   4140
tgaaacaaaa atggtaactt ttcattagtg gattatttag agttatagta gttgtttcca   4200
gaaaacactt cctcacaatt gtacttccca atcaaatcat gtgatcatac agttattccc   4260
atgaaaggca gaatgtttgt ttcaaaatta atctagtttt ctgtacattt aaatttgaga   4320
```

-continued

```
aggtgacaac tggctctttt ccagtcttcc ttcatgtcag ttttctgata gaccactatt   4380
ggcaaacagt atctgtcaac taccaaatgt gtaaaatttt ctgtatttca ctttgtctta   4440
tttgtaaata gtgaactaaa acttttggca gatcagcaac atttgctgag cctgtttttt   4500
aagctaatgt gtattcttac taatgttcct atcaagaatg gatttgtaat atatgctgtc   4560
tatttctaat gttcacattc atattttgag gttctatctt attttaatag agaacagact   4620
tctcaaaaaa tcttcagaag cagcttatta ttgaaatatc gaaatattga aataaacccg   4680
gtggggttag attactcatc tgtccaccaa gtgggacatt tgcatggact gggggcttaa   4740
aggacttaga agagacctgt aagtaaatcc tgaaaatgag ccaatcccca cttgaatggt   4800
tactggagta aacccacctt taccacccca attacagcac ccgaggccga taaaccaact   4860
tggctctggt tcatttttct tttcttcatt tgtgatgctc agattcaaaa tgtgtgttct   4920
acactgttac aggcttctct tttgtttgat taaagatttt agtcctactt ttgtatggac   4980
acattagaat attcagagac caaaatagaa gaatttgctg ttagatattt ttcagaagtc   5040
agcagatttg tggcaaatca tttatttgcc tttttaaaaa ttcatttaag cagttcagag   5100
agtagactac tcagaaaatt atttcacgta attgtctaag aggtcaatat tttttaatgc   5160
atattgaatc aaataaagtg ctctaaagaa attattatac aaattccttt gggttgtttt   5220
tcttttctta acaaggggtg ggggtaaaca ggaatatgat tcaggctttc tggttgtgta   5280
tttaaagagt attgatttta ttattactat tgatttactt tattcctggc ttcctttttca   5340
cttttctttc aatttttaaa aaataattta agccgttgaa aatataccaa actgttgaaa   5400
cattttactc aaattttaaa ttcctaaaaa tgttttttaa taagagggag aaaattattt   5460
aaaaatactt atgcctatgc caatttccct ctttttttcac aaaatccatg atttcagttt   5520
gtaagtagac atatatctaa gggcacattt ttggaaagtg aggaatagca gcagtataac   5580
ttcattttgt caggcctttg agttctaata ttttgtattg ctcttcaaat ggatcctttt   5640
aaaaaaattg tagataatga gtcataaata gattctgcca actgaggggga gaaacatttt   5700
aagtaaatat ttttcagtat ttggggcctt aaaaaaataat tgtgtttcct taaaattaca   5760
tgttagatag agtttttagg ttttttttggt tttaagattg gttaaagcaa tttaaaagcc   5820
actttttttgt caacatttaa tagcctccac ttctgttaag ataatgtata ctgctgagga   5880
attactatta atagctatca acataccacc attaaattaa ggtattcact ttagattttt   5940
tattaaagct tttttcttgc acactgatcg ttgtgtttct aagctgattt tttcagctct   6000
aatataccta tggttaaaaa gtataaaaac ttaaattgat atttagatat atgttttcct   6060
attagtttat gttttaaaaa gacaaaattg tatctgtcag tccctgaagg cagtttgttt   6120
ttatactctc tcacatttgt atttgttttt taaatggcag tattttagaa gatttggaga   6180
aaagtccaca taataatgtt ttcttaaaag cttttaaagt ttttgctgta cttcaattta   6240
cttcttccat cagaaaacta agaacaaagt gttgctcagt ctgttccgct gacctaaatt   6300
tgtgttttca gcacttggct cagccaattc actgagtgaa ggaattgctt tatgaggcaa   6360
agcatgtgaa agttctaaag tatggttaga ttgtaggtcg tgctctatat ggaaacatca   6420
aaccattact acagagaaat gataaggcat tggatccact attgaaatta ttatttttgg   6480
atcaacaagt tggtactttc tgacttctgt atcttaacat aagggaattt taggtaatgc   6540
taagtcagtt gtctcatttt ttgtgataag ttttggaatt tttagttaat tgaaataaat   6600
aatgctttta aatagaagta aaaggtttat aagtgtgcaa attgtagatt tatcaattac   6660
```

```
ctcagcaggt atcctgccat gtaattatta gtgattagtg ttaataagat aatagattca   6720
ggtcttccaa ctatgccctt ggattgtggc ctactgtatg ttattaaatg gtctcttact   6780
atccaaaatg ggagtagatg ctgtggcccc gtctcccttg gcttttacgt cccatatcca   6840
cccccattca tgtacaacat gtgaaatata aaaatctcat ttcttgtcaa aatcagcact   6900
gcttatttgc atactcagca tcggatcagt gagtagtttt ataaaaaatc cacgcaccca   6960
actcccttag ttaaaacaga ttcttaattc ataccatgaa ttcttaattt ctgtaccatc   7020
tatgttaatg atctgctgaa ggtgactcaa gattttcaag gtgtaataca gtttgatcat   7080
gtaccggacc tggatattta atttttttc cctcacagtt aatctcctcc ttgataaagc   7140
aataacactg ctttgagtct gttgcctaat agcatgtcag aatcctctcc tggatggtga   7200
ttttatagga aagtttgtat gcatatcacc cagtctatct tttaaaaatt aagaaattta   7260
aatgtatgct ggaagtaatg acactatatt gtggcatttt attttaaaaa ttggggaaag   7320
ttgcatattt ttttaaaagt aagtgtttga gtaaaaaaat tgaaggtact tttttaagga   7380
aaaaaattta tatgccacag tttacataga catttcagat tcaacacgta ctcttgaata   7440
taatggtttc ttttacttgg tcaaaatgca tgtatagcat ttctttcatc ttagttcctt   7500
gtgtttgcct atgtggtcct ttatatattt tttattgtat cgaagaaaca aaactatctt   7560
caaaaataag ttaatttgga tatatttgtc atatcaaact acaaagtgta caaagttaag   7620
tttagccctt ttctagaaag tgatctttaa aattaaaaat gctcctcttt taaattcacc   7680
aaatttatgt gtgggaaggc accaaaatga ttttgtaagt gccactgcaa tattcccttt   7740
caagtgtggc ctaaatttca atcttaagga tggaatgcat gtctgctcct tgttctgaaa   7800
aatgtaggca tctactacat tttaaaacac agtgaaacat atacataagc ctataaaaaa   7860
agatttgtgc aatttgaaag cctgttaatt ttttatgtag acatacctac acacgaaagg   7920
gttaaattca cagccttact agttccttgc ttccagtatt tcaattggtc tcctcccctc   7980
attattatta ttactactag tactattatt tttgcacata gttaactgcc cttcaatatg   8040
attcttaaaa agtgctgttt ctgtggtatc gtattctcta aataatcata tttaattttt   8100
taaaacaagg ttgcagtttc taattgtttc gttcctgtgt ttttgctggt gtgtaataaa   8160
agcaagtttt ttcttttcat ggttatttaa tacattagct gcctgtaaat aattcttgtt   8220
ataatgctct ggaatgtgtt gtagaagttg tattagatta gttttaaacc cttgtttgaa   8280
agccacattg ttttggttat ttctattaaa ttagaaaatt gaaaaagttt tcaaatgaa    8339
```

<210> SEQ ID NO 44
<211> LENGTH: 8288
<212> TYPE: DNA
<213> ORGANISM: Homo sapiens
<220> FEATURE:
<221> NAME/KEY: misc_feature
<223> OTHER INFORMATION: TRIM33 transcript variant b (NM_033020.2)

<400> SEQUENCE: 44

```
ctgcggctgg ggctgggggc ggcggcggcg gcgacgcggg cggcgggcgg cgcggggcgg     60
tccggcgggt tcaaagagga aaacatggcg gaaaacaaag gcggcggcga ggctgagagc    120
ggcggcgggg gcagcggcag cgcgccggta actgccgggg ccgccgggcc cgccgcgcag    180
gaggcggagc cgcctctcac cgcggtgctg gtggaggagg aggaggagga aggcggcagg    240
gccggcgctg agggcggcgc ggccgggccc gacgacgggg gggtggccgc ggcctcctcg    300
ggctcggccc aggctgcttc atctcctgcg gcctcagtgg gcactggagt tgccgggggc    360
```

-continued

```
gcagtatcga cgccggctcc agctccagcc tcggctcccg ctccgggtcc ctcggcaggg    420
ccgcctcctg gaccgccagc ctcgctcctg gacacctgcg ccgtgtgtca gcagagcttg    480
cagagccggc gtgaggcgga gcccaagctg ctgccctgtc ttcactcctt ctgcctgcgc    540
tgcctgcccg agccggagcg ccagctcagc gtgcccatcc cgggggcag caacggcgac    600
atccagcaag ttggtgtaat acggtgccca gtatgccgcc aagaatgcag acagatagac    660
cttgtggata attattttgt gaaagacaca tctgaagctc ctagcagttc tgatgaaaaa    720
tcagaacagg tatgtactag ttgtgaagac aatgcaagtg cagttggctt ttgtgtagaa    780
tgtggagagt ggctatgtaa gacatgtatc gaagcacatc aaagagtaaa atttactaaa    840
gatcacttga tcaggaagaa agaagatgtc tcagagtctg ttggagcatc tggtcaacgc    900
cctgttttct gccctgtaca caaacaagaa cagttgaaac ttttctgtga aacatgtgat    960
agattgacat gtagagactg tcagctattg gaacacaaag aacataggta tcagtttttg   1020
gaagaagctt ttcaaaatca gaagggtgca attgagaatc tactggcgaa acttcttgag   1080
aagaagaatt atgttcattt tgcagctact caggtgcaga ataggataaa agaagtaaat   1140
gagactaaca aacgagtaga acaggaaatt aaagtggcca ttttcaccct tatcaatgaa   1200
attaataaga aaggaaaatc tctcttacaa cagctagaga atgttacaaa ggaaagacag   1260
atgaagttac tacagcagca gaatgacatc acaggccttt cccggcaggt gaagcatgtt   1320
atgaacttca caaattgggc aattgcaagt ggcagcagca cagcactact atacagcaag   1380
cgactgatta ctttccagtt gcgtcatatt ttgaaagcac ggtgtgatcc tgtccctgct   1440
gctaatggag caatacgttt ccattgtgat cccaccttct gggcaaagaa tgtagtcaat   1500
ttaggtaatc tagtaataga gagtaaacca gctcctggtt atactcctaa tgttgtagtt   1560
gggcaagttc ctccagggac aaaccacatt agtaaaaccc ctggacagat taacttagca   1620
cagcttcgac tccagcacat gcaacaacaa gtatatgcac agaaacatca gcagttgcaa   1680
cagatgagga tgcagcaacc accagcacct gtaccaacta caacaacaac aacacaacag   1740
catcctagac aagcagcccc tcagatgtta caacaacagc ctcctcgatt gatcagtgtg   1800
caaacaatgc aaagaggcaa catgaactgt ggagcttttc aagcccatca gatgagactg   1860
gctcagaatg ctgccagaat accagggata cccaggcaca gcggccctca atattccatg   1920
atgcagccac acctccaaag acaacactca aacccagggc atgctggacc ctttcccgta   1980
gtatcggtac acaacaccac aatcaaccca acgagcccta ctacagcaac tatggcaaat   2040
gcaaaccgag gtcccaccag cccatctgtt acagcaatag agctaatccc ctcagttacc   2100
aatccagaaa accttccatc gctgccagat attccaccca tacagttgga agatgctggc   2160
tcaagtagtt tagataatct actaagtaga tacatctcag gcagtcacct acccccacag   2220
cctacaagca ccatgaatcc ttctccaggt ccctctgccc tttctccggg atcatcaggt   2280
ttatccaatt ctcacacacc tgtgagaccc ccaagtactt ctagtactgg cagtcgaggc   2340
agctgtgggt catcaggaag aactgctgag aagacaagtc ttagtttcaa atctgatcag   2400
gtgaaggtca agcaagaacc tgggactgaa gatgaaatat gtagcttttc aggaggtgta   2460
aaacaagaaa aaacagagga tggcaggagg agtgcttgca tgttgagcag tcctgagagt   2520
agcttgacac cacctctctc aaccaacctg catctagaaa gtgaattgga tgcattggca   2580
agcctggaaa accatgtgaa aattgaacct gcagatatga atgaaagctg caaacagtca   2640
gggctcagca gccttgttaa tggaaagtcc ccaattcgaa gcctcatgca caggtcggca   2700
aggattggag gagatggcaa caataaagat gatgacccaa atgaagactg gtgtgctgtc   2760
```

tgccaaaacg gaggagatct cttgtgctgc gaaaaatgtc caaaggtctt tcatctaact 2820
tgtcatgttc caacactact tagctttcca agtggggact ggatatgcac attttgtaga 2880
gatattggaa agccagaagt tgaatatgat tgtgataatt tgcaacatag taagaagggg 2940
aaaactgcgc aggggttaag ccccgtggac caaaggaaat gtgaacgtct tctgctttac 3000
ctctattgcc atgaattaag tattgaattc caggagcctg ttcctgcttc gataccaaac 3060
tactataaaa ttataaagaa accaatggat ttatccaccg tgaaaaagaa gcttcagaaa 3120
aaacattccc aacactacca aatcccggat gactttgtgg ccgatgtccg tttgatcttc 3180
aagaactgtg aaaggtttaa tgaagctgat tcagaagtag ctcaggcagg gaaagcagtt 3240
gcattgtact ttgaagataa actcacagag atctactcag acaggacctt cgcacctttg 3300
ccagagtttg agcaggaaga ggatgatggt gaggtaactg aggactctga tgaagacttt 3360
atacagcccc gcagaaaacg cctaaagtca gatgagagac cagtacatat aaagtaaaat 3420
gacatggatt taaatcaatt gtttaaaaaa aaaaaaacga aaaaaaaaaa aaaaacacaa 3480
aaaacccaga aaacttttaa gtgttgctgg aatatcctgc ctacagtggg cacctccttg 3540
aagaagctga tagcttttac acagtattag attgaaataa tggacagaaa cacattcttg 3600
tcaagaaagg gggagagaag tctgtttgca agtttcaaag caaaaagcaa aagtgaaatg 3660
atttgaggat ttctgttcta atggagatga ttctctgatt gttagaaatg gcaaatattg 3720
atgattgtgt gctattgatt ggtgcaggat acttggtata cgagtaaata cttgagactc 3780
gtgtcacttg ataaatttc tttttggact aggtcgcaca gttattaaaa caacttttaa 3840
ccctccccct tcacacacat acatatcagg ttgttttcta gttaaaaacc caagtagctc 3900
agattctact ttaatgtcag tgcagatttg cattgaatca tgccattatg tttttctca 3960
tttttatgct gttgggtctt agtttttaaa ttgatataaa gaactcagca atggttttat 4020
tttctactca tacttagggt ttaggaaaca ctaccactag ttatcattta atcaacttca 4080
atggtctact gaaacaaaaa tggtaacttt tcattagtgg attatttaga gttatagtag 4140
ttgtttccag aaaacacttc ctcacaattg tacttcccaa tcaaatcatg tgatcataca 4200
gttattccca tgaaaggcag aatgtttgtt tcaaaattaa tctagttttc tgtacattta 4260
aatttgagaa ggtgacaact ggctcttttc cagtcttcct tcatgtcagt tttctgatag 4320
accactattg gcaaacagta tctgtcaact accaaatgtg taaaattttc tgtatttcac 4380
tttgtcttat ttgtaaatag tgaactaaaa cttttggcag atcagcaaca tttgctgagc 4440
ctgtttttta agctaatgtg tattcttact aatgttccta tcaagaatgg atttgtaata 4500
tatgctgtct atttctaatg ttcacattca tattttgagg ttctatctta ttttaataga 4560
gaacagactt ctcaaaaaat cttcagaagc agcttattat tgaaatatcg aaatattgaa 4620
ataaacccgg tggggttaga ttactcatct gtccaccaag tgggacattt gcatggactg 4680
ggggcttaaa ggacttagaa gagacctgta agtaaatcct gaaaatgagc caatccccac 4740
ttgaatggtt actggagtaa acccaccttt accaccccaa ttacagcacc cgaggccgat 4800
aaaccaactt ggctctggtt catttttctt ttcttcattt gtgatgctca gattcaaaat 4860
gtgtgttcta cactgttaca ggcttctctt ttgtttgatt aaagatttta gtcctacttt 4920
tgtatggaca cattagaata ttcagagacc aaaatagaag aatttgctgt tagatatttt 4980
tcagaagtca gcagatttgt ggcaaatcat ttatttgcct ttttaaaaat tcatttaagc 5040
agttcagaga gtagactact cagaaaatta tttcacgtaa ttgtctaaga ggtcaatatt 5100

```
ttttaatgca tattgaatca aataaagtgc tctaaagaaa ttattataca aattcctttg   5160
ggttgttttt cttttcttaa caaggggtgg gggtaaacag gaatatgatt caggctttct   5220
ggttgtgtat ttaaagagta ttgattttat tattactatt gatttacttt attcctggct   5280
tccttttcac ttttctttca atttttaaaa aataatttaa gccgttgaaa atataccaaa   5340
ctgttgaaac attttactca aattttaaat tcctaaaaat gtttttaat aagagggaga   5400
aaattattta aaaatactta tgcctatgcc aatttccctc tttttcaca aaatccatga   5460
tttcagtttg taagtagaca tatatctaag ggcacatttt tggaaagtga ggaatagcag   5520
cagtataact tcattttgtc aggcctttga gttctaatat tttgtattgc tcttcaaatg   5580
gatcctttta aaaaaattgt agataatgag tcataaatag attctgccaa ctgaggggag   5640
aaacatttta agtaaatatt tttcagtatt tggggcctta aaaaataatt gtgtttcctt   5700
aaaattacat gttagataga gtttttaggt ttttttggtt ttaagattgg ttaaagcaat   5760
ttaaaagcca ctttttgtc aacatttaat agcctccact tctgttaaga taatgtatac   5820
tgctgaggaa ttactattaa tagctatcaa cataccacca ttaaattaag gtattcactt   5880
tagattttt attaaagctt ttttcttgca cactgatcgt tgtgtttcta agctgatttt   5940
ttcagctcta atatacctat ggttaaaaag tataaaaact taaattgata tttagatata   6000
tgttttccta ttagtttatg ttttaaaaag acaaaattgt atctgtcagt ccctgaaggc   6060
agtttgtttt tatactctct cacatttgta tttgtttttt aaatggcagt attttagaag   6120
atttggagaa aagtccacat aataatgttt tcttaaaagc ttttaaagtt tttgctgtac   6180
ttcaatttac ttcttccatc agaaaactaa gaacaaagtg ttgctcagtc tgttccgctg   6240
acctaaattt gtgttttcag cacttggctc agccaattca ctgagtgaag gaattgcttt   6300
atgaggcaaa gcatgtgaaa gttctaaagt atggttagat tgtaggtcgt gctctatatg   6360
gaaacatcaa accattacta cagagaaatg ataaggcatt ggatccacta ttgaaattat   6420
tatttttgga tcaacaagtt ggtactttct gacttctgta tcttaacata agggaatttt   6480
aggtaatgct aagtcagttg tctcattttt tgtgataagt tttggaattt ttagttaatt   6540
gaaataaata atgcttttaa atagaagtaa aaggtttata agtgtgcaaa ttgtagattt   6600
atcaattacc tcagcaggta tcctgccatg taattattag tgattagtgt taataagata   6660
atagattcag gtcttccaac tatgcccttg gattgtggcc tactgtatgt tattaaatgg   6720
tctcttacta tccaaaatgg gagtagatgc tgtggccccg tctcccttgg cttttacgtc   6780
ccatatccac ccccattcat gtacaacatg tgaaatataa aaatctcatt tcttgtcaaa   6840
atcagcactg cttatttgca tactcagcat cggatcagtg agtagtttta taaaaaatcc   6900
acgcacccaa ctcccttagt taaaacagat tcttaattca taccatgaat tcttaatttc   6960
tgtaccatct atgttaatga tctgctgaag gtgactcaag attttcaagg tgtaatacag   7020
tttgatcatg taccggacct ggatatttaa tttttttcc ctcacagtta atctcctcct   7080
tgataaagca ataacactgc tttgagtctg ttgcctaata gcatgtcaga atcctctcct   7140
ggatggtgat tttataggaa agtttgtatg catatcaccc agtctatctt ttaaaaatta   7200
agaaatttaa atgtatgctg gaagtaatga cactatattg tggcatttta ttttaaaaat   7260
tggggaaagt tgcatatttt tttaaaagta agtgtttgag taaaaaaatt gaaggtactt   7320
ttttaaggaa aaaaatttat atgccacagt ttacatagac atttcagatt caacacgtac   7380
tcttgaatat aatggtttct tttacttggt caaaatgcat gtatagcatt tctttcatct   7440
tagttccttg tgtttgccta tgtggtcctt tatatatttt ttattgtatc gaagaaacaa   7500
```

```
aactatcttc aaaaataagt taatttggat atatttgtca tatcaaacta caaagtgtac   7560

aaagttaagt ttagcccttt tctagaaagt gatctttaaa attaaaaatg ctcctctttt   7620

aaattcacca aatttatgtg tgggaaggca ccaaaatgat tttgtaagtg ccactgcaat   7680

attccctttc aagtgtggcc taaatttcaa tcttaaggat ggaatgcatg tctgctcctt   7740

gttctgaaaa atgtaggcat ctactacatt ttaaaacaca gtgaaacata tacataagcc   7800

tataaaaaaa gatttgtgca atttgaaagc ctgttaattt tttatgtaga catacctaca   7860

cacgaaaggg ttaaattcac agccttacta gttccttgct tccagtattt caattggtct   7920

cctcccctca ttattattat tactactagt actattattt ttgcacatag ttaactgccc   7980

ttcaatatga ttcttaaaaa gtgctgtttc tgtggtatcg tattctctaa ataatcatat   8040

ttaatttttt aaaacaaggt tgcagtttct aattgtttcg ttcctgtgtt tttgctggtg   8100

tgtaataaaa gcaagttttt tcttttcatg gttatttaat acattagctg cctgtaaata   8160

attcttgtta taatgctctg gaatgtgttg tagaagttgt attagattag ttttaaaccc   8220

ttgtttgaaa gccacattgt tttggttatt tctattaaat tagaaaattg aaaaagtttt   8280

caaatgaa                                                            8288
```

<210> SEQ ID NO 45
<211> LENGTH: 1127
<212> TYPE: PRT
<213> ORGANISM: Homo sapiens
<220> FEATURE:
<221> NAME/KEY: misc_feature
<223> OTHER INFORMATION: TRIM33 isoform alpha (NP_056990.3)

<400> SEQUENCE: 45

```
Met Ala Glu Asn Lys Gly Gly Gly Glu Ala Glu Ser Gly Gly Gly Gly
1               5                   10                  15

Ser Gly Ser Ala Pro Val Thr Ala Gly Ala Ala Gly Pro Ala Ala Gln
            20                  25                  30

Glu Ala Glu Pro Pro Leu Thr Ala Val Leu Val Glu Glu Glu Glu Glu
        35                  40                  45

Glu Gly Gly Arg Ala Gly Ala Glu Gly Gly Ala Ala Gly Pro Asp Asp
    50                  55                  60

Gly Gly Val Ala Ala Ala Ser Ser Gly Ser Ala Gln Ala Ala Ser Ser
65                  70                  75                  80

Pro Ala Ala Ser Val Gly Thr Gly Val Ala Gly Gly Ala Val Ser Thr
                85                  90                  95

Pro Ala Pro Ala Pro Ala Ser Ala Pro Ala Pro Gly Pro Ser Ala Gly
            100                 105                 110

Pro Pro Pro Gly Pro Pro Ala Ser Leu Leu Asp Thr Cys Ala Val Cys
        115                 120                 125

Gln Gln Ser Leu Gln Ser Arg Arg Glu Ala Glu Pro Lys Leu Leu Pro
    130                 135                 140

Cys Leu His Ser Phe Cys Leu Arg Cys Leu Pro Glu Pro Glu Arg Gln
145                 150                 155                 160

Leu Ser Val Pro Ile Pro Gly Gly Ser Asn Gly Asp Ile Gln Gln Val
                165                 170                 175

Gly Val Ile Arg Cys Pro Val Cys Arg Gln Glu Cys Arg Gln Ile Asp
            180                 185                 190

Leu Val Asp Asn Tyr Phe Val Lys Asp Thr Ser Glu Ala Pro Ser Ser
        195                 200                 205
```

-continued

```
Ser Asp Glu Lys Ser Glu Gln Val Cys Thr Ser Cys Glu Asp Asn Ala
    210                 215                 220

Ser Ala Val Gly Phe Cys Val Glu Cys Gly Glu Trp Leu Cys Lys Thr
225                 230                 235                 240

Cys Ile Glu Ala His Gln Arg Val Lys Phe Thr Lys Asp His Leu Ile
                245                 250                 255

Arg Lys Lys Glu Asp Val Ser Glu Ser Val Gly Ala Ser Gly Gln Arg
            260                 265                 270

Pro Val Phe Cys Pro Val His Lys Gln Glu Gln Leu Lys Leu Phe Cys
        275                 280                 285

Glu Thr Cys Asp Arg Leu Thr Cys Arg Asp Cys Gln Leu Leu Glu His
    290                 295                 300

Lys Glu His Arg Tyr Gln Phe Leu Glu Glu Ala Phe Gln Asn Gln Lys
305                 310                 315                 320

Gly Ala Ile Glu Asn Leu Leu Ala Lys Leu Leu Glu Lys Lys Asn Tyr
                325                 330                 335

Val His Phe Ala Ala Thr Gln Val Gln Asn Arg Ile Lys Glu Val Asn
            340                 345                 350

Glu Thr Asn Lys Arg Val Glu Gln Glu Ile Lys Val Ala Ile Phe Thr
        355                 360                 365

Leu Ile Asn Glu Ile Asn Lys Lys Gly Lys Ser Leu Leu Gln Gln Leu
    370                 375                 380

Glu Asn Val Thr Lys Glu Arg Gln Met Lys Leu Leu Gln Gln Gln Asn
385                 390                 395                 400

Asp Ile Thr Gly Leu Ser Arg Gln Val Lys His Val Met Asn Phe Thr
                405                 410                 415

Asn Trp Ala Ile Ala Ser Gly Ser Ser Thr Ala Leu Leu Tyr Ser Lys
            420                 425                 430

Arg Leu Ile Thr Phe Gln Leu Arg His Ile Leu Lys Ala Arg Cys Asp
        435                 440                 445

Pro Val Pro Ala Ala Asn Gly Ala Ile Arg Phe His Cys Asp Pro Thr
    450                 455                 460

Phe Trp Ala Lys Asn Val Val Asn Leu Gly Asn Leu Val Ile Glu Ser
465                 470                 475                 480

Lys Pro Ala Pro Gly Tyr Thr Pro Asn Val Val Val Gly Gln Val Pro
                485                 490                 495

Pro Gly Thr Asn His Ile Ser Lys Thr Pro Gly Gln Ile Asn Leu Ala
            500                 505                 510

Gln Leu Arg Leu Gln His Met Gln Gln Gln Val Tyr Ala Gln Lys His
        515                 520                 525

Gln Gln Leu Gln Gln Met Arg Met Gln Gln Pro Pro Ala Pro Val Pro
    530                 535                 540

Thr Thr Thr Thr Thr Thr Gln Gln His Pro Arg Gln Ala Ala Pro Gln
545                 550                 555                 560

Met Leu Gln Gln Gln Pro Pro Arg Leu Ile Ser Val Gln Thr Met Gln
                565                 570                 575

Arg Gly Asn Met Asn Cys Gly Ala Phe Gln Ala His Gln Met Arg Leu
            580                 585                 590

Ala Gln Asn Ala Ala Arg Ile Pro Gly Ile Pro Arg His Ser Gly Pro
        595                 600                 605

Gln Tyr Ser Met Met Gln Pro His Leu Gln Arg Gln His Ser Asn Pro
    610                 615                 620

Gly His Ala Gly Pro Phe Pro Val Val Ser Val His Asn Thr Thr Ile
```

-continued

```
625                 630                 635                 640

Asn Pro Thr Ser Pro Thr Thr Ala Thr Met Ala Asn Ala Asn Arg Gly
                645                 650                 655

Pro Thr Ser Pro Ser Val Thr Ala Ile Glu Leu Ile Pro Ser Val Thr
            660                 665                 670

Asn Pro Glu Asn Leu Pro Ser Leu Pro Asp Ile Pro Pro Ile Gln Leu
        675                 680                 685

Glu Asp Ala Gly Ser Ser Ser Leu Asp Asn Leu Leu Ser Arg Tyr Ile
    690                 695                 700

Ser Gly Ser His Leu Pro Pro Gln Pro Thr Ser Thr Met Asn Pro Ser
705                 710                 715                 720

Pro Gly Pro Ser Ala Leu Ser Pro Gly Ser Ser Gly Leu Ser Asn Ser
                725                 730                 735

His Thr Pro Val Arg Pro Pro Ser Thr Ser Ser Thr Gly Ser Arg Gly
            740                 745                 750

Ser Cys Gly Ser Ser Gly Arg Thr Ala Glu Lys Thr Ser Leu Ser Phe
        755                 760                 765

Lys Ser Asp Gln Val Lys Val Lys Gln Glu Pro Gly Thr Glu Asp Glu
    770                 775                 780

Ile Cys Ser Phe Ser Gly Gly Val Lys Gln Glu Lys Thr Glu Asp Gly
785                 790                 795                 800

Arg Arg Ser Ala Cys Met Leu Ser Ser Pro Glu Ser Ser Leu Thr Pro
                805                 810                 815

Pro Leu Ser Thr Asn Leu His Leu Glu Ser Glu Leu Asp Ala Leu Ala
            820                 825                 830

Ser Leu Glu Asn His Val Lys Ile Glu Pro Ala Asp Met Asn Glu Ser
        835                 840                 845

Cys Lys Gln Ser Gly Leu Ser Ser Leu Val Asn Gly Lys Ser Pro Ile
    850                 855                 860

Arg Ser Leu Met His Arg Ser Ala Arg Ile Gly Gly Asp Gly Asn Asn
865                 870                 875                 880

Lys Asp Asp Asp Pro Asn Glu Asp Trp Cys Ala Val Cys Gln Asn Gly
                885                 890                 895

Gly Asp Leu Leu Cys Cys Glu Lys Cys Pro Lys Val Phe His Leu Thr
            900                 905                 910

Cys His Val Pro Thr Leu Leu Ser Phe Pro Ser Gly Asp Trp Ile Cys
        915                 920                 925

Thr Phe Cys Arg Asp Ile Gly Lys Pro Glu Val Glu Tyr Asp Cys Asp
    930                 935                 940

Asn Leu Gln His Ser Lys Lys Gly Lys Thr Ala Gln Gly Leu Ser Pro
945                 950                 955                 960

Val Asp Gln Arg Lys Cys Glu Arg Leu Leu Leu Tyr Leu Tyr Cys His
                965                 970                 975

Glu Leu Ser Ile Glu Phe Gln Glu Pro Val Pro Ala Ser Ile Pro Asn
            980                 985                 990

Tyr Tyr Lys Ile Ile Lys Lys Pro  Met Asp Leu Ser Thr  Val Lys Lys
        995                 1000                 1005

Lys Leu  Gln Lys Lys His Ser  Gln His Tyr Gln Ile  Pro Asp Asp
    1010                 1015                 1020

Phe Val  Ala Asp Val Arg Leu  Ile Phe Lys Asn Cys  Glu Arg Phe
    1025                 1030                 1035

Asn Glu  Met Met Lys Val Val  Gln Val Tyr Ala Asp  Thr Gln Glu
    1040                 1045                 1050
```

```
Ile Asn  Leu Lys Ala Asp Ser  Glu Val Ala Gln Ala  Gly Lys Ala
    1055                 1060                 1065

Val Ala  Leu Tyr Phe Glu Asp  Lys Leu Thr Glu Ile  Tyr Ser Asp
    1070                 1075                 1080

Arg Thr  Phe Ala Pro Leu Pro  Glu Phe Glu Gln Glu  Glu Asp Asp
    1085                 1090                 1095

Gly Glu  Val Thr Glu Asp Ser  Asp Glu Asp Phe Ile  Gln Pro Arg
    1100                 1105                 1110

Arg Lys  Arg Leu Lys Ser Asp  Glu Arg Pro Val His  Ile Lys
    1115                 1120                 1125


<210> SEQ ID NO 46
<211> LENGTH: 1110
<212> TYPE: PRT
<213> ORGANISM: Homo sapiens
<220> FEATURE:
<221> NAME/KEY: misc_feature
<223> OTHER INFORMATION: TRIM33 isoform beta (NP_148980.2)

<400> SEQUENCE: 46

Met Ala Glu Asn Lys Gly Gly Gly Glu Ala Glu Ser Gly Gly Gly Gly
1               5                   10                  15

Ser Gly Ser Ala Pro Val Thr Ala Gly Ala Ala Gly Pro Ala Ala Gln
            20                  25                  30

Glu Ala Glu Pro Pro Leu Thr Ala Val Leu Val Glu Glu Glu Glu Glu
        35                  40                  45

Glu Gly Gly Arg Ala Gly Ala Glu Gly Gly Ala Ala Gly Pro Asp Asp
    50                  55                  60

Gly Gly Val Ala Ala Ala Ser Ser Gly Ser Ala Gln Ala Ala Ser Ser
65                  70                  75                  80

Pro Ala Ala Ser Val Gly Thr Gly Val Ala Gly Gly Ala Val Ser Thr
                85                  90                  95

Pro Ala Pro Ala Pro Ala Ser Ala Pro Ala Pro Gly Pro Ser Ala Gly
            100                 105                 110

Pro Pro Pro Gly Pro Pro Ala Ser Leu Leu Asp Thr Cys Ala Val Cys
        115                 120                 125

Gln Gln Ser Leu Gln Ser Arg Arg Glu Ala Glu Pro Lys Leu Leu Pro
    130                 135                 140

Cys Leu His Ser Phe Cys Leu Arg Cys Leu Pro Glu Pro Glu Arg Gln
145                 150                 155                 160

Leu Ser Val Pro Ile Pro Gly Gly Ser Asn Gly Asp Ile Gln Gln Val
                165                 170                 175

Gly Val Ile Arg Cys Pro Val Cys Arg Gln Glu Cys Arg Gln Ile Asp
            180                 185                 190

Leu Val Asp Asn Tyr Phe Val Lys Asp Thr Ser Glu Ala Pro Ser Ser
        195                 200                 205

Ser Asp Glu Lys Ser Glu Gln Val Cys Thr Ser Cys Glu Asp Asn Ala
    210                 215                 220

Ser Ala Val Gly Phe Cys Val Glu Cys Gly Glu Trp Leu Cys Lys Thr
225                 230                 235                 240

Cys Ile Glu Ala His Gln Arg Val Lys Phe Thr Lys Asp His Leu Ile
                245                 250                 255

Arg Lys Lys Glu Asp Val Ser Glu Ser Val Gly Ala Ser Gly Gln Arg
            260                 265                 270

Pro Val Phe Cys Pro Val His Lys Gln Glu Gln Leu Lys Leu Phe Cys
```

-continued

```
        275                 280                 285

Glu Thr Cys Asp Arg Leu Thr Cys Arg Asp Cys Gln Leu Leu Glu His
    290                 295                 300

Lys Glu His Arg Tyr Gln Phe Leu Glu Glu Ala Phe Gln Asn Gln Lys
305                 310                 315                 320

Gly Ala Ile Glu Asn Leu Leu Ala Lys Leu Leu Glu Lys Lys Asn Tyr
                325                 330                 335

Val His Phe Ala Ala Thr Gln Val Gln Asn Arg Ile Lys Glu Val Asn
            340                 345                 350

Glu Thr Asn Lys Arg Val Glu Gln Glu Ile Lys Val Ala Ile Phe Thr
        355                 360                 365

Leu Ile Asn Glu Ile Asn Lys Lys Gly Lys Ser Leu Leu Gln Gln Leu
    370                 375                 380

Glu Asn Val Thr Lys Glu Arg Gln Met Lys Leu Leu Gln Gln Gln Asn
385                 390                 395                 400

Asp Ile Thr Gly Leu Ser Arg Gln Val Lys His Val Met Asn Phe Thr
                405                 410                 415

Asn Trp Ala Ile Ala Ser Gly Ser Ser Thr Ala Leu Leu Tyr Ser Lys
            420                 425                 430

Arg Leu Ile Thr Phe Gln Leu Arg His Ile Leu Lys Ala Arg Cys Asp
        435                 440                 445

Pro Val Pro Ala Ala Asn Gly Ala Ile Arg Phe His Cys Asp Pro Thr
    450                 455                 460

Phe Trp Ala Lys Asn Val Val Asn Leu Gly Asn Leu Val Ile Glu Ser
465                 470                 475                 480

Lys Pro Ala Pro Gly Tyr Thr Pro Asn Val Val Val Gly Gln Val Pro
                485                 490                 495

Pro Gly Thr Asn His Ile Ser Lys Thr Pro Gly Gln Ile Asn Leu Ala
            500                 505                 510

Gln Leu Arg Leu Gln His Met Gln Gln Gln Val Tyr Ala Gln Lys His
        515                 520                 525

Gln Gln Leu Gln Gln Met Arg Met Gln Gln Pro Pro Ala Pro Val Pro
    530                 535                 540

Thr Thr Thr Thr Thr Thr Gln Gln His Pro Arg Gln Ala Ala Pro Gln
545                 550                 555                 560

Met Leu Gln Gln Gln Pro Pro Arg Leu Ile Ser Val Gln Thr Met Gln
                565                 570                 575

Arg Gly Asn Met Asn Cys Gly Ala Phe Gln Ala His Gln Met Arg Leu
            580                 585                 590

Ala Gln Asn Ala Ala Arg Ile Pro Gly Ile Pro Arg His Ser Gly Pro
        595                 600                 605

Gln Tyr Ser Met Met Gln Pro His Leu Gln Arg Gln His Ser Asn Pro
    610                 615                 620

Gly His Ala Gly Pro Phe Pro Val Val Ser Val His Asn Thr Thr Ile
625                 630                 635                 640

Asn Pro Thr Ser Pro Thr Thr Ala Thr Met Ala Asn Ala Asn Arg Gly
                645                 650                 655

Pro Thr Ser Pro Ser Val Thr Ala Ile Glu Leu Ile Pro Ser Val Thr
            660                 665                 670

Asn Pro Glu Asn Leu Pro Ser Leu Pro Asp Ile Pro Pro Ile Gln Leu
        675                 680                 685

Glu Asp Ala Gly Ser Ser Ser Leu Asp Asn Leu Leu Ser Arg Tyr Ile
    690                 695                 700
```

```
Ser Gly Ser His Leu Pro Pro Gln Pro Thr Ser Thr Met Asn Pro Ser
705                 710                 715                 720

Pro Gly Pro Ser Ala Leu Ser Pro Gly Ser Ser Gly Leu Ser Asn Ser
                725                 730                 735

His Thr Pro Val Arg Pro Pro Ser Thr Ser Ser Thr Gly Ser Arg Gly
            740                 745                 750

Ser Cys Gly Ser Ser Gly Arg Thr Ala Glu Lys Thr Ser Leu Ser Phe
        755                 760                 765

Lys Ser Asp Gln Val Lys Val Lys Gln Glu Pro Gly Thr Glu Asp Glu
    770                 775                 780

Ile Cys Ser Phe Ser Gly Gly Val Lys Gln Glu Lys Thr Glu Asp Gly
785                 790                 795                 800

Arg Arg Ser Ala Cys Met Leu Ser Ser Pro Glu Ser Ser Leu Thr Pro
                805                 810                 815

Pro Leu Ser Thr Asn Leu His Leu Glu Ser Glu Leu Asp Ala Leu Ala
            820                 825                 830

Ser Leu Glu Asn His Val Lys Ile Glu Pro Ala Asp Met Asn Glu Ser
        835                 840                 845

Cys Lys Gln Ser Gly Leu Ser Ser Leu Val Asn Gly Lys Ser Pro Ile
    850                 855                 860

Arg Ser Leu Met His Arg Ser Ala Arg Ile Gly Gly Asp Gly Asn Asn
865                 870                 875                 880

Lys Asp Asp Asp Pro Asn Glu Asp Trp Cys Ala Val Cys Gln Asn Gly
                885                 890                 895

Gly Asp Leu Leu Cys Cys Glu Lys Cys Pro Lys Val Phe His Leu Thr
            900                 905                 910

Cys His Val Pro Thr Leu Leu Ser Phe Pro Ser Gly Asp Trp Ile Cys
        915                 920                 925

Thr Phe Cys Arg Asp Ile Gly Lys Pro Glu Val Glu Tyr Asp Cys Asp
    930                 935                 940

Asn Leu Gln His Ser Lys Lys Gly Lys Thr Ala Gln Gly Leu Ser Pro
945                 950                 955                 960

Val Asp Gln Arg Lys Cys Glu Arg Leu Leu Leu Tyr Leu Tyr Cys His
                965                 970                 975

Glu Leu Ser Ile Glu Phe Gln Glu Pro Val Pro Ala Ser Ile Pro Asn
            980                 985                 990

Tyr Tyr Lys Ile Ile Lys Lys Pro  Met Asp Leu Ser Thr  Val Lys Lys
        995                 1000                 1005

Lys Leu  Gln Lys Lys His Ser  Gln His Tyr Gln Ile  Pro Asp Asp
    1010                 1015                 1020

Phe Val  Ala Asp Val Arg Leu  Ile Phe Lys Asn Cys  Glu Arg Phe
    1025                 1030                 1035

Asn Glu  Ala Asp Ser Glu Val  Ala Gln Ala Gly Lys  Ala Val Ala
    1040                 1045                 1050

Leu Tyr  Phe Glu Asp Lys Leu  Thr Glu Ile Tyr Ser  Asp Arg Thr
    1055                 1060                 1065

Phe Ala  Pro Leu Pro Glu Phe  Glu Gln Glu Glu Asp  Asp Gly Glu
    1070                 1075                 1080

Val Thr  Glu Asp Ser Asp Glu  Asp Phe Ile Gln Pro  Arg Arg Lys
    1085                 1090                 1095

Arg Leu  Lys Ser Asp Glu Arg  Pro Val His Ile Lys
    1100                 1105                 1110
```